US008546547B2

(12) United States Patent
Traversa et al.

(10) Patent No.: US 8,546,547 B2
(45) Date of Patent: *Oct. 1, 2013

(54) POLYMER CONJUGATES OF BOX-A OF HMGB1 AND BOX-A VARIANTS OF HMGB1

(75) Inventors: Silvio Traversa, Palazzo Canavese (IT); Chiara Lorenzetto, Villafranca Plemonte (IT); Valentina Mainero, Ivrea (IT); Sebastiano Morena, Chivasso (IT); Silvano Fumero, Ivrea (IT); Luca Beccaria, Ivrea (IT)

(73) Assignee: Creabilis Therapeutics S.p.A., Colleretto Giacosa (IT)

( * ) Notice: Subject to any disclaimer, the term of this patent is extended or adjusted under 35 U.S.C. 154(b) by 1008 days.

This patent is subject to a terminal disclaimer.

(21) Appl. No.: 12/441,478

(22) PCT Filed: Sep. 14, 2007

(86) PCT No.: PCT/EP2007/008029
§ 371 (c)(1),
(2), (4) Date: Mar. 16, 2009

(87) PCT Pub. No.: WO2008/031612
PCT Pub. Date: Mar. 20, 2008

(65) Prior Publication Data
US 2009/0324677 A1   Dec. 31, 2009

Related U.S. Application Data

(60) Provisional application No. 60/904,776, filed on Mar. 5, 2007.

(30) Foreign Application Priority Data

Sep. 15, 2006   (EP) .................................... 06019362

(51) Int. Cl.
*C07K 14/00* (2006.01)
(52) U.S. Cl.
USPC ......................................... 530/402; 530/350
(58) Field of Classification Search
None
See application file for complete search history.

(56) References Cited

FOREIGN PATENT DOCUMENTS

| WO | 02/060929 A2 | 8/2002 |
|---|---|---|
| WO | 02/074337 A1 | 9/2002 |
| WO | 02/092004 A2 | 11/2002 |
| WO | 2004046345 A2 | 6/2004 |
| WO | 2004/056852 S2 | 7/2004 |
| WO | 2006/012373 A2 | 2/2006 |
| WO | 2006/024547 A2 | 3/2006 |
| WO | 2007/022999 A1 | 3/2007 |

OTHER PUBLICATIONS

Yang et al., "PEGylation Confers Greatly Extended Half-Life and Attenuated Immunogenicity to Recombinant Methioninase in Primates", Cancer Research, 64, 6673-6678, Sep. 15, 2004.

Pasut, G. and F. M. Veronese, "Polymer-drug conjugation, recent achievements and general strategies", Prog. Polym. Sci. 32, 2007, pp. 933-961.

Zalipsky, S.: „Chemistry of polyethylene glycol conjugates with biologically active molecules, Advanced Drug Delivery Reviews, vol. 16, 1995, pp. 157-182.

Brocchini, S. et al.: "Disulfide bridge based PEGylation of proteins", Advanced Drug Delivery Reviews, vol. 60, 2008, p. 3-12.

Monfardini, C. and F. M. Veronese, "Stabilization of Substances in Circulation", Bioconjugate Chem., 1998, vol. 9, pp. 418-450.

Edwards, C. K. III et al.: "Design of PEGylated soluble tumor necrosis factor receptor type I (PEG sTNF-RI) for chronic inflammatory diseases", Advanced Drug Delivery Reviews, vol. 55, 2003, pp. 1315-1336.

Arduini, R. M. et al.: "Expression, purification, and characterization of rat interferon-β, and preparation of an N-terminally PEGylated form with improved pharmacokinetic parameters", Protein Expression and Purification, vol. 34, 2004, pp. 229-242.

Torchilin, V. P. et al.: "Immobilized thrombolytic enzymes for systemic and local application", Annals of the New York Academy of Sciences, 501(1), pp. 481-486.

Caliceti, P. et al.: "Physicochemical and biological properties of monofunctional hydroxy terminating poly(N-vinylpyrrolidone) conjugated superoxide dismutase", Journal of Bioactive and Compatible Polymers, vol. 10, issue 2, Apr. 1995, pp. 103-120, (only Abstract available).

Roberts, M. J. et al.: "Chemistry for peptide and protein PEGylation", Adv. Drug Delivery Reviews, 54 (2002), p. 459-476.

Letter dated Nov. 17, 2009 from Studio Ferrario with observations concerning the parallel European patent appplication No. 07 818 168.2.

Pasut et al., "Protein, peptide and non-peptide drug PEGylation for therapeutic application", Expert Opin. Ther. Patents, 2004, vol. 14, No. 6, pp. 859-894.

Tsubery et al., "Prolonging the Action of Protein and Peptide Drugs by a Novel Approach of reversible Polyethylene glycol Modification", The Journal of Biological Chemistry, vol. 279, No. 37, Sep. 10, 2004, pp. 38118-38124.

Yamada et al., "New high mobility group box 1 assay system", Clinica Chimica Acta, vol. 372, No. 1-2, Jun. 23, 2006, pp. 173-178. (Abstract only).

Official communication of Sep. 10, 2012 against European patent No. 2 068 935, with a letter from the Italian firm Bianchetti Bracco Minoja dated Sep. 5, 2012 5 pgs.

Notice of Reasons for Rejection in Japanese application No. 2009-527748 dated Sep. 25, 2012, 5 pgs.

*Primary Examiner* — Michael Pak
(74) *Attorney, Agent, or Firm* — Rothwell, Figg, Ernst & Manbeck, P.C.

(57) ABSTRACT

The present invention relates to novel polymer conjugates of polypeptide variants of the HMGB1 high affinity binding domain Box-A (HMGB1 Box-A) or of a biologically active fragment of HMGB1 Box-A. Further, the invention relates to novel polymer conjugates of polypeptide variants of the HMGB1 high affinity binding domain Box-A (HMGB1 Box-A). Moreover, the present invention concerns the use of said polymer conjugates of polypeptide molecules of HMGB1 Box-A to diagnose, prevent, alleviate and/or treat pathologies associated with extracellular HMGB1 and/or associated with an increased expression of RAGE.

6 Claims, 98 Drawing Sheets

Figure 1a

Box A 84 amino acids

\# Protection against proteolysis
If sequence:

GKGDPKKPRGKMSSYAFFVQTCREEHKKKHPDASVNFSEFSKKCSERWKTMSAKE
KGKFEDMAKADKARYEREMKTYIPPKGET

In bold amino acids sensitive to proteases proteolysis

Figure 1b

Box A 84 amino acids
\# Mutant list:

| | | | |
|---|---|---|---|
| K2N | K27Q | E55Q | E73N |
| K2Q | K28N | E55H | M74I |
| D4N | K28Q | E55N | M74V |
| D4Q | K29N | K56N | K75N |
| P5A | K29Q | K56Q | K75Q |
| P5S | P31A | K58N | Y77H |
| K6N | P31S | K58Q | Y77I |
| K6Q | D32N | F59I | P79A |
| K7N | D32Q | F59V | P79S |
| K7Q | F37I | E60Q | P80A |
| P8A | F37V | E60H | P80S |
| P8S | E39Q | E60N | K81N |
| R9H | E39H | D61N | K81Q |
| R9Q | E39N | D61Q | E83Q |
| K11N | F40I | M62I | E83H |
| K11Q | F40V | M62V | E83N |
| M12I | K42N | K64N | |
| M12V | K42Q | K64Q | |
| Y15H | K43N | D66N | |
| Y15I | K43Q | D66Q | |
| F17I | E46Q | K67N | |
| F17V | E46H | K67Q | |
| F18I | E46N | R69H | |
| F18V | R47H | R69Q | |
| R23H | R47Q | Y70H | |
| R23Q | W48Y | Y70I | |
| E24Q | W48S | E71Q | |
| E24H | K49N | E71H | |
| E24N | K49Q | E71N | |
| E25Q | M51I | R72H | |
| E25H | M51V | R72Q | |
| E25N | K54N | E73Q | |
| K27N | K54Q | E73H | |

Figure 1b continued

Box A 84 amino acid sequences:

> sequence 1 Wild type
GKGDPKKPRGKMSSYAFFVQTCREEHKKKHPDASVNFSEFSKKCSERWKTMSAKEKGKFEDMAKAD
KARYEREMKTYIPPKGET > sequence 2 K2N
GNGDPKKPRGKMSSYAFFVQTCREEHKKKHPDASVNFSEFSKKCSERWKTMSAKEKGKFEDMAKAD
KARYEREMKTYIPPKGET > sequence 3 K2Q
GQGDPKKPRGKMSSYAFFVQTCREEHKKKHPDASVNFSEFSKKCSERWKTMSAKEKGKFEDMAKAD
KARYEREMKTYIPPKGET > sequence 4 D4N
GKGNPKKPRGKMSSYAFFVQTCREEHKKKHPDASVNFSEFSKKCSERWKTMSAKEKGKFEDMAKAD
KARYEREMKTYIPPKGET > sequence 5 D4Q
GKGQPKKPRGKMSSYAFFVQTCREEHKKKHPDASVNFSEFSKKCSERWKTMSAKEKGKFEDMAKAD
KARYEREMKTYIPPKGET > sequence 6 P5A
GKGDAKKPRGKMSSYAFFVQTCREEHKKKHPDASVNFSEFSKKCSERWKTMSAKEKGKFEDMAKAD
KARYEREMKTYIPPKGET > sequence 7 P5S
GKGDSKKPRGKMSSYAFFVQTCREEHKKKHPDASVNFSEFSKKCSERWKTMSAKEKGKFEDMAKAD
KARYEREMKTYIPPKGET > sequence 8 K6N
GKGDPNKPRGKMSSYAFFVQTCREEHKKKHPDASVNFSEFSKKCSERWKTMSAKEKGKFEDMAKAD
KARYEREMKTYIPPKGET > sequence 9 K6Q
GKGDPQKPRGKMSSYAFFVQTCREEHKKKHPDASVNFSEFSKKCSERWKTMSAKEKGKFEDMAKAD
KARYEREMKTYIPPKGET > sequence 10 K7N
GKGDPKNPRGKMSSYAFFVQTCREEHKKKHPDASVNFSEFSKKCSERWKTMSAKEKGKFEDMAKAD
KARYEREMKTYIPPKGET > sequence 11 K7Q
GKGDPKQPRGKMSSYAFFVQTCREEHKKKHPDASVNFSEFSKKCSERWKTMSAKEKGKFEDMAKAD
KARYEREMKTYIPPKGET > sequence 12 P8A
GKGDPKKARGKMSSYAFFVQTCREEHKKKHPDASVNFSEFSKKCSERWKTMSAKEKGKFEDMAKAD
KARYEREMKTYIPPKGET > sequence 13 P8S
GKGDPKKSRGKMSSYAFFVQTCREEHKKKHPDASVNFSEFSKKCSERWKTMSAKE

Figure 1b continued

KGKFEDMAKADKARYEREMKTYIPPKGET

> sequence 14 R9H
GKGDPKKPHGKMSSYAFFVQTCREEHKKKHPDASVNFSEFSKKCSERWKTMSAKEKGKFEDMAKAD
KARYEREMKTYIPPKGET > sequence 15 R9Q
GKGDPKKPQGKMSSYAFFVQTCREEHKKKHPDASVNFSEFSKKCSERWKTMSAKEKGKFEDMAKAD
KARYEREMKTYIPPKGET > sequence 16 K11N
GKGDPKKPRGNMSSYAFFVQTCREEHKKKHPDASVNFSEFSKKCSERWKTMSAKEKGKFEDMAKAD
KARYEREMKTYIPPKGET > sequence 17 K11Q
GKGDPKKPRGQMSSYAFFVQTCREEHKKKHPDASVNFSEFSKKCSERWKTMSAKEKGKFEDMAKAD
KARYEREMKTYIPPKGET > sequence 18 M12I
GKGDPKKPRGKISSYAFFVQTCREEHKKKHPDASVNFSEFSKKCSERWKTMSAKEKGKFEDMAKADK
ARYEREMKTYIPPKGET > sequence 19 M12V
GKGDPKKPRGKVSSYAFFVQTCREEHKKKHPDASVNFSEFSKKCSERWKTMSAKEKGKFEDMAKADK
ARYEREMKTYIPPKGET > sequence 20 Y15H
GKGDPKKPRGKMSSHAFFVQTCREEHKKKHPDASVNFSEFSKKCSERWKTMSAKEKGKFEDMAKAD
KARYEREMKTYIPPKGET > sequence 21 Y15I
GKGDPKKPRGKMSSIAFFVQTCREEHKKKHPDASVNFSEFSKKCSERWKTMSAKEKGKFEDMAKADK
ARYEREMKTYIPPKGET > sequence 22 F17I
GKGDPKKPRGKMSSYAIFVQTCREEHKKKHPDASVNFSEFSKKCSERWKTMSAKEKGKFEDMAKADK
ARYEREMKTYIPPKGET > sequence 23 F17V
GKGDPKKPRGKMSSYAVFVQTCREEHKKKHPDASVNFSEFSKKCSERWKTMSAKEKGKFEDMAKAD
KARYEREMKTYIPPKGET > sequence 24 F18I
GKGDPKKPRGKMSSYAFIVQTCREEHKKKHPDASVNFSEFSKKCSERWKTMSAKEKGKFEDMAKADK
ARYEREMKTYIPPKGET > sequence 25 F18V
GKGDPKKPRGKMSSYAFVVQTCREEHKKKHPDASVNFSEFSKKCSERWKTMSAKEKGKFEDMAKAD
KARYEREMKTYIPPKGET > sequence 26 R23H
GKGDPKKPRGKMSSYAFFVQTCHEEHKKKHPDASVNFSEFSKKCSERWKTMSAKEKGKFEDMAKAD
KARYEREMKTYIPPKGET

Figure 1b continued

> sequence 27 R23Q
GKGDPKKPRGKMSSYAFFVQTCQEEHKKKHPDASVNFSEFSKKCSERWKTMSAKEGKFEDMAKADK

AYEREMKTYIPPKKGET

> sequence 28 E24Q
GKGDPKKPRGKMSSYAFFVQTCRQEHKKKHPDASVNFSEFSKKCSERWKTMSAKEKGKFEDMAKAD
KARYEREMKTYIPPKGET > sequence 29 E24H
GKGDPKKPRGKMSSYAFFVQTCRHEHKKKHPDASVNFSEFSKKCSERWKTMSAKEKGKFEDMAKAD
KARYEREMKTYIPPKGET > sequence 30 E24N
GKGDPKKPRGKMSSYAFFVQTCRNEHKKKHPDASVNFSEFSKKCSERWKTMSAKEKGKFEDMAKAD
KARYEREMKTYIPPKGET > sequence 31 E25Q
GKGDPKKPRGKMSSYAFFVQTCREQHKKKHPDASVNFSEFSKKCSERWKTMSAKEKGKFEDMAKAD
KARYEREMKTYIPPKGET > sequence 32 E25H
GKGDPKKPRGKMSSYAFFVQTCREHHKKKHPDASVNFSEFSKKCSERWKTMSAKEKGKFEDMAKAD
KARYEREMKTYIPPKGET > sequence 33 E25N
GKGDPKKPRGKMSSYAFFVQTCRENHKKKHPDASVNFSEFSKKCSERWKTMSAKEKGKFEDMAKAD
KARYEREMKTYIPPKGET > sequence 34 K27N
GKGDPKKPRGKMSSYAFFVQTCREEHNKKHPDASVNFSEFSKKCSERWKTMSAKEKGKFEDMAKAD
KARYEREMKTYIPPKGET > sequence 35 K27Q
GKGDPKKPRGKMSSYAFFVQTCREEHQKKHPDASVNFSEFSKKCSERWKTMSAKEKGKFEDMAKAD
KARYEREMKTYIPPKGET > sequence 36 K28N
GKGDPKKPRGKMSSYAFFVQTCREEHKNKHPDASVNFSEFSKKCSERWKTMSAKEKGKFEDMAKAD
KARYEREMKTYIPPKGET > sequence 37 K28Q
GKGDPKKPRGKMSSYAFFVQTCREEHKQKHPDASVNFSEFSKKCSERWKTMSAKEKGKFEDMAKAD
KARYEREMKTYIPPKGET > sequence 38 K29N
GKGDPKKPRGKMSSYAFFVQTCREEHKKNHPDASVNFSEFSKKCSERWKTMSAKEKGKFEDMAKAD
KARYEREMKTYIPPKGET > sequence 39 K29Q
GKGDPKKPRGKMSSYAFFVQTCREEHKKQHPDASVNFSEFSKKCSERWKTMSAKEKGKFEDMAKAD
KARYEREMKTYIPPKGET

Figure 1b continued

> sequence 40 P31A
GKGDPKKPRGKMSSYAFFVQTCREEHKKKHADASVNFSEFSKKCSERWKTMSAKEKGKFEDMAKAD
KARYEREMKTYIPPKGET > sequence 41 P31S
GKGDPKKPRGKMSSYAFFVQTCREEHKKKHSDASVNFSEFSKKCSERWKTMSAKEKGKFEDMAKAD
KARYEREMKTYIPPKGET > sequence 42 D32N
GKGDPKKPRGKMSSYAFFVQTCREEHKKKHPNASVNFSEFSKKCSERWKTMSAKEKGKFEDMAKAD
KARYEREMKTYIPPKGET > sequence 43 D32Q
GKGDPKKPRGKMSSYAFFVQTCREEHKKKHPQASVNFSEFSKKCSERWKTMSAKEKGKFEDMAKAD
KARYEREMKTYIPPKGET > sequence 44 F37I
GKGDPKKPRGKMSSYAFFVQTCREEHKKKHPDASVNISEFSKKCSERWKTMSAKEKGKFEDMAKADK
ARYEREMKTYIPPKGET > sequence 45 F37V
GKGDPKKPRGKMSSYAFFVQTCREEHKKKHPDASVNVSEFSKKCSERWKTMSAKEKGKFEDMAKAD
KARYEREMKTYIPPKGET > sequence 46 E39Q
GKGDPKKPRGKMSSYAFFVQTCREEHKKKHPDASVNFSQFSKKCSERWKTMSAKEKGKFEDMAKAD
KARYEREMKTYIPPKGET > sequence 47 E39H
GKGDPKKPRGKMSSYAFFVQTCREEHKKKHPDASVNFSHFSKKCSERWKTMSAKEKGKFEDMAKAD
KARYEREMKTYIPPKGET > sequence 48 E39N
GKGDPKKPRGKMSSYAFFVQTCREEHKKKHPDASVNFSNFSKKCSERWKTMSAKEKGKFEDMAKAD
KARYEREMKTYIPPKGET > sequence 49 F40I
GKGDPKKPRGKMSSYAFFVQTCREEHKKKHPDASVNFSEISKKCSERWKTMSAKEKGKFEDMAKADK
ARYEREMKTYIPPKGET > sequence 50 F40V
GKGDPKKPRGKMSSYAFFVQTCREEHKKKHPDASVNFSEVSKKCSERWKTMSAKEKGKFEDMAKAD
KARYEREMKTYIPPKGET > sequence 51 K42N
GKGDPKKPRGKMSSYAFFVQTCREEHKKKHPDASVNFSEFSNKCSERWKTMSAKEKGKFEDMAKAD
KARYEREMKTYIPPKGET > sequence 52 K42Q
GKGDPKKPRGKMSSYAFFVQTCREEHKKKHPDASVNFSEFSQKCSERWKTMSAKEKGKFEDMAKAD
KARYEREMKTYIPPKGET > sequence 53 K43N
GKGDPKKPRGKMSSYAFFVQTCREEHKKKHPDASVNFSEFSKNCSERWKTMSAKEKGKFEDMAKAD
KARYEREMKTYIPPKGET

Figure 1b continued

> sequence 54 K43Q
GKGDPKKPRGKMSSYAFFVQTCREEHKKKHPDASVNFSEFSKQCSERWKTMSAKEKGKFEDMAKAD
KARYEREMKTYIPPKGET > sequence 55 E46Q
GKGDPKKPRGKMSSYAFFVQTCREEHKKKHPDASVNFSEFSKKCSQRWKTMSAKEKGKFEDMAKAD
KARYEREMKTYIPPKGET > sequence 56 E46H
GKGDPKKPRGKMSSYAFFVQTCREEHKKKHPDASVNFSEFSKKCSHRWKTMSAKEKGKFEDMAKAD
KARYEREMKTYIPPKGET > sequence 57 E46N
GKGDPKKPRGKMSSYAFFVQTCREEHKKKHPDASVNFSEFSKKCSNRWKTMSAKEKGKFEDMAKAD
KARYEREMKTYIPPKGET > sequence 58 R47H
GKGDPKKPRGKMSSYAFFVQTCREEHKKKHPDASVNFSEFSKKCSEHWKTMSAKEKGKFEDMAKAD
KARYEREMKTYIPPKGET > sequence 59 R47Q
GKGDPKKPRGKMSSYAFFVQTCREEHKKKHPDASVNFSEFSKKCSEQWKTMSAKEKGKFEDMAKAD
KARYEREMKTYIPPKGET > sequence 60 W48Y
GKGDPKKPRGKMSSYAFFVQTCREEHKKKHPDASVNFSEFSKKCSERYKTMSAKEKGKFEDMAKADK
ARYEREMKTYIPPKGET > sequence 61 W48S
GKGDPKKPRGKMSSYAFFVQTCREEHKKKHPDASVNFSEFSKKCSERSKTMSAKEKGKFEDMAKADK
ARYEREMKTYIPPKGET > sequence 62 K49N
GKGDPKKPRGKMSSYAFFVQTCREEHKKKHPDASVNFSEFSKKCSERWNTMSAKEKGKFEDMAKAD
KARYEREMKTYIPPKGET > sequence 63 K49Q
GKGDPKKPRGKMSSYAFFVQTCREEHKKKHPDASVNFSEFSKKCSERWQTMSAKEKGKFEDMAKAD
KARYEREMKTYIPPKGET > sequence 64 M51I
GKGDPKKPRGKMSSYAFFVQTCREEHKKKHPDASVNFSEFSKKCSERWKTISAKEKGKFEDMAKADK
ARYEREMKTYIPPKGET > sequence 65 M51V
GKGDPKKPRGKMSSYAFFVQTCREEHKKKHPDASVNFSEFSKKCSERWKTVSAKEKGKFEDMAKADK
ARYEREMKTYIPPKGET > sequence 66 K54N
GKGDPKKPRGKMSSYAFFVQTCREEHKKKHPDASVNFSEFSKKCSERWKTMSANEKGKFEDMAKAD
KARYEREMKTYIPPKGET > sequence 67 K54Q
GKGDPKKPRGKMSSYAFFVQTCREEHKKKHPDASVNFSEFSKKCSERWKTMSAQEKGKFEDMAKAD

Figure 1b continued

KARYEREMKTYIPPKGET

> sequence 68 E55Q
GKGDPKKPRGKMSSYAFFVQTCREEHKKKHPDASVNFSEFSKKCSERWKTMSAKQKGKFEDMAKAD
KARYEREMKTYIPPKGET > sequence 69 E55H
GKGDPKKPRGKMSSYAFFVQTCREEHKKKHPDASVNFSEFSKKCSERWKTMSAKHKGKFEDMAKAD
KARYEREMKTYIPPKGET > sequence 70 E55N
GKGDPKKPRGKMSSYAFFVQTCREEHKKKHPDASVNFSEFSKKCSERWKTMSAKNKGKFEDMAKAD
KARYEREMKTYIPPKGET > sequence 71 K56N
GKGDPKKPRGKMSSYAFFVQTCREEHKKKHPDASVNFSEFSKKCSERWKTMSAKENGKFEDMAKAD
KARYEREMKTYIPPKGET > sequence 72 K56Q
GKGDPKKPRGKMSSYAFFVQTCREEHKKKHPDASVNFSEFSKKCSERWKTMSAKEQGKFEDMAKAD
KARYEREMKTYIPPKGET > sequence 73 K58N
GKGDPKKPRGKMSSYAFFVQTCREEHKKKHPDASVNFSEFSKKCSERWKTMSAKEKGNFEDMAKAD
KARYEREMKTYIPPKGET > sequence 74 K58Q
GKGDPKKPRGKMSSYAFFVQTCREEHKKKHPDASVNFSEFSKKCSERWKTMSAKEKGQFEDMAKAD
KARYEREMKTYIPPKGET > sequence 75 F59I
GKGDPKKPRGKMSSYAFFVQTCREEHKKKHPDASVNFSEFSKKCSERWKTMSAKEKGKIEDMAKADK
ARYEREMKTYIPPKGET > sequence 76 F59V
GKGDPKKPRGKMSSYAFFVQTCREEHKKKHPDASVNFSEFSKKCSERWKTMSAKEKGKVEDMAKAD
KARYEREMKTYIPPKGET > sequence 77 E60Q
GKGDPKKPRGKMSSYAFFVQTCREEHKKKHPDASVNFSEFSKKCSERWKTMSAKEKGKFQDMAKAD
KARYEREMKTYIPPKGET > sequence 78 E60H
GKGDPKKPRGKMSSYAFFVQTCREEHKKKHPDASVNFSEFSKKCSERWKTMSAKEKGKFHDMAKAD
KARYEREMKTYIPPKGET > sequence 79 E60N
GKGDPKKPRGKMSSYAFFVQTCREEHKKKHPDASVNFSEFSKKCSERWKTMSAKEKGKFNDMAKAD
KARYEREMKTYIPPKGET > sequence 80 D61N
GKGDPKKPRGKMSSYAFFVQTCREEHKKKHPDASVNFSEFSKKCSERWKTMSAKEKGKFENMAKAD
KARYEREMKTYIPPKGET > sequence 81 D61Q

Figure 1b continued

GKGDPKKPRGKMSSYAFFVQTCREEHKKKHPDASVNFSEFSKKCSERWKTMSAKEKGKFEQMAKAD
KARYEREMKTYIPPKGET

> sequence 82 M62I
GKGDPKKPRGKMSSYAFFVQTCREEHKKKHPDASVNFSEFSKKCSERWKTMSAKEKGKFEDIAKADK
ARYEREMKTYIPPKGET > sequence 83 M62V
GKGDPKKPRGKMSSYAFFVQTCREEHKKKHPDASVNFSEFSKKCSERWKTMSAKEKGKFEDVAKADK
ARYEREMKTYIPPKGET > sequence 84 K64N
GKGDPKKPRGKMSSYAFFVQTCREEHKKKHPDASVNFSEFSKKCSERWKTMSAKEKGKFEDMANAD
KARYEREMKTYIPPKGET > sequence 85 K64Q
GKGDPKKPRGKMSSYAFFVQTCREEHKKKHPDASVNFSEFSKKCSERWKTMSAKEKGKFEDMAQAD
KARYEREMKTYIPPKGET > sequence 86 D66N
GKGDPKKPRGKMSSYAFFVQTCREEHKKKHPDASVNFSEFSKKCSERWKTMSAKEKGKFEDMAKAN
KARYEREMKTYIPPKGET > sequence 87 D66Q
GKGDPKKPRGKMSSYAFFVQTCREEHKKKHPDASVNFSEFSKKCSERWKTMSAKEKGKFEDMAKAQ
KARYEREMKTYIPPKGET > sequence 88 K67N
GKGDPKKPRGKMSSYAFFVQTCREEHKKKHPDASVNFSEFSKKCSERWKTMSAKEKGKFEDMAKAD
NARYEREMKTYIPPKGET > sequence 89 K67Q
GKGDPKKPRGKMSSYAFFVQTCREEHKKKHPDASVNFSEFSKKCSERWKTMSAKEKGKFEDMAKAD
QARYEREMKTYIPPKGET > sequence 90 R69H
GKGDPKKPRGKMSSYAFFVQTCREEHKKKHPDASVNFSEFSKKCSERWKTMSAKEKGKFEDMAKAD
KAHYEREMKTYIPPKGET > sequence 91 R69Q
GKGDPKKPRGKMSSYAFFVQTCREEHKKKHPDASVNFSEFSKKCSERWKTMSAKEKGKFEDMAKAD
KAQYEREMKTYIPPKGET > sequence 92 Y70H
GKGDPKKPRGKMSSYAFFVQTCREEHKKKHPDASVNFSEFSKKCSERWKTMSAKEKGKFEDMAKAD
KARHEREMKTYIPPKGET > sequence 93 Y70I
GKGDPKKPRGKMSSYAFFVQTCREEHKKKHPDASVNFSEFSKKCSERWKTMSAKEKGKFEDMAKAD
KARIEREMKTYIPPKGET > sequence 94 E71Q
GKGDPKKPRGKMSSYAFFVQTCREEHKKKHPDASVNFSEFSKKCSERWKTMSAKEKGKFEDMAKAD
KARYQREMKTYIPPKGET

Figure 1b continued

> sequence 95 E71H
GKGDPKKPRGKMSSYAFFVQTCREEHKKKHPDASVNFSEFSKKCSERWKTMSAKEKGKFEDMAKAD
KARYHREMKTYIPPKGET > sequence 96 E71N
GKGDPKKPRGKMSSYAFFVQTCREEHKKKHPDASVNFSEFSKKCSERWKTMSAKEKGKFEDMAKAD
KARYNREMKTYIPPKGET > sequence 97 R72H
GKGDPKKPRGKMSSYAFFVQTCREEHKKKHPDASVNFSEFSKKCSERWKTMSAKEKGKFEDMAKAD
KARYEHEMKTYIPPKGET > sequence 98 R72Q
GKGDPKKPRGKMSSYAFFVQTCREEHKKKHPDASVNFSEFSKKCSERWKTMSAKEKGKFEDMAKAD
KARYEQEMKTYIPPKGET > sequence 99 E73Q
GKGDPKKPRGKMSSYAFFVQTCREEHKKKHPDASVNFSEFSKKCSERWKTMSAKEKGKFEDMAKAD
KARYERQMKTYIPPKGET > sequence 100 E73H
GKGDPKKPRGKMSSYAFFVQTCREEHKKKHPDASVNFSEFSKKCSERWKTMSAKEKGKFEDMAKAD
KARYERHMKTYIPPKGET > sequence 101 E73N
GKGDPKKPRGKMSSYAFFVQTCREEHKKKHPDASVNFSEFSKKCSERWKTMSAKEKGKFEDMAKAD
KARYERNMKTYIPPKGET > sequence 102 M74I
GKGDPKKPRGKMSSYAFFVQTCREEHKKKHPDASVNFSEFSKKCSERWKTMSAKEKGKFEDMAKAD
KARYEREIKTYIPPKGET > sequence 103 M74V
GKGDPKKPRGKMSSYAFFVQTCREEHKKKHPDASVNFSEFSKKCSERWKTMSAKEKGKFEDMAKAD
KARYEREVKTYIPPKGET > sequence 104 K75N
GKGDPKKPRGKMSSYAFFVQTCREEHKKKHPDASVNFSEFSKKCSERWKTMSAKEKGKFEDMAKAD
KARYEREMNTYIPPKGET > sequence 105 K75Q
GKGDPKKPRGKMSSYAFFVQTCREEHKKKHPDASVNFSEFSKKCSERWKTMSAKEKGKFEDMAKAD
KARYEREMQTYIPPKGET > sequence 106 Y77H
GKGDPKKPRGKMSSYAFFVQTCREEHKKKHPDASVNFSEFSKKCSERWKTMSAKEKGKFEDMAKAD
KARYEREMKTHIPPKGET > sequence 107 Y77I
GKGDPKKPRGKMSSYAFFVQTCREEHKKKHPDASVNFSEFSKKCSERWKTMSAKEKGKFEDMAKAD
KARYEREMKTIIPPKGET > sequence 108 P79A
GKGDPKKPRGKMSSYAFFVQTCREEHKKKHPDASVNFSEFSKKCSERWKTMSAKEKGKFEDMAKAD
KARYEREMKTYIAPKGET

Figure 1b continued

> sequence 109 P79S
GKGDPKKPRGKMSSYAFFVQTCREEHKKKHPDASVNFSEFSKKCSERWKTMSAKEKGKFEDMAKAD
KARYEREMKTYISPKGET > sequence 110 P80A
GKGDPKKPRGKMSSYAFFVQTCREEHKKKHPDASVNFSEFSKKCSERWKTMSAKEKGKFEDMAKAD
KARYEREMKTYIPAKGET > sequence 111 P80S
GKGDPKKPRGKMSSYAFFVQTCREEHKKKHPDASVNFSEFSKKCSERWKTMSAKEKGKFEDMAKAD
KARYEREMKTYIPSKGET > sequence 112 K81N
GKGDPKKPRGKMSSYAFFVQTCREEHKKKHPDASVNFSEFSKKCSERWKTMSAKEKGKFEDMAKAD
KARYEREMKTYIPPNGET > sequence 113 K81Q
GKGDPKKPRGKMSSYAFFVQTCREEHKKKHPDASVNFSEFSKKCSERWKTMSAKEKGKFEDMAKAD
KARYEREMKTYIPPQGET > sequence 114 E83Q
GKGDPKKPRGKMSSYAFFVQTCREEHKKKHPDASVNFSEFSKKCSERWKTMSAKEKGKFEDMAKAD
KARYEREMKTYIPPKGQT > sequence 115 E83H
GKGDPKKPRGKMSSYAFFVQTCREEHKKKHPDASVNFSEFSKKCSERWKTMSAKEKGKFEDMAKAD
KARYEREMKTYIPPKGHT > sequence 116 E83N
GKGDPKKPRGKMSSYAFFVQTCREEHKKKHPDASVNFSEFSKKCSERWKTMSAKEKGKFEDMAKAD
KARYEREMKTYIPPKGNT

Figure 2a

Box A 77 amino acids

\# Protection against proteolysis
If sequence:

PRGKMSSYAFFVQTCREEHKKKHPDASVNFSEFSKKCSERWKTMSAKEKGKFEDM
AKADKARYEREMKTYIPPKGET

In bold amino acids sensitive to proteases proteolysis

Figure 2b

Box A 77 amino acids
\# Mutant list:

| | | | |
|---|---|---|---|
| P1A | F30V | E53H | P73S |
| P1S | E32Q | E53N | K74N |
| R2H | E32H | D54N | K74Q |
| R2Q | E32N | D54Q | E76Q |
| K4N | F33I | M55I | E76H |
| K4Q | F33V | M55V | E76N |
| M5I | K35N | K57N | |
| M5V | K35Q | K57Q | |
| Y8H | K36N | D59N | |
| Y8I | K36Q | D59Q | |
| F10I | E39Q | K60N | |
| F10V | E39H | K60Q | |
| F11I | E39N | R62H | |
| F11V | R40H | R62Q | |
| R16H | R40Q | Y63H | |
| R16Q | W41Y | Y63I | |
| E17Q | W41S | E64Q | |
| E17H | K42N | E64H | |
| E17N | K42Q | E64N | |
| E18Q | M44I | R65H | |
| E18H | M44V | R65Q | |
| E18N | K47N | E66Q | |
| K20N | K47Q | E66H | |
| K20Q | E48Q | E66N | |
| K21N | E48H | M67I | |
| K21Q | E48N | M67V | |
| K22N | K49N | K68N | |
| K22Q | K49Q | K68Q | |
| P24A | K51N | Y70H | |
| P24S | K51Q | Y70I | |
| D25N | F52I | P72A | |
| D25Q | F52V | P72S | |
| F30I | E53Q | P73A | |

Figure 2b continued

Box A 77 amino acid sequences

> sequence 117 Wild type

PRGKMSSYAFFVQTCREEHKKKHPDASVNFSEFSKKCSERWKTMSAKEKGKFEDMAKADKARYEREM
KTYIPPKGET

> sequence 118 P1A

ARGKMSSYAFFVQTCREEHKKKHPDASVNFSEFSKKCSERWKTMSAKEKGKFEDMAKADKARYEREM
KTYIPPKGET

> sequence 119 P1S

SRGKMSSYAFFVQTCREEHKKKHPDASVNFSEFSKKCSERWKTMSAKEKGKFEDMAKADKARYEREM
KTYIPPKGET

> sequence 120 R2H

PHGKMSSYAFFVQTCREEHKKKHPDASVNFSEFSKKCSERWKTMSAKEKGKFEDMAKADKARYEREM
KTYIPPKGET

> sequence 121 R2Q

PQGKMSSYAFFVQTCREEHKKKHPDASVNFSEFSKKCSERWKTMSAKEKGKFEDMAKADKARYERE
MKTYIPPKGET

> sequence 122 K4N

PRGNMSSYAFFVQTCREEHKKKHPDASVNFSEFSKKCSERWKTMSAKEKGKFEDMAKADKARYEREM
KTYIPPKGET

> sequence 123 K4Q

PRGQMSSYAFFVQTCREEHKKKHPDASVNFSEFSKKCSERWKTMSAKEKGKFEDMAKADKARYERE
MKTYIPPKGET

> sequence 124 M5I

PRGKISSYAFFVQTCREEHKKKHPDASVNFSEFSKKCSERWKTMSAKEKGKFEDMAKADKARYEREM
KTYIPPKGET

> sequence 125 M5V

PRGKVSSYAFFVQTCREEHKKKHPDASVNFSEFSKKCSERWKTMSAKEKGKFEDMAKADKARYEREM
KTYIPPKGET

> sequence 126 Y8H

PRGKMSSHAFFVQTCREEHKKKHPDASVNFSEFSKKCSERWKTMSAKEKGKFEDMAKADKARYERE
MKTYIPPKGET

> sequence 127 Y8I

PRGKMSSIAFFVQTCREEHKKKHPDASVNFSEFSKKCSERWKTMSAKEKGKFEDMAKADKARYEREM
KTYIPPKGET

> sequence 128 F10I

PRGKMSSYAIFVQTCREEHKKKHPDASVNFSEFSKKCSERWKTMSAKEKGKFEDMAKADKARYEREM
KTYIPPKGET

> sequence 129 F10V

PRGKMSSYAVFVQTCREEHKKKHPDASVNFSEFSKKCSERWKTMSAKEKGKFEDMAKADKARYERE

Figure 2b continued

MKTYIPPKGET

> sequence 130 F11I
PRGKMSSYAFIVQTCREEHKKKHPDASVNFSEFSKKCSERWKTMSAKEKGKFEDMAKADKARYEREM
KTYIPPKGET > sequence 131 F11V
PRGKMSSYAFVVQTCREEHKKKHPDASVNFSEFSKKCSERWKTMSAKEKGKFEDMAKADKARYERE
MKTYIPPKGET > sequence 132 R16H
PRGKMSSYAFFVQTCHEEHKKKHPDASVNFSEFSKKCSERWKTMSAKEKGKFEDMAKADKARYEREM
KTYIPPKGET > sequence 133 R16Q
PRGKMSSYAFFVQTCQEEHKKKHPDASVNFSEFSKKCSERWKTMSAKEKGKFEDMAKADKARYERE
MKTYIPPKGET > sequence 134 E17Q
PRGKMSSYAFFVQTCRQEHKKKHPDASVNFSEFSKKCSERWKTMSAKEKGKFEDMAKADKARYERE
MKTYIPPKGET > sequence 135 E17H
PRGKMSSYAFFVQTCRHEHKKKHPDASVNFSEFSKKCSERWKTMSAKEKGKFEDMAKADKARYERE
MKTYIPPKGET > sequence 136 E17N
PRGKMSSYAFFVQTCRNEHKKKHPDASVNFSEFSKKCSERWKTMSAKEKGKFEDMAKADKARYERE
MKTYIPPKGET > sequence 137 E18Q
PRGKMSSYAFFVQTCREQHKKKHPDASVNFSEFSKKCSERWKTMSAKEKGKFEDMAKADKARYERE
MKTYIPPKGET > sequence 138 E18H
PRGKMSSYAFFVQTCREHHKKKHPDASVNFSEFSKKCSERWKTMSAKEKGKFEDMAKADKARYERE
MKTYIPPKGET > sequence 139 E18N
PRGKMSSYAFFVQTCRENHKKKHPDASVNFSEFSKKCSERWKTMSAKEKGKFEDMAKADKARYERE
MKTYIPPKGET > sequence 140 K20N
PRGKMSSYAFFVQTCREEHNKKHPDASVNFSEFSKKCSERWKTMSAKEKGKFEDMAKADKARYEREM
KTYIPPKGET > sequence 141 K20Q
PRGKMSSYAFFVQTCREEHQKKHPDASVNFSEFSKKCSERWKTMSAKEKGKFEDMAKADKARYERE
MKTYIPPKGET > sequence 142 K21N
PRGKMSSYAFFVQTCREEHKNKHPDASVNFSEFSKKCSERWKTMSAKEKGKFEDMAKADKARYEREM
KTYIPPKGET > sequence 143 K21Q
PRGKMSSYAFFVQTCREEHKQKHPDASVNFSEFSKKCSERWKTMSAKEKGKFEDMAKADKARYERE

Figure 2b continued

MKTYIPPKGET

> sequence 144 K22N
PRGKMSSYAFFVQTCREEHKKNHPDASVNFSEFSKKCSERWKTMSAKEKGKFEDMAKADKARYEREM
KTYIPPKGET > sequence 145 K22Q
PRGKMSSYAFFVQTCREEHKKQHPDASVNFSEFSKKCSERWKTMSAKEKGKFEDMAKADKARYERE
MKTYIPPKGET > sequence 146 P24A
PRGKMSSYAFFVQTCREEHKKKHADASVNFSEFSKKCSERWKTMSAKEKGKFEDMAKADKARYEREM
KTYIPPKGET > sequence 147 P24S
PRGKMSSYAFFVQTCREEHKKKHSDASVNFSEFSKKCSERWKTMSAKEKGKFEDMAKADKARYEREM
KTYIPPKGET > sequence 148 D25N
PRGKMSSYAFFVQTCREEHKKKHPNASVNFSEFSKKCSERWKTMSAKEKGKFEDMAKADKARYEREM
KTYIPPKGET > sequence 149 D25Q
PRGKMSSYAFFVQTCREEHKKKHPQASVNFSEFSKKCSERWKTMSAKEKGKFEDMAKADKARYERE
MKTYIPPKGET > sequence 150 F30I
PRGKMSSYAFFVQTCREEHKKKHPDASVNISEFSKKCSERWKTMSAKEKGKFEDMAKADKARYEREM
KTYIPPKGET > sequence 151 F30V
PRGKMSSYAFFVQTCREEHKKKHPDASVNVSEFSKKCSERWKTMSAKEKGKFEDMAKADKARYERE
MKTYIPPKGET > sequence 152 E32Q
PRGKMSSYAFFVQTCREEHKKKHPDASVNFSQFSKKCSERWKTMSAKEKGKFEDMAKADKARYERE
MKTYIPPKGET > sequence 153 E32H
PRGKMSSYAFFVQTCREEHKKKHPDASVNFSHFSKKCSERWKTMSAKEKGKFEDMAKADKARYERE
MKTYIPPKGET > sequence 154 E32N
PRGKMSSYAFFVQTCREEHKKKHPDASVNFSNFSKKCSERWKTMSAKEKGKFEDMAKADKARYERE
MKTYIPPKGET > sequence 155 F33I
PRGKMSSYAFFVQTCREEHKKKHPDASVNFSEISKKCSERWKTMSAKEKGKFEDMAKADKARYEREM
KTYIPPKGET > sequence 156 F33V
PRGKMSSYAFFVQTCREEHKKKHPDASVNFSEVSKKCSERWKTMSAKEKGKFEDMAKADKARYERE
MKTYIPPKGET > sequence 157 K35N
PRGKMSSYAFFVQTCREEHKKKHPDASVNFSEFSNKCSERWKTMSAKEKGKFEDMAKADKARYEREM

Figure 2b continued

KTYIPPKGET

> sequence 158 K35Q
PRGKMSSYAFFVQTCREEHKKKHPDASVNFSEFSQKCSERWKTMSAKEKGKFEDMAKADKARYERE
MKTYIPPKGET > sequence 159 K36N
PRGKMSSYAFFVQTCREEHKKKHPDASVNFSEFSKNCSERWKTMSAKEKGKFEDMAKADKARYEREM
KTYIPPKGET > sequence 160 K36Q
PRGKMSSYAFFVQTCREEHKKKHPDASVNFSEFSKQCSERWKTMSAKEKGKFEDMAKADKARYERE
MKTYIPPKGET > sequence 161 E39Q
PRGKMSSYAFFVQTCREEHKKKHPDASVNFSEFSKKCSQRWKTMSAKEKGKFEDMAKADKARYERE
MKTYIPPKGET > sequence 162 E39H
PRGKMSSYAFFVQTCREEHKKKHPDASVNFSEFSKKCSHRWKTMSAKEKGKFEDMAKADKARYERE
MKTYIPPKGET > sequence 163 E39N
PRGKMSSYAFFVQTCREEHKKKHPDASVNFSEFSKKCSNRWKTMSAKEKGKFEDMAKADKARYERE
MKTYIPPKGET > sequence 164 R40H
PRGKMSSYAFFVQTCREEHKKKHPDASVNFSEFSKKCSEHWKTMSAKEKGKFEDMAKADKARYEREM
KTYIPPKGET > sequence 165 R40Q
PRGKMSSYAFFVQTCREEHKKKHPDASVNFSEFSKKCSEQWKTMSAKEKGKFEDMAKADKARYERE
MKTYIPPKGET > sequence 166 W41Y
PRGKMSSYAFFVQTCREEHKKKHPDASVNFSEFSKKCSERYKTMSAKEKGKFEDMAKADKARYEREM
KTYIPPKGET > sequence 167 W41S
PRGKMSSYAFFVQTCREEHKKKHPDASVNFSEFSKKCSERSKTMSAKEKGKFEDMAKADKARYEREM
KTYIPPKGET > sequence 168 K42N
PRGKMSSYAFFVQTCREEHKKKHPDASVNFSEFSKKCSERWNTMSAKEKGKFEDMAKADKARYEREM
KTYIPPKGET > sequence 169 K42Q
PRGKMSSYAFFVQTCREEHKKKHPDASVNFSEFSKKCSERWQTMSAKEKGKFEDMAKADKARYERE
MKTYIPPKGET > sequence 170 M44I
PRGKMSSYAFFVQTCREEHKKKHPDASVNFSEFSKKCSERWKTISAKEKGKFEDMAKADKARYEREM
KTYIPPKGET > sequence 171 M44V

Figure 2b continued

PRGKMSSYAFFVQTCREEHKKKHPDASVNFSEFSKKCSERWKTVSAKEKGKFEDMAKADKARYEREM
KTYIPPKGET

> sequence 172 K47N
PRGKMSSYAFFVQTCREEHKKKHPDASVNFSEFSKKCSERWKTMSANEKGKFEDMAKADKARYEREM
KTYIPPKGET > sequence 173 K47Q
PRGKMSSYAFFVQTCREEHKKKHPDASVNFSEFSKKCSERWKTMSAQEKGKFEDMAKADKARYERE
MKTYIPPKGET > sequence 174 E48Q
PRGKMSSYAFFVQTCREEHKKKHPDASVNFSEFSKKCSERWKTMSAKQKGKFEDMAKADKARYERE
MKTYIPPKGET > sequence 175 E48H
PRGKMSSYAFFVQTCREEHKKKHPDASVNFSEFSKKCSERWKTMSAKHKGKFEDMAKADKARYERE
MKTYIPPKGET > sequence 176 E48N
PRGKMSSYAFFVQTCREEHKKKHPDASVNFSEFSKKCSERWKTMSAKNKGKFEDMAKADKARYERE
MKTYIPPKGET > sequence 177 K49N
PRGKMSSYAFFVQTCREEHKKKHPDASVNFSEFSKKCSERWKTMSAKENGKFEDMAKADKARYEREM
KTYIPPKGET > sequence 178 K49Q
PRGKMSSYAFFVQTCREEHKKKHPDASVNFSEFSKKCSERWKTMSAKEQGKFEDMAKADKARYERE
MKTYIPPKGET > sequence 179 K51N
PRGKMSSYAFFVQTCREEHKKKHPDASVNFSEFSKKCSERWKTMSAKEKGNFEDMAKADKARYEREM
KTYIPPKGET > sequence 180 K51Q
PRGKMSSYAFFVQTCREEHKKKHPDASVNFSEFSKKCSERWKTMSAKEKGQFEDMAKADKARYERE
MKTYIPPKGET > sequence 181 F52I
PRGKMSSYAFFVQTCREEHKKKHPDASVNFSEFSKKCSERWKTMSAKEKGIEDMAKADKARYEREM
KTYIPPKGET > sequence 182 F52V
PRGKMSSYAFFVQTCREEHKKKHPDASVNFSEFSKKCSERWKTMSAKEKGVEDMAKADKARYERE
MKTYIPPKGET > sequence 183 E53Q
PRGKMSSYAFFVQTCREEHKKKHPDASVNFSEFSKKCSERWKTMSAKEKGKFQDMAKADKARYERE
MKTYIPPKGET > sequence 184 E53H
PRGKMSSYAFFVQTCREEHKKKHPDASVNFSEFSKKCSERWKTMSAKEKGKFHDMAKADKARYERE
MKTYIPPKGET

Figure 2b continued

> sequence 185 E53N
PRGKMSSYAFFVQTCREEHKKKHPDASVNFSEFSKKCSERWKTMSAKEKGKFNDMAKADKARYERE
MKTYIPPKGET > sequence 186 D54N
PRGKMSSYAFFVQTCREEHKKKHPDASVNFSEFSKKCSERWKTMSAKEKGKFENMAKADKARYEREM
KTYIPPKGET > sequence 187 D54Q
PRGKMSSYAFFVQTCREEHKKKHPDASVNFSEFSKKCSERWKTMSAKEKGKFEQMAKADKARYERE
MKTYIPPKGET > sequence 188 M55I
PRGKMSSYAFFVQTCREEHKKKHPDASVNFSEFSKKCSERWKTMSAKEKGKFEDIAKADKARYEREM
KTYIPPKGET > sequence 189 M55V
PRGKMSSYAFFVQTCREEHKKKHPDASVNFSEFSKKCSERWKTMSAKEKGKFEDVAKADKARYEREM
KTYIPPKGET > sequence 190 K57N
PRGKMSSYAFFVQTCREEHKKKHPDASVNFSEFSKKCSERWKTMSAKEKGKFEDMANADKARYEREM
KTYIPPKGET > sequence 191 K57Q
PRGKMSSYAFFVQTCREEHKKKHPDASVNFSEFSKKCSERWKTMSAKEKGKFEDMAQADKARYERE
MKTYIPPKGET > sequence 192 D59N
PRGKMSSYAFFVQTCREEHKKKHPDASVNFSEFSKKCSERWKTMSAKEKGKFEDMAKANKARYEREM
KTYIPPKGET > sequence 193 D59Q
PRGKMSSYAFFVQTCREEHKKKHPDASVNFSEFSKKCSERWKTMSAKEKGKFEDMAKAQKARYERE
MKTYIPPKGET > sequence 194 K60N
PRGKMSSYAFFVQTCREEHKKKHPDASVNFSEFSKKCSERWKTMSAKEKGKFEDMAKADNARYEREM
KTYIPPKGET > sequence 195 K60Q
PRGKMSSYAFFVQTCREEHKKKHPDASVNFSEFSKKCSERWKTMSAKEKGKFEDMAKADQARYERE
MKTYIPPKGET > sequence 196 R62H
PRGKMSSYAFFVQTCREEHKKKHPDASVNFSEFSKKCSERWKTMSAKEKGKFEDMAKADKAHYEREM
KTYIPPKGET > sequence 197 R62Q
PRGKMSSYAFFVQTCREEHKKKHPDASVNFSEFSKKCSERWKTMSAKEKGKFEDMAKADKAQYERE
MKTYIPPKGET > sequence 198 Y63H
PRGKMSSYAFFVQTCREEHKKKHPDASVNFSEFSKKCSERWKTMSAKEKGKFEDMAKADKARHERE
MKTYIPPKGET

Figure 2b continued

> sequence 199 Y63I
PRGKMSSYAFFVQTCREEHKKKHPDASVNFSEFSKKCSERWKTMSAKEKGKFEDMAKADKARIEREM
KTYIPPKGET > sequence 200 E64Q
PRGKMSSYAFFVQTCREEHKKKHPDASVNFSEFSKKCSERWKTMSAKEKGKFEDMAKADKARYQRE
MKTYIPPKGET > sequence 201 E64H
PRGKMSSYAFFVQTCREEHKKKHPDASVNFSEFSKKCSERWKTMSAKEKGKFEDMAKADKARYHRE
MKTYIPPKGET > sequence 202 E64N
PRGKMSSYAFFVQTCREEHKKKHPDASVNFSEFSKKCSERWKTMSAKEKGKFEDMAKADKARYNRE
MKTYIPPKGET > sequence 203 R65H
PRGKMSSYAFFVQTCREEHKKKHPDASVNFSEFSKKCSERWKTMSAKEKGKFEDMAKADKARYEHEM
KTYIPPKGET > sequence 204 R65Q
PRGKMSSYAFFVQTCREEHKKKHPDASVNFSEFSKKCSERWKTMSAKEKGKFEDMAKADKARYEQE
MKTYIPPKGET > sequence 205 E66Q
PRGKMSSYAFFVQTCREEHKKKHPDASVNFSEFSKKCSERWKTMSAKEKGKFEDMAKADKARYERQ
MKTYIPPKGET > sequence 206 E66H
PRGKMSSYAFFVQTCREEHKKKHPDASVNFSEFSKKCSERWKTMSAKEKGKFEDMAKADKARYERH
MKTYIPPKGET > sequence 207 E66N
PRGKMSSYAFFVQTCREEHKKKHPDASVNFSEFSKKCSERWKTMSAKEKGKFEDMAKADKARYERN
MKTYIPPKGET > sequence 208 M67I
PRGKMSSYAFFVQTCREEHKKKHPDASVNFSEFSKKCSERWKTMSAKEKGKFEDMAKADKARYEREI
KTYIPPKGET > sequence 209 M67V
PRGKMSSYAFFVQTCREEHKKKHPDASVNFSEFSKKCSERWKTMSAKEKGKFEDMAKADKARYEREV
KTYIPPKGET > sequence 210 K68N
PRGKMSSYAFFVQTCREEHKKKHPDASVNFSEFSKKCSERWKTMSAKEKGKFEDMAKADKARYEREM
NTYIPPKGET > sequence 211 K68Q
PRGKMSSYAFFVQTCREEHKKKHPDASVNFSEFSKKCSERWKTMSAKEKGKFEDMAKADKARYEREM
QTYIPPKGET > sequence 212 Y70H
PRGKMSSYAFFVQTCREEHKKKHPDASVNFSEFSKKCSERWKTMSAKEKGKFEDMAKADKARYEREM

Figure 2b continued

KTHIPPKGET

> sequence 213 Y70I
PRGKMSSYAFFVQTCREEHKKKHPDASVNFSEFSKKCSERWKTMSAKEKGKFEDMAKADKARYEREM
KTIIPPKGET > sequence 214 P72A
PRGKMSSYAFFVQTCREEHKKKHPDASVNFSEFSKKCSERWKTMSAKEKGKFEDMAKADKARYEREM
KTYIAPKGET > sequence 215 P72S
PRGKMSSYAFFVQTCREEHKKKHPDASVNFSEFSKKCSERWKTMSAKEKGKFEDMAKADKARYEREM
KTYISPKGET > sequence 216 P73A
PRGKMSSYAFFVQTCREEHKKKHPDASVNFSEFSKKCSERWKTMSAKEKGKFEDMAKADKARYEREM
KTYIPAKGET > sequence 217 P73S
PRGKMSSYAFFVQTCREEHKKKHPDASVNFSEFSKKCSERWKTMSAKEKGKFEDMAKADKARYEREM
KTYIPSKGET > sequence 218 K74N
PRGKMSSYAFFVQTCREEHKKKHPDASVNFSEFSKKCSERWKTMSAKEKGKFEDMAKADKARYEREM
KTYIPPNGET > sequence 219 K74Q
PRGKMSSYAFFVQTCREEHKKKHPDASVNFSEFSKKCSERWKTMSAKEKGKFEDMAKADKARYEREM
KTYIPPQGET > sequence 220 E76Q
PRGKMSSYAFFVQTCREEHKKKHPDASVNFSEFSKKCSERWKTMSAKEKGKFEDMAKADKARYEREM
KTYIPPKGQT > sequence 221 E76H
PRGKMSSYAFFVQTCREEHKKKHPDASVNFSEFSKKCSERWKTMSAKEKGKFEDMAKADKARYEREM
KTYIPPKGHT > sequence 222 E76N
PRGKMSSYAFFVQTCREEHKKKHPDASVNFSEFSKKCSERWKTMSAKEKGKFEDMAKADKARYEREM
KTYIPPKGNT

Figure 3a

Box A 54 amino acids

\# Protection against proteolysis
If sequence:

PDASVNFSEFSKKCSERWKTMSAKEKGKFEDMAKADKARYEREMKTYIPPKGET

In bold amino acids sensitive to proteases proteolysis

Figure 3b

Box A 54 amino acids
\# Mutant list:

| | | |
|---|---|---|
| P1A | F29I | P50A |
| P1S | F29V | P50S |
| D2N | E30Q | K51N |
| D2Q | E30H | K51Q |
| F7I | E30N | E53Q |
| F7V | D31N | E53H |
| E9Q | D31Q | E53N |
| E9H | M32I | |
| E9N | M32V | |
| F10I | K34N | |
| F10V | K34Q | |
| K12N | D36N | |
| K12Q | D36Q | |
| K13N | K37N | |
| K13Q | K37Q | |
| E16Q | R39H | |
| E16H | R39Q | |
| E16N | Y40H | |
| R17H | Y40I | |
| R17Q | E41Q | |
| W18Y | E41H | |
| W18S | E41N | |
| K19N | R42H | |
| K19Q | R42Q | |
| M21I | E43Q | |
| M21V | E43H | |
| K24N | E43N | |
| K24Q | M44I | |
| E25Q | M44V | |
| E25H | K45N | |
| E25N | K45Q | |
| K26N | Y47H | |
| K26Q | Y47I | |
| K28N | P49A | |
| K28Q | P49S | |

Figure 3b continued

Box A 54 amino acid sequences:

> sequence 223 Wild type

PDASVNFSEFSKKCSERWKTMSAKEKGKFEDMAKADKARYEREMKTYIPPKGET

> sequence 224 P1A
ADASVNFSEFSKKCSERWKTMSAKEKGKFEDMAKADKARYEREMKTYIPPKGET

> sequence 225 P1S
SDASVNFSEFSKKCSERWKTMSAKEKGKFEDMAKADKARYEREMKTYIPPKGET

> sequence 226 D2N
PNASVNFSEFSKKCSERWKTMSAKEKGKFEDMAKADKARYEREMKTYIPPKGET

> sequence 227 D2Q
PQASVNFSEFSKKCSERWKTMSAKEKGKFEDMAKADKARYEREMKTYIPPKGET

> sequence 228 F7I
PDASVNISEFSKKCSERWKTMSAKEKGKFEDMAKADKARYEREMKTYIPPKGET

> sequence 229 F7V
PDASVNVSEFSKKCSERWKTMSAKEKGKFEDMAKADKARYEREMKTYIPPKGET

> sequence 230 E9Q
PDASVNFSQFSKKCSERWKTMSAKEKGKFEDMAKADKARYEREMKTYIPPKGET

> sequence 231 E9H
PDASVNFSHFSKKCSERWKTMSAKEKGKFEDMAKADKARYEREMKTYIPPKGET

> sequence 232 E9N
PDASVNFSNFSKKCSERWKTMSAKEKGKFEDMAKADKARYEREMKTYIPPKGET

> sequence 233 F10I
PDASVNFSEISKKCSERWKTMSAKEKGKFEDMAKADKARYEREMKTYIPPKGET

> sequence 234 F10V
PDASVNFSEVSKKCSERWKTMSAKEKGKFEDMAKADKARYEREMKTYIPPKGET

> sequence 235 K12N
PDASVNFSEFSNKCSERWKTMSAKEKGKFEDMAKADKARYEREMKTYIPPKGET

> sequence 236 K12Q
PDASVNFSEFSQKCSERWKTMSAKEKGKFEDMAKADKARYEREMKTYIPPKGET

> sequence 237 K13N
PDASVNFSEFSKNCSERWKTMSAKEKGKFEDMAKADKARYEREMKTYIPPKGET

> sequence 238 K13Q
PDASVNFSEFSKQCSERWKTMSAKEKGKFEDMAKADKARYEREMKTYIPPKGET

> sequence 239 E16Q
PDASVNFSEFSKKCSQRWKTMSAKEKGKFEDMAKADKARYEREMKTYIPPKGET

Figure 3b continued

> sequence 240 E16H
PDASVNFSEFSKKCSHRWKTMSAKEKGKFEDMAKADKARYEREMKTYIPPKGET

> sequence 241 E16N
PDASVNFSEFSKKCSNRWKTMSAKEKGKFEDMAKADKARYEREMKTYIPPKGET

> sequence 242 R17H
PDASVNFSEFSKKCSEHWKTMSAKEKGKFEDMAKADKARYEREMKTYIPPKGET

> sequence 243 R17Q
PDASVNFSEFSKKCSEQWKTMSAKEKGKFEDMAKADKARYEREMKTYIPPKGET

> sequence 244 W18Y
PDASVNFSEFSKKCSERYKTMSAKEKGKFEDMAKADKARYEREMKTYIPPKGET

> sequence 245 W18S
PDASVNFSEFSKKCSERSKTMSAKEKGKFEDMAKADKARYEREMKTYIPPKGET

> sequence 246 K19N
PDASVNFSEFSKKCSERWNTMSAKEKGKFEDMAKADKARYEREMKTYIPPKGET

> sequence 247 K19Q
PDASVNFSEFSKKCSERWQTMSAKEKGKFEDMAKADKARYEREMKTYIPPKGET

> sequence 248 M21I
PDASVNFSEFSKKCSERWKTISAKEKGKFEDMAKADKARYEREMKTYIPPKGET

> sequence 249 M21V
PDASVNFSEFSKKCSERWKTVSAKEKGKFEDMAKADKARYEREMKTYIPPKGET

> sequence 250 K24N
PDASVNFSEFSKKCSERWKTMSANEKGKFEDMAKADKARYEREMKTYIPPKGET

> sequence 251 K24Q
PDASVNFSEFSKKCSERWKTMSAQEKGKFEDMAKADKARYEREMKTYIPPKGET

> sequence 252 E25Q
PDASVNFSEFSKKCSERWKTMSAKQKGKFEDMAKADKARYEREMKTYIPPKGET

> sequence 253 E25H
PDASVNFSEFSKKCSERWKTMSAKHKGKFEDMAKADKARYEREMKTYIPPKGET

> sequence 254 E25N
PDASVNFSEFSKKCSERWKTMSAKNKGKFEDMAKADKARYEREMKTYIPPKGET

> sequence 255 K26N
PDASVNFSEFSKKCSERWKTMSAKENGKFEDMAKADKARYEREMKTYIPPKGET

> sequence 256 K26Q
PDASVNFSEFSKKCSERWKTMSAKEQGKFEDMAKADKARYEREMKTYIPPKGET

> sequence 257 K28N
PDASVNFSEFSKKCSERWKTMSAKEKGNFEDMAKADKARYEREMKTYIPPKGET

> sequence 258 K28Q

Figure 3b continued

PDASVNFSEFSKKCSERWKTMSAKEKGQFEDMAKADKARYEREMKTYIPPKGET

> sequence 259 F29I
PDASVNFSEFSKKCSERWKTMSAKEKGKIEDMAKADKARYEREMKTYIPPKGET

> sequence 260 F29V
PDASVNFSEFSKKCSERWKTMSAKEKGKVEDMAKADKARYEREMKTYIPPKGET

> sequence 261 E30Q
PDASVNFSEFSKKCSERWKTMSAKEKGKFQDMAKADKARYEREMKTYIPPKGET

> sequence 262 E30H
PDASVNFSEFSKKCSERWKTMSAKEKGKFHDMAKADKARYEREMKTYIPPKGET

> sequence 263 E30N
PDASVNFSEFSKKCSERWKTMSAKEKGKFNDMAKADKARYEREMKTYIPPKGET

> sequence 264 D31N
PDASVNFSEFSKKCSERWKTMSAKEKGKFENMAKADKARYEREMKTYIPPKGET

> sequence 265 D31Q
PDASVNFSEFSKKCSERWKTMSAKEKGKFEQMAKADKARYEREMKTYIPPKGET

> sequence 266 M32I
PDASVNFSEFSKKCSERWKTMSAKEKGKFEDIAKADKARYEREMKTYIPPKGET

> sequence 267 M32V
PDASVNFSEFSKKCSERWKTMSAKEKGKFEDVAKADKARYEREMKTYIPPKGET

> sequence 268 K34N
PDASVNFSEFSKKCSERWKTMSAKEKGKFEDMANADKARYEREMKTYIPPKGET

> sequence 269 K34Q
PDASVNFSEFSKKCSERWKTMSAKEKGKFEDMAQADKARYEREMKTYIPPKGET

> sequence 270 D36N
PDASVNFSEFSKKCSERWKTMSAKEKGKFEDMAKANKARYEREMKTYIPPKGET

> sequence 271 D36Q
PDASVNFSEFSKKCSERWKTMSAKEKGKFEDMAKAQKARYEREMKTYIPPKGET

> sequence 272 K37N
PDASVNFSEFSKKCSERWKTMSAKEKGKFEDMAKADNARYEREMKTYIPPKGET

> sequence 273 K37Q
PDASVNFSEFSKKCSERWKTMSAKEKGKFEDMAKADQARYEREMKTYIPPKGET

> sequence 274 R39H
PDASVNFSEFSKKCSERWKTMSAKEKGKFEDMAKADKAHYEREMKTYIPPKGET

> sequence 275 R39Q
PDASVNFSEFSKKCSERWKTMSAKEKGKFEDMAKADKAQYEREMKTYIPPKGET

> sequence 276 Y40H
PDASVNFSEFSKKCSERWKTMSAKEKGKFEDMAKADKARHEREMKTYIPPKGET

Figure 3b continued

\> sequence 277 Y40I
PDASVNFSEFSKKCSERWKTMSAKEKGKFEDMAKADKARIEREMKTYIPPKGET

\> sequence 278 E41Q
PDASVNFSEFSKKCSERWKTMSAKEKGKFEDMAKADKARYQREMKTYIPPKGET

\> sequence 279 E41H
PDASVNFSEFSKKCSERWKTMSAKEKGKFEDMAKADKARYHREMKTYIPPKGET

\> sequence 280 E41N
PDASVNFSEFSKKCSERWKTMSAKEKGKFEDMAKADKARYNREMKTYIPPKGET

\> sequence 281 R42H
PDASVNFSEFSKKCSERWKTMSAKEKGKFEDMAKADKARYEHEMKTYIPPKGET

\> sequence 282 R42Q
PDASVNFSEFSKKCSERWKTMSAKEKGKFEDMAKADKARYEQEMKTYIPPKGET

\> sequence 283 E43Q
PDASVNFSEFSKKCSERWKTMSAKEKGKFEDMAKADKARYERQMKTYIPPKGET

\> sequence 284 E43H
PDASVNFSEFSKKCSERWKTMSAKEKGKFEDMAKADKARYERHMKTYIPPKGET

\> sequence 285 E43N
PDASVNFSEFSKKCSERWKTMSAKEKGKFEDMAKADKARYERNMKTYIPPKGET

\> sequence 286 M44I
PDASVNFSEFSKKCSERWKTMSAKEKGKFEDMAKADKARYEREIKTYIPPKGET

\> sequence 287 M44V
PDASVNFSEFSKKCSERWKTMSAKEKGKFEDMAKADKARYEREVKTYIPPKGET

\> sequence 288 K45N
PDASVNFSEFSKKCSERWKTMSAKEKGKFEDMAKADKARYEREMNTYIPPKGET

\> sequence 289 K45Q
PDASVNFSEFSKKCSERWKTMSAKEKGKFEDMAKADKARYEREMQTYIPPKGET

\> sequence 290 Y47H
PDASVNFSEFSKKCSERWKTMSAKEKGKFEDMAKADKARYEREMKTHIPPKGET

\> sequence 291 Y47I
PDASVNFSEFSKKCSERWKTMSAKEKGKFEDMAKADKARYEREMKTIIPPKGET

\> sequence 292 P49A
PDASVNFSEFSKKCSERWKTMSAKEKGKFEDMAKADKARYEREMKTYIAPKGET

\> sequence 293 P49S
PDASVNFSEFSKKCSERWKTMSAKEKGKFEDMAKADKARYEREMKTYISPKGET

\> sequence 294 P50A
PDASVNFSEFSKKCSERWKTMSAKEKGKFEDMAKADKARYEREMKTYIPAKGET

Figure 3b continued

> sequence 295 P50S
PDASVNFSEFSKKCSERWKTMSAKEKGKFEDMAKADKARYEREMKTYIPSKGET

> sequence 296 K51N
PDASVNFSEFSKKCSERWKTMSAKEKGKFEDMAKADKARYEREMKTYIPPNGET

> sequence 297 K51Q
PDASVNFSEFSKKCSERWKTMSAKEKGKFEDMAKADKARYEREMKTYIPPQGET

> sequence 298 E53Q
PDASVNFSEFSKKCSERWKTMSAKEKGKFEDMAKADKARYEREMKTYIPPKGQT

> sequence 299 E53H
PDASVNFSEFSKKCSERWKTMSAKEKGKFEDMAKADKARYEREMKTYIPPKGHT

> sequence 300 E53N
PDASVNFSEFSKKCSERWKTMSAKEKGKFEDMAKADKARYEREMKTYIPPKGNT

Figure 4a

Box A 84 amino acid of HMGB1 *Anopheles gambia* (XP_311154)

\# Protection against proteolysis
If sequence:

GKVKDNKPRGRMTAYAFFVQTCREEHKKKHPEEQVIFAEFSRKCAERWKTMLDKEK
QRFHEMAEKDKARYELEMQSYVPPKGAV

In bold amino acids sensitive to proteases proteolysis

Figure 4b

Box A 84 amino acid
\# Mutant list:

| | | | | |
|---|---|---|---|---|
| K2N | E24H | F40V | K56N | E71H |
| K2Q | E24N | R42H | K56Q | E71N |
| K4N | E25Q | R42Q | R58H | L72I |
| K4Q | E25H | K43N | R58Q | L72V |
| D5N | E25N | K43Q | F59I | E73Q |
| D5Q | K27N | E46Q | F59V | E73H |
| K7N | K27Q | E46H | E61Q | E73N |
| K7Q | K28N | E46N | E61H | M74I |
| P8A | K28Q | R47H | E61N | M74V |
| P8S | K29N | R47Q | M62I | Y77H |
| R9H | K29Q | W48Y | M62V | Y77I |
| R9Q | P31A | W48S | E64Q | P79A |
| R11H | P31S | K49N | E64H | P79S |
| R11Q | E32Q | K49Q | E64N | P80A |
| M12I | E32H | M51I | K65N | P80S |
| M12V | E32N | M51V | K65Q | K81N |
| Y15H | E33Q | L52I | D66N | K81Q |
| Y15I | E33H | L52V | D66Q | |
| F17I | E33N | D53N | K67N | |
| F17V | F37I | D53Q | K67Q | |
| F18I | F37V | K54N | R69H | |
| F18V | E39Q | K54Q | R69Q | |
| R23H | E39H | E55Q | Y70H | |
| R23Q | E39N | E55H | Y70I | |
| E24Q | F40I | E55N | E71Q | |

Figure 4b continued

> SEQUENCE 301 Wild type
GKVKDNKPRGRMTAYAFFVQTCREEHKKKHPEEQVIFAEFSRKCAERWKTMLDKEKQRFHEMAEKDK
ARYELEMQSYVPPKGAV >> SEQUENCE 302 K2N
GNVKDNKPRGRMTAYAFFVQTCREEHKKKHPEEQVIFAEFSRKCAERWKTMLDKEKQRFHEMAEKDK
ARYELEMQSYVPPKGAV >> SEQUENCE 303 K2Q
GQVKDNKPRGRMTAYAFFVQTCREEHKKKHPEEQVIFAEFSRKCAERWKTMLDKEKQRFHEMAEKDK
ARYELEMQSYVPPKGAV >> SEQUENCE 304 K4N
GKVNDNKPRGRMTAYAFFVQTCREEHKKKHPEEQVIFAEFSRKCAERWKTMLDKEKQRFHEMAEKDK
ARYELEMQSYVPPKGAV >> SEQUENCE 305 K4Q
GKVQDNKPRGRMTAYAFFVQTCREEHKKKHPEEQVIFAEFSRKCAERWKTMLDKEKQRFHEMAEKDK
ARYELEMQSYVPPKGAV >> SEQUENCE 306 D5N
GKVKNNKPRGRMTAYAFFVQTCREEHKKKHPEEQVIFAEFSRKCAERWKTMLDKEKQRFHEMAEKDK
ARYELEMQSYVPPKGAV >> SEQUENCE 307 D5Q
GKVKQNKPRGRMTAYAFFVQTCREEHKKKHPEEQVIFAEFSRKCAERWKTMLDKEKQRFHEMAEKDK
ARYELEMQSYVPPKGAV >> SEQUENCE 308 K7N
GKVKDNNPRGRMTAYAFFVQTCREEHKKKHPEEQVIFAEFSRKCAERWKTMLDKEKQRFHEMAEKDK
ARYELEMQSYVPPKGAV >> SEQUENCE 309 K7Q
GKVKDNQPRGRMTAYAFFVQTCREEHKKKHPEEQVIFAEFSRKCAERWKTMLDKEKQRFHEMAEKDK
ARYELEMQSYVPPKGAV >> SEQUENCE 310 P8A
GKVKDNKARGRMTAYAFFVQTCREEHKKKHPEEQVIFAEFSRKCAERWKTMLDKEKQRFHEMAEKDK
ARYELEMQSYVPPKGAV >> SEQUENCE 311 P8S
GKVKDNKSRGRMTAYAFFVQTCREEHKKKHPEEQVIFAEFSRKCAERWKTMLDKEKQRFHEMAEKDK
ARYELEMQSYVPPKGAV >> SEQUENCE 312 R9H
GKVKDNKPHGRMTAYAFFVQTCREEHKKKHPEEQVIFAEFSRKCAERWKTMLDKEKQRFHEMAEKDK
ARYELEMQSYVPPKGAV >> SEQUENCE 313 R9Q
GKVKDNKPQGRMTAYAFFVQTCREEHKKKHPEEQVIFAEFSRKCAERWKTMLDKEKQRFHEMAEKDK
ARYELEMQSYVPPKGAV >> SEQUENCE 314 R11H
GKVKDNKPRGHMTAYAFFVQTCREEHKKKHPEEQVIFAEFSRKCAERWKTMLDKEKQRFHEMAEKDK

Figure 4b continued

ARYELEMQSYVPPKGAV

>> SEQUENCE 315 R11Q
GKVKDNKPRGQMTAYAFFVQTCREEHKKKHPEEQVIFAEFSRKCAERWKTMLDKEKQRFHEMAEKDK
ARYELEMQSYVPPKGAV

>> SEQUENCE 316 M12I
GKVKDNKPRGRITAYAFFVQTCREEHKKKHPEEQVIFAEFSRKCAERWKTMLDKEKQRFHEMAEKDKA
RYELEMQSYVPPKGAV

>> SEQUENCE 317 M12V
GKVKDNKPRGRVTAYAFFVQTCREEHKKKHPEEQVIFAEFSRKCAERWKTMLDKEKQRFHEMAEKDK
ARYELEMQSYVPPKGAV

>> SEQUENCE 318 Y15H
GKVKDNKPRGRMTAHAFFVQTCREEHKKKHPEEQVIFAEFSRKCAERWKTMLDKEKQRFHEMAEKDK
ARYELEMQSYVPPKGAV

>> SEQUENCE 319 Y15I
GKVKDNKPRGRMTAIAFFVQTCREEHKKKHPEEQVIFAEFSRKCAERWKTMLDKEKQRFHEMAEKDKA
RYELEMQSYVPPKGAV

>> SEQUENCE 320 F17I
GKVKDNKPRGRMTAYAIFVQTCREEHKKKHPEEQVIFAEFSRKCAERWKTMLDKEKQRFHEMAEKDKA
RYELEMQSYVPPKGAV

>> SEQUENCE 321 F17V
GKVKDNKPRGRMTAYAVFVQTCREEHKKKHPEEQVIFAEFSRKCAERWKTMLDKEKQRFHEMAEKDK
ARYELEMQSYVPPKGAV

>> SEQUENCE 322 F18I
GKVKDNKPRGRMTAYAFIVQTCREEHKKKHPEEQVIFAEFSRKCAERWKTMLDKEKQRFHEMAEKDKA
RYELEMQSYVPPKGAV

>> SEQUENCE 323 F18V
GKVKDNKPRGRMTAYAFVVQTCREEHKKKHPEEQVIFAEFSRKCAERWKTMLDKEKQRFHEMAEKDK
ARYELEMQSYVPPKGAV

>> SEQUENCE 324 R23H
GKVKDNKPRGRMTAYAFFVQTCHEEHKKKHPEEQVIFAEFSRKCAERWKTMLDKEKQRFHEMAEKDK
ARYELEMQSYVPPKGAV

>> SEQUENCE 325 R23Q
GKVKDNKPRGRMTAYAFFVQTCQEEHKKKHPEEQVIFAEFSRKCAERWKTMLDKEKQRFHEMAEKDK
ARYELEMQSYVPPKGAV

>> SEQUENCE 326 E24Q
GKVKDNKPRGRMTAYAFFVQTCRQEHKKKHPEEQVIFAEFSRKCAERWKTMLDKEKQRFHEMAEKDK
ARYELEMQSYVPPKGAV

>> SEQUENCE 327 E24H
GKVKDNKPRGRMTAYAFFVQTCRHEHKKKHPEEQVIFAEFSRKCAERWKTMLDKEKQRFHEMAEKDK
ARYELEMQSYVPPKGAV

>> SEQUENCE 328 E24N

Figure 4b continued

GKVKDNKPRGRMTAYAFFVQTCRNEHKKKHPEEQVIFAEFSRKCAERWKTMLDKEKQRFHEMAEKDK
ARYELEMQSYVPPKGAV

>> SEQUENCE 329 E25Q
GKVKDNKPRGRMTAYAFFVQTCREQHKKKHPEEQVIFAEFSRKCAERWKTMLDKEKQRFHEMAEKDK
ARYELEMQSYVPPKGAV

>> SEQUENCE 330 E25H
GKVKDNKPRGRMTAYAFFVQTCREHHKKKHPEEQVIFAEFSRKCAERWKTMLDKEKQRFHEMAEKDK
ARYELEMQSYVPPKGAV

>> SEQUENCE 331 E25N
GKVKDNKPRGRMTAYAFFVQTCRENHKKKHPEEQVIFAEFSRKCAERWKTMLDKEKQRFHEMAEKDK
ARYELEMQSYVPPKGAV

>> SEQUENCE 332 K27N
GKVKDNKPRGRMTAYAFFVQTCREEHNKKHPEEQVIFAEFSRKCAERWKTMLDKEKQRFHEMAEKDK
ARYELEMQSYVPPKGAV

>> SEQUENCE 333 K27Q
GKVKDNKPRGRMTAYAFFVQTCREEHQKKHPEEQVIFAEFSRKCAERWKTMLDKEKQRFHEMAEKDK
ARYELEMQSYVPPKGAV

>> SEQUENCE 334 K28N
GKVKDNKPRGRMTAYAFFVQTCREEHKNKHPEEQVIFAEFSRKCAERWKTMLDKEKQRFHEMAEKDK
ARYELEMQSYVPPKGAV

>> SEQUENCE 335 K28Q
GKVKDNKPRGRMTAYAFFVQTCREEHKQKHPEEQVIFAEFSRKCAERWKTMLDKEKQRFHEMAEKDK
ARYELEMQSYVPPKGAV

>> SEQUENCE 336 K29N
GKVKDNKPRGRMTAYAFFVQTCREEHKKNHPEEQVIFAEFSRKCAERWKTMLDKEKQRFHEMAEKDK
ARYELEMQSYVPPKGAV

>> SEQUENCE 337 K29Q
GKVKDNKPRGRMTAYAFFVQTCREEHKKQHPEEQVIFAEFSRKCAERWKTMLDKEKQRFHEMAEKDK
ARYELEMQSYVPPKGAV

>> SEQUENCE 338 P31A
GKVKDNKPRGRMTAYAFFVQTCREEHKKKHAEEQVIFAEFSRKCAERWKTMLDKEKQRFHEMAEKDK
ARYELEMQSYVPPKGAV

>> SEQUENCE 339 P31S
GKVKDNKPRGRMTAYAFFVQTCREEHKKKHSEEQVIFAEFSRKCAERWKTMLDKEKQRFHEMAEKDK
ARYELEMQSYVPPKGAV

>> SEQUENCE 340 E32Q
GKVKDNKPRGRMTAYAFFVQTCREEHKKKHPQEQVIFAEFSRKCAERWKTMLDKEKQRFHEMAEKDK
ARYELEMQSYVPPKGAV

>> SEQUENCE 341 E32H
GKVKDNKPRGRMTAYAFFVQTCREEHKKKHPHEQVIFAEFSRKCAERWKTMLDKEKQRFHEMAEKDK

Figure 4b continued

ARYELEMQSYVPPKGAV

>> SEQUENCE 342 E32N
GKVKDNKPRGRMTAYAFFVQTCREEHKKKHPNEQVIFAEFSRKCAERWKTMLDKEKQRFHEMAEKDK
ARYELEMQSYVPPKGAV

>> SEQUENCE 343 E33Q
GKVKDNKPRGRMTAYAFFVQTCREEHKKKHPEQQVIFAEFSRKCAERWKTMLDKEKQRFHEMAEKDK
ARYELEMQSYVPPKGAV

>> SEQUENCE 344 E33H
GKVKDNKPRGRMTAYAFFVQTCREEHKKKHPEHQVIFAEFSRKCAERWKTMLDKEKQRFHEMAEKDK
ARYELEMQSYVPPKGAV

>> SEQUENCE 345 E33N
GKVKDNKPRGRMTAYAFFVQTCREEHKKKHPENQVIFAEFSRKCAERWKTMLDKEKQRFHEMAEKDK
ARYELEMQSYVPPKGAV

>> SEQUENCE 346 F37I
GKVKDNKPRGRMTAYAFFVQTCREEHKKKHPEEQVIIAEFSRKCAERWKTMLDKEKQRFHEMAEKDKA
RYELEMQSYVPPKGAV

>> SEQUENCE 347 F37V
GKVKDNKPRGRMTAYAFFVQTCREEHKKKHPEEQVIVAEFSRKCAERWKTMLDKEKQRFHEMAEKDK
ARYELEMQSYVPPKGAV

>> SEQUENCE 348 E39Q
GKVKDNKPRGRMTAYAFFVQTCREEHKKKHPEEQVIFAQFSRKCAERWKTMLDKEKQRFHEMAEKDK
ARYELEMQSYVPPKGAV

>> SEQUENCE 349 E39H
GKVKDNKPRGRMTAYAFFVQTCREEHKKKHPEEQVIFAHFSRKCAERWKTMLDKEKQRFHEMAEKDK
ARYELEMQSYVPPKGAV

>> SEQUENCE 350 E39N
GKVKDNKPRGRMTAYAFFVQTCREEHKKKHPEEQVIFANFSRKCAERWKTMLDKEKQRFHEMAEKDK
ARYELEMQSYVPPKGAV

>> SEQUENCE 351 F40I
GKVKDNKPRGRMTAYAFFVQTCREEHKKKHPEEQVIFAEISRKCAERWKTMLDKEKQRFHEMAEKDKA
RYELEMQSYVPPKGAV

>> SEQUENCE 352 F40V
GKVKDNKPRGRMTAYAFFVQTCREEHKKKHPEEQVIFAEVSRKCAERWKTMLDKEKQRFHEMAEKDK
ARYELEMQSYVPPKGAV

>> SEQUENCE 353 R42H
GKVKDNKPRGRMTAYAFFVQTCREEHKKKHPEEQVIFAEFSHKCAERWKTMLDKEKQRFHEMAEKDK
ARYELEMQSYVPPKGAV

>> SEQUENCE 354 R42Q
GKVKDNKPRGRMTAYAFFVQTCREEHKKKHPEEQVIFAEFSQKCAERWKTMLDKEKQRFHEMAEKDK
ARYELEMQSYVPPKGAV

>> SEQUENCE 355 K43N

Figure 4b continued

GKVKDNKPRGRMTAYAFFVQTCREEHKKKHPEEQVIFAEFSRNCAERWKTMLDKEKQRFHEMAEKDK
ARYELEMQSYVPPKGAV

>> SEQUENCE 356 K43Q
GKVKDNKPRGRMTAYAFFVQTCREEHKKKHPEEQVIFAEFSRQCAERWKTMLDKEKQRFHEMAEKDK
ARYELEMQSYVPPKGAV

>> SEQUENCE 357 E46Q
GKVKDNKPRGRMTAYAFFVQTCREEHKKKHPEEQVIFAEFSRKCAQRWKTMLDKEKQRFHEMAEKDK
ARYELEMQSYVPPKGAV

>> SEQUENCE 358 E46H
GKVKDNKPRGRMTAYAFFVQTCREEHKKKHPEEQVIFAEFSRKCAHRWKTMLDKEKQRFHEMAEKDK
ARYELEMQSYVPPKGAV

>> SEQUENCE 359 E46N
GKVKDNKPRGRMTAYAFFVQTCREEHKKKHPEEQVIFAEFSRKCANRWKTMLDKEKQRFHEMAEKDK
ARYELEMQSYVPPKGAV

>> SEQUENCE 360 R47H
GKVKDNKPRGRMTAYAFFVQTCREEHKKKHPEEQVIFAEFSRKCAEHWKTMLDKEKQRFHEMAEKDK
ARYELEMQSYVPPKGAV

>> SEQUENCE 361 R47Q
GKVKDNKPRGRMTAYAFFVQTCREEHKKKHPEEQVIFAEFSRKCAEQWKTMLDKEKQRFHEMAEKDK
ARYELEMQSYVPPKGAV

>> SEQUENCE 362 W48Y
GKVKDNKPRGRMTAYAFFVQTCREEHKKKHPEEQVIFAEFSRKCAERYKTMLDKEKQRFHEMAEKDK
ARYELEMQSYVPPKGAV

>> SEQUENCE 363 W48S
GKVKDNKPRGRMTAYAFFVQTCREEHKKKHPEEQVIFAEFSRKCAERSKTMLDKEKQRFHEMAEKDK
ARYELEMQSYVPPKGAV

>> SEQUENCE 364 K49N
GKVKDNKPRGRMTAYAFFVQTCREEHKKKHPEEQVIFAEFSRKCAERWNTMLDKEKQRFHEMAEKDK
ARYELEMQSYVPPKGAV

>> SEQUENCE 365 K49Q
GKVKDNKPRGRMTAYAFFVQTCREEHKKKHPEEQVIFAEFSRKCAERWQTMLDKEKQRFHEMAEKDK
ARYELEMQSYVPPKGAV

>> SEQUENCE 366 M51I
GKVKDNKPRGRMTAYAFFVQTCREEHKKKHPEEQVIFAEFSRKCAERWKTILDKEKQRFHEMAEKDKA
RYELEMQSYVPPKGAV

>> SEQUENCE 367 M51V
GKVKDNKPRGRMTAYAFFVQTCREEHKKKHPEEQVIFAEFSRKCAERWKTVLDKEKQRFHEMAEKDK
ARYELEMQSYVPPKGAV

>>> SEQUENCE 368 L52I
GKVKDNKPRGRMTAYAFFVQTCREEHKKKHPEEQVIFAEFSRKCAERWKTMIDKEKQRFHEMAEKDKA
RYELEMQSYVPPKGAV

Figure 4b continued

\>> SEQUENCE 369 L52V
GKVKDNKPRGRMTAYAFFVQTCREEHKKKHPEEQVIFAEFSRKCAERWKTMVDKEKQRFHEMAEKDKARYELEMQSYVPPKGAV

\>> SEQUENCE 370 D53N
GKVKDNKPRGRMTAYAFFVQTCREEHKKKHPEEQVIFAEFSRKCAERWKTMLNKEKQRFHEMAEKDKARYELEMQSYVPPKGAV

\>> SEQUENCE 371 D53Q
GKVKDNKPRGRMTAYAFFVQTCREEHKKKHPEEQVIFAEFSRKCAERWKTMLQKEKQRFHEMAEKDKARYELEMQSYVPPKGAV

\>> SEQUENCE 372 K54N
GKVKDNKPRGRMTAYAFFVQTCREEHKKKHPEEQVIFAEFSRKCAERWKTMLDNEKQRFHEMAEKDKARYELEMQSYVPPKGAV

\>> SEQUENCE 373 K54Q
GKVKDNKPRGRMTAYAFFVQTCREEHKKKHPEEQVIFAEFSRKCAERWKTMLDQEKQRFHEMAEKDKARYELEMQSYVPPKGAV

\>> SEQUENCE 374 E55Q
GKVKDNKPRGRMTAYAFFVQTCREEHKKKHPEEQVIFAEFSRKCAERWKTMLDKQKQRFHEMAEKDKARYELEMQSYVPPKGAV

\>> SEQUENCE 375 E55H
GKVKDNKPRGRMTAYAFFVQTCREEHKKKHPEEQVIFAEFSRKCAERWKTMLDKHKQRFHEMAEKDKARYELEMQSYVPPKGAV

\>> SEQUENCE 376 E55N
GKVKDNKPRGRMTAYAFFVQTCREEHKKKHPEEQVIFAEFSRKCAERWKTMLDKNKQRFHEMAEKDKARYELEMQSYVPPKGAV

\>> SEQUENCE 377 K56N
GKVKDNKPRGRMTAYAFFVQTCREEHKKKHPEEQVIFAEFSRKCAERWKTMLDKENQRFHEMAEKDKARYELEMQSYVPPKGAV

\>> SEQUENCE 378 K56Q
GKVKDNKPRGRMTAYAFFVQTCREEHKKKHPEEQVIFAEFSRKCAERWKTMLDKEQQRFHEMAEKDKARYELEMQSYVPPKGAV

\>> SEQUENCE 379 R58H
GKVKDNKPRGRMTAYAFFVQTCREEHKKKHPEEQVIFAEFSRKCAERWKTMLDKEKQHFHEMAEKDKARYELEMQSYVPPKGAV

\>> SEQUENCE 380 R58Q
GKVKDNKPRGRMTAYAFFVQTCREEHKKKHPEEQVIFAEFSRKCAERWKTMLDKEKQQFHEMAEKDKARYELEMQSYVPPKGAV

\>> SEQUENCE 381 F59I
GKVKDNKPRGRMTAYAFFVQTCREEHKKKHPEEQVIFAEFSRKCAERWKTMLDKEKQRIHEMAEKDKARYELEMQSYVPPKGAV

\>> SEQUENCE 382 F59V
GKVKDNKPRGRMTAYAFFVQTCREEHKKKHPEEQVIFAEFSRKCAERWKTMLDKEKQRVHEMAEKDKARYELEMQSYVPPKGAV

Figure 4b continued

>> SEQUENCE 383 E61Q
GKVKDNKPRGRMTAYAFFVQTCREEHKKKHPEEQVIFAEFSRKCAERWKTMLDKEKQRFHQMAEKDK
ARYELEMQSYVPPKGAV

>> SEQUENCE 384 E61H
GKVKDNKPRGRMTAYAFFVQTCREEHKKKHPEEQVIFAEFSRKCAERWKTMLDKEKQRFHHMAEKDK
ARYELEMQSYVPPKGAV

>> SEQUENCE 385 E61N
GKVKDNKPRGRMTAYAFFVQTCREEHKKKHPEEQVIFAEFSRKCAERWKTMLDKEKQRFHNMAEKDK
ARYELEMQSYVPPKGAV

>> SEQUENCE 386 M62I
GKVKDNKPRGRMTAYAFFVQTCREEHKKKHPEEQVIFAEFSRKCAERWKTMLDKEKQRFHEIAEKDKA
RYELEMQSYVPPKGAV

>> SEQUENCE 387 M62V
GKVKDNKPRGRMTAYAFFVQTCREEHKKKHPEEQVIFAEFSRKCAERWKTMLDKEKQRFHEVAEKDK
ARYELEMQSYVPPKGAV

>> SEQUENCE 388 E64Q
GKVKDNKPRGRMTAYAFFVQTCREEHKKKHPEEQVIFAEFSRKCAERWKTMLDKEKQRFHEMAQKDK
ARYELEMQSYVPPKGAV

>> SEQUENCE 389 E64H
GKVKDNKPRGRMTAYAFFVQTCREEHKKKHPEEQVIFAEFSRKCAERWKTMLDKEKQRFHEMAHKDK
ARYELEMQSYVPPKGAV

>> SEQUENCE 390 E64N
GKVKDNKPRGRMTAYAFFVQTCREEHKKKHPEEQVIFAEFSRKCAERWKTMLDKEKQRFHEMANKDK
ARYELEMQSYVPPKGAV

>> SEQUENCE 391 K65N
GKVKDNKPRGRMTAYAFFVQTCREEHKKKHPEEQVIFAEFSRKCAERWKTMLDKEKQRFHEMAENDK
ARYELEMQSYVPPKGAV

>> SEQUENCE 392 K65Q
GKVKDNKPRGRMTAYAFFVQTCREEHKKKHPEEQVIFAEFSRKCAERWKTMLDKEKQRFHEMAEQDK
ARYELEMQSYVPPKGAV

>> SEQUENCE 393 D66N
GKVKDNKPRGRMTAYAFFVQTCREEHKKKHPEEQVIFAEFSRKCAERWKTMLDKEKQRFHEMAEKNK
ARYELEMQSYVPPKGAV

>> SEQUENCE 394 D66Q
GKVKDNKPRGRMTAYAFFVQTCREEHKKKHPEEQVIFAEFSRKCAERWKTMLDKEKQRFHEMAEKQK
ARYELEMQSYVPPKGAV

>> SEQUENCE 395 K67N
GKVKDNKPRGRMTAYAFFVQTCREEHKKKHPEEQVIFAEFSRKCAERWKTMLDKEKQRFHEMAEKDN
ARYELEMQSYVPPKGAV

>> SEQUENCE 396 K67Q
GKVKDNKPRGRMTAYAFFVQTCREEHKKKHPEEQVIFAEFSRKCAERWKTMLDKEKQRFHEMAEKDQ

Figure 4b continued

ARYELEMQSYVPPKGAV

>> SEQUENCE 397 R69H
GKVKDNKPRGRMTAYAFFVQTCREEHKKKHPEEQVIFAEFSRKCAERWKTMLDKEKQRFHEMAEKDK
AHYELEMQSYVPPKGAV

>> SEQUENCE 398 R69Q
GKVKDNKPRGRMTAYAFFVQTCREEHKKKHPEEQVIFAEFSRKCAERWKTMLDKEKQRFHEMAEKDK
AQYELEMQSYVPPKGAV

>> SEQUENCE 399 Y70H
GKVKDNKPRGRMTAYAFFVQTCREEHKKKHPEEQVIFAEFSRKCAERWKTMLDKEKQRFHEMAEKDK
ARHELEMQSYVPPKGAV

>> SEQUENCE 400 Y70I
GKVKDNKPRGRMTAYAFFVQTCREEHKKKHPEEQVIFAEFSRKCAERWKTMLDKEKQRFHEMAEKDK
ARIELEMQSYV

>> SEQUENCE 401 E71Q
GKVKDNKPRGRMTAYAFFVQTCREEHKKKHPEEQVIFAEFSRKCAERWKTMLDKEKQRFHEMAEKDK
ARYQLEMQSYVPPKGAV

>> SEQUENCE 402 E71H
GKVKDNKPRGRMTAYAFFVQTCREEHKKKHPEEQVIFAEFSRKCAERWKTMLDKEKQRFHEMAEKDK
ARYHLEMQSYVPPKGAV

>> SEQUENCE 403 E71N
GKVKDNKPRGRMTAYAFFVQTCREEHKKKHPEEQVIFAEFSRKCAERWKTMLDKEKQRFHEMAEKDK
ARYNLEMQSYVPPKGAV

>> SEQUENCE 404 L72I
GKVKDNKPRGRMTAYAFFVQTCREEHKKKHPEEQVIFAEFSRKCAERWKTMLDKEKQRFHEMAEKDK
ARYEIEMQSYVPPKGAV

>> SEQUENCE 405 L72V
GKVKDNKPRGRMTAYAFFVQTCREEHKKKHPEEQVIFAEFSRKCAERWKTMLDKEKQRFHEMAEKDK
ARYEVEMQSYVPPKGAV

>> SEQUENCE 406 E73Q
GKVKDNKPRGRMTAYAFFVQTCREEHKKKHPEEQVIFAEFSRKCAERWKTMLDKEKQRFHEMAEKDK
ARYELQMQSYVPPKGAV

>> SEQUENCE 407 E73H
GKVKDNKPRGRMTAYAFFVQTCREEHKKKHPEEQVIFAEFSRKCAERWKTMLDKEKQRFHEMAEKDK
ARYELHMQSYVPPKGAV

>> SEQUENCE 408 E73N
GKVKDNKPRGRMTAYAFFVQTCREEHKKKHPEEQVIFAEFSRKCAERWKTMLDKEKQRFHEMAEKDK
ARYELNMQSYVPPKGAV

>> SEQUENCE 409 M74I
GKVKDNKPRGRMTAYAFFVQTCREEHKKKHPEEQVIFAEFSRKCAERWKTMLDKEKQRFHEMAEKDK
ARYELEIQSYVPPKGAV

>> SEQUENCE 410 M74V
GKVKDNKPRGRMTAYAFFVQTCREEHKKKHPEEQVIFAEFSRKCAERWKTMLDKEKQRFHEMAEKDK

Figure 4b continued

ARYELEVQSYVPPKGAV

>> SEQUENCE 411 Y77H
GKVKDNKPRGRMTAYAFFVQTCREEHKKKHPEEQVIFAEFSRKCAERWKTMLDKEKQRFHEMAEKDK
ARYELEMQSHVPPKGAV

>> SEQUENCE 412 Y77I
GKVKDNKPRGRMTAYAFFVQTCREEHKKKHPEEQVIFAEFSRKCAERWKTMLDKEKQRFHEMAEKDK
ARYELEMQSIVPPKGAV

>> SEQUENCE 413 P79A
GKVKDNKPRGRMTAYAFFVQTCREEHKKKHPEEQVIFAEFSRKCAERWKTMLDKEKQRFHEMAEKDK
ARYELEMQSYVAPKGAV

>> SEQUENCE 414 P79S
GKVKDNKPRGRMTAYAFFVQTCREEHKKKHPEEQVIFAEFSRKCAERWKTMLDKEKQRFHEMAEKDK
ARYELEMQSYVSPKGAV

>> SEQUENCE 415 P80A
GKVKDNKPRGRMTAYAFFVQTCREEHKKKHPEEQVIFAEFSRKCAERWKTMLDKEKQRFHEMAEKDK
ARYELEMQSYVPAKGAV

>> SEQUENCE 416 P80S
GKVKDNKPRGRMTAYAFFVQTCREEHKKKHPEEQVIFAEFSRKCAERWKTMLDKEKQRFHEMAEKDK
ARYELEMQSYVPSKGAV

>> SEQUENCE417 K81N
GKVKDNKPRGRMTAYAFFVQTCREEHKKKHPEEQVIFAEFSRKCAERWKTMLDKEKQRFHEMAEKDK
ARYELEMQSYVPPNGAV

>> SEQUENCE 418 K81Q
GKVKDNKPRGRMTAYAFFVQTCREEHKKKHPEEQVIFAEFSRKCAERWKTMLDKEKQRFHEMAEKDK
ARYELEMQSYVPPQGAV

Figure 5a

Box A 77 amino acid of HMGB1 *Anopheles gambia* (XP_311154)

Protection against proteolysis
If sequence:

PRGRMTAYAFFVQTCREEHKKKHPEEQVIFAEFSRKCAERWKTMLDKEKQRFHEMA
EKDKARYELEMQSYVPPKGAV

In bold amino acids sensitive to proteases proteolysis

Figure 5b

Box A 77 amino acid of HMGB1 *Anopheles gambia* (XP_311154)

Mutant list:

| | | | |
|---|---|---|---|
| P1A | E26N | R51Q | P73A |
| P1S | F30I | F52I | P73S |
| R2H | F30V | F52V | K74N |
| R2Q | E32Q | E54Q | K74Q |
| R4H | E32H | E54H | |
| R4Q | E32N | E54N | |
| M5I | F33I | M55I | |
| M5V | F33V | M55V | |
| Y8H | R35H | E57Q | |
| Y8I | R35Q | E57H | |
| F10I | K36N | E57N | |
| F10V | K36Q | K58N | |
| F11I | E39Q | K58Q | |
| F11V | E39H | D59N | |
| R16H | E39N | D59Q | |
| R16Q | R40H | K60N | |
| E17Q | R40Q | K60Q | |
| E17H | W41Y | R62H | |
| E17N | W41S | R62Q | |
| E18Q | K42N | Y63H | |
| E18H | K42Q | Y63I | |
| E18N | M44I | E64Q | |
| K20N | M44V | E64H | |
| K20Q | L45I | E64N | |
| K21N | L45V | L65I | |
| K21Q | D46N | L65V | |
| K22N | D46Q | E66Q | |
| K22Q | K47N | E66H | |
| P24A | K47Q | E66N | |
| P24S | E48Q | M67I | |
| E25Q | E48H | M67V | |
| E25H | E48N | Y70H | |
| E25N | K49N | Y70I | |
| E26Q | K49Q | P72A | |
| E26H | R51H | P72S | |

Figure 5b continued

> SEQUENCE 419 Wild type
PRGRMTAYAFFVQTCREEHKKKHPEEQVIFAEFSRKCAERWKTMLDKEKQRFHEMAEKDKARYELEM
QSYVPPKGAV > > SEQUENCE 420 P1A
ARGRMTAYAFFVQTCREEHKKKHPEEQVIFAEFSRKCAERWKTMLDKEKQRFHEMAEKDKARYELEM
QSYVPPKGAV > SEQUENCE 421 P1S
SRGRMTAYAFFVQTCREEHKKKHPEEQVIFAEFSRKCAERWKTMLDKEKQRFHEMAEKDKARYELEM
QSYVPPKGAV > SEQUENCE 422 R2H
PHGRMTAYAFFVQTCREEHKKKHPEEQVIFAEFSRKCAERWKTMLDKEKQRFHEMAEKDKARYELEM
QSYVPPKGAV > SEQUENCE 423 R2Q
PQGRMTAYAFFVQTCREEHKKKHPEEQVIFAEFSRKCAERWKTMLDKEKQRFHEMAEKDKARYELEM
QSYVPPKGAV > SEQUENCE 424 R4H
PRGHMTAYAFFVQTCREEHKKKHPEEQVIFAEFSRKCAERWKTMLDKEKQRFHEMAEKDKARYELEM
QSYVPPKGAV > SEQUENCE 425 R4Q
PRGQMTAYAFFVQTCREEHKKKHPEEQVIFAEFSRKCAERWKTMLDKEKQRFHEMAEKDKARYELEM
QSYVPPKGAV > SEQUENCE 426 M5I
PRGRITAYAFFVQTCREEHKKKHPEEQVIFAEFSRKCAERWKTMLDKEKQRFHEMAEKDKARYELEMQ
SYVPPKGAV > SEQUENCE 427 M5V
PRGRVTAYAFFVQTCREEHKKKHPEEQVIFAEFSRKCAERWKTMLDKEKQRFHEMAEKDKARYELEM
QSYVPPKGAV > SEQUENCE 428 Y8H
PRGRMTAHAFFVQTCREEHKKKHPEEQVIFAEFSRKCAERWKTMLDKEKQRFHEMAEKDKARYELEM
QSYVPPKGAV > SEQUENCE 429 Y8I
PRGRMTAIAFFVQTCREEHKKKHPEEQVIFAEFSRKCAERWKTMLDKEKQRFHEMAEKDKARYELEMQ
SYVPPKGAV > SEQUENCE 430 F10I
PRGRMTAYAIFVQTCREEHKKKHPEEQVIFAEFSRKCAERWKTMLDKEKQRFHEMAEKDKARYELEMQ
SYVPPKGAV > SEQUENCE 431 F10V
PRGRMTAYAVFVQTCREEHKKKHPEEQVIFAEFSRKCAERWKTMLDKEKQRFHEMAEKDKARYELEM
QSYVPPKGAV

Figure 5b continued

> SEQUENCE 432 F11I
PRGRMTAYAFIVQTCREEHKKKHPEEQVIFAEFSRKCAERWKTMLDKEKQRFHEMAEKDKARYELEMQ
SYVPPKGAV

> SEQUENCE 433 F11V
PRGRMTAYAFVVQTCREEHKKKHPEEQVIFAEFSRKCAERWKTMLDKEKQRFHEMAEKDKARYELEM
QSYVPPKGAV

> SEQUENCE 434 R16H
PRGRMTAYAFFVQTCHEEHKKKHPEEQVIFAEFSRKCAERWKTMLDKEKQRFHEMAEKDKARYELEM
QSYVPPKGAV

> SEQUENCE 435 R16Q
PRGRMTAYAFFVQTCQEEHKKKHPEEQVIFAEFSRKCAERWKTMLDKEKQRFHEMAEKDKARYELEM
QSYVPPKGAV

> SEQUENCE 436 E17Q
PRGRMTAYAFFVQTCRQEHKKKHPEEQVIFAEFSRKCAERWKTMLDKEKQRFHEMAEKDKARYELEM
QSYVPPKGAV

> SEQUENCE 437 E17H
PRGRMTAYAFFVQTCRHEHKKKHPEEQVIFAEFSRKCAERWKTMLDKEKQRFHEMAEKDKARYELEM
QSYVPPKGAV

> SEQUENCE 438 E17N
PRGRMTAYAFFVQTCRNEHKKKHPEEQVIFAEFSRKCAERWKTMLDKEKQRFHEMAEKDKARYELEM
QSYVPPKGAV

> SEQUENCE 439 E18Q
PRGRMTAYAFFVQTCREQHKKKHPEEQVIFAEFSRKCAERWKTMLDKEKQRFHEMAEKDKARYELEM
QSYVPPKGAV

> SEQUENCE 440 E18H
PRGRMTAYAFFVQTCREHHKKKHPEEQVIFAEFSRKCAERWKTMLDKEKQRFHEMAEKDKARYELEM
QSYVPPKGAV

> SEQUENCE 441 E18N
PRGRMTAYAFFVQTCRENHKKKHPEEQVIFAEFSRKCAERWKTMLDKEKQRFHEMAEKDKARYELEM
QSYVPPKGAV

> SEQUENCE 442 K20N
PRGRMTAYAFFVQTCREEHNKKHPEEQVIFAEFSRKCAERWKTMLDKEKQRFHEMAEKDKARYELEM
QSYVPPKGAV

> SEQUENCE 443 K20Q
PRGRMTAYAFFVQTCREEHQKKHPEEQVIFAEFSRKCAERWKTMLDKEKQRFHEMAEKDKARYELEM
QSYVPPKGAV

> SEQUENCE 444 K21N
PRGRMTAYAFFVQTCREEHKNKHPEEQVIFAEFSRKCAERWKTMLDKEKQRFHEMAEKDKARYELEM
QSYVPPKGAV

> SEQUENCE 445 K21Q
PRGRMTAYAFFVQTCREEHKQKHPEEQVIFAEFSRKCAERWKTMLDKEKQRFHEMAEKDKARYELEM
QSYVPPKGAV

Figure 5b continued

> SEQUENCE 446 K22N
PRGRMTAYAFFVQTCREEHKKNHPEEQVIFAEFSRKCAERWKTMLDKEKQRFHEMAEKDKARYELEM
QSYVPPKGAV

> SEQUENCE 447 K22Q
PRGRMTAYAFFVQTCREEHKKQHPEEQVIFAEFSRKCAERWKTMLDKEKQRFHEMAEKDKARYELEM
QSYVPPKGAV

> SEQUENCE 448 P24A
PRGRMTAYAFFVQTCREEHKKKHAEEQVIFAEFSRKCAERWKTMLDKEKQRFHEMAEKDKARYELEM
QSYVPPKGAV

> SEQUENCE 449 P24S
PRGRMTAYAFFVQTCREEHKKKHSEEQVIFAEFSRKCAERWKTMLDKEKQRFHEMAEKDKARYELEM
QSYVPPKGAV

> SEQUENCE 450 E25Q
PRGRMTAYAFFVQTCREEHKKKHPQEQVIFAEFSRKCAERWKTMLDKEKQRFHEMAEKDKARYELEM
QSYVPPKGAV

> SEQUENCE 451 E25H
PRGRMTAYAFFVQTCREEHKKKHPHEQVIFAEFSRKCAERWKTMLDKEKQRFHEMAEKDKARYELEM
QSYVPPKGAV

> SEQUENCE 452 E25N
PRGRMTAYAFFVQTCREEHKKKHPNEQVIFAEFSRKCAERWKTMLDKEKQRFHEMAEKDKARYELEM
QSYVPPKGAV

> SEQUENCE 453 E26Q
PRGRMTAYAFFVQTCREEHKKKHPEQQVIFAEFSRKCAERWKTMLDKEKQRFHEMAEKDKARYELEM
QSYVPPKGAV

> SEQUENCE 454 E26H
PRGRMTAYAFFVQTCREEHKKKHPEHQVIFAEFSRKCAERWKTMLDKEKQRFHEMAEKDKARYELEM
QSYVPPKGAV

> SEQUENCE 455 E26N
PRGRMTAYAFFVQTCREEHKKKHPENQVIFAEFSRKCAERWKTMLDKEKQRFHEMAEKDKARYELEM
QSYVPPKGAV

> SEQUENCE 456 F30I
PRGRMTAYAFFVQTCREEHKKKHPEEQVIIAEFSRKCAERWKTMLDKEKQRFHEMAEKDKARYELEMQ
SYVPPKGAV

> SEQUENCE 457 F30V
PRGRMTAYAFFVQTCREEHKKKHPEEQVIVAEFSRKCAERWKTMLDKEKQRFHEMAEKDKARYELEM
QSYVPPKGAV

> SEQUENCE 458 E32Q
PRGRMTAYAFFVQTCREEHKKKHPEEQVIFAQFSRKCAERWKTMLDKEKQRFHEMAEKDKARYELEM
QSYVPPKGAV

> SEQUENCE 459 E32H
PRGRMTAYAFFVQTCREEHKKKHPEEQVIFAHFSRKCAERWKTMLDKEKQRFHEMAEKDKARYELEM
QSYVPPKGAV

Figure 5b continued

> SEQUENCE 460 E32N
PRGRMTAYAFFVQTCREEHKKKHPEEQVIFANFSRKCAERWKTMLDKEKQRFHEMAEKDKARYELEM
QSYVPPKGAV

> SEQUENCE 461 F33I
PRGRMTAYAFFVQTCREEHKKKHPEEQVIFAEISRKCAERWKTMLDKEKQRFHEMAEKDKARYELEMQ
SYVPPKGAV

> SEQUENCE 462 F33V
PRGRMTAYAFFVQTCREEHKKKHPEEQVIFAEVSRKCAERWKTMLDKEKQRFHEMAEKDKARYELEM
QSYVPPKGAV

> SEQUENCE 463 R35H
PRGRMTAYAFFVQTCREEHKKKHPEEQVIFAEFSHKCAERWKTMLDKEKQRFHEMAEKDKARYELEM
QSYVPPKGAV

> SEQUENCE 464 R35Q
PRGRMTAYAFFVQTCREEHKKKHPEEQVIFAEFSQKCAERWKTMLDKEKQRFHEMAEKDKARYELEM
QSYVPPKGAV

> SEQUENCE 465 K36N
PRGRMTAYAFFVQTCREEHKKKHPEEQVIFAEFSRNCAERWKTMLDKEKQRFHEMAEKDKARYELEM
QSYVPPKGAV

> SEQUENCE 466 K36Q
PRGRMTAYAFFVQTCREEHKKKHPEEQVIFAEFSRQCAERWKTMLDKEKQRFHEMAEKDKARYELEM
QSYVPPKGAV

> SEQUENCE 467 E39Q
PRGRMTAYAFFVQTCREEHKKKHPEEQVIFAEFSRKCAQRWKTMLDKEKQRFHEMAEKDKARYELEM
QSYVPPKGAV

> SEQUENCE 468 E39H
PRGRMTAYAFFVQTCREEHKKKHPEEQVIFAEFSRKCAHRWKTMLDKEKQRFHEMAEKDKARYELEM
QSYVPPKGAV

> SEQUENCE 469 E39N
PRGRMTAYAFFVQTCREEHKKKHPEEQVIFAEFSRKCANRWKTMLDKEKQRFHEMAEKDKARYELEM
QSYVPPKGAV

> SEQUENCE 470 R40H
PRGRMTAYAFFVQTCREEHKKKHPEEQVIFAEFSRKCAEHWKTMLDKEKQRFHEMAEKDKARYELEM
QSYVPPKGAV

> SEQUENCE 471 R40Q
PRGRMTAYAFFVQTCREEHKKKHPEEQVIFAEFSRKCAEQWKTMLDKEKQRFHEMAEKDKARYELEM
QSYVPPKGAV

> SEQUENCE 472 W41Y
PRGRMTAYAFFVQTCREEHKKKHPEEQVIFAEFSRKCAERYKTMLDKEKQRFHEMAEKDKARYELEMQ
SYVPPKGAV

> SEQUENCE 473 W41S

Figure 5b continued

PRGRMTAYAFFVQTCREEHKKKHPEEQVIFAEFSRKCAERSKTMLDKEKQRFHEMAEKDKARYELEMQSYVPPKGAV

> SEQUENCE 474 K42N
PRGRMTAYAFFVQTCREEHKKKHPEEQVIFAEFSRKCAERWNTMLDKEKQRFHEMAEKDKARYELEMQSYVPPKGAV

> SEQUENCE 475 K42Q
PRGRMTAYAFFVQTCREEHKKKHPEEQVIFAEFSRKCAERWQTMLDKEKQRFHEMAEKDKARYELEMQSYVPPKGAV

> SEQUENCE 476 M44I
PRGRMTAYAFFVQTCREEHKKKHPEEQVIFAEFSRKCAERWKTILDKEKQRFHEMAEKDKARYELEMQSYVPPKGAV

> SEQUENCE 477 M44V
PRGRMTAYAFFVQTCREEHKKKHPEEQVIFAEFSRKCAERWKTVLDKEKQRFHEMAEKDKARYELEMQSYVPPKGAV

> SEQUENCE 478 L45I
PRGRMTAYAFFVQTCREEHKKKHPEEQVIFAEFSRKCAERWKTMIDKEKQRFHEMAEKDKARYELEMQSYVPPKGAV

> SEQUENCE 479 L45V
PRGRMTAYAFFVQTCREEHKKKHPEEQVIFAEFSRKCAERWKTMVDKEKQRFHEMAEKDKARYELEMQSYVPPKGAV

> SEQUENCE 480 D46N
PRGRMTAYAFFVQTCREEHKKKHPEEQVIFAEFSRKCAERWKTMLNKEKQRFHEMAEKDKARYELEMQSYVPPKGAV

> SEQUENCE 481 D46Q
PRGRMTAYAFFVQTCREEHKKKHPEEQVIFAEFSRKCAERWKTMLQKEKQRFHEMAEKDKARYELEMQSYVPPKGAV

> SEQUENCE 482 K47N
PRGRMTAYAFFVQTCREEHKKKHPEEQVIFAEFSRKCAERWKTMLDNEKQRFHEMAEKDKARYELEMQSYVPPKGAV

> SEQUENCE 483 K47Q
PRGRMTAYAFFVQTCREEHKKKHPEEQVIFAEFSRKCAERWKTMLDQEKQRFHEMAEKDKARYELEMQSYVPPKGAV

> SEQUENCE 484 E48Q
PRGRMTAYAFFVQTCREEHKKKHPEEQVIFAEFSRKCAERWKTMLDKQKQRFHEMAEKDKARYELEMQSYVPPKGAV

> SEQUENCE 485 E48H
PRGRMTAYAFFVQTCREEHKKKHPEEQVIFAEFSRKCAERWKTMLDKHKQRFHEMAEKDKARYELEMQSYVPPKGAV

> SEQUENCE 486 E48N
PRGRMTAYAFFVQTCREEHKKKHPEEQVIFAEFSRKCAERWKTMLDKNKQRFHEMAEKDKARYELEMQSYVPPKGAV

Figure 5b continued

> SEQUENCE 487 K49N
PRGRMTAYAFFVQTCREEHKKKHPEEQVIFAEFSRKCAERWKTMLDKENQRFHEMAEKDKARYELEM
QSYVPPKGAV

> SEQUENCE 488 K49Q
PRGRMTAYAFFVQTCREEHKKKHPEEQVIFAEFSRKCAERWKTMLDKEQQRFHEMAEKDKARYELEM
QSYVPPKGAV

> SEQUENCE 489 R51H
PRGRMTAYAFFVQTCREEHKKKHPEEQVIFAEFSRKCAERWKTMLDKEKQHFHEMAEKDKARYELEM
QSYVPPKGAV

> SEQUENCE 490 R51Q
PRGRMTAYAFFVQTCREEHKKKHPEEQVIFAEFSRKCAERWKTMLDKEKQQFHEMAEKDKARYELEM
QSYVPPKGAV

> SEQUENCE 491 F52I
PRGRMTAYAFFVQTCREEHKKKHPEEQVIFAEFSRKCAERWKTMLDKEKQRIHEMAEKDKARYELEMQ
SYVPPKGAV

> SEQUENCE 492 F52V
PRGRMTAYAFFVQTCREEHKKKHPEEQVIFAEFSRKCAERWKTMLDKEKQRVHEMAEKDKARYELEM
QSYVPPKGAV

> SEQUENCE 493 E54Q
PRGRMTAYAFFVQTCREEHKKKHPEEQVIFAEFSRKCAERWKTMLDKEKQRFHQMAEKDKARYELEM
QSYVPPKGAV

> SEQUENCE 494 E54H
PRGRMTAYAFFVQTCREEHKKKHPEEQVIFAEFSRKCAERWKTMLDKEKQRFHHMAEKDKARYELEM
QSYVPPKGAV

> SEQUENCE 495 E54N
PRGRMTAYAFFVQTCREEHKKKHPEEQVIFAEFSRKCAERWKTMLDKEKQRFHNMAEKDKARYELEM
QSYVPPKGAV

> SEQUENCE 496 M55I
PRGRMTAYAFFVQTCREEHKKKHPEEQVIFAEFSRKCAERWKTMLDKEKQRFHEIAEKDKARYELEMQ
SYVPPKGAV

> SEQUENCE 497 M55V
PRGRMTAYAFFVQTCREEHKKKHPEEQVIFAEFSRKCAERWKTMLDKEKQRFHEVAEKDKARYELEM
QSYVPPKGAV

> SEQUENCE 498 E57Q
PRGRMTAYAFFVQTCREEHKKKHPEEQVIFAEFSRKCAERWKTMLDKEKQRFHEMAQKDKARYELEM
QSYVPPKGAV

> SEQUENCE 499 E57H
PRGRMTAYAFFVQTCREEHKKKHPEEQVIFAEFSRKCAERWKTMLDKEKQRFHEMAHKDKARYELEM
QSYVPPKGAV

> SEQUENCE 500 E57N
PRGRMTAYAFFVQTCREEHKKKHPEEQVIFAEFSRKCAERWKTMLDKEKQRFHEMANKDKARYELEM
QSYVPPKGAV

Figure 5b continued

> SEQUENCE 501 K58N
PRGRMTAYAFFVQTCREEHKKKHPEEQVIFAEFSRKCAERWKTMLDKEKQRFHEMAENDKARYELEM
QSYVPPKGAV

> SEQUENCE 502 K58Q
PRGRMTAYAFFVQTCREEHKKKHPEEQVIFAEFSRKCAERWKTMLDKEKQRFHEMAEQDKARYELEM
QSYVPPKGAV

> SEQUENCE 503 D59N
PRGRMTAYAFFVQTCREEHKKKHPEEQVIFAEFSRKCAERWKTMLDKEKQRFHEMAEKNKARYELEM
QSYVPPKGAV

> SEQUENCE 504 D59Q
PRGRMTAYAFFVQTCREEHKKKHPEEQVIFAEFSRKCAERWKTMLDKEKQRFHEMAEKQKARYELEM
QSYVPPKGAV

> SEQUENCE 505 K60N
PRGRMTAYAFFVQTCREEHKKKHPEEQVIFAEFSRKCAERWKTMLDKEKQRFHEMAEKDNARYELEM
QSYVPPKGAV

> SEQUENCE 506 K60Q
PRGRMTAYAFFVQTCREEHKKKHPEEQVIFAEFSRKCAERWKTMLDKEKQRFHEMAEKDQARYELEM
QSYVPPKGAV

> SEQUENCE 507 R62H
PRGRMTAYAFFVQTCREEHKKKHPEEQVIFAEFSRKCAERWKTMLDKEKQRFHEMAEKDKAHYELEM
QSYVPPKGAV

> SEQUENCE 508 R62Q
PRGRMTAYAFFVQTCREEHKKKHPEEQVIFAEFSRKCAERWKTMLDKEKQRFHEMAEKDKAQYELEM
QSYVPPKGAV

> SEQUENCE 509 Y63H
PRGRMTAYAFFVQTCREEHKKKHPEEQVIFAEFSRKCAERWKTMLDKEKQRFHEMAEKDKARHELEM
QSYVPPKGAV

> SEQUENCE 510 Y63I
PRGRMTAYAFFVQTCREEHKKKHPEEQVIFAEFSRKCAERWKTMLDKEKQRFHEMAEKDKARIELEMQ
SYVPPKGAV

> SEQUENCE 511 E64Q
PRGRMTAYAFFVQTCREEHKKKHPEEQVIFAEFSRKCAERWKTMLDKEKQRFHEMAEKDKARYQLEM
QSYVPPKGAV

> SEQUENCE 512 E64H
PRGRMTAYAFFVQTCREEHKKKHPEEQVIFAEFSRKCAERWKTMLDKEKQRFHEMAEKDKARYHLEM
QSYVPPKGAV

> SEQUENCE 513 E64N
PRGRMTAYAFFVQTCREEHKKKHPEEQVIFAEFSRKCAERWKTMLDKEKQRFHEMAEKDKARYNLEM
QSYVPPKGAV

> SEQUENCE 514 L65I
PRGRMTAYAFFVQTCREEHKKKHPEEQVIFAEFSRKCAERWKTMLDKEKQRFHEMAEKDKARYEIEMQ

Figure 5b continued

SYVPPKGAV

> SEQUENCE 515 L65V
PRGRMTAYAFFVQTCREEHKKKHPEEQVIFAEFSRKCAERWKTMLDKEKQRFHEMAEKDKARYEVEM
QSYVPPKGAV

> SEQUENCE 516 E66Q
PRGRMTAYAFFVQTCREEHKKKHPEEQVIFAEFSRKCAERWKTMLDKEKQRFHEMAEKDKARYELQM
QSYVPPKGAV

> SEQUENCE 517 E66H
PRGRMTAYAFFVQTCREEHKKKHPEEQVIFAEFSRKCAERWKTMLDKEKQRFHEMAEKDKARYELHM
QSYVPPKGAV

> SEQUENCE 518 E66N
PRGRMTAYAFFVQTCREEHKKKHPEEQVIFAEFSRKCAERWKTMLDKEKQRFHEMAEKDKARYELNM
QSYVPPKGAV

> SEQUENCE 519 M67I
PRGRMTAYAFFVQTCREEHKKKHPEEQVIFAEFSRKCAERWKTMLDKEKQRFHEMAEKDKARYELEIQ
SYVPPKGAV

> SEQUENCE 520 M67V
PRGRMTAYAFFVQTCREEHKKKHPEEQVIFAEFSRKCAERWKTMLDKEKQRFHEMAEKDKARYELEV
QSYVPPKGAV

> SEQUENCE 521 Y70H
PRGRMTAYAFFVQTCREEHKKKHPEEQVIFAEFSRKCAERWKTMLDKEKQRFHEMAEKDKARYELEM
QSHVPPKGAV

> SEQUENCE 522 Y70I
PRGRMTAYAFFVQTCREEHKKKHPEEQVIFAEFSRKCAERWKTMLDKEKQRFHEMAEKDKARYELEM
QSIVPPKGAV

> SEQUENCE 523 P72A
PRGRMTAYAFFVQTCREEHKKKHPEEQVIFAEFSRKCAERWKTMLDKEKQRFHEMAEKDKARYELEM
QSYVAPKGAV

>SEQUENCE 524 P72S
PRGRMTAYAFFVQTCREEHKKKHPEEQVIFAEFSRKCAERWKTMLDKEKQRFHEMAEKDKARYELEM
QSYVSPKGAV

>SEQUENCE 525 P73A
PRGRMTAYAFFVQTCREEHKKKHPEEQVIFAEFSRKCAERWKTMLDKEKQRFHEMAEKDKARYELEM
QSYVPAKGAV

>SEQUENCE 526 P73S
PRGRMTAYAFFVQTCREEHKKKHPEEQVIFAEFSRKCAERWKTMLDKEKQRFHEMAEKDKARYELEM
QSYVPSKGAV

> SEQUENCE 527 K74N
PRGRMTAYAFFVQTCREEHKKKHPEEQVIFAEFSRKCAERWKTMLDKEKQRFHEMAEKDKARYELEM
QSYVPPNGAV

> SEQUENCE 528 K74Q
PRGRMTAYAFFVQTCREEHKKKHPEEQVIFAEFSRKCAERWKTMLDKEKQRFHEMAEKDKARYELEM

Figure 5b continued

QSYVPPQGAV

Figure 6a

Box A 54 amino acid of HMGB1 *Anopheles gambia* (XP_311154)

Protection against proteolysis
If sequence:

PEEQVIFAEFSRKCAERWKTMLDKEKQRFHEMAEKDKARYELEMQSYVPPKGAV

In bold amino acids sensitive to proteases proteolysis

Figure 6b

Box A 54 amino acid of HMGB1 *Anopheles gambia* (XP_311154)

Mutant list:

| | | |
|---|---|---|
| P1A | K24N | E43Q |
| P1S | K24Q | E43H |
| E2Q | E25Q | E43N |
| E2H | E25H | M44I |
| E2N | E25N | M44V |
| E3Q | K26N | Y47H |
| E3H | K26Q | Y47I |
| E3N | R28H | P49A |
| F7I | R28Q | P49S |
| F7V | F29I | P50A |
| E9Q | F29V | P50S |
| E9H | E31Q | K51N |
| E9N | E31H | K51Q |
| F10I | E31N | |
| F10V | M32I | |
| R12H | M32V | |
| R12Q | E34Q | |
| K13N | E34H | |
| K13Q | E34N | |
| E16Q | K35N | |
| E16H | K35Q | |
| E16N | D36N | |
| R17H | D36Q | |
| R17Q | K37N | |
| W18Y | K37Q | |
| W18S | R39H | |
| K19N | R39Q | |
| K19Q | Y40H | |
| M21I | Y40I | |
| M21V | E41Q | |
| L22I | E41H | |
| L22V | E41N | |
| D23N | L42I | |
| D23Q | L42V | |

Figure 6b continued

> SEQUENCE 529 Wild type

PEEQVIFAEFSRKCAERWKTMLDKEKQRFHEMAEKDKARYELEMQSYVPPKGAV

> SEQUENCE 530 P1A
AEEQVIFAEFSRKCAERWKTMLDKEKQRFHEMAEKDKARYELEMQSYVPPKGAV

> SEQUENCE 531 P1S
SEEQVIFAEFSRKCAERWKTMLDKEKQRFHEMAEKDKARYELEMQSYVPPKGAV

> SEQUENCE 532 E2Q
PQEQVIFAEFSRKCAERWKTMLDKEKQRFHEMAEKDKARYELEMQSYVPPKGAV

> SEQUENCE 533 E2H
PHEQVIFAEFSRKCAERWKTMLDKEKQRFHEMAEKDKARYELEMQSYVPPKGAV

> SEQUENCE 534 E2N
PNEQVIFAEFSRKCAERWKTMLDKEKQRFHEMAEKDKARYELEMQSYVPPKGAV

> SEQUENCE 535 E3Q
PEQQVIFAEFSRKCAERWKTMLDKEKQRFHEMAEKDKARYELEMQSYVPPKGAV

> SEQUENCE 536 E3H
PEHQVIFAEFSRKCAERWKTMLDKEKQRFHEMAEKDKARYELEMQSYVPPKGAV

> SEQUENCE 537 E3N
PENQVIFAEFSRKCAERWKTMLDKEKQRFHEMAEKDKARYELEMQSYVPPKGAV

> SEQUENCE 538 F7I
PEEQVIIAEFSRKCAERWKTMLDKEKQRFHEMAEKDKARYELEMQSYVPPKGAV

> SEQUENCE 539 F7V
PEEQVIVAEFSRKCAERWKTMLDKEKQRFHEMAEKDKARYELEMQSYVPPKGAV

> SEQUENCE 540 E9Q
PEEQVIFAQFSRKCAERWKTMLDKEKQRFHEMAEKDKARYELEMQSYVPPKGAV

> SEQUENCE 541 E9H
PEEQVIFAHFSRKCAERWKTMLDKEKQRFHEMAEKDKARYELEMQSYVPPKGAV

> SEQUENCE 542 E9N
PEEQVIFANFSRKCAERWKTMLDKEKQRFHEMAEKDKARYELEMQSYVPPKGAV

> SEQUENCE 543 F10I
PEEQVIFAEISRKCAERWKTMLDKEKQRFHEMAEKDKARYELEMQSYVPPKGAV

> SEQUENCE 544 F10V
PEEQVIFAEVSRKCAERWKTMLDKEKQRFHEMAEKDKARYELEMQSYVPPKGAV

> SEQUENCE 545 R12H
PEEQVIFAEFSHKCAERWKTMLDKEKQRFHEMAEKDKARYELEMQSYVPPKGAV

> SEQUENCE 546 R12Q
PEEQVIFAEFSQKCAERWKTMLDKEKQRFHEMAEKDKARYELEMQSYVPPKGAV

Figure 6b continued

> SEQUENCE 547 K13N
PEEQVIFAEFSRNCAERWKTMLDKEKQRFHEMAEKDKARYELEMQSYVPPKGAV

> SEQUENCE 548 K13Q
PEEQVIFAEFSRQCAERWKTMLDKEKQRFHEMAEKDKARYELEMQSYVPPKGAV

> SEQUENCE 549 E16Q
PEEQVIFAEFSRKCAQRWKTMLDKEKQRFHEMAEKDKARYELEMQSYVPPKGAV

> SEQUENCE 550 E16H
PEEQVIFAEFSRKCAHRWKTMLDKEKQRFHEMAEKDKARYELEMQSYVPPKGAV

> SEQUENCE 551 E16N
PEEQVIFAEFSRKCANRWKTMLDKEKQRFHEMAEKDKARYELEMQSYVPPKGAV

> SEQUENCE 552 R17H
PEEQVIFAEFSRKCAEHWKTMLDKEKQRFHEMAEKDKARYELEMQSYVPPKGAV

> SEQUENCE 553 R17Q
PEEQVIFAEFSRKCAEQWKTMLDKEKQRFHEMAEKDKARYELEMQSYVPPKGAV

> SEQUENCE 554 W18Y
PEEQVIFAEFSRKCAERYKTMLDKEKQRFHEMAEKDKARYELEMQSYVPPKGAV

> SEQUENCE 555 W18S
PEEQVIFAEFSRKCAERSKTMLDKEKQRFHEMAEKDKARYELEMQSYVPPKGAV

> SEQUENCE 556 K19N
PEEQVIFAEFSRKCAERWNTMLDKEKQRFHEMAEKDKARYELEMQSYVPPKGAV

> SEQUENCE 557 K19Q
PEEQVIFAEFSRKCAERWQTMLDKEKQRFHEMAEKDKARYELEMQSYVPPKGAV

> SEQUENCE 558 M21I
PEEQVIFAEFSRKCAERWKTILDKEKQRFHEMAEKDKARYELEMQSYVPPKGAV

> SEQUENCE 559 M21V
PEEQVIFAEFSRKCAERWKTVLDKEKQRFHEMAEKDKARYELEMQSYVPPKGAV

> SEQUENCE 560 L22I
PEEQVIFAEFSRKCAERWKTMIDKEKQRFHEMAEKDKARYELEMQSYVPPKGAV

> SEQUENCE 561 L22V
PEEQVIFAEFSRKCAERWKTMVDKEKQRFHEMAEKDKARYELEMQSYVPPKGAV

> SEQUENCE 562 D23N
PEEQVIFAEFSRKCAERWKTMLNKEKQRFHEMAEKDKARYELEMQSYVPPKGAV

> SEQUENCE 563 D23Q
PEEQVIFAEFSRKCAERWKTMLQKEKQRFHEMAEKDKARYELEMQSYVPPKGAV

> SEQUENCE 564 K24N
PEEQVIFAEFSRKCAERWKTMLDNEKQRFHEMAEKDKARYELEMQSYVPPKGAV

> SEQUENCE 565 K24Q
PEEQVIFAEFSRKCAERWKTMLDQEKQRFHEMAEKDKARYELEMQSYVPPKGAV

> SEQUENCE 566 E25Q

Figure 6b continued

PEEQVIFAEFSRKCAERWKTMLDKQKQRFHEMAEKDKARYELEMQSYVPPKGAV

>SEQUENCE 567 E25H
PEEQVIFAEFSRKCAERWKTMLDKHKQRFHEMAEKDKARYELEMQSYVPPKGAV

>SEQUENCE 568 E25N
PEEQVIFAEFSRKCAERWKTMLDKNKQRFHEMAEKDKARYELEMQSYVPPKGAV

>SEQUENCE 569 K26N
PEEQVIFAEFSRKCAERWKTMLDKENQRFHEMAEKDKARYELEMQSYVPPKGAV

>SEQUENCE 570 K26Q
PEEQVIFAEFSRKCAERWKTMLDKEQQRFHEMAEKDKARYELEMQSYVPPKGAV

>SEQUENCE 571 R28H
PEEQVIFAEFSRKCAERWKTMLDKEKQHFHEMAEKDKARYELEMQSYVPPKGAV

>SEQUENCE 572 R28Q
PEEQVIFAEFSRKCAERWKTMLDKEKQQFHEMAEKDKARYELEMQSYVPPKGAV

>SEQUENCE 573 F29I
PEEQVIFAEFSRKCAERWKTMLDKEKQRIHEMAEKDKARYELEMQSYVPPKGAV

>SEQUENCE 574 F29V
PEEQVIFAEFSRKCAERWKTMLDKEKQRVHEMAEKDKARYELEMQSYVPPKGAV

>SEQUENCE 575 E31Q
PEEQVIFAEFSRKCAERWKTMLDKEKQRFHQMAEKDKARYELEMQSYVPPKGAV

>SEQUENCE 576 E31H
PEEQVIFAEFSRKCAERWKTMLDKEKQRFHHMAEKDKARYELEMQSYVPPKGAV

>SEQUENCE 577 E31N
PEEQVIFAEFSRKCAERWKTMLDKEKQRFHNMAEKDKARYELEMQSYVPPKGAV

>SEQUENCE 578 M32I
PEEQVIFAEFSRKCAERWKTMLDKEKQRFHEIAEKDKARYELEMQSYVPPKGAV

>SEQUENCE 579 M32V
PEEQVIFAEFSRKCAERWKTMLDKEKQRFHEVAEKDKARYELEMQSYVPPKGAV

>SEQUENCE 580 E34Q
PEEQVIFAEFSRKCAERWKTMLDKEKQRFHEMAQKDKARYELEMQSYVPPKGAV

>SEQUENCE 581 E34H
PEEQVIFAEFSRKCAERWKTMLDKEKQRFHEMAHKDKARYELEMQSYVPPKGAV

>SEQUENCE 582 E34N
PEEQVIFAEFSRKCAERWKTMLDKEKQRFHEMANKDKARYELEMQSYVPPKGAV

>SEQUENCE 583 K35N
PEEQVIFAEFSRKCAERWKTMLDKEKQRFHEMAENDKARYELEMQSYVPPKGAV

>SEQUENCE 584 K35Q
PEEQVIFAEFSRKCAERWKTMLDKEKQRFHEMAEQDKARYELEMQSYVPPKGAV

>SEQUENCE 585 D36N

Figure 6b continued

PEEQVIFAEFSRKCAERWKTMLDKEKQRFHEMAEKNKARYELEMQSYVPPKGAV

> SEQUENCE 586 D36Q
PEEQVIFAEFSRKCAERWKTMLDKEKQRFHEMAEKQKARYELEMQSYVPPKGAV

> SEQUENCE 587 K37N
PEEQVIFAEFSRKCAERWKTMLDKEKQRFHEMAEKDNARYELEMQSYVPPKGAV

> SEQUENCE 588 K37Q
PEEQVIFAEFSRKCAERWKTMLDKEKQRFHEMAEKDQARYELEMQSYVPPKGAV

> SEQUENCE 589 R39H
PEEQVIFAEFSRKCAERWKTMLDKEKQRFHEMAEKDKAHYELEMQSYVPPKGAV

> SEQUENCE 590 R39Q
PEEQVIFAEFSRKCAERWKTMLDKEKQRFHEMAEKDKAQYELEMQSYVPPKGAV

> SEQUENCE 591 Y40H
PEEQVIFAEFSRKCAERWKTMLDKEKQRFHEMAEKDKARHELEMQSYVPPKGAV

> SEQUENCE 592 Y40I
PEEQVIFAEFSRKCAERWKTMLDKEKQRFHEMAEKDKARIELEMQSYVPPKGAV

> SEQUENCE 593 E41Q
PEEQVIFAEFSRKCAERWKTMLDKEKQRFHEMAEKDKARYQLEMQSYVPPKGAV

> SEQUENCE 594 E41H
PEEQVIFAEFSRKCAERWKTMLDKEKQRFHEMAEKDKARYHLEMQSYVPPKGAV

> SEQUENCE 595 E41N
PEEQVIFAEFSRKCAERWKTMLDKEKQRFHEMAEKDKARYNLEMQSYVPPKGAV

> SEQUENCE 596 L42I
PEEQVIFAEFSRKCAERWKTMLDKEKQRFHEMAEKDKARYEIEMQSYVPPKGAV

> SEQUENCE 597 L42V
PEEQVIFAEFSRKCAERWKTMLDKEKQRFHEMAEKDKARYEVEMQSYVPPKGAV

> SEQUENCE 598 E43Q
PEEQVIFAEFSRKCAERWKTMLDKEKQRFHEMAEKDKARYELQMQSYVPPKGAV

> SEQUENCE 599 E43H
PEEQVIFAEFSRKCAERWKTMLDKEKQRFHEMAEKDKARYELHMQSYVPPKGAV

> SEQUENCE 600 E43N
PEEQVIFAEFSRKCAERWKTMLDKEKQRFHEMAEKDKARYELNMQSYVPPKGAV

> SEQUENCE 601 M44I
PEEQVIFAEFSRKCAERWKTMLDKEKQRFHEMAEKDKARYELEIQSYVPPKGAV

> SEQUENCE 602 M44V
PEEQVIFAEFSRKCAERWKTMLDKEKQRFHEMAEKDKARYELEVQSYVPPKGAV

> SEQUENCE 603 Y47H
PEEQVIFAEFSRKCAERWKTMLDKEKQRFHEMAEKDKARYELEMQSHVPPKGAV

> SEQUENCE 604 Y47I
PEEQVIFAEFSRKCAERWKTMLDKEKQRFHEMAEKDKARYELEMQSIVPPKGAV

Figure 6b continued

> SEQUENCE 605 P49A
PEEQVIFAEFSRKCAERWKTMLDKEKQRFHEMAEKDKARYELEMQSYVAPKGAV

> SEQUENCE 606 P49S
PEEQVIFAEFSRKCAERWKTMLDKEKQRFHEMAEKDKARYELEMQSYVSPKGAV

> SEQUENCE 607 P50A
PEEQVIFAEFSRKCAERWKTMLDKEKQRFHEMAEKDKARYELEMQSYVPAKGAV

> SEQUENCE 608 P50S
PEEQVIFAEFSRKCAERWKTMLDKEKQRFHEMAEKDKARYELEMQSYVPSKGAV

> SEQUENCE 609 K51N
PEEQVIFAEFSRKCAERWKTMLDKEKQRFHEMAEKDKARYELEMQSYVPPNGAV

> SEQUENCE 610 K51Q
PEEQVIFAEFSRKCAERWKTMLDKEKQRFHEMAEKDKARYELEMQSYVPPQGAV

Table 7.1

|  | MEAN (cells/filter) | Std deviation | SEM |
|---|---|---|---|
| w/o FBS | 22,04 | 1,119 | 0,3956 |
| HMGB1 1 nM | 51,13 | 2,702 | 0,9552 |
| HMGB1 1 nM + CT500 1nM | 21,71 | 1,803 | 0,6376 |
| HMGB1 1 nM + CT501 1nM | 19,94 | 1,400 | 0,4950 |
| HMGB1 1 nM + CT568 1 nM | 29,19 | 2,506 | 0,8861 |
| HMGB1 1 nM + CT5691 nM | 28,06 | 3,812 | 1,348 |
| HMGB1 1 nM + CT570 1 nM | 30,00 | 4,559 | 1,612 |
| HMGB1 1 nM + CT571 1 nM | 35,94 | 2,528 | 0,8936 |
| HMGB1 1 nM + CT502 1 nM | 25,31 | 3,218 | 1,138 |
| HMGB1 1 nM + CT572 1 nM | 26,63 | 2,489 | 0,8801 |
| HMGB1 1 nM + CT503 1 nM | 18,75 | 3,012 | 1,065 |
| HMGB1 1 nM + CT573 1 nM | 26,31 | 4,383 | 1,550 |
| HMGB1 1 nM + CT504 1 nM | 26,00 | 4,149 | 1,467 |
| HMGB1 1 nM + CT574 1 nM | 31,19 | 2,789 | 0,9862 |
| HMGB1 1 nM + CT575 1 nM | 29,13 | 3,824 | 1,352 |
| HMGB1 1 nM + CT576 1 nM | 30,19 | 2,404 | 0,8501 |
| HMGB1 1 nM + CT505 1 nM | 18,13 | 2,900 | 1,025 |

Figure 7.1

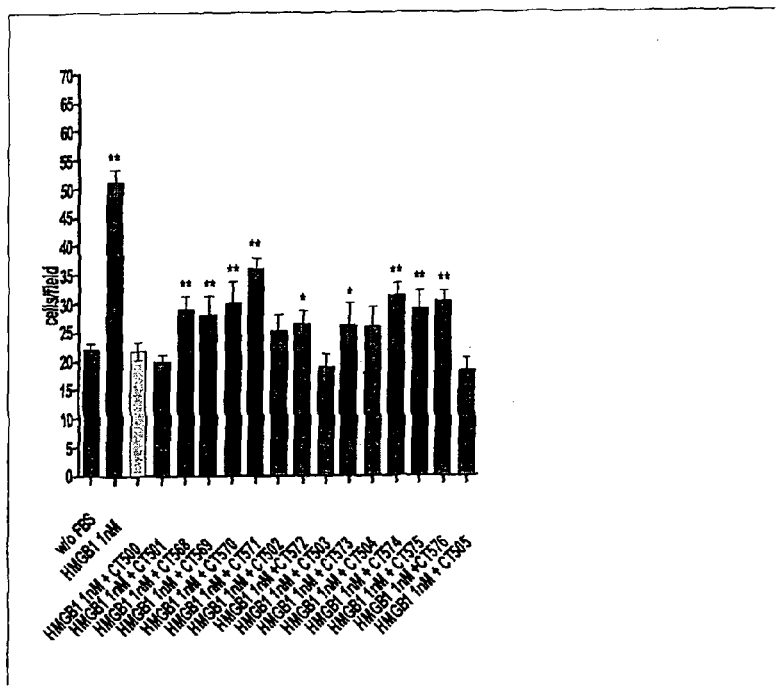

LEGEND:
- higher activity compared to CT500
- similar activity compared to CT500
- lower activity compared to CT500
- * $p < 0.05$
- ** $p < 0.01$ Table 7.2

|  | MEAN (cells/filter) | Std deviation | SEM |
|---|---|---|---|
| w/o FBS | 20,25 | 1,035 | 0,3660 |
| HMGB1 1 nM | 64,42 | 8,556 | 3,025 |
| HMGB1 1 nM + CT500 1nM | 23,33 | 3,505 | 1,239 |
| HMGB1 1 nM + CT577 1 nM | 34,75 | 2,171 | 0,7676 |
| HMGB1 1 nM + CT578 1 nM | 29,56 | 3,396 | 1,201 |
| HMGB1 1 nM + CT506 1 nM | 25,31 | 3,936 | 1,392 |
| HMGB1 1 nM + CT579 1 nM | 51,31 | 4,140 | 1,464 |
| HMGB1 1 nM + CT580 1 nM | 30,44 | 3,469 | 1,226 |
| HMGB1 1 nM + CT581 1 nM | 30,44 | 3,469 | 1,226 |
| HMGB1 1 nM + CT507 1 nM | 24,81 | 4,183 | 1,479 |
| HMGB1 1 nM + CT582 1 nM | 38,22 | 5,205 | 1,840 |
| HMGB1 1 nM + CT584 1 nM | 30,56 | 2,796 | 0,9885 |
| HMGB1 1 nM + CT508 1 nM | 25,63 | 2,838 | 1,003 |
| HMGB1 1 nM + CT509 1 nM | 28,88 | 1,827 | 0,6461 |
| HMGB1 1 nM + CT510 1 nM | 25,50 | 5,285 | 1,868 |
| HMGB1 1 nM + CT585 1 nM | 40,63 | 4,719 | 1,668 |

Figure 7.2

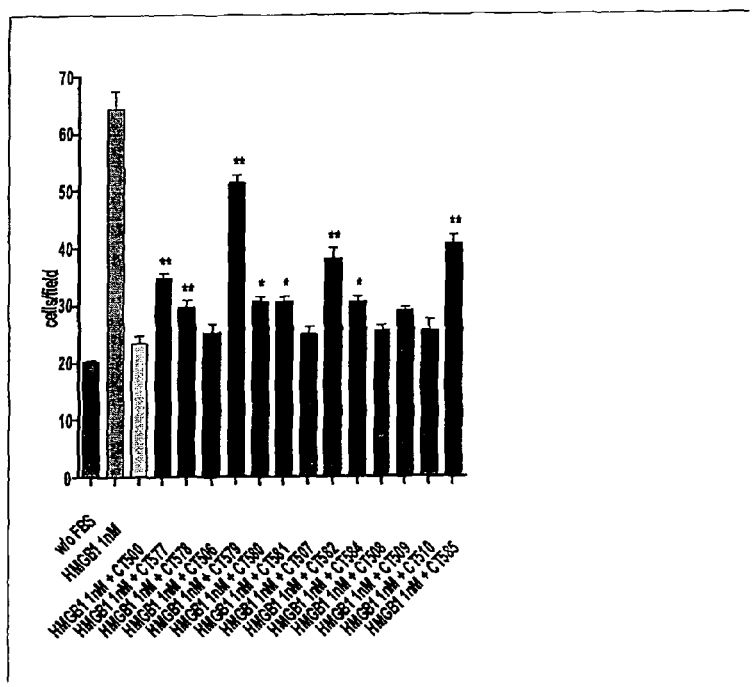

LEGEND:
- higher activity compared to CT500
- similar activity compared to CT500
- lower activity compared to CT500
- \* $p < 0.05$
- \*\* $p < 0.01$ Table 7.3

| | MEAN (cells/filter) | Std deviation | SEM |
|---|---|---|---|
| w/o FBS | 20,38 | 2,285 | 0,8078 |
| HMGB1 1 nM | 72,54 | 5,188 | 1,834 |
| HMGB1 1 nM + CT500 0.5 nM | 33,31 | 2,375 | 0,8395 |
| HMGB1 1 nM + CT511 0.5 nM | 26,31 | 5,669 | 2,004 |
| HMGB1 1 nM + CT512 0.5 nM | 26,56 | 2,872 | 1,015 |
| HMGB1 1 nM + CT513 0.5 nM | 25,93 | 1,512 | 0,5714 |
| HMGB1 1 nM + CT514 0.5 nM | 35,29 | 2,233 | 0,8441 |
| HMGB1 1 nM + CT586 0.5 nM | 60,06 | 5,179 | 1,831 |
| HMGB1 1 nM + CT515 0.5 nM | 24,56 | 3,959 | 1,400 |
| HMGB1 1 nM + CT516 0.5 nM | 29,09 | 2,949 | 1,043 |
| HMGB1 1 nM + CT517 0.5 nM | 27,25 | 3,229 | 1,142 |
| HMGB1 1 nM + CT518 0.5 nM | 29,25 | 2,632 | 0,9306 |
| HMGB1 1 nM + CT519 0.5 nM | 26,81 | 3,712 | 1,313 |
| HMGB1 1 nM + CT520 0.5 nM | 27,31 | 3,047 | 1,077 |
| HMGB1 1 nM + CT521 0.5 nM | 29,13 | 2,888 | 1,021 |
| HMGB1 1 nM + CT522 0.5 nM | 25,69 | 3,391 | 1,199 |

Figure 7.3

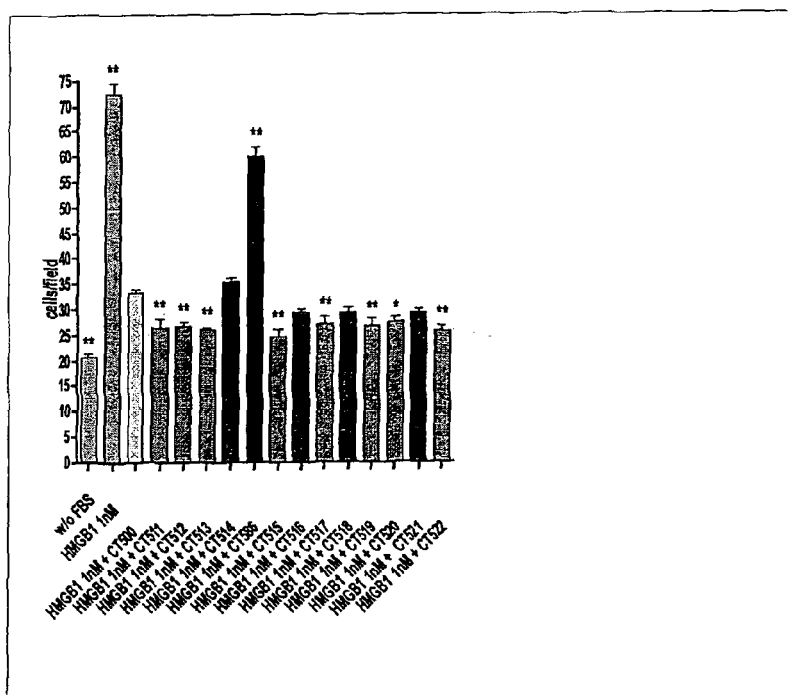

LEGEND:
- higher activity compared to CT500
- similar activity compared to CT500
- lower activity compared to CT500
- \* $p < 0.05$
- \*\* $p < 0.01$ Table 7.4

|  | MEAN (cells/filter) | Std deviation | SEM |
|---|---|---|---|
| w/o FBS | 20,27 | 2,250 | 0,7955 |
| HMGB1 1 nM | 66,58 | 6,732 | 2,380 |
| HMGB1 1 nM + CT500 0.5 nM | 36,50 | 3,045 | 1,076 |
| HMGB1 1 nM + CT523 0.5 nM | 34,06 | 3,849 | 1,361 |
| HMGB1 1 nM + CT524 0.5 nM | 39,57 | 6,380 | 2,411 |
| HMGB1 1 nM + CT525 0.5 nM | 41,06 | 4,229 | 1,495 |
| HMGB1 1 nM + CT526 0.5 nM | 34,13 | 4,764 | 1,684 |
| HMGB1 1 nM + CT527 0.5 nM | 29,88 | 3,182 | 1,125 |
| HMGB1 1 nM + CT528 0.5 nM | 41,50 | 2,878 | 1,018 |
| HMGB1 1 nM + CT588 0.5 nM | 60,13 | 5,848 | 2,067 |
| HMGB1 1 nM + CT529 0.5 nM | 30,13 | 3,357 | 1,187 |
| HMGB1 1 nM + CT530 0.5 nM | 35,63 | 2,504 | 0,8851 |
| HMGB1 1 nM + CT589 0.5 nM | 43,88 | 3,227 | 1,141 |
| HMGB1 1 nM + CT590 0.5 nM | 47,00 | 2,535 | 0,8964 |
| HMGB1 1 nM + CT531 0.5 nM | 35,25 | 8,045 | 2,844 |
| HMGB1 1 nM + CT591 0.5 nM | 43,56 | 3,267 | 1,155 |
| HMGB1 1 nM + CT532 0.5 nM | 26,50 | 3,094 | 1,094 |

Figure 7.4

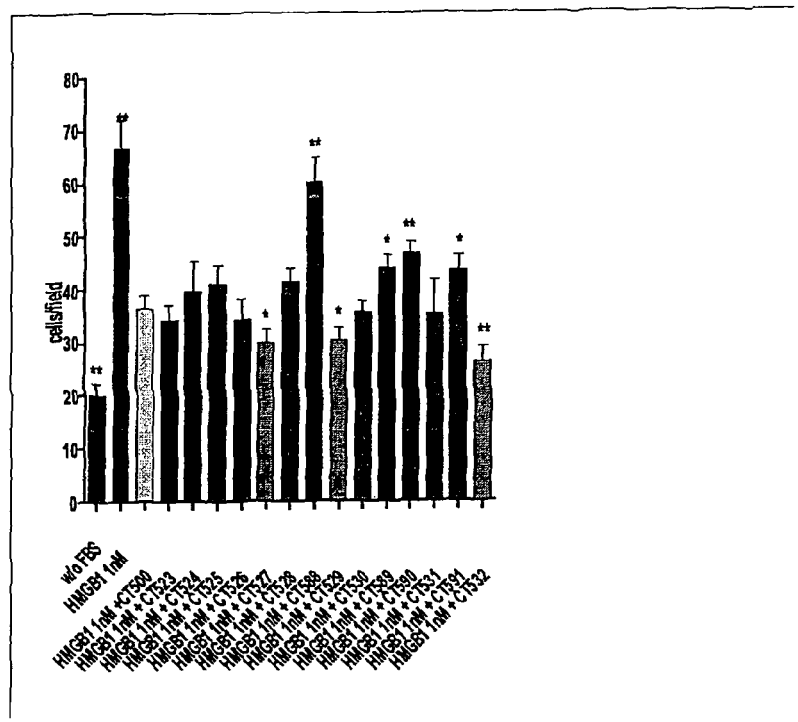

LEGEND:
- higher activity compared to CT500
- similar activity compared to CT500
- lower activity compared to CT500
- * $p < 0.05$
- ** $p < 0.01$ Table 7.5

|  | MEAN (cells/filter) | Std deviation | SEM |
|---|---|---|---|
| w/o FBS | 18,48 | 1,694 | 0,5988 |
| HMGB1 1 nM | 76,81 | 5,000 | 1,768 |
| HMGB1 1 nM + CT500 0.5 nM | 35,90 | 0,738 | 0,2790 |
| HMGB1 1 nM + CT592 0.5 nM | 43,00 | 4,041 | 1,528 |
| HMGB1 1 nM + CT533 0.5 nM | 35,88 | 4,883 | 1,726 |
| HMGB1 1 nM + CT593 0.5 nM | 47,14 | 1,574 | 0,5948 |
| HMGB1 1 nM + CT534 0.5 nM | 34,00 | 3,742 | 1,323 |
| HMGB1 1 nM + CT535 0.5 nM | 33,21 | 3,534 | 1,336 |
| HMGB1 1 nM + CT536 0.5 nM | 28,00 | 1,558 | 0,5510 |
| HMGB1 1 nM + CT537 0.5 nM | 28,88 | 2,925 | 1,034 |
| HMGB1 1 nM + CT594 0.5 nM | 45,31 | 3,391 | 1,199 |
| HMGB1 1 nM + CT538 0.5 nM | 31,93 | 3,421 | 1,293 |
| HMGB1 1 nM + CT539 0.5 nM | 34,41 | 3,265 | 1,154 |
| HMGB1 1 nM + CT540 0.5 nM | 29,81 | 1,850 | 0,6542 |
| HMGB1 1 nM + CT541 0.5 nM | 27,44 | 2,195 | 0,7760 |
| HMGB1 1 nM + CT542 0.5 nM | 32,19 | 5,411 | 1,913 |

Figure 7.5

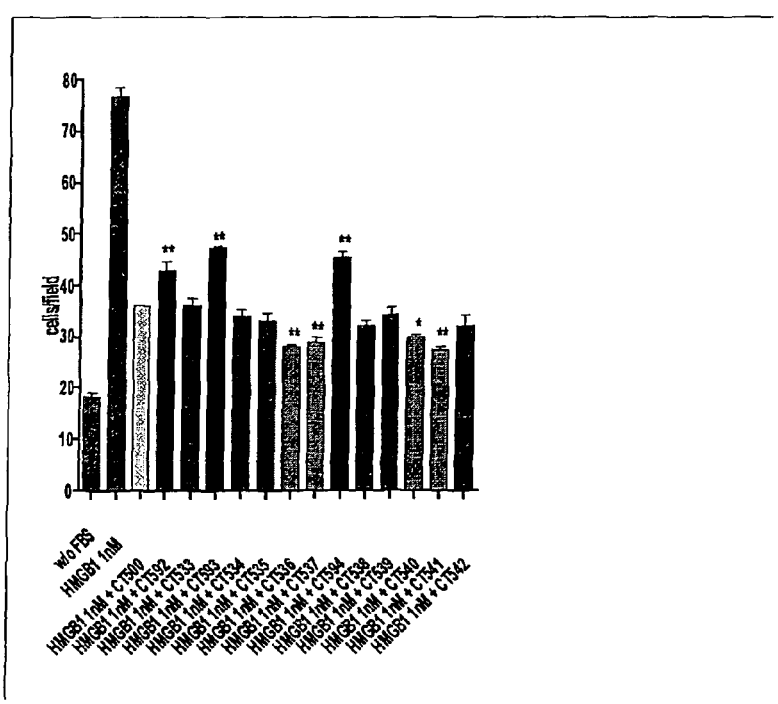

LEGEND:
- higher activity compared to CT500
- similar activity compared to CT500
- lower activity compared to CT500
- \* $p < 0.05$
- \*\* $p < 0.01$ Table 7.6

|  | MEAN (cells/filter) | Std deviation | SEM |
|---|---|---|---|
| w/o FBS | 15,25 | 2,231 | 0,7887 |
| HMGB1 1 nM | 90,04 | 5,400 | 1,909 |
| HMGB1 1 nM + CT500 0.5 nM | 34,04 | 1,713 | 0,6057 |
| HMGB1 1 nM + CT596 0.5 nM | 55,56 | 3,479 | 1,230 |
| HMGB1 1 nM + CT597 0.5 nM | 92,79 | 11,77 | 4,449 |
| HMGB1 1 nM + CT598 0.5 nM | 64,38 | 4,446 | 1,572 |
| HMGB1 1 nM + CT599 0.5 nM | 58,81 | 6,681 | 2,362 |
| HMGB1 1 nM + CT600 0.5 nM | 95,86 | 7,063 | 2,670 |
| HMGB1 1 nM + CT601 0.5 nM | 67,44 | 7,302 | 2,582 |
| HMGB1 1 nM + CT602 0.5 nM | 49,63 | 2,532 | 0,8952 |
| HMGB1 1 nM + CT603 0.5 nM | 41,56 | 3,923 | 1,387 |
| HMGB1 1 nM + CT543 0.5 nM | 41,44 | 2,884 | 1,020 |
| HMGB1 1 nM + CT544 0.5 nM | 30,63 | 1,620 | 0,5728 |
| HMGB1 1 nM + CT545 0.5 nM | 40,13 | 3,583 | 1,267 |
| HMGB1 1 nM + CT546 0.5 nM | 34,88 | 4,051 | 1,432 |
| HMGB1 1 nM + CT547 0.5 nM | 41,64 | 4,661 | 1,762 |
| HMGB1 1 nM + CT604 0.5 nM | 61,88 | 5,330 | 1,885 |

Figure 7.6

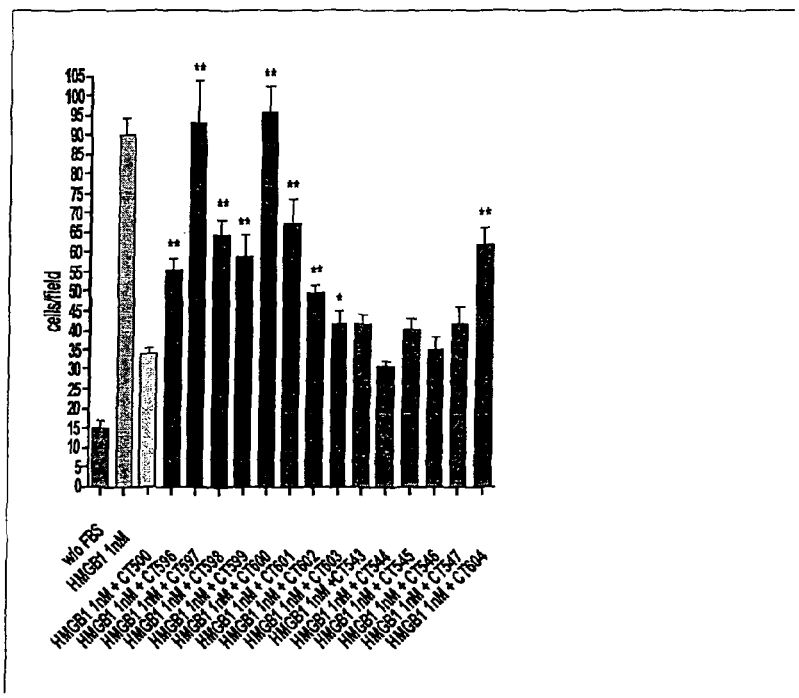

LEGEND:
- higher activity compared to CT500
- similar activity compared to CT500
- lower activity compared to CT500
- *  $p < 0.05$
- ** $p < 0.01$ Table 7.7

|  | MEAN (cells/filter) | Std deviation | SEM |
|---|---|---|---|
| w/o FBS | 24,33 | 1,869 | 0,6607 |
| HMGB1 1 nM | 90,58 | 2,888 | 1,021 |
| HMGB1 1 nM + CT500 0.5 nM | 44,33 | 4,673 | 1,652 |
| HMGB1 1 nM + CT548 0.5 nM | 45,38 | 3,068 | 1,085 |
| HMGB1 1 nM + CT549 0.5 nM | 44,56 | 4,362 | 1,542 |
| HMGB1 1 nM + CT605 0.5 nM | 84,63 | 5,643 | 1,995 |
| HMGB1 1 nM + CT606 0.5 nM | 83,19 | 5,182 | 1,832 |
| HMGB1 1 nM + CT607 0.5 nM | 68,00 | 4,132 | 1,461 |
| HMGB1 1 nM + CT608 0.5 nM | 89,50 | 6,503 | 2,299 |
| HMGB1 1 nM + CT609 0.5 nM | 89,56 | 3,110 | 1,100 |
| HMGB1 1 nM + CT610 0.5 nM | 82,19 | 5,398 | 1,908 |
| HMGB1 1 nM + CT550 0.5 nM | 28,06 | 3,479 | 1,230 |
| HMGB1 1 nM + CT551 0.5 nM | 37,50 | 4,862 | 1,719 |
| HMGB1 1 nM + CT611 0.5 nM | 55,88 | 4,060 | 1,435 |
| HMGB1 1 nM + CT552 0.5 nM | 42,94 | 3,510 | 1,241 |
| HMGB1 1 nM + CT553 0.5 nM | 40,25 | 4,097 | 1,449 |
| HMGB1 1 nM + CT554 0.5 nM | 43,69 | 2,235 | 0,7902 |

Figure 7.7

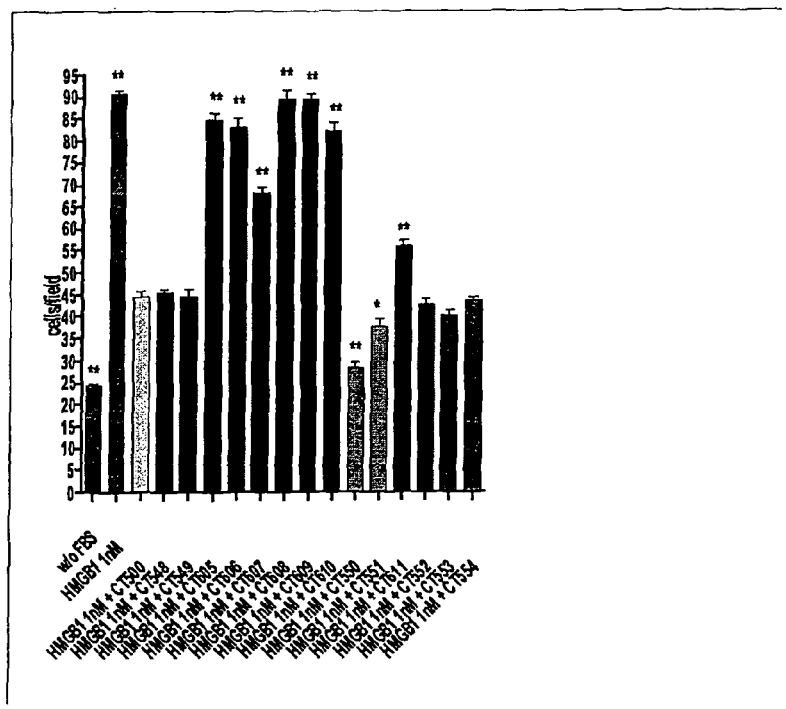

LEGEND:
- higher activity compared to CT500
- similar activity compared to CT500
- lower activity compared to CT500
- \* $p < 0.05$
- \*\* $p < 0.01$ Table 7.8

|  | MEAN (cells/filter) | Std deviation | SEM |
|---|---|---|---|
| w/o FBS | 17,10 | 2,428 | 0,859 |
| HMGB1 1 nM | 75,90 | 3,613 | 1,277 |
| HMGB1 1 nM + CT500 0.5 nM | 33,33 | 2,643 | 0,934 |
| HMGB1 1 nM + CT555 0.5 nM | 26,13 | 2,151 | 0,760 |
| HMGB1 1 nM + CT556 0.5 nM | 30,13 | 2,774 | 0,981 |
| HMGB1 1 nM + CT557 0.5 nM | 33,63 | 5,397 | 1,908 |
| HMGB1 1 nM + CT558 0.5 nM | 25,00 | 3,064 | 1,573 |
| HMGB1 1 nM + CT559 0.5 nM | 26,94 | 4,448 | 1,083 |
| HMGB1 1 nM + CT612 0.5 nM | 65,13 | 4,948 | 1,749 |
| HMGB1 1 nM + CT560 0.5 nM | 27,50 | 2,891 | 1,022 |
| HMGB1 1 nM + CT561 0.5 nM | 27,13 | 2,973 | 1,051 |
| HMGB1 1 nM + CT613 0.5 nM | 43,06 | 2,337 | 0,826 |
| HMGB1 1 nM + CT562 0.5 nM | 28,19 | 1,602 | 0,567 |
| HMGB1 1 nM + CT563 0.5 nM | 27,75 | 3,381 | 1,195 |
| HMGB1 1 nM + CT564 0.5 nM | 23,38 | 1,747 | 0,618 |
| HMGB1 1 nM + CT565 0.5 nM | 29,00 | 2,121 | 0,750 |
| HMGB1 1 nM + CT566 0.5 nM | 27,75 | 2,220 | 0,785 |

Figure 7.8

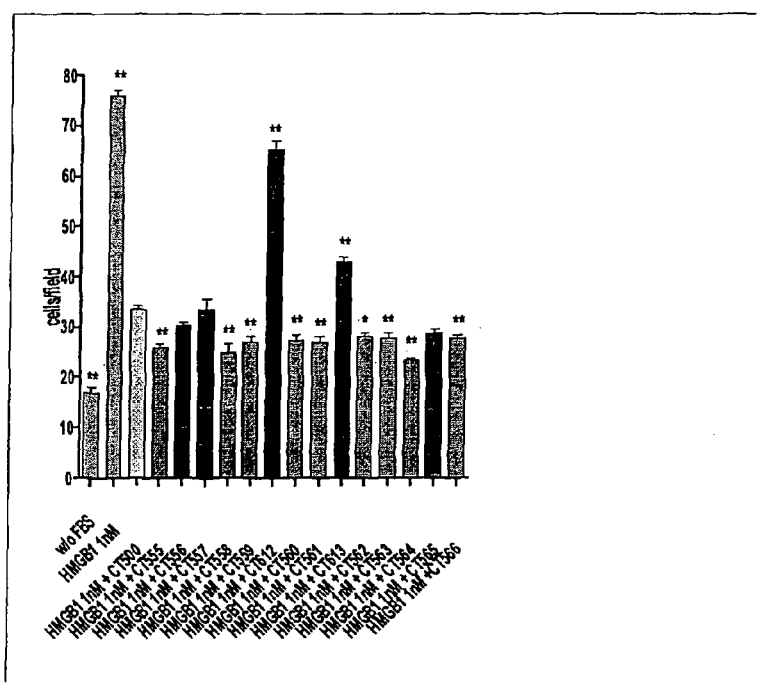

LEGEND:
- higher activity compared to CT500
- similar activity compared to CT500
- lower activity compared to CT500
- \* $p < 0.05$
- \*\* $p < 0.01$ Table 7.9
|  | MEAN (cells/filter) | Std deviation | SEM |
|---|---|---|---|
| w/o FBS | 14,04 | 1,315 | 0,4648 |
| HMGB1 1 nM | 62,96 | 1,864 | 0,659 |
| HMGB1 1 nM + CT500 0.5 nM | 21,71 | 2,155 | 0,815 |
| HMGB1 1 nM + CT567 0.5 nM | 19,31 | 2,052 | 0,725 |
| HMGB1 1 nM + CT614 0.5 nM | 28,71 | 2,119 | 0,801 |
| HMGB1 1 nM + CT615 0.5 nM | 39,81 | 2,154 | 0,761 |
Figure 7.9
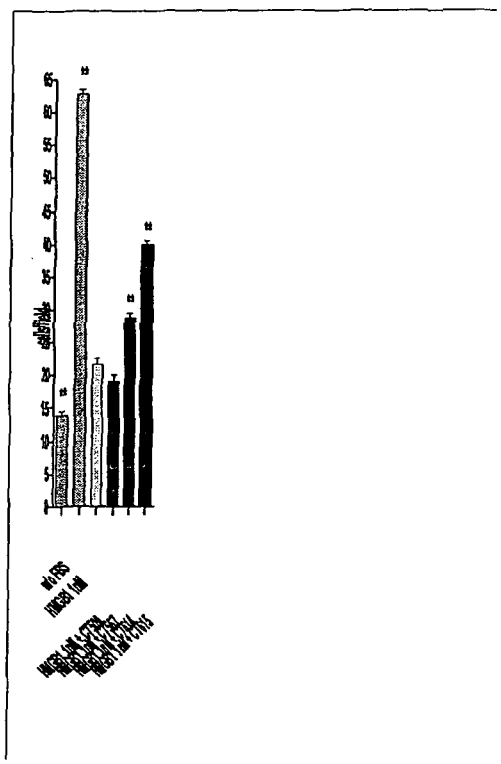
LEGEND:
- higher activity compared to CT500
- similar activity compared to CT500
- lower activity compared to CT500
- \* $p < 0.05$
- \*\* $p < 0.01$ Figure 8
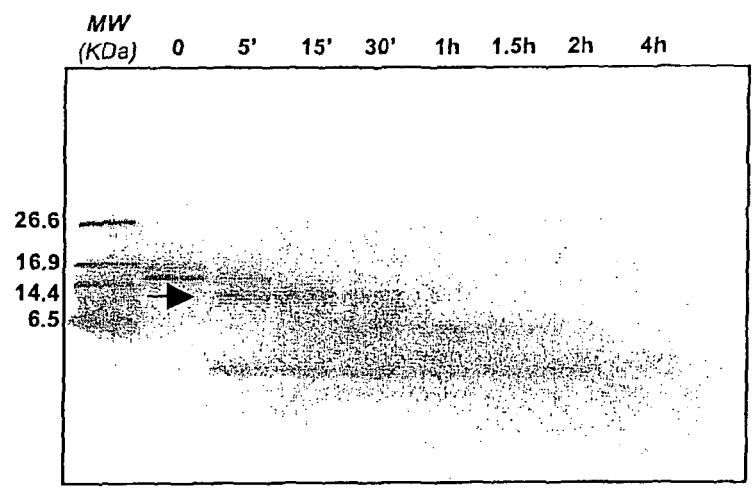
Figure 9.1
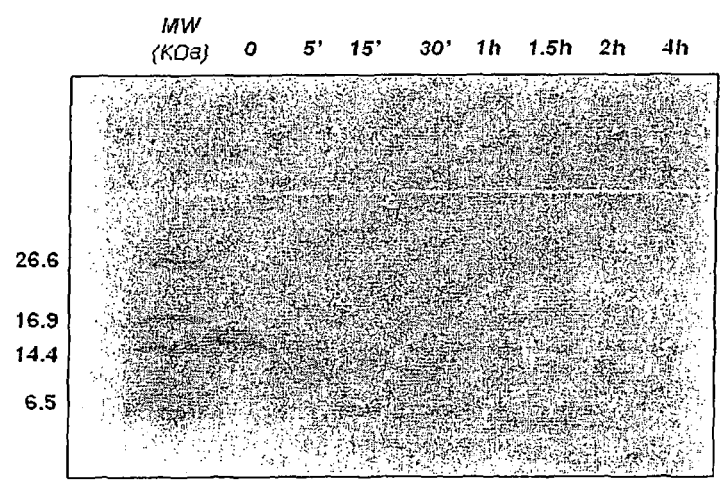

Figure 9.2
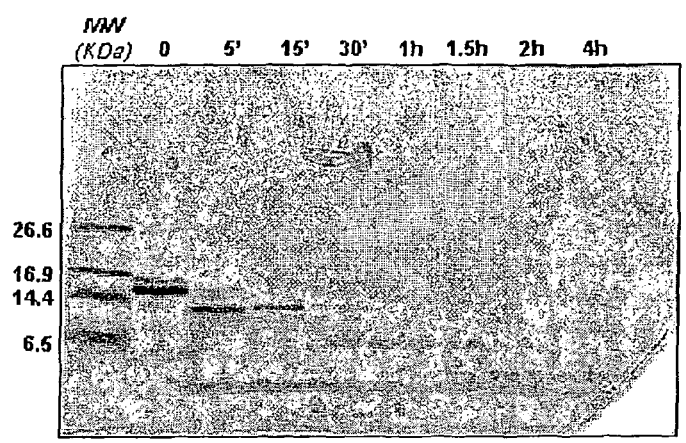
Figure 9.3
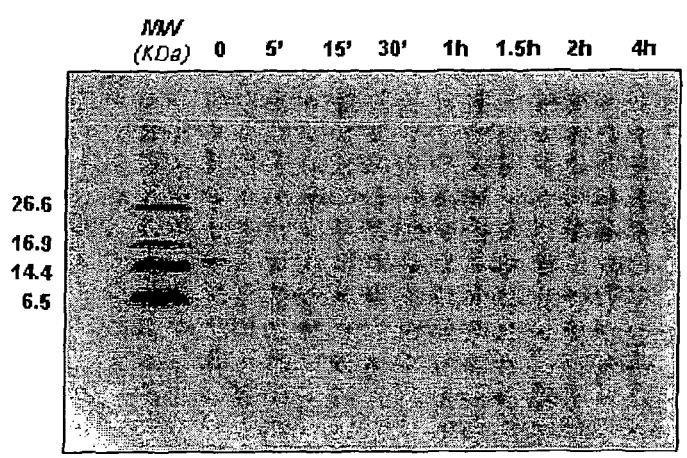

Figure 9.4
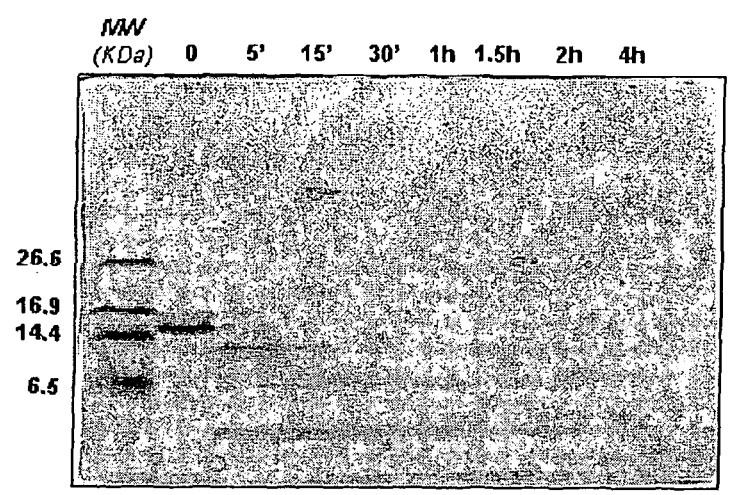
Figure 9.5
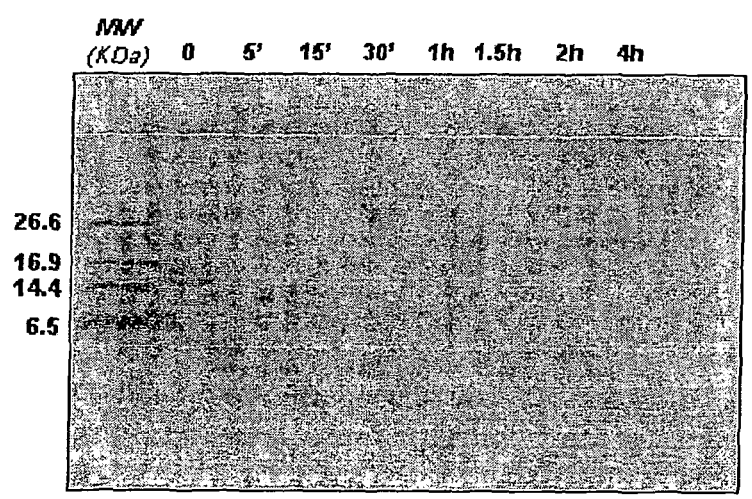

Figure 9.6
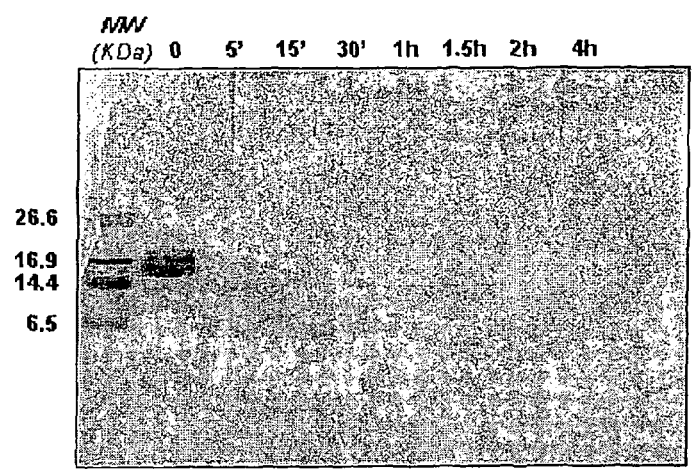
Figure 9.7
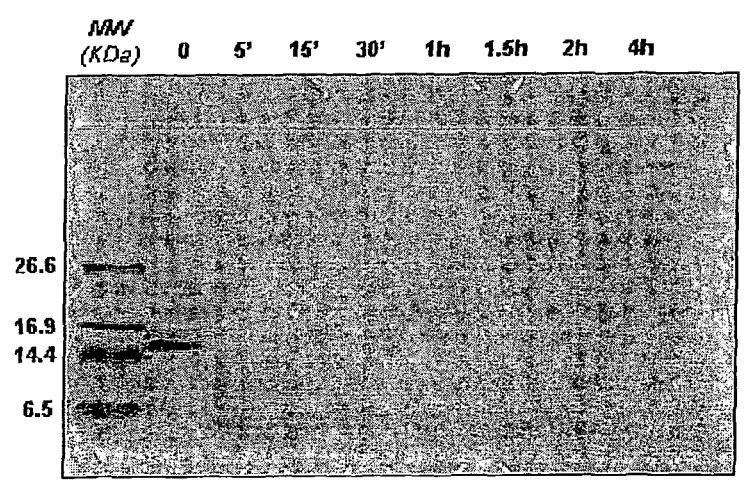

Figure 9.8
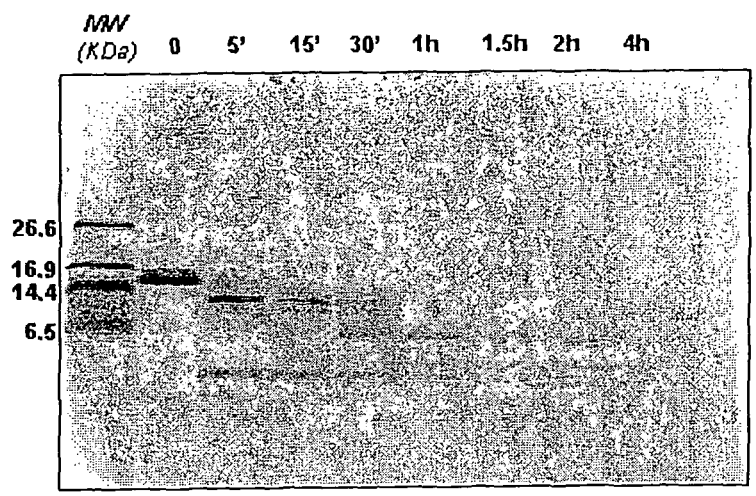
Figure 9.9
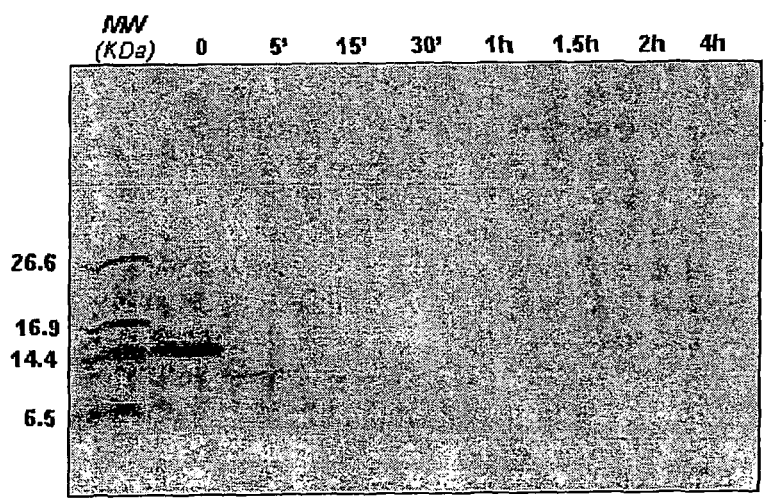

Figure 9.10
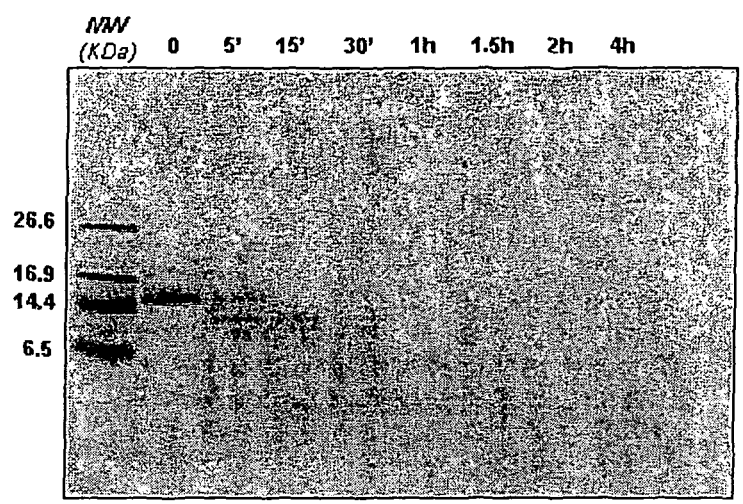
Figure 9.11
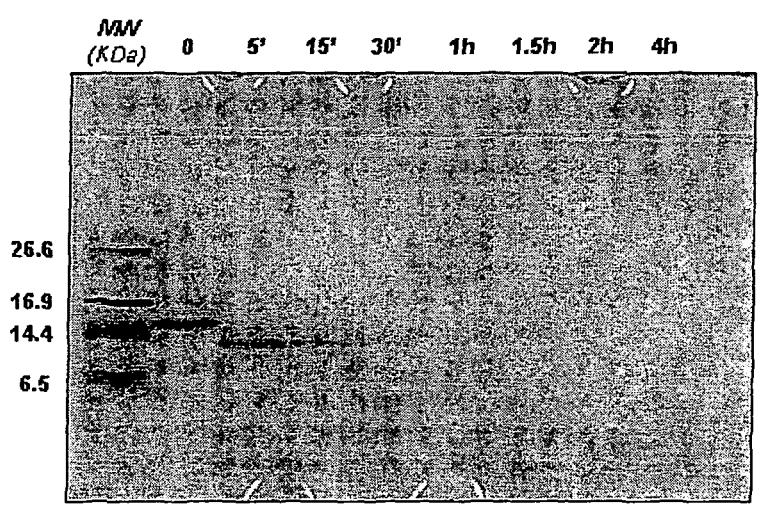

Figure 9.12
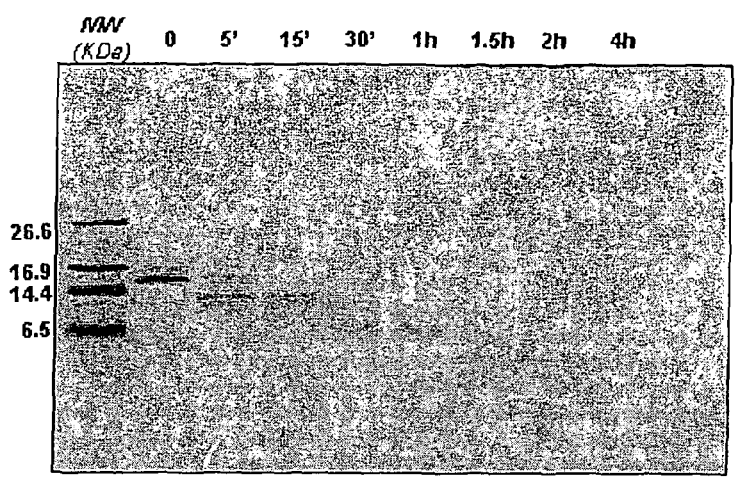
Figure 9.13
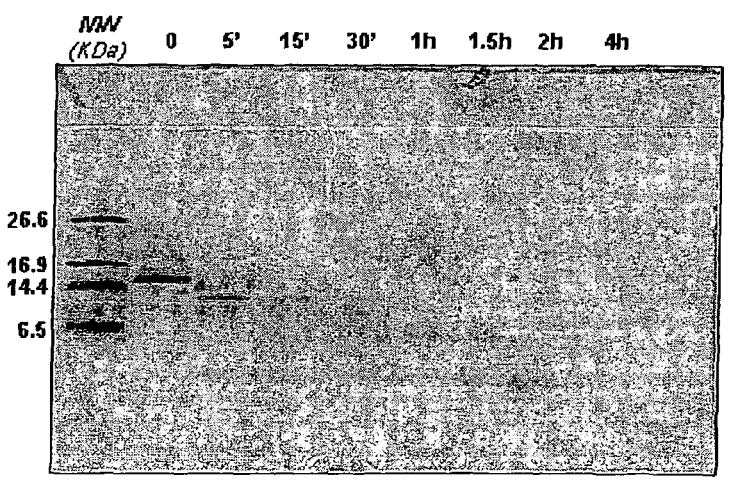

Figure 9.14
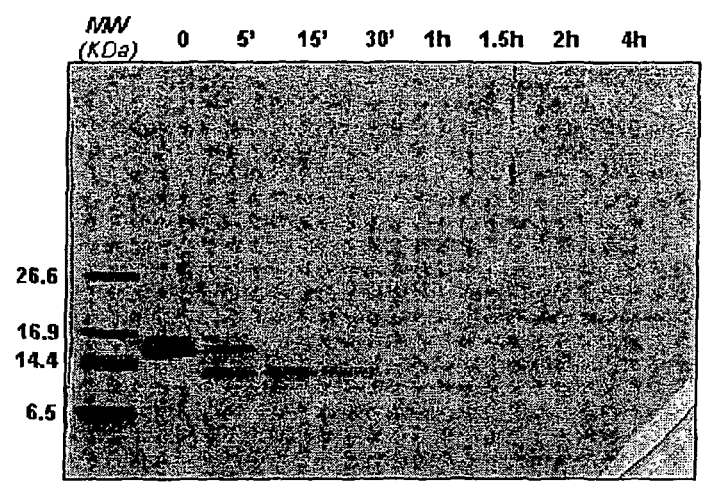
Figure 9.15
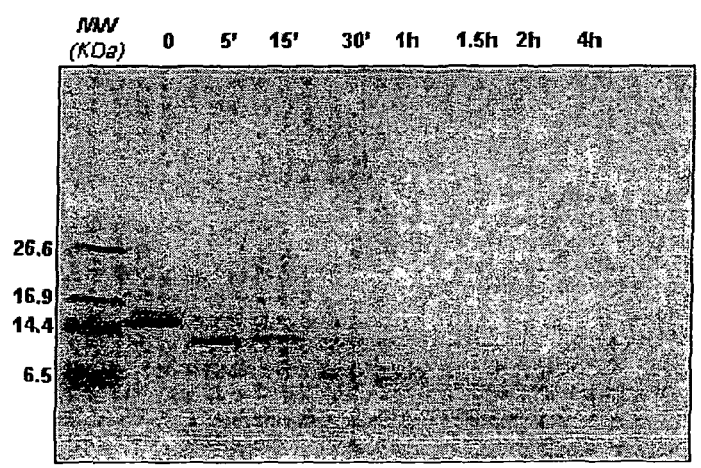

Figure 9.16
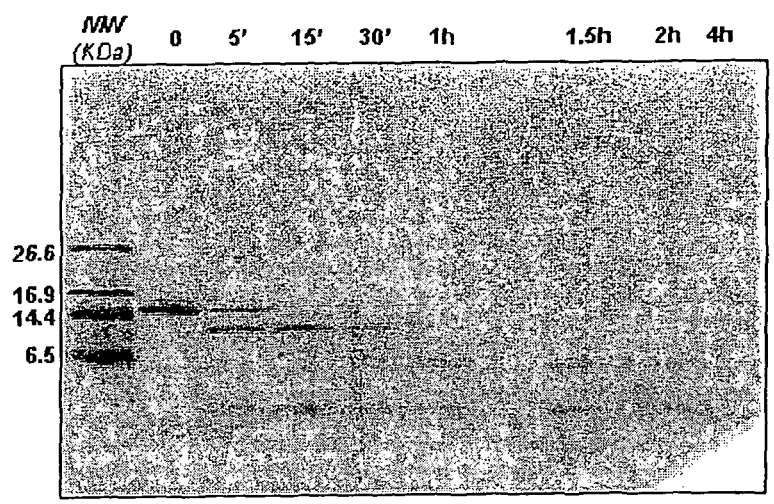
Figure 9.17
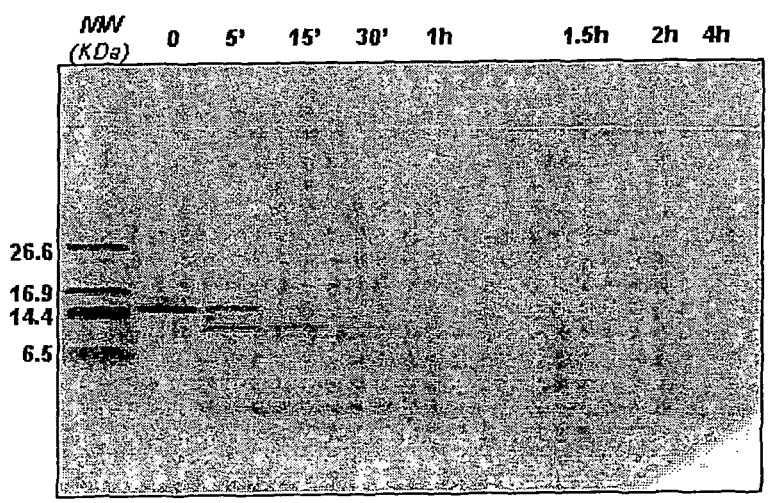

Figure 9.18
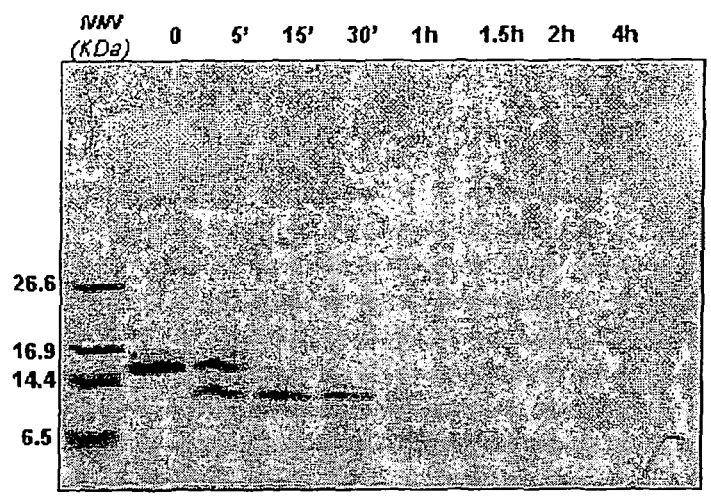
Figure 9.19
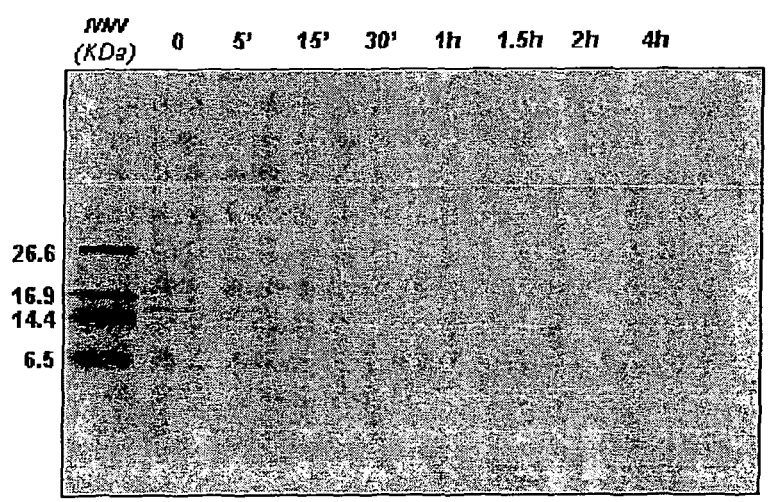

Figure 9.20
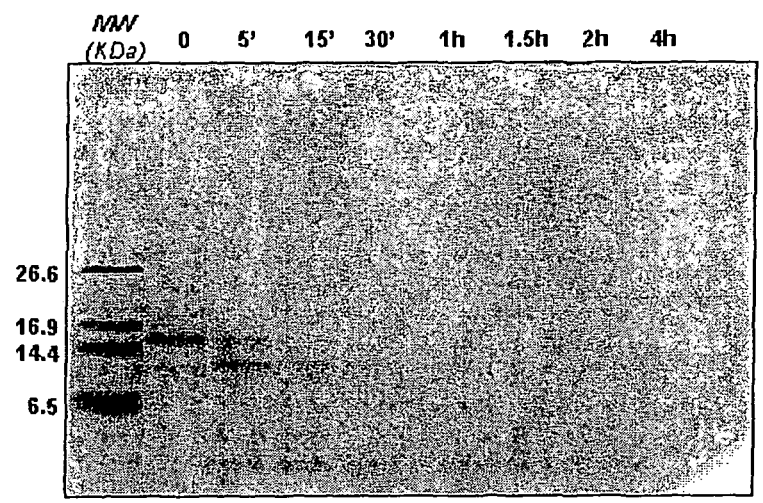
Figure 9.21
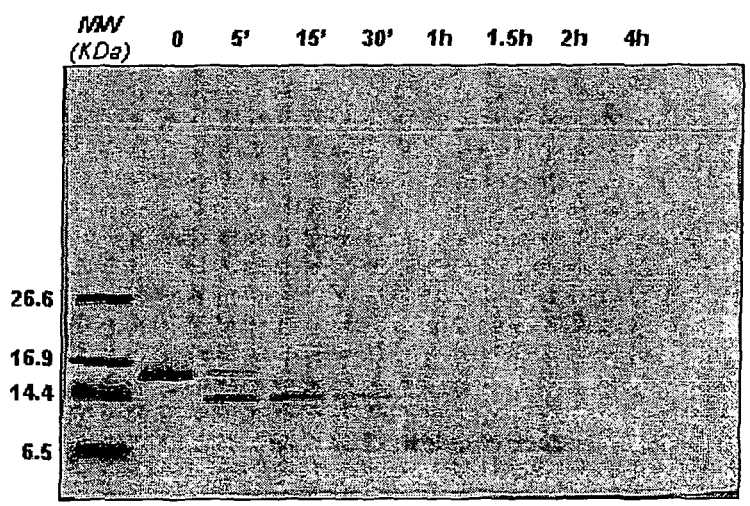

Figure 9.22
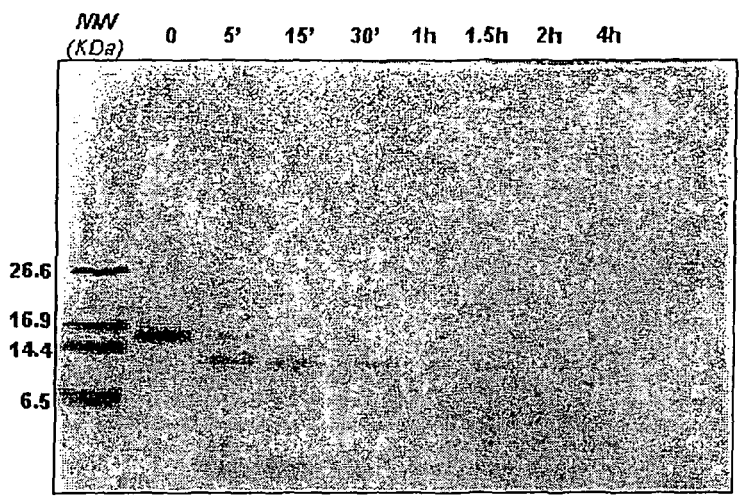
Figure 9.23
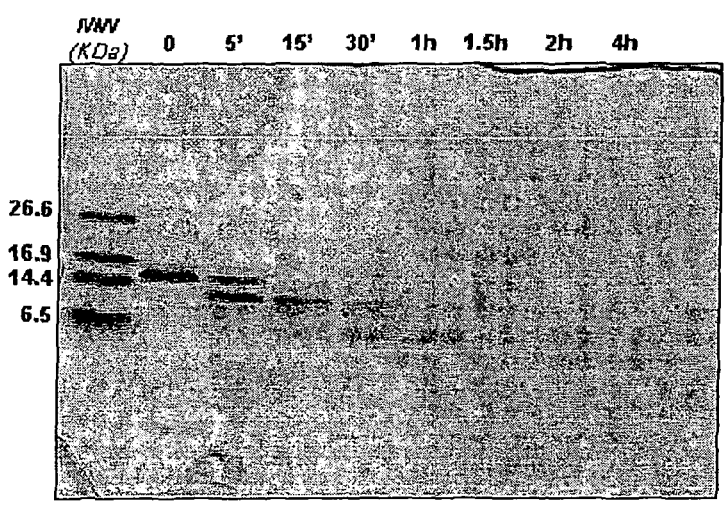

Figure 9.24
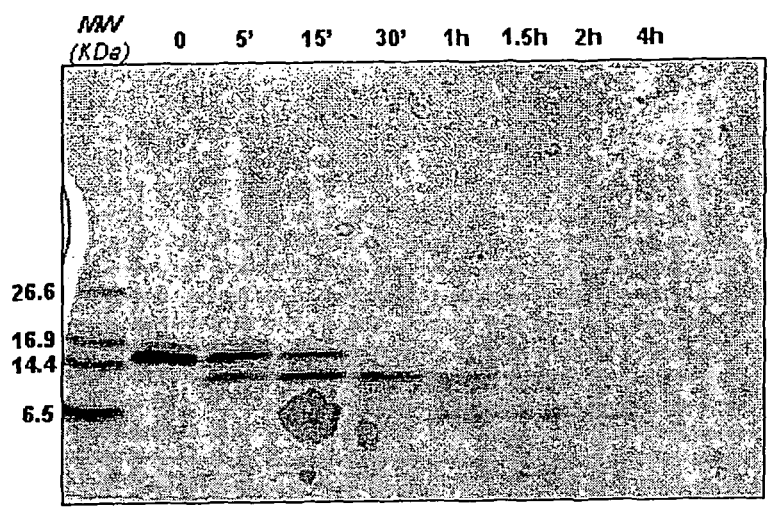
Figure 9.25
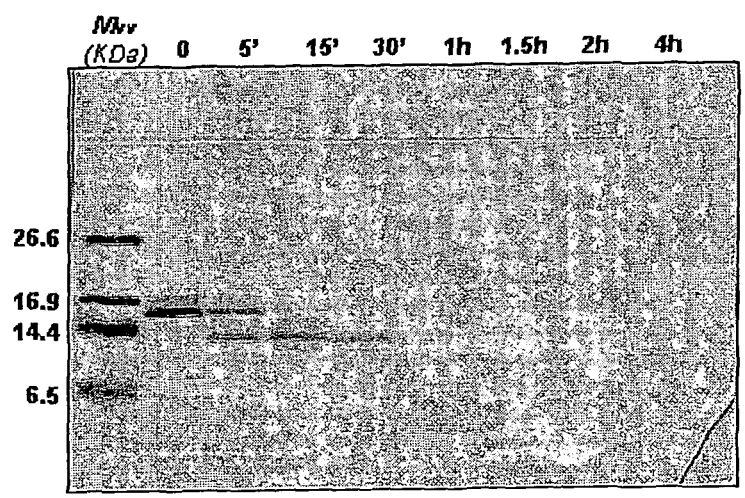

Figure 9.26
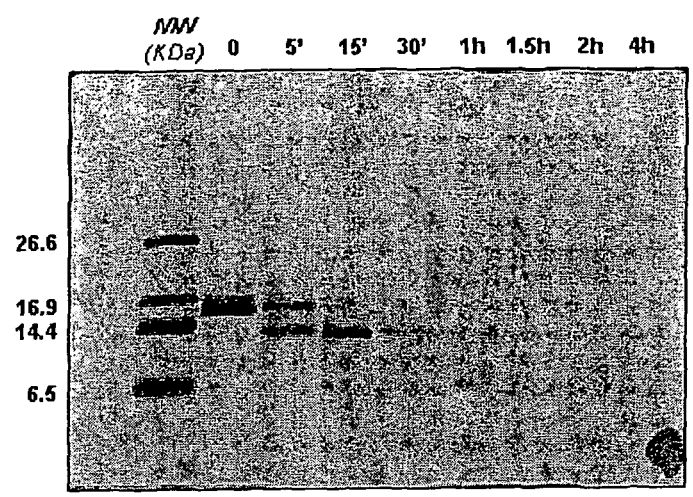
Figure 9.27
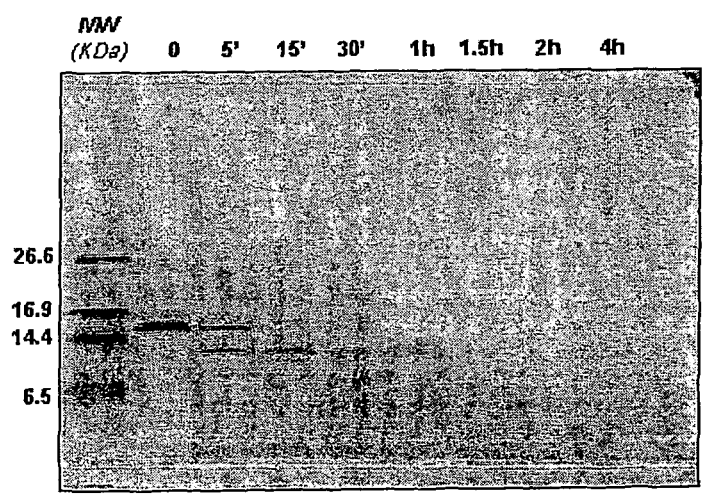

Figure 9.28
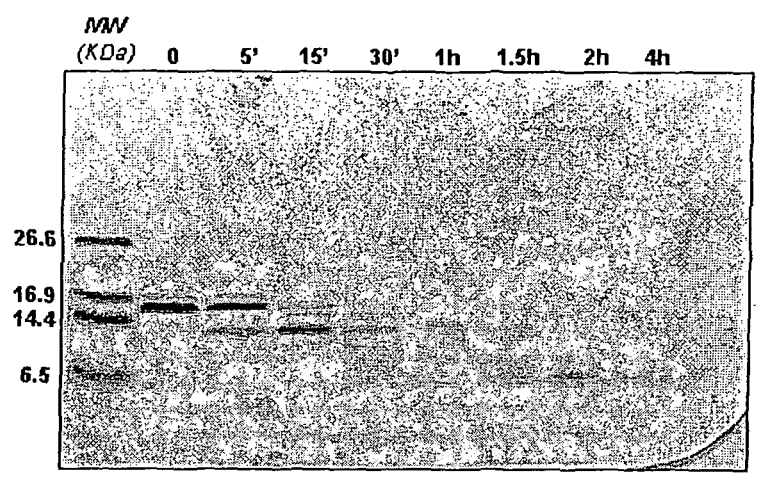
Figure 9.29
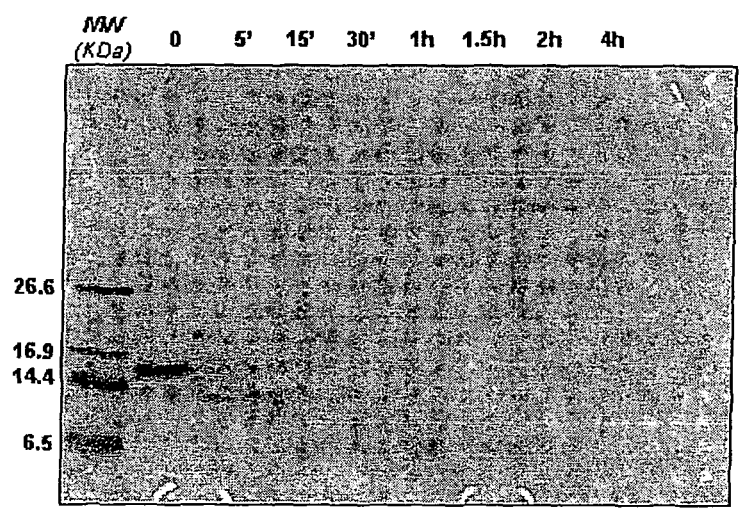

Figure 9.30
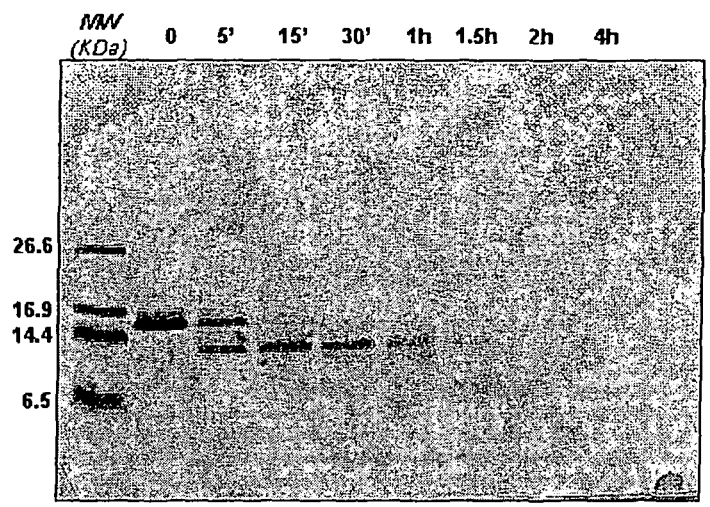
Figure 9.31
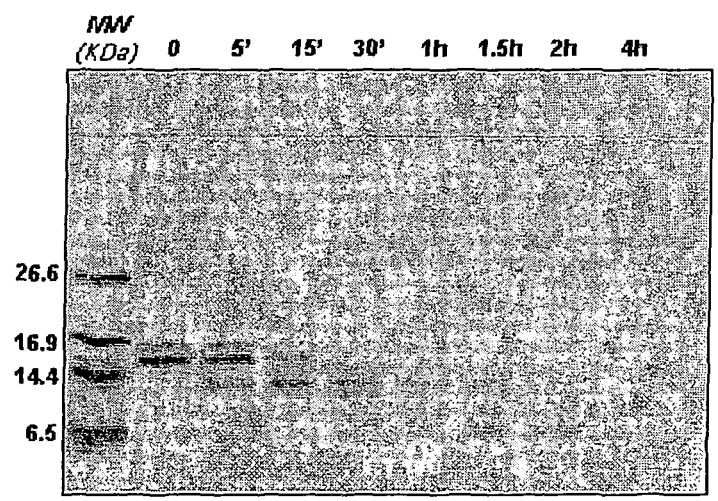

Figure 9.32
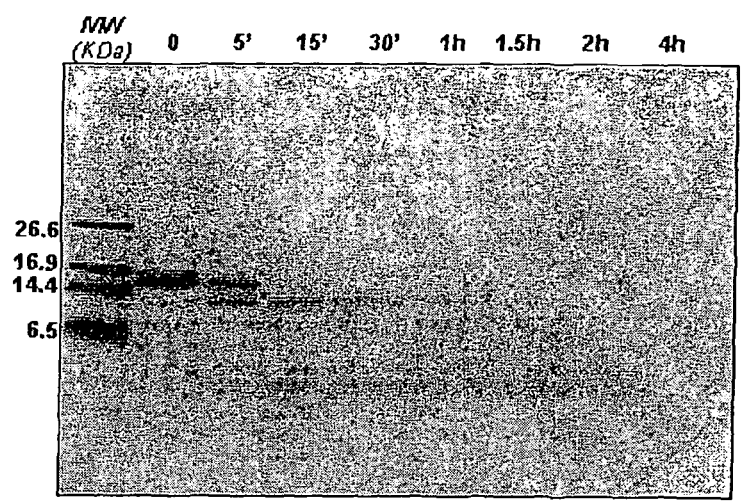
Figure 9.33
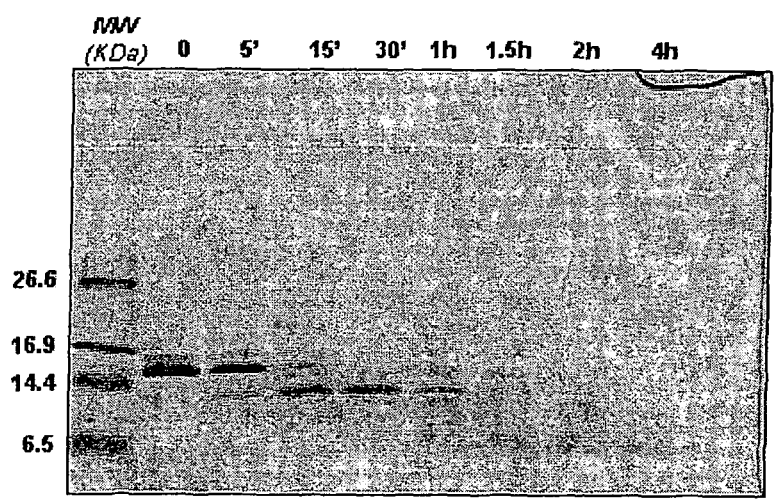

Figure 9.34
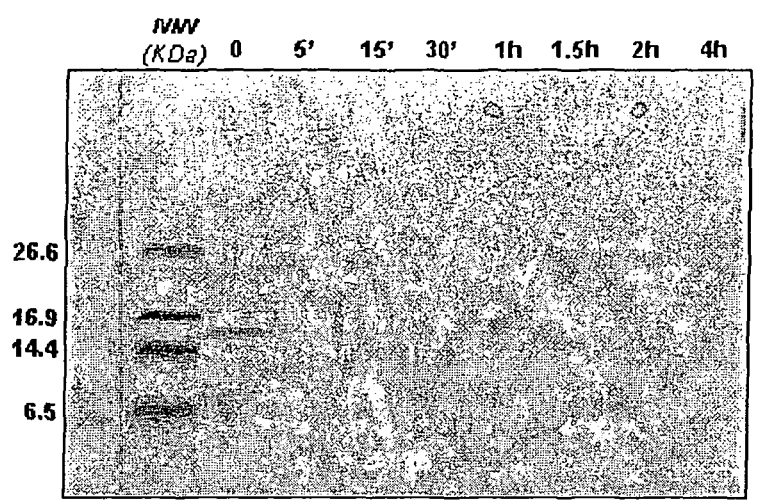
Figure 9.35
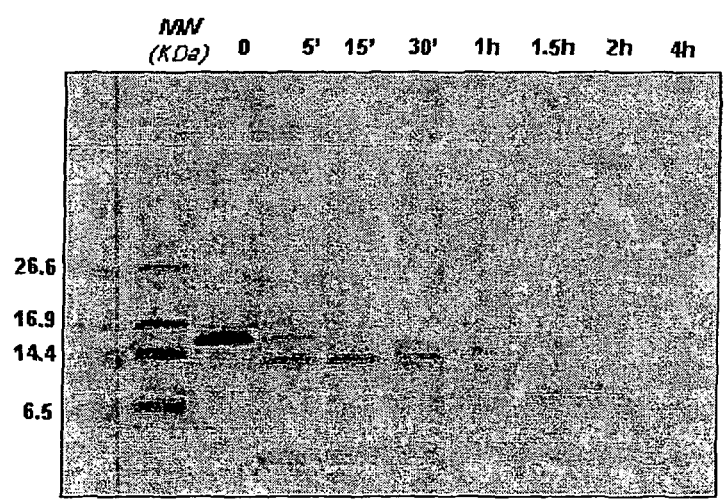

Figure 9.36
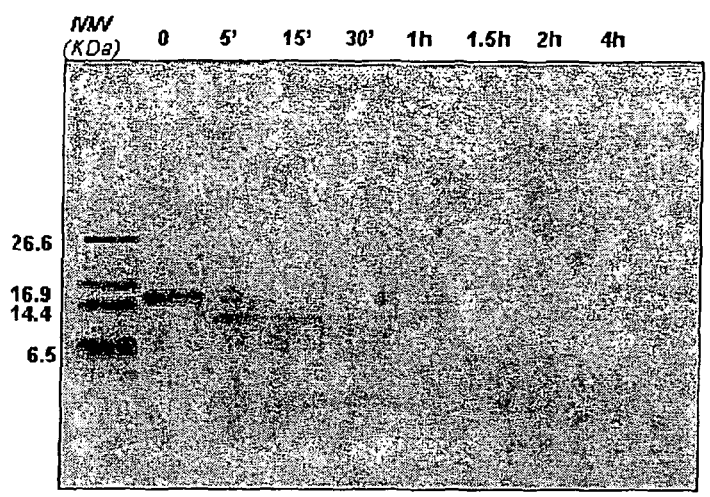
Figure 9.37
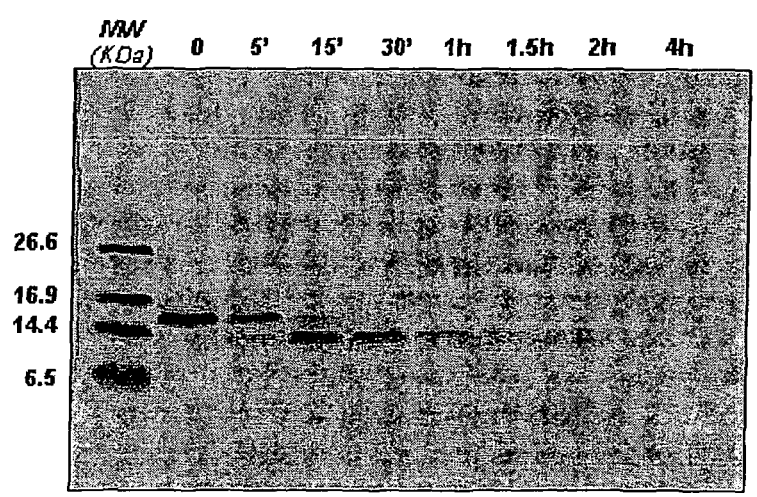

Figure 9.38
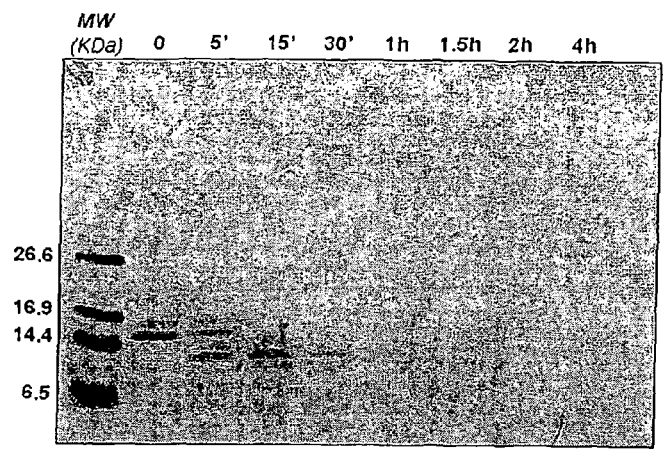
Figure 9.39
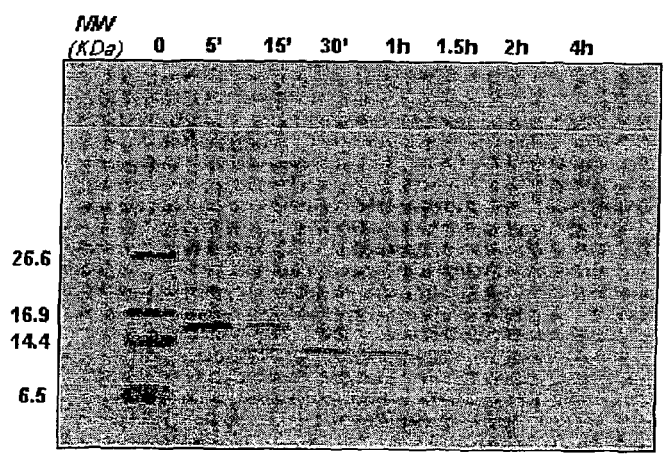

Figure 9.40
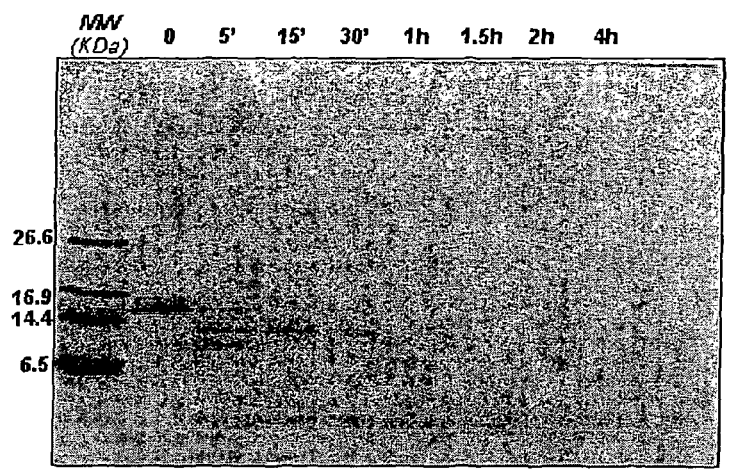
Figure 9.41
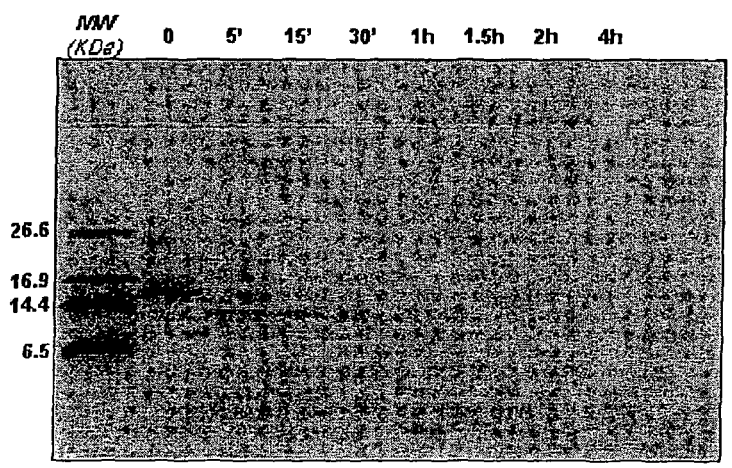

Figure 9.42
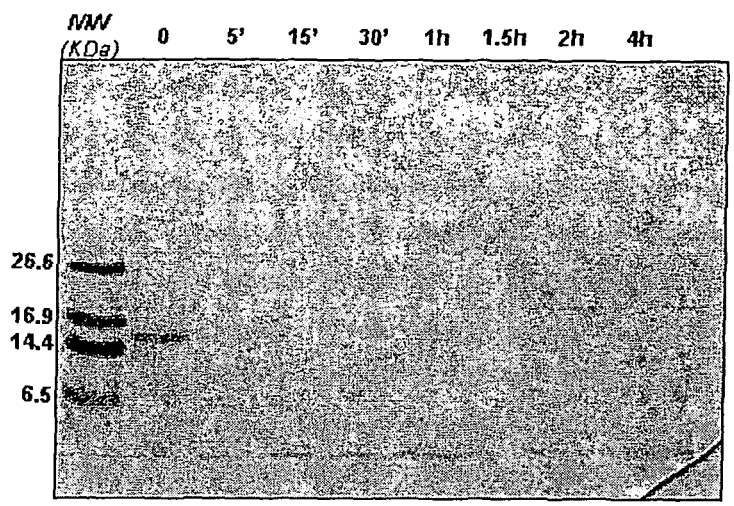
Figure 9.43
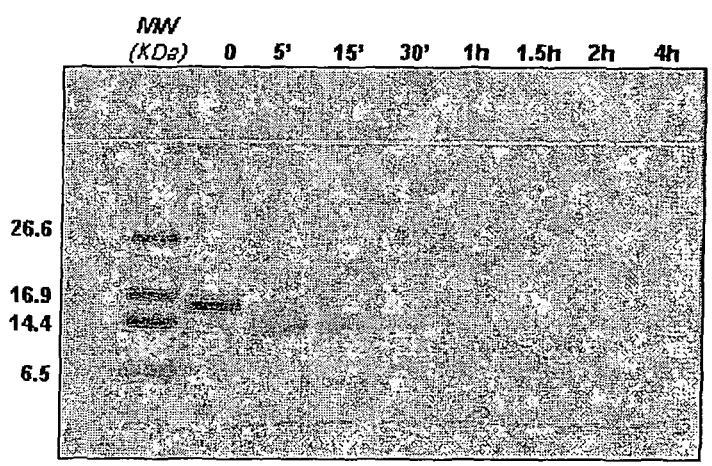

Figure 9.44
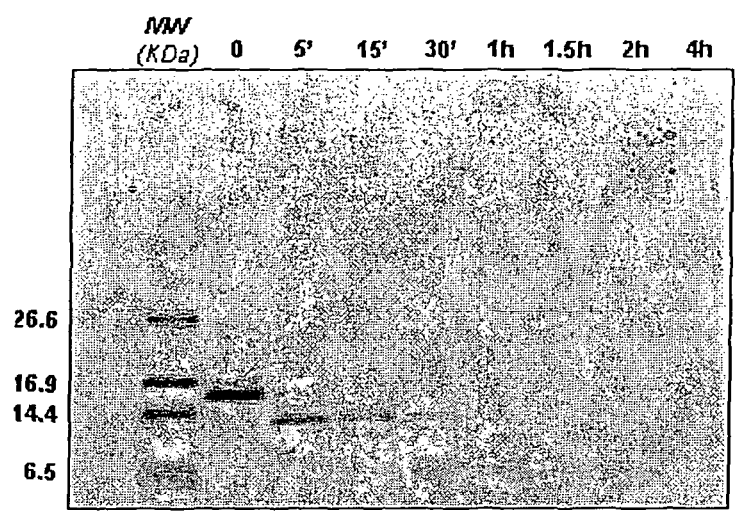
Figure 9.45
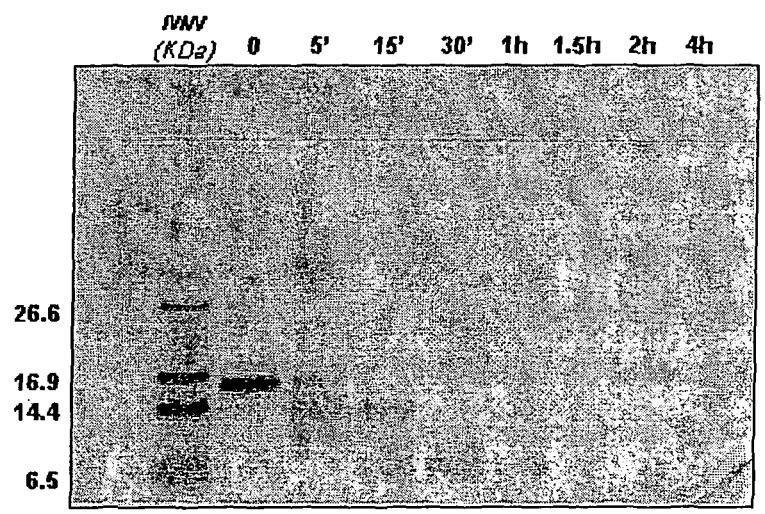

Figure 9.46
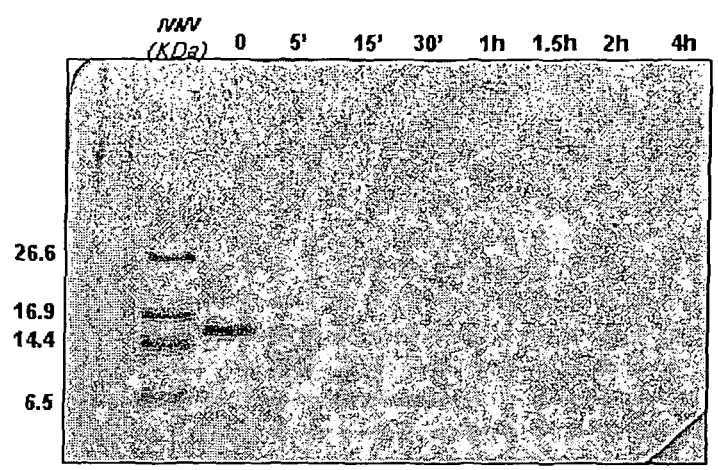
Figure 9.47
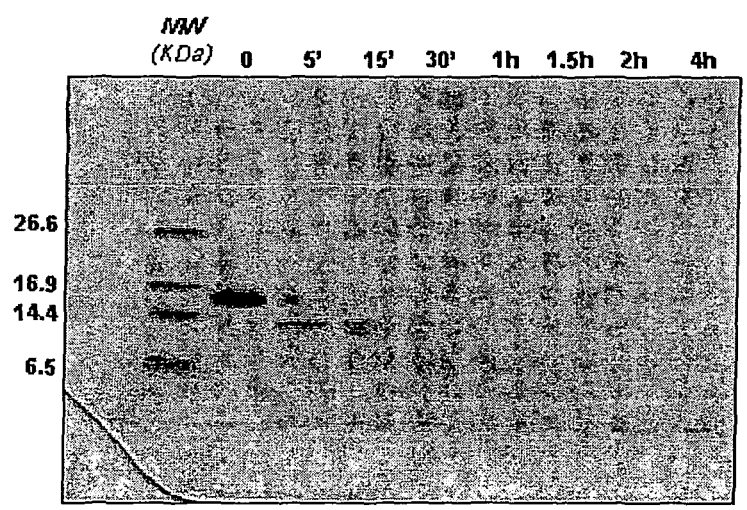

Figure 9.48
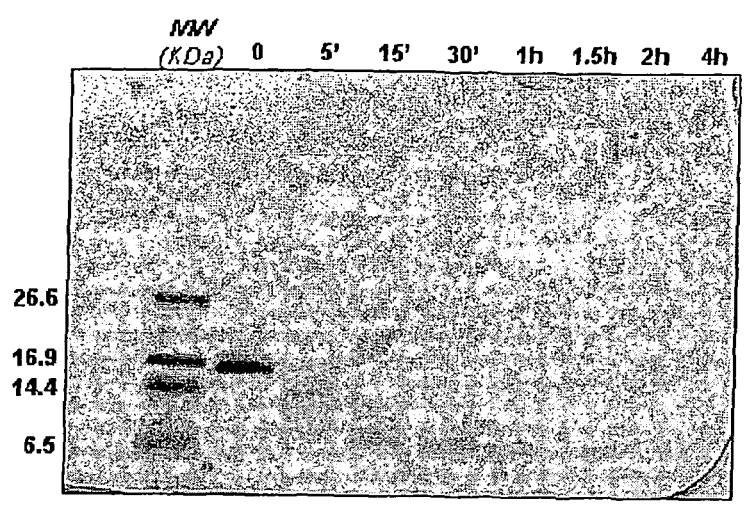
Figure 9.49
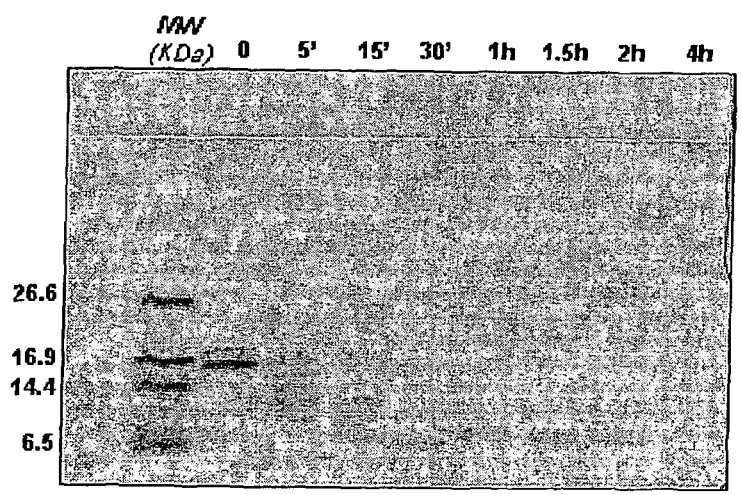

Figure 9.50
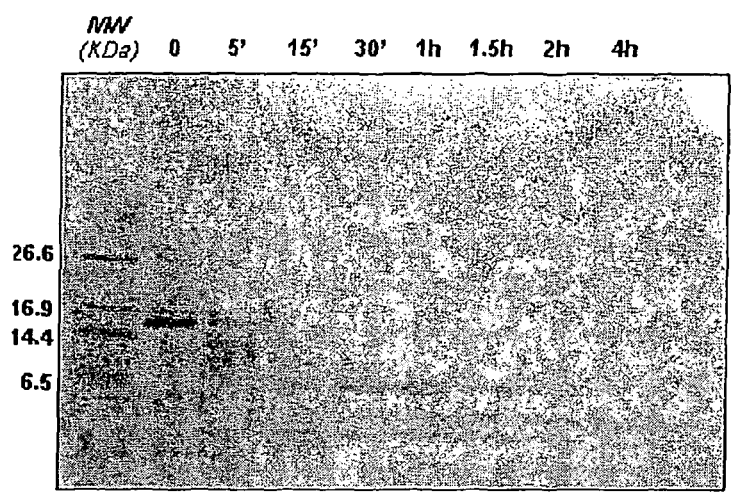
Figure 9.51
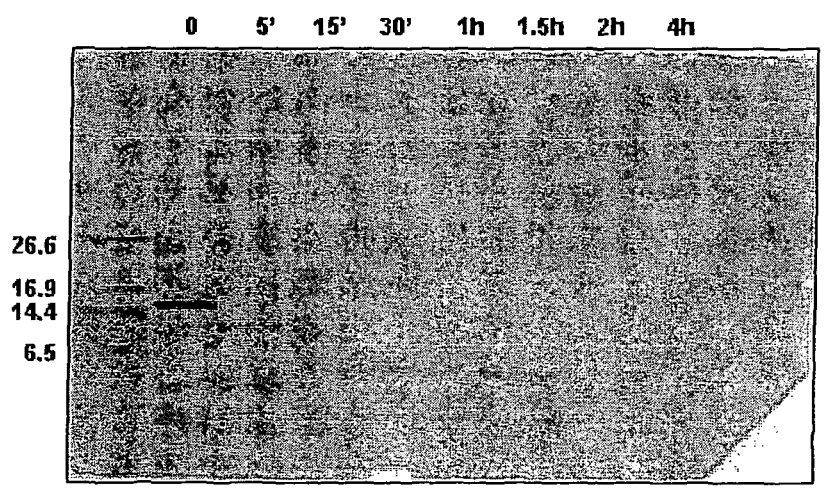

Figure 9.52
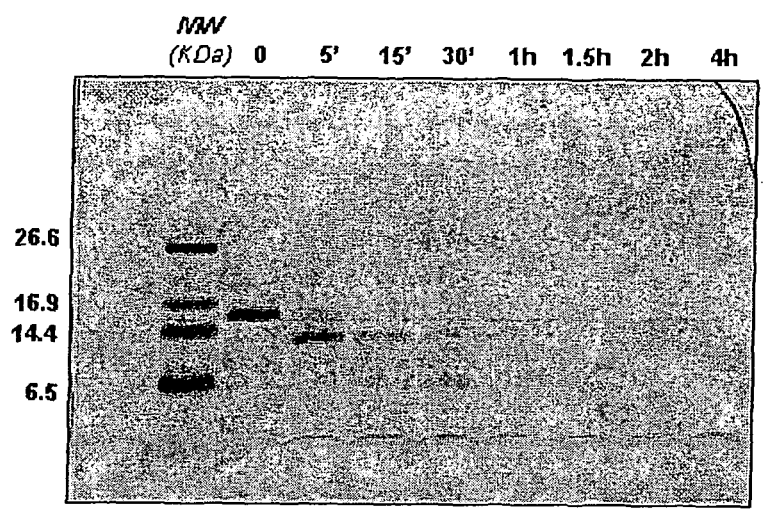
Figure 9.53
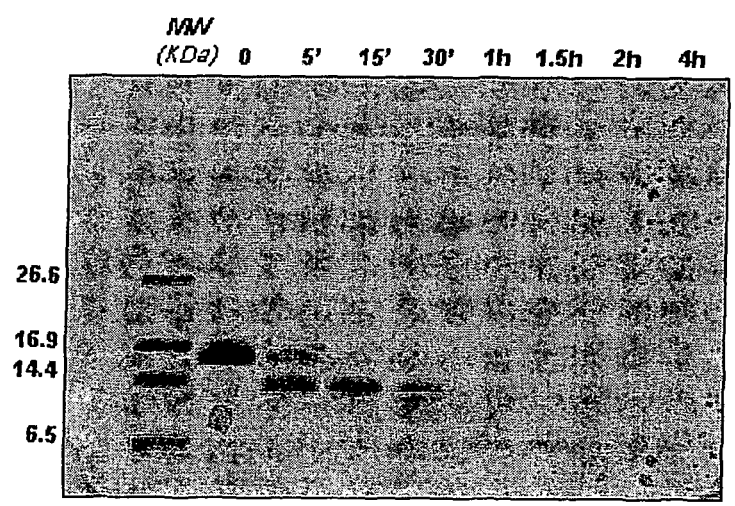

Figure 9.54
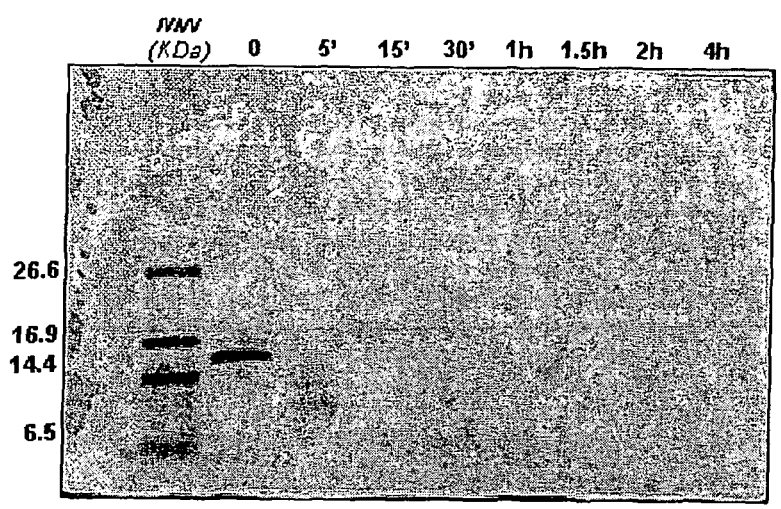
Figure 9.55
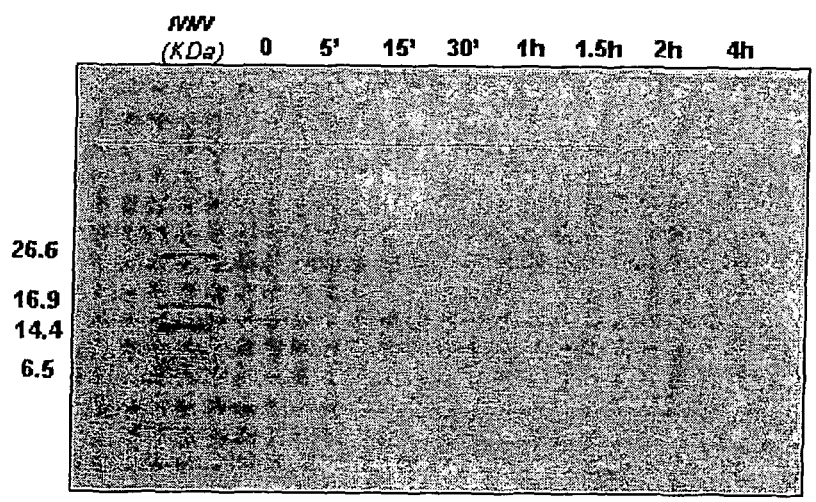

Figure 9.56
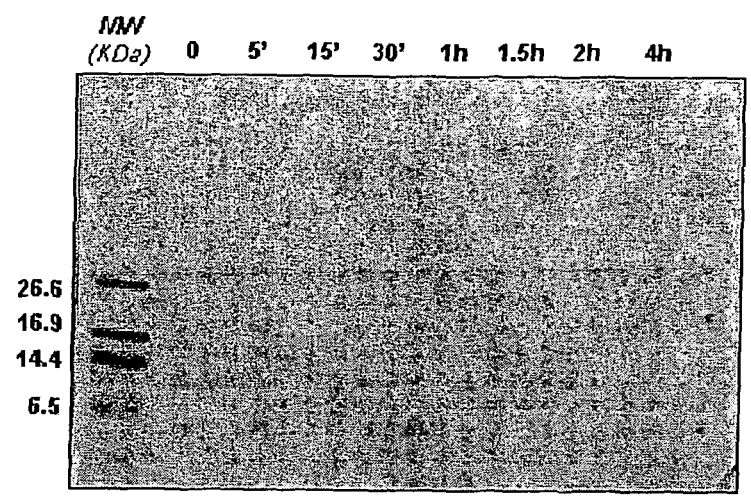
Figure 9.57
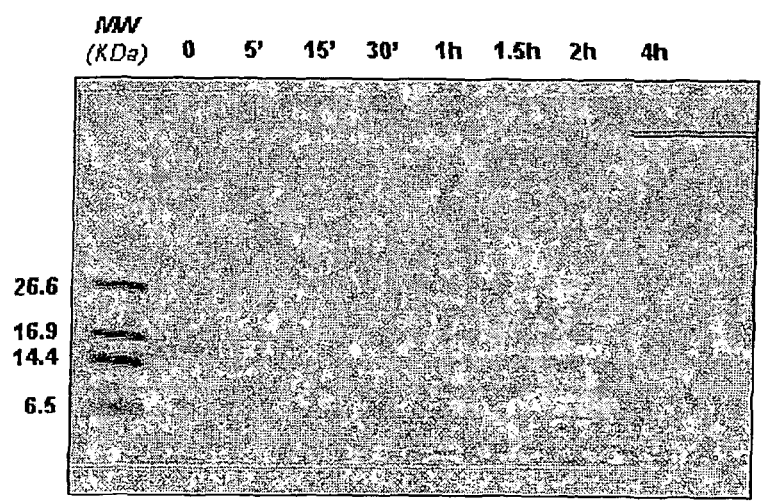

Figure 9.58
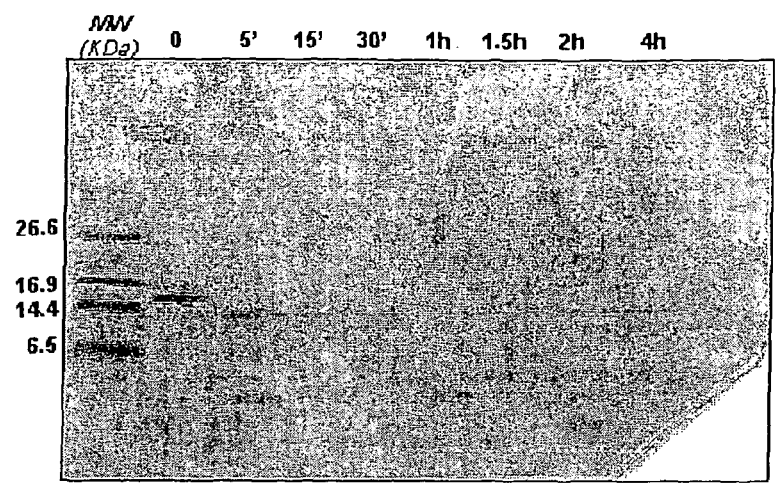
Figure 9.59
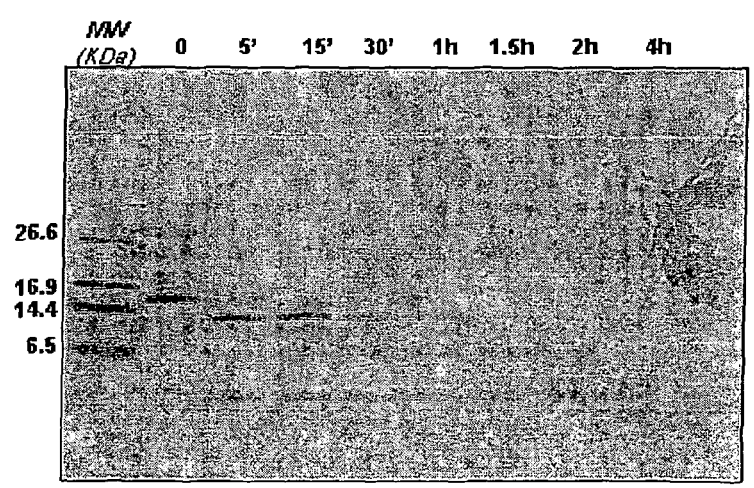

Figure 9.60
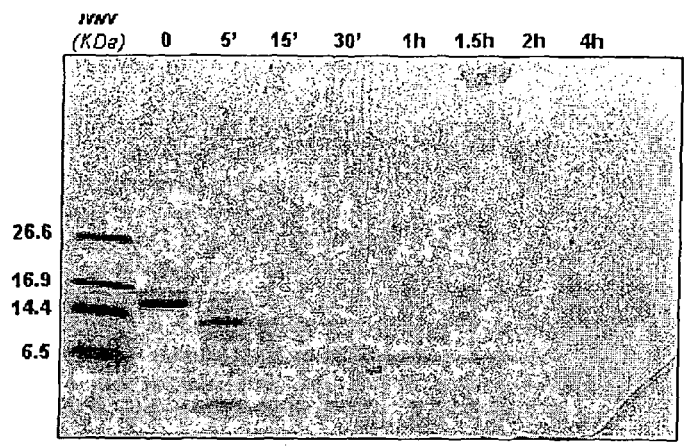
Figure 9.61
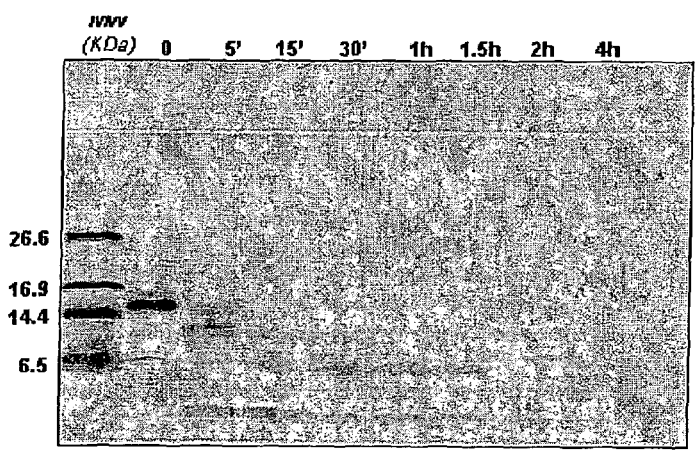

Figure 9.62
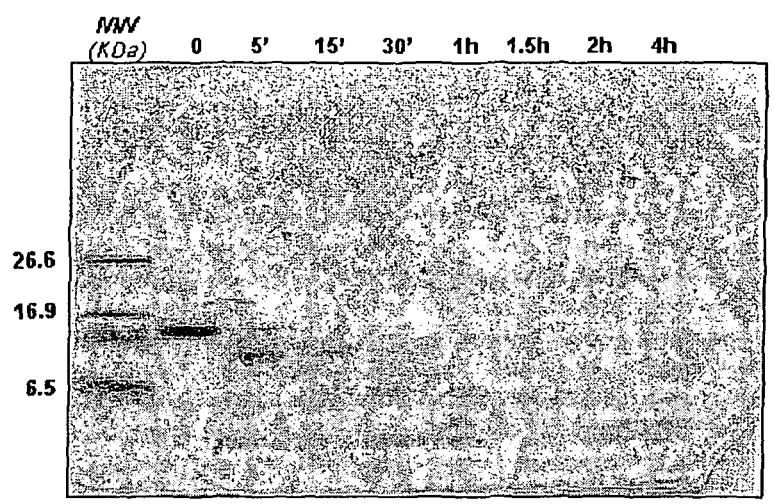
Figure 9.63
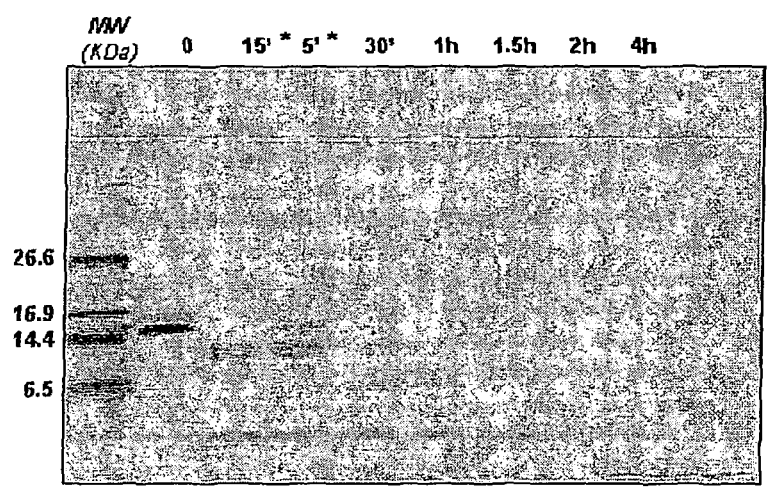

Figure 9.64
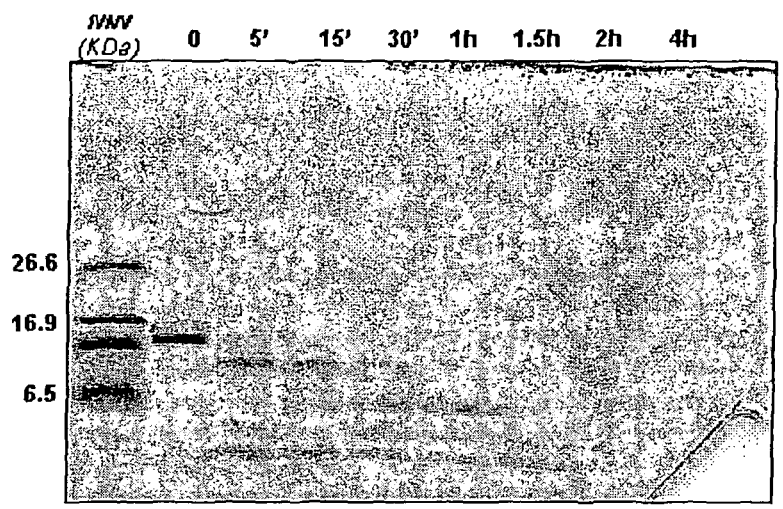
Figure 9.65
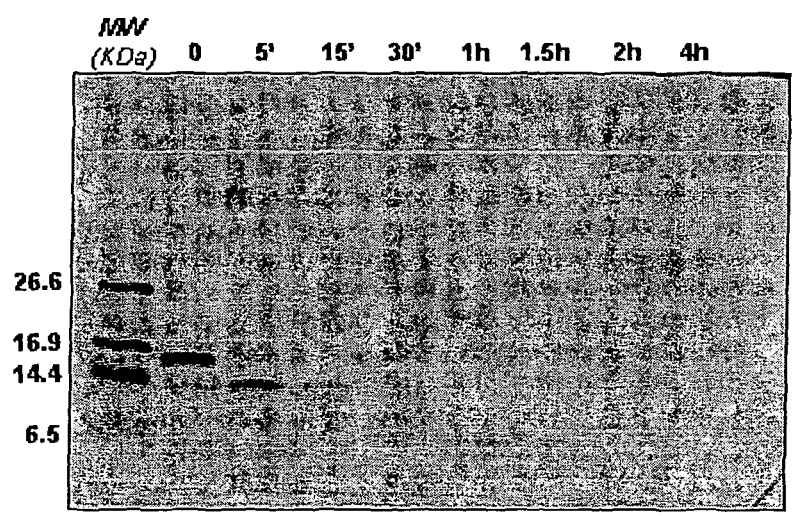

Figure 9.66
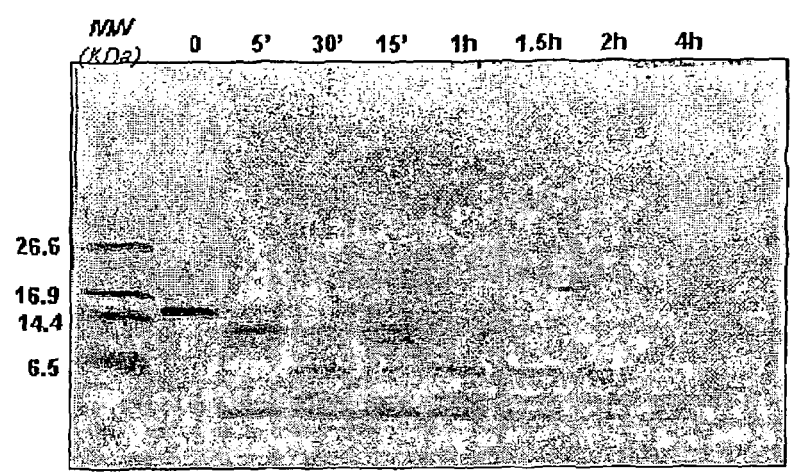
Figure 9.67
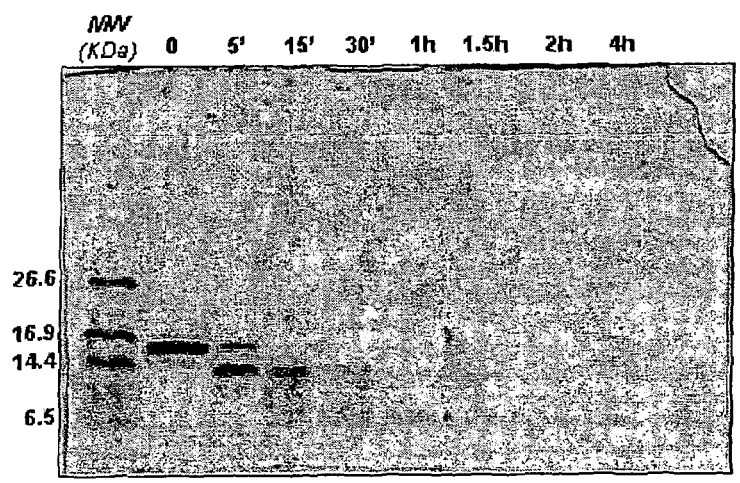

Figure 10: CT500 and variants protease resistance summary table

| Variants | TIMEPOINTS | | | | | | | |
|---|---|---|---|---|---|---|---|---|
| | 0 | 5' | 15' | 30' | 1h | 1.5h | 2h | 4h |
| CT500 | x | x | x | x | | | | |
| CT501 | x | x | x | x | | | | |
| CT502 | x | x | x | x | | | | |
| CT503 | x | x | x | x | | | | |
| CT504 | x | x | x | | | | | |
| CT505 | x | x | x | x | | | | |
| CT506 | x | x | x | | | | | |
| CT507 | x | x | | | | | | |
| CT508 | x | x | x | x | | | | |
| CT509 | x | x | x | | | | | |
| CT510 | x | x | x | x | | | | |
| CT511 | x | x | x | x | | | | |
| CT512 | x | x | x | x | | | | |
| CT513 | x | x | x | x | | | | |
| CT514 | x | x | x | x | x | | | |
| CT515 | x | x | x | x | x | | | |
| CT516 | x | x | x | x | x | | | |
| CT517 | x | x | x | x | x | | | |
| CT518 | x | x | x | x | x | | | |
| CT519 | x | x | x | | | | | |
| CT520 | x | x | x | x | | | | |
| CT521 | x | x | x | x | x | | | |

| Variants | TIMEPOINTS | | | | | | | |
|---|---|---|---|---|---|---|---|---|
| | 0 | 5' | 15' | 30' | 1h | 1.5h | 2h | 4h |
| CT522 | x | x | x | x | x | | | |
| CT523 | x | x | x | x | x | | | |
| CT524 | x | x | x | x | x | x | | |
| CT525 | x | x | x | x | | | | |
| CT526 | x | x | x | x | x | | | |
| CT527 | x | x | x | x | x | | | |
| CT528 | x | x | x | x | x | x | | |
| CT529 | x | x | x | x | | | | |
| CT530 | x | x | x | x | x | x | | |
| CT531 | x | x | x | x | x | x | | |
| CT532 | x | x | x | x | x | | | |
| CT533 | x | x | x | x | x | x | x | |
| CT534 | x | | | | | | | |
| CT535 | x | x | x | x | x | | | |
| CT536 | x | x | x | x | | | | |
| CT537 | x | x | x | x | x | x | x | |
| CT538 | x | x | | x | | | | |
| CT539 | x | x | x | x | x | x | | |
| CT540 | x | x | x | x | x | | | |
| CT541 | x | x | x | x | | | | |
| CT542 | x | | | | | | | |
| CT543 | x | x | x | x | | | | |
| CT544 | x | x | x | x | | | | |
| CT545 | x | x | x | | | | | |
| CT546 | x | x | x | | | | | |
| CT547 | x | x | x | x | | | | |
| CT548 | x | x | | | | | | |
| CT549 | x | x | | | | | | |
| CT550 | x | x | x | | | | | |
| CT551 | x | x | | | | | | |
| CT552 | x | x | x | x | | | | |
| CT553 | x | x | x | x | | | | |
| CT554 | x | x | | | | | | |

Figure 10 (continued)

| Variants | TIMEPOINTS | | | | | | | |
|---|---|---|---|---|---|---|---|---|
| CT555 | x | | | | | | | |
| CT556 | x | | | | | | | |
| CT557 | x | x | | | | | | |
| CT558 | x | x | | | | | | |
| CT559 | x | x | x | x | x | | | |
| CT560 | x | x | x | x | | | | |
| CT561 | x | x | x | x | | | | |
| CT562 | x | x | x | x | | | | |
| CT563 | x | x | x | x | | | | |
| CT564 | x | x | x | x | | | | |
| CT565 | x | x | x | x | | | | |
| CT566 | x | x | x | x | | | | |
| CT567 | x | x | x | x | | | | |

POLYMER CONJUGATES OF BOX-A OF HMGB1 AND BOX-A VARIANTS OF HMGB1

CROSS REFERENCE TO RELATED APPLICATION

This application is a 35 U.S.C. 371 National Phase Entry Application from PCT/EP2007/008029, filed Sep. 14, 2007, which claims the benefit of European Patent Application No. 06019362.0 filed on Sep. 15, 2006 and U.S. Ser. No. 60/904,776 filed Mar. 5, 2007, the disclosures of which are incorporated herein in their entirety by reference.

The present invention relates to novel polymer conjugates of the HMGB1 high affinity binding domain Box-A (HMGB1 Box-A) or of a biologically active fragment of HMGB1 Box-A. Further, the invention relates to novel polymer conjugates of polypeptide variants of the HMGB1 high affinity binding domain Box-A (HMGB1 Box-A) or of the biologically active fragments of HMGB1 Box-A. Moreover, the present invention concerns the use of said polymer conjugates to diagnose, prevent, alleviate and/or treat pathologies associated with extracellular HMGB1 and/or associated with an increased expression of RAGE.

The HMGB1 protein belongs to the family of high mobility group (HMG) proteins. HMG proteins, so-called due to their high electrophoretic mobility in polyacrylamide gels, are the most ubiquitous non-histone proteins associated with isolated chromatin in eukaryotic cells. These proteins play a generalized "architectural" role in DNA bending, looping, folding and wrapping, since they either distort, bend or modify DNA structures and complexes with transcription factors or histones (Andersson et al., 2002; Agresti et al., 2003; Degryse et al., 2003). The high mobility group 1 (HMGB1) protein is usually a nuclear factor, in particular a transcriptional regulatory molecule causing DNA bending and facilitating the binding of several transcriptional complexes.

Structurally, the HMGB1 protein is a protein of approximately 25 kDa with a highly conserved sequence among mammals, whereby 2 out of 214 amino acids have conservative substitutions in all mammalian species. HMGB1 is ubiquitously present in all vertebrate nuclei and in particular can be found in fibroblasts, neurons, hepatocytes, glia and in cells derived from hematopoietic stem cells, including monocytes/macrophages, neutrophils and platelets. The HMGB1 molecule has a tripartite structure composed of three distinct domains: two DNA binding domains called HMG Box-A and Box-B, and an acid carboxyl terminus, making it bipolarly charged.

The two HMGB1 boxes are involved in the protein's function as non-sequence-specific architectural DNA-binding elements, conferring the ability to bind DNA into recognized distorted DNA structures and stabilizing nucleosome assembly, remodelling and sliding. Both the A- and B-HMG boxes are made up of highly conserved 84 amino acid residues, are strongly positively charged and are arranged in three α-helices having a similar L-shaped fold. The long arm of the "L" contains the N-terminal extended strand and helix III (Andersson et al. 2002; Agresti et al., 2003; Thomas, J. O. 2001), while the short arm comprises helices I and II. Structure-function analysis reveals that the pro-inflammatory cytokine domain of HMGB1 is the B-Box and in particular the sequence of its first 20 amino acids. The A-Box is an extremely weak agonist of the inflammatory cytokine release triggered by HMGB1 and competitively inhibits the pro-inflammatory activities of the B-Box and of the whole protein. Therefore, from a pharmacological point of view, the A-Box acts as an antagonist of the pathological conditions induced and/or sustained by the B-Box and HMGB1.

The third domain, the carboxyl terminus or acidic tail, is extremely negatively charged since it contains 30 repetitive aspartic and glutamic acid residues, and is linked to the boxes by a basic region of about 20 residues. Mouse and rat HMGB1 differ from the human form by only two substitutions that are located in this continuous C-terminal stretch.

Besides its nuclear location and role as a transcription factor regulator, HMGB1 has also been found in the extracellular medium, actively released by activated cells of the immune systems (monocytes and macrophages) or passively released by damaged or necrotic cells (Andersson et al., 2002; Scaffidi et al., 2002; Bonaldi et al., 2002; Taniguchi et al., 2003; Friedman et al., 2003; Palumbo et al., 2004).

Extracellularly released HMGB1 acts as a potent cytokine and as an extremely potent macrophage-stimulating factor. HMGB1 acts directly by binding to the cell membrane, inducing signaling and chemotaxis, having a chemokine-like function (Yang et al., 2001) and further acting indirectly by up-regulating the expression and secretion of pro-inflammatory cytokines. This makes extracellular HMGB1 protein a potent chemotactic and immunoregulatory protein which promotes an effective inflammatory immune response. Furthermore, other proteins belonging to the family of HMG proteins, and which are able to bend DNA, are released together with HMGB1 in the extracellular medium. These proteins are inter alia HMGB2, HMGB3, HMG-1L10, HMG-4L and SP100-HMG. They share with HMGB1 highly homologous amino acid sequences. Like HMGB1, they trigger/sustain inflammatory pathologies interacting with the same receptors, leading to the same downstream pathways of interaction.

In healthy cells, HMGB1 migrates to the cytoplasm both by passive and active transport. However, all cultured cells and resting monocytes contain the vast majority of HMGB1 in the nucleus, indicating that in baseline conditions import is much more effective than export. Cells might transport HMGB1 from the nucleus by acetylating lysine residues which are abundant in HMGB1, thereby neutralizing their basic charge and rendering them unable to function as nuclear localization signals. Nuclear HMGB1 hyperacetylation determines the relocation of this protein from the nucleus to the cytoplasm (in the fibroblasts, for example) or its accumulation into secretory endolysosomes (in activated monocytes and macrophages, for example) and subsequent redirection towards release through a non-classical vesicle-mediated secretory pathway. HMGB1 secretion by already activated monocytes is then triggered by bioactive lysophosphatidylcholine (LPC), which is generated later in the inflammation site from phosphatidylcholine through the action of the secretory phospholipase sPLA2 produced by monocytes several hours after activation. Therefore, secretion of HMGB1 seems to be induced by two signals (Bonaldi et al., 2003) and to take place in three steps: 1) at first, an inflammatory signal promotes HMGB1 acetylation and its relocation from the nucleus to the cytoplasm (step 1) and storage in cytoplasmic secretory vesicles (step 2); then, a secretion signal (extracellular ATP or lysophosphatidylcholine) promotes exocytosis (third step) (Andersson et al., 2002; Scaffidi et al. 2002; Gardella et al., 2002; Bonaldi et al., 2003; Friedman et al., 2003).

Released HMGB1 has been identified as one of the ligands binding to the RAGE receptor. This receptor is expressed in most cell types, and at a high level mainly in endothelial cells, in vascular smooth muscle cells, in monocytes and macrophages and in mononuclear phagocytes. Recognition involves the C-terminal of HMGB1. The interaction of HMGB1 and RAGE triggers a sustained period of cellular activation mediated by RAGE up-regulation and receptor-dependent signaling. In particular, the interaction of HMGB1 and RAGE activates several intracellular signal transduction pathways, including mitogen-activated protein kinases (MAPKs), Cdc42, p21ras, Rac and the nuclear translocation factor κB (NF-κB), the transcription factor classically linked to inflammatory processes (Schmidt et al., 2001).

According to several experimental evidences, released HMGB1 may also interact with receptors belonging to one or more subclass(es) of the family of the Toll-like receptors. Further, HMGB1 may also interact with the functional N-terminal lectin-like domain (D1) of thrombomodulin. Due to the ability of the functional D1 domain of thrombomodulin to intercept and bind circulating HMGB1, the interaction with the RAGE receptors and the Toll-like receptors is prevented.

When released in vivo, HMGB1 is an extremely potent cytokine and a potent macrophage-stimulating factor. In fact, like other cytokine mediators of endotoxemia, HMGB1 activates in vitro a cascade of multiple pro-inflammatory cytokines (TNF, IL-1α, IL-1β, IL-1Ra, IL-6, IL-8, MIP-1α and MIP-1β) from human macrophages. Therefore, HMGB1 acts as a late mediator during acute inflammation and participates in an important way in the pathogenesis of systemic inflammation after the early mediator response has been resolved.

Moreover, the observed RAGE upregulation in proinflammatory environments and the proved increased expression of this receptor in a variety of acute and chronic inflammatory diseases provide support for RAGE as an attractive target for future medical interventions related to inflammation.

The observed pro-inflammatory effects of HMGB1 in vitro and the correlation between circulating HMGB1 levels and the development of the pathogenic sequence of systemic inflammation in vivo indicate that therapeutically targeting of this cytokine-like molecule should be of relevant clinical value, suggesting novel therapeutic approaches by a "late" administration of (selective) antagonists/inhibitors of the extracellular activities of HMGB1.

Therefore, several attempts were performed in order to block this extracellular HMGB1 chemo-cytokine protein. Several important approaches were addressed to the administration of antibodies against HMGB1, of antibodies against HMGB1 fragments (for example HMGB1 Boxes) of antibodies to RAGE, of soluble RAGE (sRAGE), of ethyl pyruvate (Czura et al., 2003; Lotze et al., 2003) and N-terminal lectin-like domain (D1) of thrombomodulin.

HMGB1 A-Box, one of the two DNA-binding domains in HMGB1, has been identified as a specific antagonist of HMGB1: highly purified recombinant A-Box has protected mice from lethal experimental sepsis even when initial treatment has been delayed for 24 hours after pathology induction, further suggesting that HMGB1 antagonists may be administered successfully in a clinically relevant window wider than the one used for other known cytokines (Yang et al., 2004).

Structural function analysis of HMGB1-truncated mutants has revealed that the A-Box domain of HMGB1 competitively displaces the saturable binding of HMGB1 to macrophages, specifically antagonizing HMGB1 activities. As has been already seen with the protective activity of anti-HMGB1 antibodies, the administration of the A-Box rescues mice from sepsis even when treatment has been initiated as late as 24 hours after surgical induction of sepsis (Yang H. et al., 2004). HMGB1 antagonists or inhibitors selected from the group of antibodies or antibody fragments that bind to an HMGB1 protein, HMGB1 gene antisense sequences and HMGB1 receptor antagonists are known from U.S. Pat. No. 6,468,533, WO 02/074337 and US 2003/0144201.

A promising attempt for inhibiting and/or antagonizing the extracellular HMGB1 chemo-cytokine protein is therefore based on the experimental evidence that the two high affinity binding domains for DNA, i.e. HMGB1 Box-A and HMGB1 Box-B, which are present in the HMGB1 molecule, have two opposing roles in the protein released in the extracellular space. The main activity of HMGB1 Box-B is to mediate the pro-inflammatory activities attributed to the HMGB1 protein. On the other hand, HMGB1 Box-A acts as an antagonist competing with the pro-inflammatory activity of the Box-B domain.

The patent application WO 2006/024547 discloses polypeptide variants of the HMGB1 Box-A, or of biologically active fragments of HMGB1 Box-A, which are obtained through systematic mutations of single amino acids of the wild-type HMGB1 Box-A protein. Therefore, WO 2006/024547 provides new agents as selective inhibitors and/or antagonists of extracellular HMGB1 and their use to prevent, alleviate and/or treat the broad spectrum of pathological conditions associated and induced by the extracellular HMGB1 chemokine and/or by the cascade of multiple inflammatory cytokines caused by the extracellular release of the HMGB1 chemokine proteins.

The efficacy of administration of synthetic protein drugs may be hampered in vivo by factors such as solubility at physiological pH, rapid elimination by glomerulal filtration, cellular clearance and metabolism as well as readily absorption. The efficacy of oral administration is, for example, hampered since proteins are digested if taken orally. The efficacy of systemic administration on the other hand is hampered since proteins under 65-70 kDa are cleared rapidly from the body. In many cases, such disadvantageous effects lead to reduced patient compliance and to reduced drug efficacy preventing an effective therapeutic use of such protein agents.

A successful strategy for improving the efficacy and the duration of the protein agent effects and for reducing potential toxicological effects is the covalent binding of a biologically active protein agent to diverse polymers. One of the polymers that is most often used in the art for improving the pharmacologic and toxicologic properties of an active agent is polyethyleneglycol, PEG in short. Polyethyleneglycol (PEG) polymers are amphiphilic, non-toxic and immunologically inert and can be conjugated to pharmaceuticals to manipulate many of the pharmacokinetic and toxicologic properties.

In the art, many covalent modification of therapeutic useful proteins with polyethyleneglycol (PEG) are reported. Covalent attachment of PEG to a protein ("pegylation") is useful in order to extend the circulation half life of proteins, since it increases the proteins effective size and reduces it rate of clearance from the body. Moreover, PEG modification of a protein increases the protein solubility, stability and decreases the protein immunogenicity.

The problem underlying the present invention was therefore the provision of novel therapeutically useful protein agents, which act as selective antagonist and/or inhibitors of extracellular HMGB1. The scope of the present invention was therefore to exploit the peculiar characteristics of some polymers, in particular of PEG, in order to develop new administration forms of the HMGB-1 high affinity binding domain Box-A (HMGB1 Box-A), which show the same if not an even higher pharmacological activity and moreover, an improved pharmacokinetic and toxicologic performance in comparison to the non-conjugation HMGB1 Box-A polypeptide and which permit to achieve the best availability of HMGB1

Box-A or of a biologically active fragment thereof in various possible administration routes.

The present invention is therefore directed to a novel polymer conjugate of the human and/or non-human wild type HMGB1 high affinity binding domain Box-A (HMGB1 Box-A) or of a biological active fragment of HMGB1 Box-A. The amino acid sequence of human HMGB1 Box-A is shown in SEQ ID NO:1. A preferred non-human HMGB1 Box-A is the *Anapheles gambia* HMGB1 Box-A, the sequence of which is shown in SEQ ID NO:301.

A further aspect of the present invention is directed to a polymer conjugate of a polypeptide variant of the human and/or non-human HMGB1 high affinity binding domain Box-A or of a biologically active fragment of HMGB1 Box-A, whereby the amino acid sequence of said polypeptide variant differs from the amino acid sequence of the wild type HMGB1 Box-A by the mutation of one or more single amino acids.

In the context of the present invention, "HMGB1" includes the non-acetylated form or/and the acetylated form of HMGB1. Likewise, "HMGB1 homologous proteins" include the non-acetylated form or/and the acetylated form of HMGB1 homologous proteins. Preferred HMGB1 homologous proteins are HMGB2, HMGB3, HMG-1L10, HMG-4L or/and SP100-HMG.

The novel polymer conjugates of the present invention show an increased water solubility, an improved pharmaceutical manageability, an improved pharmacokinetic and bioavailability and/or a decreased toxicity and/or immunogenicity in comparison to the non-conjugated HMGB1 polypeptide or polypeptide variant. Moreover, it was surprisingly found that the conjugation of the HMGB1 Box-A polypeptide or polypeptide variant and/or fragment does not alter the biological activity of the protein.

The polymer moiety according to the present invention has to be biocompatible, can be of natural or semi-synthetic or synthetic origin and can have a linear or branched structure. Exemplary polymers include without limitation polyalkylene glycols, polyalkylene oxides, polyacrylic acid, polyacrylates, polyacrylamide or N-alkyl derivatives thereof, polymethacrylic acid, polymethacrylates, polyethylacrylic acid, polyethylacrylates, polyvinylpyrrolidone, poly(vinylalcohol), polyglycolic acid, polylactic acid, poly (lactic-co-glycolic) acid, dextran, chitosan, polyaminoacids.

In a very preferred embodiment of the present invention, the polymer is polyethylene glycol (PEG) or polyethylene glycol, wherein the terminal OH group can optionally be modified, e.g. with $C_1$-$C_5$ alkyl groups or $C_1$-$C_5$ acyl groups, preferably with $C_1$-, $C_2$- or $C_3$ alkyl groups or $C_1$-, $C_2$- or $C_3$ acyl groups. Preferably, the modified polyethylene glycol is methoxy-polyethylene-glycol (mPEG).

The polymer used according to the present invention has a molecular weight ranking from 100 to 100,000 Da, preferably from 5,000 to 50,000 Da. In a very preferred embodiment of the invention, the polymer is PEG, which preferably has a terminal OH and/or methoxy group, with a molecular weight ranking from 10,000 to 40,000 Da, and preferably from 20,000 to 40,000 Da. In the most preferred embodiment, a PEG, which preferably has a terminal OH and/or methoxy group, with an average molecular weight of 20,000 Da or of 40,000 Da is used in the present invention.

The polymer moiety of the polymer conjugate of the invention is conjugated to the HMGB1 polypeptide or polypeptide variant by a covalent chemical bond in order to provide a stable conjugate.

Preferred conjugation sites on the HMGB1 Box-A moiety are selected from a lysine, cysteine, histidine, arginine, tyrosine, serine, threonine, aspartate and glutamate residue or from the N-terminal amino group of the protein moiety.

The polymer conjugate of the present invention may be mono-, di- and multi-pegylated conjugates. Preferably, the polymer conjugates of the invention are mono-pegylated.

The polymer moiety is usually covalently linked to the HMGB1 Box-A moiety through a linker group. In particular, in the context of the present invention the term linker group means a group which is obtained by the chemical reaction between polypeptide moiety and polymer moiety. The linker group can be any residue known to those skilled in the art of polymer conjugation, obtained by the reaction of the active group on the amino acid residue of the HMGB1 Box-A moiety and the polymer or the polymer activated by a reactive group. Exemplary linker groups include without limitation alkylene, amine, amide, carbamate, carboxylate, carbonyl, ester, ether, thioether and disulfide groups. Preferably, the linker group is an amine bond, which is obtained by the reaction of the N-terminal amino acid residue with the polymer moiety activated with an aldehyde reactive group and subsequent reduction.

Moreover, the linker group may optionally contain one or more spacer groups. In the context of the present invention, a spacer group is defined as a bifunctional group, having on both termini a reactive functional end-group. With the one reactive end-group, the spacer reacts with the polymer moiety or with the reactive group on the polymer moiety. With the further functional group on the other terminus, the spacer group binds to the functional group on the amino acid residue of the HMGB1 Box-A moiety. Suitable spacer groups are known to those skilled in the art. Examples of spacer groups include, but are not limited to hetero-, bi-functional small molecules or polymer. For example, the spacer group may be represented by bifunctional $C_6$-$C_{12}$ alkyl groups or heterobifunctional alkyl groups containing from 1-3 heteroatoms selected from N, S and O or an intermediary short bifunctional PEG chain.

Covalent attachment of the polymer to the HMGB1 Box-A moiety to obtain the polymer conjugate of the invention may be accomplished by known chemical synthesis techniques. For example, in one exemplary embodiment of the present invention, the polymer conjugation can be accomplished by reacting a N-hydroxy succinimide polymer (es. NHS-PEG) with the free amine groups on the amino acid residues, preferably on the lysine residues, or at the N-terminal amino acid of the HMGB1 Box-A polypeptide. Alternatively, the polymer conjugation is achieved by reaction of a PEG aldehyde to the N-terminus of the polypeptide by reductive amination. Further, the polymer conjugates can also be obtained by reacting a PEG-maleimide to a Cys residue of the HMGB1 Box-A polypeptide or polypeptide variant.

In the context of the present invention, the term "HMGB1 Box-A moiety" indicates within the polymer conjugate compound the polypeptide moiety. Hence, this term refers to the wild-type HMGB1 Box-A and to biologically active fragments thereof as well as to polypeptide variants of HMGB1 Box-A and of biologically active fragments thereof.

In the context of the present invention, where reference is made to the term "HMGB1 Box-A or amino acid sequence of HMGB1 Box-A", it is referred to both human and non-human HMGB1 Box-A. In a preferred embodiment of the present invention, the HMGB1 Box-A moiety is derived from the wild type of human HMGB1 Box-A protein and from the wild type of *Anopheles gambia* HMGB1 Box-A protein.

"Biologically active fragments of HMGB1 Box-A" as used herein are meant to encompass parts of the known wild type HMGB1 Box-A protein, for which at least one of the biological activities of the corresponding mature protein is still observable when known tests are being used. Preferably, a fragment of the mature protein is considered as biologically active if an antagonist activity with respect to the pro-inflammatory activity of the HMGB1 B-Box and the HMGB1 protein as a whole can be determined. Biologically active fragments of native HMGB1 Box-A are fragments of at least 20, 25, 30, 35, 45, 50, 55, 60, 65, 70, 75 or 80 amino acids. Preferred biologically active fragments of native HMGB1 Box-A used in the context of the present invention comprises fragments of at least 77 or of at least 54 amino acids, respectively.

The term "mutation" as used in the context of the present invention can be understood as substitution, deletion and/or addition of single amino acid in the target sequence. Preferably, the mutation of the target sequence in the present invention is a substitution. The substitution can occur with different genetically encoded amino acid or by non-genetically encoded amino acids. Examples for non-genetically encoded amino acids are homocystein, hydroxyproline, ornithin, hydroxylysine, citrulline, carnitine, etc.

In a most preferred embodiment of the present invention, the polypeptide variants of HMGB1 Box-A or of a biologically active fragment thereof are obtained by using a directed evolution process, which technology is extensively described in WO 2004/7022593 and in several further patent applications (PCT/FR00/03503, PCT/FR01/01366, U.S. Ser. No. 10/022,249, U.S. Ser. No. 10/022,390, U.S. Ser. No. 10/375,192, U.S. 60/409,898, U.S. 60/457,135, U.S. 60/410,258 and U.S. 60/410,263), all in the name of Nautilus Biotech S.A. (Paris, France), which are herein incorporated by reference.

The polypeptide variants of the present invention obtained by using directed evolution technology are mutant proteins which differ from the amino acid sequence of the wild type HMGB1 Box-A by the mutation of one or more single amino acid. In a very preferred embodiment of the present invention, only one amino acid replacement occurs on the sequence of the native protein. It is, however, encompassed by the subject of the present invention that the native protein can be further optimized by replacement of a plurality, e.g. two or more, of amino acid replacements. The modified polypeptide variants can therefore differ from the wild type protein sequence by amino acid replacements on 1-10, preferably 2, 3, 4, 5 and 6 different amino acid target positions.

In particular, the very preferred polypeptide variants of HMGB1 Box-A or of a biologically active fragment thereof used as HMGB1 Box-A moiety of the polymer conjugates of the invention are those described in the application WO 2006/024547.

Accordingly, in one preferred embodiment of the invention, the HMGB1 Box-A moiety of the polymer conjugate is derived starting from human HMGB1 Box-A. In particular, one group of polypeptide variants is derived from single mutations introduced into the full-length amino acid sequence (84 amino acids) from Human HMGB1 Box-A (SEQ ID NO:1) (FIG. 1a). These preferred polypeptide variants are defined in sequences SEQ ID Nos:2-116 (FIG. 1b).

Other preferred polypeptide variants are obtained starting from biologically active fragments of human HMGB1 Box-A of 77 amino acids (SEQ ID NO:117) (FIG. 2a) and 54 amino acids (SEQ ID NO:223) (FIG. 3a), respectively. The polypeptide variants of Box-A of human HMGB1 fragment of 77 amino acids are defined in sequences SEQ ID NOs:118 to 222 (FIG. 2b). The polypeptide variants of Box-A of human HMGB1 fragment of 54 amino acids are defined in sequences SEQ ID NOs:224 to 300 (FIG. 3b).

In a further preferred embodiment of the invention, the HMGB1 Box-A moiety of the polymer conjugate is derived starting from *Anopheles gambia* HMGB1 Box-A. In particular, one group of polypeptide variants is derived from single mutations introduced into the full-length amino acid sequence (84 amino acids) from *Anopheles gambia* HMGB1 Box-A (SEQ ID NO:301) (FIG. 4a). These polypeptide variants are identified in the sequences SEQ ID Nos:302 to 418 (FIG. 4b). Other preferred polypeptide variants are generated starting from biologically active fragments of *Anopheles gambia* HMGB1 Box-A of 77 amino acids (SEQ ID NO:419) (FIG. 5a) and 54 amino acids (SEQ ID NO:529) (FIG. 6a), respectively. The polypeptide variants of Box-A of HMGB1 fragment of 77 amino acids are defined in sequences SEQ ID Nos:420 to 528 (FIG. 5b). The polypeptide variants of Box-A of HMGB1 *Anopheles gambia* (XP_311154) fragment of 54 amino acids are defined in sequences SEQ ID Nos:530 to 610 (FIG. 6b).

In order to identify the most preferred polypeptide variants of HMGB1 Box-A used as HMGB1 Box-A moiety of the polymer conjugates of the invention, studies have been conducted to determine the polypeptide variants which show both a similar or even improved activity and an increased protease resistance compared to the wild-type HMGB1 Box-A protein. For this purpose, the activity of Box-A polypeptide variants of the human HMGB1 Box-A of SEQ ID NO:1 in inhibiting HMGB1-induced NIH/3T3 cell migration was determined in chemotaxis assays in comparison to the antagonistic activity of human HMGB1 Box-A wild-type itself (Example 1 and FIGS. 7.1 to 7.9). Moreover, for those polypeptide variants, which show a similar or even higher antagonistic activity than the native HMGB1 Box-A protein of SEQ ID NO:1, the in vitro resistance to protease digestion was determined by incubation of each of these polypeptide variants, with a mixture of trypsin, a-chymotrypsin, endoproteinase Asp-N and endoproteinase Glu-C (sigma). This protease resistance test is described in Example 2 and the results of protease resistance profile of said variants in comparison to native HMGB1 Box-A are shown in FIGS. 9.1 to 9.67.

From the results it can be gathered that the preferred polypeptide variants of HMGB1 Box-A useful as HMGB1 Box-A moiety of the polymer conjugate of the present invention are those variants which show a similar or higher antagonistic activity together with an increased protease resistance. In particular, the preferred polypeptide variants are the polypeptides of SEQ ID NOs: 33, 35, 37-39, 42-45, 47-49, 52, 55, 57, 59, 62, 64, 67, 69 and 104. Among these preferred polypeptide variants, the most preferred variants are those defined in SEQ ID Nos:45, 49, 52, 55, 59, 64 and 67. These very preferred polypeptide variants show a dramatically improved proteinase resistance profile compared with the wild-type human HMGB1 Box-A of SEQ ID NO:1 (cf. results of Example 2).

It is noted that the amino acids which occur in the various amino acid sequences appearing herein are identified according to their known one-letter code abbreviations. It should be further noted that all amino acid residue sequences represented herein by their one-letter abbreviation code have a left-to-right orientation in the conventional direction of amino-terminus to carboxyl-terminus.

In the present invention, it was surprisingly found that the above described polymer conjugates exhibit an improved pharmacokinetic and toxicologic performance, leading to an improved bioavailability compared to the non-conjugated HMGB1 Box-A polypeptide moiety. A particular advantageous effect of the polymer conjugation of the HMGB1 Box-A polypeptides and variants thereof, and in particular of the pegylation of these polypeptides, in comparison with the non-conjugated form, is the increase of the hydrodynamic volume of the proteins. This leads to a significant and unexpected improvement of the pharmacokinetic properties of the conjugated compounds due to the avoidance of renal clearance, i.e. reduction of glomerular filtration.

Moreover, the polymer conjugates of the invention exhibit increased resistance to the proteolytic activity of proteases and/or peptidases, in particular exhibit an increased resistance to the proteolytic activity of the human proteases and/or peptidases, in particular of the human serum proteases and/or human gastro-intestinal proteases or peptidases.

In particular, the resistance to proteolysis is at least 10%, 20%, 30%, 40%, 50%, 70%, 80%, 90%, 95% or higher compared to the non-conjugated HMGB1 Box-A. Protease resistance was measured at different timepoints (between 5 minutes and 8 hours) at 25° C. after incubation of 20 µg of Box-A wild type or variants with a mixture of proteases at 1% w/w of total proteins. The mixture of the proteases was prepared freshly at each assay from stock solutions of endoproteinase Glu-C (SIGMA) 200 µg/ml; trypsin (SIGMA) 400 µg/ml and α-chymotrypsin (SIGMA) 400 µg/ml. After protease incubation the reaction was stopped adding 10 µl of anti-proteases solution (Roche) and the samples were stored at −20° C. for the biological activity assay.

As a consequence of the increased stability due to the increased resistance to proteases activity, the polymer conjugates of the present invention also exhibit a longer half-life in body fluids compared to the non-conjugated HMGB1 Box-A. In particular, the half-life in serum and/or in blood is increased, whereby an increase of at least 10 minutes, 20 minutes, 30 minutes, 60 minutes or even longer, compared to the non-conjugated HMGB1 Box-A is observed.

Due to the increase of the hydrodynamic volume of the proteins and also due to an increased resistance to proteolysis and thus the higher stability, the polymer conjugates of the invention also exhibit improved therapeutic and biological properties and activity. In fact, they show a more favorable pharmacokinetic and pharmacodynamic profile than non-conjugated HMGB1 Box-A protein and protein variants.

The invention is therefore directed to the use of the above-mentioned polymer conjugates of HMGB1 Box-A as an active agent in a medicament.

A still further aspect of the invention is hence the use of the inventive polymer conjugates for the manufacture of a medicament for the prevention and/or treatment of extracellular HMGB1-associated pathologies or pathologies associated with the HMGB1 homologous proteins. In particular, the HMGB1 associated pathologies are pathologies which are mediated by a multiple inflammatory cytokine cascade.

The broad spectrum of pathological conditions induced by the HMGB1-chemokine and by the HMGB1-induced cascade of inflammatory cytokines are grouped in the following categories: inflammatory disease, autoimmune disease, systemic inflammatory response syndrome, reperfusion injury after organ transplantation, cardiovascular affections, obstetric and gynecologic disease, infectious (viral and bacterial) disease, allergic and atopic disease, solid and non-solid tumor pathologies, transplant rejection diseases, congenital diseases, dermatological diseases, neurological diseases, cachexia, renal diseases, iatrogenic intoxication conditions, metabolic and idiopathic diseases.

HMGB1-associated pathologies according to the present invention are preferably pathological conditions mediated by activation of the inflammatory cytokine cascade. Non limiting examples of conditions which can be usefully treated using the present invention include the broad spectrum of pathological conditions induced by the HMGB1-chemokine and by the HMGB1-induced cascade of inflammatory cytokines grouped in the following categories: restenosis and other cardiovascular diseases, reperfusion injury, inflammation diseases such as inflammatory bowel disease, systemic inflammation response syndrome, e.g. sepsis, adult respiratory distress syndrome, etc, autoimmune diseases such as rheumatoid arthritis and osteoarthritis, obstetric and gynecological diseases, infectious diseases, atopic diseases, such as asthma, eczema, etc, tumor pathologies, e.g. solid or non-solid tumor diseases associated with organ or tissue transplants, such as reperfusion injuries after organ transplantation, organ rejection and graft-versus-host disease, congenital diseases, dermatological diseases such as psoriasis or alopecia, neurological diseases, ophthalmological diseases, renal, metabolic or idiopathic diseases and intoxication conditions, e.g. iatrogenic toxicity and Behçet disease, wherein the above diseases are caused by, associated with and/or accompanied by HMGB1 protein release.

In particular, the pathologies belonging to inflammatory and autoimmune diseases include rheumatoid arthritis/seronegative arthropathies, osteoarthritis, inflammatory bowel disease, Crohn's disease, intestinal infarction, systemic lupus erythematosus, iridoeyelitis/uveitis, optic neuritis, idiopathic pulmonary fibrosis, systemic vasculitis/Wegener's granulomatosis, sarcoidosis, orchitis/vasectomy reversal procedures, systemic sclerosis and scleroderma. Systemic inflammatory response includes sepsis syndrome (including gram positive sepsis, gram negative sepsis, culture negative sepsis, fungal sepsis, neutropenic fever, urosepsis, septic conjunctivitis), meningococcemia, trauma hemorrhage, hums, ionizing radiation exposure, acute and chronic prostatitis, acute and chronic pancreatitis, appendicitis, peptic, gastric and duodenal ulcers, peritonitis, ulcerative, pseudomembranous, acute and ischemic cholitis, diverticulitis, achalasia, cholangitis, cholecystitis, enteritis, adult respiratory distress syndrome (ARDS). Reperfusion injury includes post-pump syndrome and ischemia-reperfusion injury. Cardiovascular disease includes cardiac stun syndrome, myocardial infarction and ischemia, atherosclerosis, thrombophlebitis, endocarditis, pericarditis, congestive heart failure and restenosis. Obstetric and gynecologic diseases include premature labour, endometriosis, miscarriage, vaginitis and infertility. Infectious diseases include HIV infection/HIV neuropathy, meningitis, B- and C-hepatitis, herpes simplex infection, septic arthritis, peritonitis, *E. coli* 0157:H7, pneumonia epiglottitis, haemolytic uremic syndrome/thrombolytic thrombocytopenic purpura, candidiasis, filariasis, amebiasis, malaria, Dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis/epidydimitis, legionella, Lyme disease, influenza A, Epstein-Barr Virus, Cytomegalovirus, viral associated hemiaphagocytic syndrome, viral encephalitis/aseptic meningitis. Allergic and atopic disease include asthma, allergy, anaphylactic shock, immune complex disease, hay fever, allergic rhinitis, eczema, allergic contact dermatitis, allergic conjunctivitis, hypersensitivity pneumonitis. Malignancies (liquid and solid tumor pathologies) include ALL, AML, CML, CLL, Hodgkin's disease, non Hodgkin's lymphoma, Kaposi's sarcoma, colorectal carcinoma, nasopharyngeal carcinoma, malignant histiocytosis and paraneoplastic syndrome/hypercalcemia of malignancy. Transplant diseases include organ transplant rejection and graft-versus-host disease. Congenital disease includes cystic fibrosis, familial hematophagocytic lymphohistiocytosis and sickle cell anemia. Dermatologic disease includes psoriasis, psoriatic arthritis and alopecia. Neurologic disease includes neurodegenerative diseases (multiple sclerosis, migraine, headache, amyloid-associated pathologies, prion diseases/Creutzfeld-Jacob disease, Alzheimer and Parkinson's diseases, multiple sclerosis, amyotrophic emilateral sclerosis) and peripheral neuropathies, migraine, headache. Renal disease includes nephrotic syndrome, hemodialysis and uremia. Iatrogenic intoxication condition includes OKT3 therapy, Anti-CD3 therapy, Cytokine therapy, Chemotherapy, Radiation therapy and chronic salicylate intoxication. Metabolic and idiopathic disease includes Wilson's disease, hemochromatosis, alpha-1 antitrypsin deficiency, diabetes and diabetes complications, weight loss, anorexia, cachexia, obesity, Hashimoto's thyroiditis, osteoporosis, hypothalamic-pituitary-adrenal axis evaluation and primary biliary cirrhosis. Ophtalmological disease include glaucoma, retinopathies and dry-eye. A miscellanea of other pathologies comprehends: multiple organ dysfunction syndrome, muscular dystrophy, septic meningitis, atherosclerosis, epiglottitis, Whipple's disease, asthma, allergy, allergic rhinitis, organ necrosis, fever, septicaemia, endotoxic shock, hyperpyrexia, eosinophilic granuloma, granulomatosis, sarcoidosis, septic abortion, urethritis, emphysema, rhinitis, alveolitis, bronchiolitis, pharyngitis, epithelial barrier dysfunctions, pneumoultramicropicsilicovolcanoconiosis, pleurisy, sinusitis, influenza, respiratory syncytial virus infection, disseminated bacteremia, hydatid cyst, dermatomyositis, burns, sunburn, urticaria, warst, wheal, vasulitis, angiitis, myocarditis, arteritis, periarteritis nodosa, rheumatic fever, celiac disease, encephalitis, cerebral embolism, Guillame-Barre syndrome, neuritis, neuralgia, iatrogenic complications/peripheral nerve lesions, spinal cord injury, paralysis, uveitis, arthriditis, arthralgias, osteomyelitis, fasciitis, Paget's disease, gout, periodontal disease, synovitis, myasthenia gravis, Goodpasture's syndrome, Behçets's syndrome, ankylosing spondylitis, Barger's disease, Retier's syndrome, bullous dermatitis (bullous pemphigoid), pemphigous and pemphigous vulgaris and alopecia.

In a further preferred embodiment, the polymer compounds of the invention are used as active agents for the prevention, alleviation and/or treatment of RAGE-related pathologies. RAGE-related pathologies are defined as pathological states associated with an increased expression of RAGE.

RAGE (Receptor for Advanced Glycation End-products) is a multi-ligand member of the immunoglobulin superfamily of cell surface molecules. It is composed of three immunoglobulin-like regions (one V-type immunoglobulin domain followed by two C-type immunoglobulin domain), a transmembrane domain and a highly charged short cytosolic tail that is essential for post-RAGE signalling. RAGE was first identified in 1992 as a binding target for AGEs, non-enzymatically glycosylated and oxidated proteins which accumulate in vascular tissue in aging and at an accelerated rate in diabetes. RAGE is expressed on a wide set of cells, including endothelial cells, smooth muscle cells, mononuclear phagocytes and neurons. While it is present at high levels during development, especially in the central nervous system, its levels decline during maturity.

As reported above, RAGE was the first receptor identified for extracellular HMGB1. HMGB1 binding on the cell surface induces the transcriptional up-regulation of RAGE. Examples of RAGE-related pathologies are diabetes and disorders associated with diabetes such as diabetic vasculopathy, neuropathy, retinopathy and other disorders, including Alzheimer's disease and immune/inflammatory reactions of the vessel walls. A very preferred example of RAGE-related pathologies in this context is diabetes of type I and/or of type II.

In a further aspect of the invention, the use of the polymer conjugates HMGB1 Box-A described above is in combination with a further active agent.

The further agent is preferably an agent capable of inhibiting an early mediator of the inflammatory cytokine cascade. Preferably, this further agent is an antagonist or inhibitor of a cytokine selected from the group consisting of TNF, IL-1α, IL-1β, IL-Ra, IL-6, IL-8, IL-10, IL 13, IL-18, IFN-γ MIP-1α, MIF-1β, MIP-2, MIF and PAF.

The further agent used in combination with the polymer conjugate, may also be an inhibitor of RAGE, e.g. an antibody directed to RAGE, a nucleic acid or nucleic acid analogue capable of inhibiting RAGE expression, e.g. an antisense molecule, a ribozyme or a RNA interference molecule, or a small synthetic molecule antagonist of the interaction of HMGB1 with RAGE, preferably of the interaction of the non-acetylated or/and acetylated form of HMGB1 with RAGE, or soluble RAGE (sRAGE). The antibody to RAGE is preferably a monoclonal antibody, more preferably a chimeric or humanized antibody or a recombinant antibody, such as a single chain antibody or an antigen-binding fragment of such an antibody. The soluble RAGE analog may be optionally present as a fusion protein, e.g. with the Fc domain of a human antibody. The small synthetic molecular antagonist of the HMGB1 interaction with RAGE preferably has a molecular weight of less than 1000 Dalton. The small synthetic molecular antagonist preferably inhibits the interaction of RAGE with the non-acetylated form or/and with the acetylated form of HMGB1 and with the non-acetylated form or/and with the acetylated form of HMGB1 homologous proteins, particularly HMGB2, HMGB3, HMG-1L10, HMG-4L or/and SP100-HMG.

The further agent used in combination with the polymer conjugate, may also be an inhibitor of the interaction of a Toll-like receptor (TLR), e.g. of TLR2, TLR4, TLR7, TLR8 or/and TLR9, with HMGB1, which inhibitor is preferably a monoclonal or polyclonal antibody, a nucleic acid or nucleic acid analogue capable of inhibiting TLR expression, e.g. an antisense molecule, a ribozyme or a RNA interference molecule, or a synthetic molecule preferably having a size of less than 1000 Dalton. The inhibitor may be a known inhibitor of a Toll-like receptor, in particular of TLR2, TLR4, TLR7, TLR8 or/and TLR9. The inhibitor preferably inhibits the interaction of the Toll-like receptor with the non-acetylated form or/and the acetylated form of HMGB1 and with the non-acetylated form or/and with the acetylated form of HMGB1 homologous proteins, in particular HMGB2, HMGB3, HMG-1L10, HMG4L or/and SP100-HMG.

In still another embodiment, the further agent is the functional N-terminal lectin-like domain (D1) of thrombomodulin. The D1 domain of thrombomodulin is able to intercept the non-acetylated form and/or the acetylated form of released HMGB1 and of released HMGB1 homologous proteins, in particular HMGB2, HMGB3, HMG-1L10, HMG-4L or/and SP100-HMG, preventing thus their interaction with RAGE and Toll-like receptors. The D1 domain of thrombomodulin may be native or mutated in order to make it resistant to proteases.

The further agent may also be a synthetic double-stranded nucleic acid or nucleic acid analogue molecule with a bent shape structure, particularly a double-stranded bent DNA, PNA or DNA/PNA chimera or hybrid or a double-stranded cruciform DNA, PNA or DNA, PNA chimera or hybrid structure, capable of binding to the HMGB1 protein. Preferred nucleic acids and nucleic analogue molecules are disclosed in a co-owned and co-pending international patent application No. PCT/EP2005/007198 filed on 4 Jul. 2005 (claiming the priority of U.S. provisional application No. 60/584,678 filed on 2 Jul. 2004), which are incorporated herein by reference. The synthetic double-stranded nucleic acid or nucleic acid analogue molecule with a bent shape structure is preferably capable of binding to the non-acetylated or/and to the acetylated form of HMGB1 and the non-acetylated or/and the acetylated form of HMGB1 homologous proteins, in particular HMGB2, HMGB3, HMG-1L10, HMG4L or/and SP100-HMG.

In a still further embodiment, the further agent used in combination with the polymer conjugate is K-252a or/and a salt or derivative thereof or a polymer conjugate of K-252a or/and of a derivative thereof. The use of K-252a or polymer conjugates of K-252a and derivatives thereof is disclosed in a co-owned and co-pending international patent application No. PCT/EP2005/008258 and filed on 25 Aug. 2005, which is herein incorporated by reference.

Therefore, a further aspect of the present invention is a pharmaceutical composition comprising an effective amount of at least one of the polymer conjugates of HMGB1 Box-A polypeptide or polypeptide variant or a biologically active fragment thereof as an active ingredient for the treatment of HMGB1-associated pathologies and pharmaceutically acceptable carriers, diluents and/or adjuvants. The pharmaceutical composition of the present invention is preferably suitable for the treatment of pathologies associated with the non-acetylated or/and the acetylated form of HMGB1 and/or of HMGB1 homologous proteins. In a further preferred embodiment, the pharmaceutical composition of the present invention comprising the at least one polymer conjugate also comprises a further agent as defined above. The pharmaceutical composition of the present invention may be used for diagnostic or for therapeutic applications.

The exact formulation, route of administration and dosage can be chosen by the individual physician in view of the patient's conditions. Administration may be achieved in a single dose or repeated doses at intervals. Dosage amount and interval may be adjusted individually in order to provide the therapeutical effect which results in amelioration of symptoms or a prolongation of the survival in a patient. The actual amount of composition administered will, of course, be dependent on the subject being treated, on the subject's weight, the severity of the affliction, the manner of administration and the judgement of the prescribing physician. A suitable daily dosage will be between 0.001 to 10 mg/kg, particularly 0.1 to 5 mg/kg.

The administration may be carried out by known methods, e.g. by injection, in particular by intravenous, intramuscular, transmucosal, subcutaneous or intraperitoneal injection and/or by oral, topical, nasal, inhalation, aerosol and/or rectal application, etc. The administration may be local or systemic.

In addition, the polymer conjugates of the Box-A of HMGB1 moiety object of this invention can be reversibly immobilized and/or adsorbed on the surface and/or inside medical devices or drug release/vehicling systems (microspheres). Medical devices and microspheres can be reversibly loaded with the polymer conjugates of this invention, through their binding, impregnation and/or adsorption on the surface of the medical device or of the microsphere or on a layer that coats its surface. When the medical device or the microsphere come into contact with biological fluids, the reversibly immobilized polymer conjugate is released. Therefore, the medical device and the microsphere act as drug-releasing tools that elute the molecule object of this invention in such a way that their release kinetics can be controlled, ensuring controlled or sustained release, as required by the treatment. The methods for coating/impregnating the medical devices and loading microspheres are well known by experts in these technologies.

Thus, a further aspect of this invention is the use of the polymer conjugates of Box-A of HMGB1, wherein conjugated molecules are reversibly immobilized on the surface of medical devices or of microspheres or are adsorbed within them. These medical instruments are preferably surgical tools, implants, catheters or stents, for example stents for angioplasty and, in particular, medicated drug-eluting stents.

Another aspect of the invention concerns a medical device reversibly coated with at least one polymer conjugate of the invention. Such a device can be selected from surgical instruments, implants, catheters or stents. Such a device may be useful for angioplasty.

The invention is further illustrated by the following figures:

FIG. 1a displays the amino acid sequence of the native Human HMGB1 Box-A made of 84 amino acid residues (SEQ ID NO:1).

FIG. 1b shows the type of replacing amino acids on the respective target positions selected to generate the polypeptide variant of the full-length human HMGB1 Box-A. Further, the specific amino acid sequences of the generated polypeptide variant are displayed in SEQ ID NOs:2 to 116.

FIG. 2a displays the amino acid sequence of the biologically active fragment of Human HMGB1 Box-A made of 77 amino acid residues (SEQ ID NO:117).

FIG. 2b shows the type of replacing amino acids on the respective target positions selected to generate the polypeptide variant of the biologically active fragment of Human HMGB1 Box-A made of 77 amino acid residues. Further the specific amino acid sequences of the generated polypeptide variant are displayed in SEQ ID NOs: 118 to 222.

FIG. 3a displays the amino acid sequence of the biologically active fragment of Human HMGB1 Box-A made of 54 amino acid residues (SEQ ID NO:223).

FIG. 3b shows the type of replacing amino acids on the respective target positions selected to generate the polypeptide variant of the biologically active fragment of Human HMGB1 Box-A made of 54 amino acid residues. Further, the specific amino acid sequences of the generated polypeptide variant are displayed in SEQ ID NOs: 224 to 300.

FIG. 4a displays the amino acid sequence of the native *Anopheles gambia* HMGB1 Box-A made of 84 amino acid residues (SEQ ID NO:301).

FIG. 4b shows the type of replacing amino acids on the respective target positions selected to generate the polypeptide variant of the full-length *Anopheles gambia* HMGB1 Box-A. Further, the specific amino acid sequences of the generated polypeptide variant are displayed in SEQ ID NOs: 302 to 418.

FIG. 5a displays the amino acid sequence of the biologically active fragment of *Anopheles gambia* HMGB1 Box-A made of 77 amino acid residues (SEQ ID NO:419).

FIG. 5b shows the type of replacing amino acids on the respective target positions selected to generate the polypeptide variant of the biologically active fragment of *Anopheles gambia* HMGB1 Box-A made of 77 amino acid residues. Further the specific amino acid sequences of the generated polypeptide variant are displayed in SEQ ID NOs: 420 to 528.

FIG. 6a displays the amino acid sequence of the biologically active fragment of *Anopheles gambia* HMGB1 Box-A made of 54 amino acid residues (SEQ ID NO:529).

FIG. 6b shows the type of replacing amino acids on the respective target positions selected to generate the polypeptide variant of the biologically active fragment of *Anopheles gambia* HMGB1 Box-A made of 54 amino acid residues. Further, the specific amino acid sequences of the generated polypeptide variant are displayed in SEQ ID NOs: 530 to 610.

Figures and Tables 7.1 to 7.9 show the results of the chemotaxis assay described of Example 1 performed on the HMGB1 Box-A polypeptide variants of SEQ ID NO:2 to SEQ ID NO:116 used as HMGB1 Box-A moiety of the polymer conjugates of the present invention. In each figure the activity of a set of polypeptide variants in the inhibition of HMGB1 induced NIH/3T3 cell migration is tested compared to the activity of human wild-type HMGB1 Box-A full-length fragment of SEQ ID NO:1. Each figure shows a table reporting the statistical analysis numerical data and a column bar graph showing the chemotaxis assay results.

FIG. 7.1 and Table 7.1 show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID NO:2 to 15 (identified in the Table and Figure with the code CT501, CT568, CT569, CT570, CT571, CT502, CT572, CT503, CT573, CT504, CT574, CT575, CT576 and CT505, respectively).

FIG. 7.2 and Table 7.2 show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID NOs:16-23 and 25-29 (identified in the Table and Figure with the code CT577, CT578, CT506, CT579, CT580, CT581, CT507, CT582, CT584, CT508, CT509, CT510 and CT585, respectively).

FIG. 7.3 and Table 7.3 show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:30-35 and 37-43 (identified in the Table and Figure with the code CT511, CT512, CT513, CT514, CT586, CT515, CT516, CT517, CT518, CT519, CT520, CT521 and CT522, respectively).

FIG. 7.4 and Table 7.4 show the bar graph and statistical data of chemotaxis migration assay results in the inhibition of HMGB1-induced NIH/3T3 cells by human HMGB1 Box-A wild type of SEQ ID NOs:44-57 (identified in the Table and Figure with the code CT523, CT524, CT525, CT526, CT527, CT528, CT588, CT529, CT530, CT589, CT590, CT531, CT591 and CT532, respectively).

FIG. 7.5 and Table 7.5 show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:58-67 and 69-71 (identified in the Table and Figure with the code CT592, CT533, CT593, CT534, CT535, CT536, CT537, CT594, CT538, CT539, CT540, CT541 and CT542, respectively).

FIG. 7.6 and Table 7.6 show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:72-85 (identified in the Table and Figure with the code CT596, CT597, CT598, CT599, CT600, CT601, CT602, CT603, CT543, CT544, CT545, CT546, CT547 and CT604, respectively).

FIG. 7.7 and Table 7.7 show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID NOs:86-99 (identified in the Table and Figure with the code CT548, CT549, CT605, CT606, CT607, CT608, CT609, CT610, CT550, CT551, CT611, CT552, CT553 and CT554, respectively).

FIG. 7.8 and Table 7.8 show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:100-113 (identified in the Table and Figure with the code CT555, CT556, CT557, CT558, CT559, CT612, CT560, CT561, CT613, CT562, CT563, CT564, CT565 and CT566, respectively).

FIG. 7.9 and Table 7.9 show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:114-116 (identified in the Table and Figure with the code CT567, CT614 and CT615, respectively).

FIG. 8 shows the image of the Tricine SDS-PAGE gel loaded with human HMGB1 Box-A wild type of SEQ ID NO:1 (CT500) at different timepoints after protease digestion of the protease resistance testing described in Example 2. The Box-A wild type protein tested for protease resistance is a His-tagged protein. After 5 minutes of digestion CT500 shows two major bands, one corresponding to the original protein in the sample and the second corresponding to the 84-aminoacid protein without the N-term His-tag (indicated on the figure with an arrow). The profile of this second band shows resistance to proteases for 30 minutes. Minor bands present on this and other gels of FIG. 9.1 to FIG. 9.67 correspond to Box-A digested fragments.

FIG. 9.1 to FIG. 9.67 show the image of the Tricine SDS-PAGE gel loaded with the polypeptide variants of the HMGB1 Box-A moiety of the polymer conjugates of the present invention at different timepoints after protease digestion of the protease resistance testing described in Example 2. Box-A polypeptide variants tested for protease resistance are Hig-tagged proteins. After 5 minutes of digestion the SDS-PAGE gel image of the polypeptide variants show two major bands, one corresponding to the original protein variant in the sample and the second corresponding to the Box-A 84 amino acid protein variant without the N-term His-tag.

FIG. 9.1 shows the Tricine SDS-PAGE of the polypeptide variant of SEQ ID NO:2 (CT501) at different timepoints after protease digestion.

FIG. 9.2 shows the Tricine SDS-PAGE of the polypeptide variant of SEQ ID NO:7 (CT502) at different timepoints after protease digestion.

FIG. 9.3 shows the Tricine SDS-PAGE of the polypeptide variant of SEQ ID NO:9 (CT503) at different timepoints after protease digestion.

FIG. 9.4 shows the Tricine SDS-PAGE of the polypeptide variant of SEQ ID NO:11 (CT504) at different timepoints after protease digestion.

FIG. 9.5 shows the Tricine SDS-PAGE of the polypeptide variant of SEQ ID NO:15 (CT505) at different timepoints after protease digestion.

FIG. 9.6 shows the Tricine SDS-PAGE of the polypeptide variant of SEQ ID NO:18 (CT506) at different timepoints after protease digestion.

FIG. 9.7: Tricine SDS-PAGE of the polypeptide variant of SEQ ID NO:22 (CT507) at different timepoints after protease digestion.

FIG. 9.8 shows the Tricine SDS-PAGE of the polypeptide variant of SEQ ID NO:26 (CT508) at different timepoints after protease digestion.

FIG. 9.9 shows the Tricine SDS-PAGE of the polypeptide variant of SEQ ID NO:27 (CT509) at different timepoints after protease digestion.

FIG. 9.10 shows the Tricine SDS-PAGE of the polypeptide variant of SEQ ID NO:28 (CT510) at different timepoints after protease digestion.

FIG. 9.11 shows the Tricine SDS-PAGE of the polypeptide variant of SEQ ID NO:30 (CT511) at different timepoints after protease digestion.

FIG. 9.12 shows the Tricine SDS-PAGE of the polypeptide variant of SEQ ID NO:31 (CT512) at different timepoints after protease digestion.

FIG. 9.13 shows the Tricine SDS-PAGE of the polypeptide variant of SEQ ID NO:32 (CT513) at different timepoints after protease digestion.

FIG. 9.14 shows the Tricine SDS-PAGE of the polypeptide variant of SEQ ID NO:33 (CT514) at different timepoints after protease digestion.

FIG. 9.15 shows the Tricine SDS-PAGE of the polypeptide variant of SEQ ID NO:35 (CT515) at different timepoints after protease digestion.

FIG. 9.16 shows the Tricine SDS-PAGE of the polypeptide variant of SEQ ID NO:37 (CT516) at different timepoints after protease digestion.

FIG. 9.17 shows the Tricine SDS-PAGE of the polypeptide variant of SEQ ID NO:38 (CT517) at different timepoints after protease digestion.

FIG. 9.18 shows the Tricine SDS-PAGE of the polypeptide variant of SEQ ID NO:39 (CT518) at different timepoints after protease digestion.

FIG. 9.19 shows the Tricine SDS-PAGE of the polypeptide variant of SEQ ID NO:40 (CT519) at different timepoints after protease digestion.

FIG. 9.20 shows the Tricine SDS-PAGE of the polypeptide variant of SEQ ID NO:41 (CT520) at different timepoints after protease digestion.

FIG. 9.21 shows the Tricine SDS-PAGE of the polypeptide variant of SEQ ID NO:42 (CT521) at different timepoints after protease digestion.

FIG. 9.22 shows the Tricine SDS-PAGE of the polypeptide variant of SEQ ID NO:43 (CT522) at different timepoints after protease digestion.

FIG. 9.23 shows the Tricine SDS-PAGE of the polypeptide variant of SEQ ID NO:44 (CT523) at different timepoints after protease digestion.

FIG. 9.24 shows the Tricine SDS-PAGE of the polypeptide variant of SEQ ID NO:45 (CT524) at different timepoints after protease digestion.

FIG. 9.25 shows the Tricine SDS-PAGE of the polypeptide variant of SEQ ID NO:46 (CT525) at different timepoints after protease digestion.

FIG. 9.26 shows the Tricine SDS-PAGE of the polypeptide variant of SEQ ID NO:47 (CT526) at different timepoints after protease digestion.

FIG. 9.27 shows the Tricine SDS-PAGE of the polypeptide variant of SEQ ID NO:48 (CT527) at different timepoints after protease digestion.

FIG. 9.28 shows the Tricine SDS-PAGE of the polypeptide variant of SEQ ID NO:49 (CT528) at different timepoints after protease digestion.

FIG. 9.29 shows the Tricine SDS-PAGE of the polypeptide variant of SEQ ID NO:51 (CT529) at different timepoints after protease digestion.

FIG. 9.30 shows the Tricine SDS-PAGE of the polypeptide variant of SEQ ID NO:52 (CT530) at different timepoints after protease digestion.

FIG. 9.31 shows the Tricine SDS-PAGE of the polypeptide variant of SEQ ID NO:55 (CT531) at different timepoints after protease digestion.

FIG. 9.32 shows the Tricine SDS-PAGE of the polypeptide variant of SEQ ID NO:57 (CT532) at different timepoints after protease digestion.

FIG. 9.33 shows the Tricine SDS-PAGE of the polypeptide variant of SEQ ID NO:59 (CT533) at different timepoints after protease digestion.

FIG. 9.34 shows the Tricine SDS-PAGE of the polypeptide variant of SEQ ID NO:61 (CT534) at different timepoints after protease digestion.

FIG. 9.35 shows the Tricine SDS-PAGE of the polypeptide variant of SEQ ID NO:62 (CT535) at different timepoints after protease digestion.

FIG. 9.36 shows the Tricine SDS-PAGE of the polypeptide variant of SEQ ID NO:63 (CT536) at different timepoints after protease digestion.

FIG. 9.37 shows the Tricine SDS-PAGE of the polypeptide variant of SEQ ID NO:64 (CT537) at different timepoints after protease digestion.

FIG. 9.38 shows the Tricine SDS-PAGE of the polypeptide variant of SEQ ID NO:66 (CT538) at different timepoints after protease digestion.

FIG. 9.39 shows the Tricine SDS-PAGE of the polypeptide variant of SEQ ID NO:67 (CT539) at different timepoints after protease digestion.

FIG. 9.40 shows the Tricine SDS-PAGE of the polypeptide variant of SEQ ID NO:69 (CT540) at different timepoints after protease digestion.

FIG. 9.41 shows the Tricine SDS-PAGE of the polypeptide variant of SEQ ID NO:70 (CT541) at different timepoints after protease digestion.

FIG. 9.42 shows the Tricine SDS-PAGE of the polypeptide variant of SEQ ID NO:71 (CT542) at different timepoints after protease digestion.

FIG. 9.43 shows the Tricine SDS-PAGE of the polypeptide variant of SEQ ID NO:80 (CT543) at different timepoints after protease digestion.

FIG. 9.44 shows the Tricine SDS-PAGE of the polypeptide variant of SEQ ID NO:81 (CT544) at different timepoints after protease digestion.

FIG. 9.45 shows the Tricine SDS-PAGE of the polypeptide variant of SEQ ID NO:82 (CT545) at different timepoints after protease digestion.

FIG. 9.46 shows the Tricine SDS-PAGE of the polypeptide variant of SEQ ID NO:83 (CT546) at different timepoints after protease digestion.

FIG. 9.47 shows the Tricine SDS-PAGE of the polypeptide variant of SEQ ID NO:84 (CT547) at different timepoints after protease digestion.

FIG. 9.48 shows the Tricine SDS-PAGE of the polypeptide variant of SEQ ID NO:86 (CT548) at different timepoints after protease digestion.

FIG. 9.49 shows the Tricine SDS-PAGE of the polypeptide variant of SEQ ID NO:87 (CT549) at different timepoints after protease digestion.

FIG. 9.50 shows the Tricine SDS-PAGE of the polypeptide variant of SEQ ID NO:94 (CT550) at different timepoints after protease digestion.

FIG. 9.51 shows the Tricine SDS-PAGE of the polypeptide variant of SEQ ID NO:95 (CT551) at different timepoints after protease digestion.

FIG. 9.52 shows the Tricine SDS-PAGE of the polypeptide variant of SEQ ID NO:97 (CT552) at different timepoints after protease digestion.

FIG. 9.53 shows the Tricine SDS-PAGE of the polypeptide variant of SEQ ID NO:98 (CT553) at different timepoints after protease digestion.

FIG. 9.54 shows the Tricine SDS-PAGE of the polypeptide variant of SEQ ID NO:99 (CT554) at different timepoints after protease digestion.

FIG. 9.55 shows the Tricine SDS-PAGE of the polypeptide variant of SEQ ID NO:100 (CT555) at different timepoints after protease digestion.

FIG. 9.56 shows the Tricine SDS-PAGE of the polypeptide variant of SEQ ID NO:101 (CT556) at different timepoints after protease digestion.

FIG. 9.57 shows the Tricine SDS-PAGE of the polypeptide variant of SEQ ID NO:102 (CT557) at different timepoints after protease digestion.

FIG. 9.58 shows the Tricine SDS-PAGE of the polypeptide variant of SEQ ID NO:103 (CT558) at different timepoints after protease digestion.

FIG. 9.59 shows the Tricine SDS-PAGE of the polypeptide variant of SEQ ID NO:104 (CT559) at different timepoints after protease digestion.

FIG. 9.60 shows the Tricine SDS-PAGE of the polypeptide variant of SEQ ID NO:106 (CT560) at different timepoints after protease digestion.

FIG. 9.61 shows the Tricine SDS-PAGE of the polypeptide variant of SEQ ID NO:107 (CT561) at different timepoints after protease digestion. ID NO:106 (CT560) at different timepoints after protease digestion.

FIG. 9.61 shows the Tricine SDS-PAGE of the polypeptide variant of SEQ ID NO:107 (CT561) at different timepoints after protease digestion.

FIG. 9.62 shows the Tricine SDS-PAGE of the polypeptide variant of SEQ ID NO:109 (CT562) at different timepoints after protease digestion.

FIG. 9.63 shows the Tricine SDS-PAGE of the polypeptide variant of SEQ ID NO:110 (CT563) at different timepoints after protease digestion.

FIG. 9.64 shows the Tricine SDS-PAGE of the polypeptide variant of SEQ ID NO:111 (CT564) at different timepoints after protease digestion.

FIG. 9.65 shows the Tricine SDS-PAGE of the polypeptide variant of SEQ ID) NO:112 (CT565) at different timepoints after protease digestion.

FIG. 9.66 shows the Tricine SDS-PAGE of the polypeptide variant of SEQ ID NO:113 (CT566) at different timepoints after protease digestion.

FIG. 9.67 shows the Tricine SDS-PAGE of the polypeptide variant of SEQ ID NO:19 (CT567) at different timepoints after protease digestion.

FIG. 10 shows a table in which the results of the Tricine SDS-PAGE are summarized. A cross indicates the presence on the gel of the band corresponding to the 84 amino acid long protein fragment of the HMGB1 Box-A wild-type or of the HMGB1 Box-A polypeptide variant.

EXAMPLES

Figure 11:
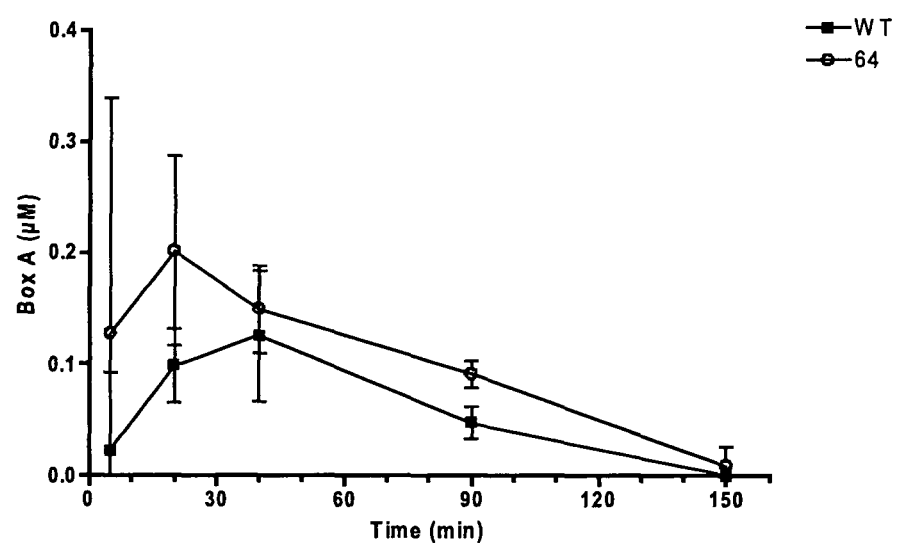
FIG. 11 shows the mean plasma concentration/time after a single subcutaneous administration of Box A wild type (WT) and Box A variant number 64 (64) at a dosage of 1 mg/kg. Data representation: Mean±SEM.

1. In Vitro Activity Testing: NIH/373 Cell Migration Assay

The purpose of the present study was to evaluate the activity of each of the HMGB1 Box-A polypeptide variants as defined in SEQ ID NOs:2-116 and to compare their activity to that of human wild type HMGB1 Box-A full-length fragment of SEQ ID NO:1 in order to select all the variants with similar or better activity than wild type.

HMGB1 Box-A activity is evaluated in vitro as inhibition of HMGB1-induced NIH/3T3 cells migration.

1.1 Materials

HMGB1 Box-A wild type and variants (Nautilus Biotech)
NIH/3T3 cells (ATCC n. CRL-1658)
D-MEM medium (GIBCO; cat. n. 31966-021)
Foetal Bovine Serum (GIBCO; cat. n. 10270-106)
Penicillin-Streptomycin 10,000 U/ml (GIBCO; cat. n. 15140-122)
L-Glutamine 200 mM (GIBCO; cat. n. 25030-024)
TrypLE Select (GIBCO; cat. n. 12563-011)
Phosphate Buffered Saline (0.138 M NaCl, 0.0027 M KCl, 0.01 M phosphate, pH 7.4)
PVP free filters (8 μm pore size; 13 mm total diameter) (Neuro Probe; cat. n. PFA8)
Human fibronectin (Roche; cat. n. 1080938)
Blind Well Chemotaxis Chambers (Neuro Probe; cat. n. BW25)
GIEMSA Stain Modified (Sigma; cat. n. GS1L)

1.2 Filters Preparation

Polycarbonate membranes PVP free filters (8 μm pore size, 13 mm total diameter) are prepared about one hour before performing the experiment by coating them with 30 μl/filter of a solution 50 μg/ml of fibronectin dispensed on the opaque side of the filter. The stock fibronectin solution is prepared by diluting the lyophilized fibronectin in ddH$_2$O to a final concentration of 1 mg/ml and by keeping the solution about 1 hour at 37° C. for complete dissolution. This stock solution can be stored at −20° C.

The filters are then left to dry under the laminar flux of the hood (about one hour).

1.3 Cells Preparation

NIH/3T3 cells are seeded the day before the experiment (approximately 22-24 hours before performing the experiment) $10^6$ cells/plate.

When the filters are ready to use, the cells are detached with Trypsin, counted and resuspended $10^6$ cells/ml in serum free culture medium.

1.4 Chemotaxis Assay

In each chemotaxis experiment 14 different polypeptide variants of the human HMGB1 Box-A full-length fragment of SEQ ID NO:1 are tested.

Growth cell medium without serum addition (w/o FBS) is used as negative control representing spontaneous migration.

1 nM HMGB1 is used as positive control. HMGB1 Box-A wild type or the tested polypeptide variants 0.5/1 nM are added to 1 nM HMGB1 to inhibit HMGB1-induced NIH/3T3 cell migration.

Negative control (w/o FBS) and positive control (1 nM HMGB1) are tested in triplicate in each experiment.

HMGB1 Box-A wild type (SEQ ID NO:1) activity in inhibiting HMGB1-induced cell migration is tested in triplicate in each experiment.

Each of the HMGB1 Box-A polypeptide variants (SEQ ID NOs:2 to 116) is tested in duplicate.

Blind Well Chemotaxis Chambers are used. The clean, dry lower well of each chamber is filled with 50 μl of DMEM without FBS added with the appropriate chemotactic agent 2and inhibitors. A slight positive meniscus should form when the well is filled; this helps prevent air bubbles from being trapped when the filter is applied. With small forceps the filter is placed over the filled well (fibronectin treated side up), being careful not to trap air bubbles and not to touch the filter with fingers. The filter retainer is screwed in by hand. Cell suspension (50000 cells/50 μl) is pipetted into the upper well and 150 μl of serum free medium are added to fill the upper well of the chamber. The filled chamber is incubated for 3 hours (37° C., 5% $CO_2$) to allow cell migration. After incubation the fluid is removed from the filter. The retainer is unscrewed and immersed in cool distilled water. The filter is lifted out with forceps, placed on a clean surface (solid paraffin) (migrated cells side up) and fixed with a needle (placed on the border area).

1.5 GIEMSA Staining of Migrated Cells

The filters are fixed with ethanol once and then washed three times under running water. A working solution of GIEMSA Stain Modified diluted 1:10 in dd$H_2O$ is prepared just before use. After washing of the filters, the staining is added and left to incubate for 20 minutes. Washing of the staining is performed under running water. The filters are then placed on slides with the migrated cells side down, and the non-migrated cells side is gently wiped off with a wet cotton swab (wipe twice, using two swabs or both ends of a double-tipped swab) being careful not to move the filter. After cleaning, a cover slide is placed on the filter and cells are counted under a microscope at 40× in 10 random fields/filter.

1.6 Data Representation and Statistical Analysis

The results of the NIH/3T3 migration assay performed are reported in the tables and bar graphs shown in Figure and Table 7.1 to Figure and Table 7.9.

Data are represented in bar columns as MEAN±95% Cl.

One-way ANOVA followed by Dunnett's post test (control column data: 1 nM HMGB1 sample+HMGB1 Box-A WT sample) is the statistical analysis performed.

When evaluating the results data, HMGB1 Box-A variants data having a post test p value<0.05 are considered significantly different from HMGB1 Box-A wild type. If the mean of the Box-A polypeptide variant is higher than that of Box-A wild type the column is coloured in red in the graph of the experiment shown in FIGS. 7.1 to 7.9. Those red columns represent HMGB1 Box-A polypeptide variants showing less activity than wild type in inhibiting HMGB1-induced cell migration.

If the mean of the polypeptide variant results lower than that of wild type Box-A then the column is coloured in light blue in the graph of the experiment shown in FIGS. 7.1 to 7.9. Those variants represent HMGB1 Box-A variants showing higher activity than HMGB1 Box-A wild type in inhibiting HMGB1-induced cell migration.

HMGB1 Box-A variants data having a post test p value>0.05 are considered not significantly different from HMGB1 Box-A wild type. The bar column of those variants are coloured in green. Those variants represent HMGB1 Box-A variants showing the same activity of wild type in inhibiting HMGB1-induced cell migration.

1.7 Results

The activity of polypeptide variants of the human HMGB1 high affinity binding domain Box-A of SEQ ID NOs:2 to 116 was evaluated in comparison to human HMGB1 Box-A wild-type of SEQ ID NO:1 as inhibition of HMGB1-induced cell migration, in order to determine the preferred polypeptide variants useful as HMGB1 Box-A moiety of the preferred polymer conjugate of the present invention.

The chemotaxis assays results revealed (FIGS. 7.1 to 7.9) that for 26 polypeptide variants the mutation according to the present invention could lead to a higher activity in cell migration inhibition in comparison with the activity of the wild-type human HMGB1 Box-A. In particular, a higher activity in cell migration inhibition was shown for the polypeptide variants of SEQ ID NOs: 30-32, 35, 38, 40-41, 43, 48, 51, 57, 63-64, 69, 70, 94, 95, 100, 103-104, 106-107, 109-111 and 113.

Moreover, the chemotaxis assays results revealed (FIGS. 7.1 to 7.9) that 41 polypeptide variants showed no changes in their activity in inhibiting HMGB1-induced cell migration compared to the activity of Box-A wild-type polypeptide. In particular, this is the case for the polypeptide variants of SEQ ID NOs: 2, 7, 9, 11, 15, 18, 22, 26-28, 33, 37, 39, 42, 44-47, 49, 52, 55, 59, 61, 62, 66-67, 71, 80-84, 86-87, 97-99, 101-102, 112 and 114.

All these Box-A polypeptide variants which exhibit a similar or a higher activity than the Box-A wild-type were tested for in vitro protease resistance, in order to choose the most resistant ones that are at least as active as Box-A wild-type (see protease resistance test in Example 2).

2. In Vitro Protease Resistance Testing

The purpose of the present study was to evaluate the in vitro protease resistance of to HMGB1 Box-A variants shown in Example 1 and to compare it to that of wild type HMGB1 Box-A of SEQ ID NO:1 in order to identify the variants with improved protease resistance with respect to wild type polypeptide.

2.1 Materials

HMGB1 His-tagged Box-A wild type and selected variants (Nautilus biotech)

Trypsin (Sigma; cat. n. T8658; lot.n. 045K5113)

α-chymotrypsin (Sigma; cat. n. C6423; lot.n. 109H74858),

Endoproteinase Asp-N (Sigma; cat. n. P3303; lot.n. 046K1049)

Endoproteinase Glu-C (Sigma; cat. n. P6181; lot.n. 075K5100)

Complete, Mini EDTA-free protease inhibitor cocktail (Roche; cat. n. 11836170 001)

Trizma base (Sigma; cat. n. T6066)

Acrylamide/bis solution 40% in water (Sigma; cat.n. 01709)

SDS (Sigma; cat. n. 71729)

Glycerol 99% (Sigma; cat. n. G9012)

Temed (Sigma; cat. n. 87689)

APS (Sigma; cat. n. A 3678)

polypeptide SDS-PAGE Molecular Weight Standards (Bio-Rad; cat. n. 161-0326)

Premixed 10× Tris/tricine/SDS Buffer (Bio-Rad; cat. n. 161-0744)

β-Mercaptoethanol (Sigma; cat. n. M7154)

Methanol (VWR; cat. n. 20864.320)

Acetic acid (VWR; cat. n. 20104.323)

Brilliant Blue R (Sigma; cat. n. B0149)

Bromophenol Blue (Sigma; cat. n. B0126)

Hydrochloric acid (Merck; cat. n. 1.00319.2511)

3× sample loading buffer for Tricine gels (composition: 150 mM Tris-HCl, pH 6.8; 12% SDS; 36% glycerol; 6% β-Mercaptoethanol; 0.04% of bromophenol blue)

2.2. Protease Mixture Preparation

A mixture of proteases containing trypsine, α-chymotrypsine, endoproteinase Asp-N and endoproteinase Glu-C is used.

Table 1 reports specificity of each of the proteases used in this study.

TABLE 1 protease specificity.

| Protease | Specificity |
| --- | --- |
| Trypsin | C-term of K, R (not if P at C-term of cutting site; slower digestion if acidic residue on either side of cutting site) |
| α-chymotrypsin | C-term of T, P, W, L (secondary hydrolysis: C-term of M, I, S, T, V, H, G, A) |
| Endoproteinase Asp-N | N-term of D, C |
| Endoproteinase Glu | C-term of E, D (not if P is at C-term of cutting site) |

Each lyophilized protease is dissolved according to manufacturer recommendations to obtain a stock solution that is aliquoted and stored at −80° C.

100 µg of trypsin are dissolved in 100 µl of $dH_2O$ to obtain a 1 µg/µl stock solution. 25 µg of α-chymotrypsine are dissolved in 50 µl of a solution 1 mM HCl, 2 mM $CaCl_2$ to obtain a 0.5 µg/µl stock solution. 2 µg of endoproteinase Asp-N are dissolved in 50 µl of $dH_2O$ to obtain a 0.04 µg/µl stock solution. 25 µg of endoproteinase Glu-C are dissolved in 50 µl of $dH_2O$ to obtain a 0.5 µg/µl stock solution.

Before performing the experiment one aliquot of each protease stock solution is left to thaw on ice.

Trypsin and endoproteinase Glu-C stock aliquots are diluted in $dH_2O$ to obtain a final working solution of 0.1 µg/µl. α-chymotrypsine stock aliquot is diluted in a solution 1 mM HCl, 2 mM $CaCl_2$ to obtain a final 0.1 µg/µl working solution. Endoproteinase Asp-N aliquot is used without dilution.

Just before performing the experiment a mixture of proteases containing 1% (in weight/weight of total Box-A contained in the sample) of each protease is freshly prepared and immediately added to HMGB1 Box-A to be digested.

2.3. HMGB1 Box-A Wild Type and Variants Protease Digestion

18 µg total of each HMGB1 Box-A (wild type or variants) are digested in each experiment.

HMGB1 Box-A to be tested is left to thaw on ice and the volume corresponding to 18 µg is taken. The volume of this solution is then brought with $dH_2O$ to a final volume of 90 µl in order to obtain the same final volume for each HMGB1 Box-A to be tested.

10 µl of this solution (corresponding to 2 µg of HMGB1 Box-A) are taken before adding the protease mixture. This sample corresponds to "time 0" not digested sample.

The remaining sample (16 µg of HMGB1 Box-A) is added with 8.8 µl (corresponding to 0.16 µg of each protease of the freshly prepared mixture; see 2.2) of protease mixture for digestion.

Protease digestion is performed at 25° C. and a volume corresponding to 2 µg of HMGB1 Box-A (originally present in the mixture) is sampled at defined time points. Digestion is stopped adding 4 µl of a solution of complete Mini EDTA-free protease inhibitor cocktail (1 tablet dissolved in 10 ml of $dH_2O$).

Timepoints for sampling are: 0, 5 minutes, 15 minutes, 30 minutes, 1 hour, 1.5 hours, 2 hours and 4 hours.

Soon after protease inhibition, samples are added with the appropriate amount of sample loading buffer 3× and incubated at 95° C. for about 3 minutes.

2.4. Tricine SDS-PAGE of Digested HMGB1 Box-A Wild Type and Variants

After protease digestion and samples preparation, time-points samples of each HMGB1 Box-A are loaded on a Tricine SDS PAGE gel (see for references: Schägger and von Jagow, "Tricine-sodium dodecyl sulphate-polyacrylamide gel electrophoresis for the separation of proteins in the range from 1 to 100 kDa", Anal. Biochem. 166, 368-379, 1987).

5 µl of Polypeptide SDS-PAGE Molecular Weight Standards (Bio-Rad) are loaded for reference on each gel.

Each well of the gel is loaded with 10 µl of sample (volume corresponding to 1 µg of HMGB1 Box-A before digestion).

Electrophoresis is performed at 30 V until the bromophenol blue has entered the separating portion of the gel, then at 120 V (Mini Protean 3 System; Bio-Rad) till the end of the run.

Gels are stained by soaking in a Coomassie Brilliant Blue R staining solution (0.1% w/v in 50% methanol, 10% acetic acid) for 1 hour and destained overnight in destaining solution (30% methanol, 10% acetic acid).

Gel images are acquired with Gel Doc 2000 (Bio-Rad) imaging system.

2.5 Results

In the above reported assay conditions HGMB1 wild-type protein resisted approximately 30 minutes to complete protease digestion. In FIG. 8 the band corresponding to the 84-amino acid full-length fragment of human HMGB1 Box-A wild-type of SEQ ID NO:1 protein is visible until 30 minutes of protease digestion.

21 Box-A polypeptide variants tested showed an increased resistance to protease (FIG. 10). In the reported assay conditions these variants resist from 1 hour to 2 hours to protease digestion. The polypeptide variants of SEQ ID NOs: 33, 35, 37, 38, 39, 42, 43, 44, 47, 48, 57, 62, 69 and 104 showed a resistance of 1 hour to protease digestion. FIGS. 9.14, 9.15, 9.16, 9.17, 9.18, 9.21, 9.22, 9.23, 9.26, 9.27, 9.32, 9.35, 9.40 and 9.59 show a band corresponding to the not His-tagged protein of 84 amino acids which is visible until 1 hour of protease digestion.

The polypeptide variants of SEQ ID NOs: 45, 49, 52, 55 and 67 showed a resistance of 1.5 hours to protease digestion. FIGS. 9.24, 9.28, 9.30, 9.31 and 9.39 show a band corresponding to the not His-tagged protein of 84 amino acids which is clearly visible 1 hour and a half after protease digestion. The polypeptide variants of SEQ ID NOs: 59 and 64 even show a resistance of up to 2 hours to protease digestion. FIGS. 9.33 and 9.37 show a band of the not His-tagged protein of 84 amino acids which is clearly visible until 2 hours after protease digestion.

3. Pharmacokinetic Study of Box A (Wild Type and Variants) and Pegylated Box a (Wild Type and Variants) after Single Subcutaneous Administration in Mice 3.1. Aim of the Study The purpose of the study was to evaluate and to compare the pharmacokinetic profile of Box A (wild type and variants) and PEGylated Box A (wild type and variants) following a single subcutaneous administration of the compounds in mice.

3.2. Materials and Methods

Test articles: Box A wild type and variants and the corresponding PEGylated molecules. PEGylated molecules were obtained reacting linear mPEG-aldehyde (40 kDa) with the N-terminus of the respective Box A molecule by reductive amination.

3.3 In Vivo Experiment

Animals: mice (Balb/c, males, 7-9 weeks old, supplied by Charles River Laboratories Italia SpA, Calco one week before the experiment) with an average body weight of 22.2-22.4 g at the moment of the experiment.

Animal husbandry: the animals were housed in a ventilated thermostatic container set to maintain temperature and relative humidity at 22° C.±2° C. and 55±15% respectively, with 12 hours light/dark cycle. Mice were housed up to 10 to a cage, in clear polycarbonate cages (Techniplast, Buguggiate, Italy); drinking water via water bottles and a commercially available laboratory rodent diet (4RF21, Mucedola s.r.l., Settimo Milanese, Italy) were supplied ad libitum.

Experimental groups: 4 (four test items), 20 animals/group, randomly grouped.

Administered dose: Box A wild type and variants were administered 1 mg/kg subcutaneously. PEGylated Box A wild type and variants were administered 5 mg/kg subcutaneously. These doses ensured equimolarity of test compounds.

Administration of the test items: test items were administered subcutaneously by using an insulin syringe fitted with a 0.45×12 mm (26G×½") needle at a volume of 0.25 mL/mouse (10 mL/kg body weight).

Test article formulation: Phosphate Buffer Saline solution

Animal Sacrifice and Blood Collection:

Blood samples were collected at the following time points after treatment:

Box A wild type and variants: 5, 20 and 40 minutes, 1.5 and 2.5 hours after administration of the test compounds;

PEGylated Box A wild type and variants: 5, 40 minutes, 1.5, 5 and 10 hours after administration of the test compounds.

Different timepoints for blood sample collection between test compounds were decided on the basis of longer expected permanence of PEGylated molecules in the bloodstream.

At each sampling time, approximately 0.4 mL blood samples were collected from the ventral aorta of each animal using an insulin syringe, under deep ether anesthesia, and transferred into polyethylene Eppendorf tubes containing 5 µL heparin (5000 UI/mL) to prevent blood clotting. Blood samples were kept in ice until centrifugation at 1400 g for 5 min. in a refrigerated centrifuge (2-4° C.). From each tube plasma samples were then recovered, put in new Eppendorf tubes and frozen at −80° C. until analysis.

3.4 Analytical Determination

Box A (wild type and variants) and PEGylated Box A (wild type and variants) plasma concentrations were determined in mouse plasma by an ELISA method.

Briefly, a coating solution was prepared by diluting a monoclonal antibody against the N-terminal of Box A to 10 ng/ml in 100 mM carbonate-bicarbonate coating buffer. 100 µL were aliquoted to every well of a Nunc Maxisorp ELISA plate, which was incubated overnight at 4° C. The plate was washed with PBS 0.05% Tween for 6 times and 300 µL of 5% milk in PBS 1% Tween were added to each well to block the remaining binding sites on the plate. The plate was incubated for 1 hour at room temperature at 300 rpm. Samples were diluted 1:20 in PBS 1% Tween.

rpm. Samples were diluted 1:20 in PBS 1% Tween.

The plate was washed 6-fold and 100 µL of standards and diluted samples were transferred to the designated wells of the coated plate and incubated at room temperature for 1 hour at 300 rpm. The plate was washed 6-fold again prior to the addition of the secondary antibody against the C-Terminal of Box A (1:200). After 1 hour of incubation and 6 washes, the biotin-goat anti-rabbit conjugate 1:20000 solution was added to every well (100 µL/well). After 1 hour of incubation (at room temperature, 300 rpm) and six washes, the plate was incubated with 100 µl/well of the streptavidin-HRP solution 1:100000 for 25 minutes at 300 rpm. The plate was washed 6 times and 100 µl of pre-warmed TMB substrate were added to each well. The signal was developed at room temperature on the bench top and, after 30 minutes, 100 µL/well of Stop Solution were added and the plate was immediately read at 450 nm.

3.5 Results

Figure 12:
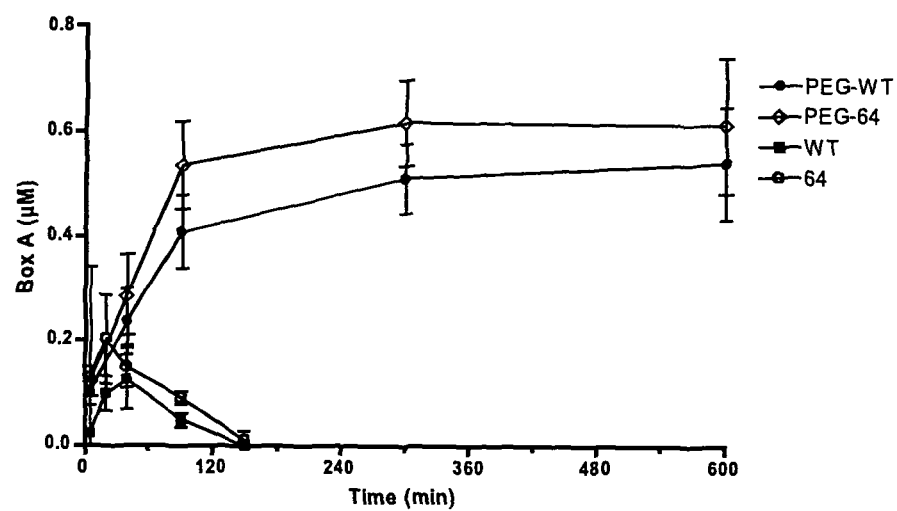
FIG. 12 shows the mean plasma concentration/time after a single subcutaneous administration of Box A wild type (WT) and Box A variant number 64 (64) at a dosage of: 1 mg/kg and of PEGylated Box A wild type (PEG-WT) and PEGylated Box A variant number 64 (PEG-64) at a dosage of 5 mg/kg. Data representation: Mean±SEM.

Mean plasma concentrations of Box A (wild type and variants) and PEGylated Box A (wild type and variants) were calculated for each of the previously described PK samples and the pharmacokinetic profile determined. The results are shown in FIGS. 11 and 12.

As example, here below are reported the PK profiles of Box A wild type and variant n. 64 (M51I) and of PEGylated Box A and PEGylated Box A variant number 64 (M51I). The results are reported as mean values±error (SEM) (4 mice for each time point, analysis in duplicate).

In the following table, the calculated $AUC_{last}$ (Area Under the Curve calculated at the last experimental point) for Box A wild type, Box A variant number 64, PEGylated Box A wild type and PEGylated Box A variant number 64 curves are reported.

TABLE 2

Calculated $AUC_{last}$ data for Box A wild type (WT), Box A variant number 64 (64), PEGylated Box A wild type (WT) and PEGylated Box A variant number 64 (PEG-64) curves.

| | $AUC_{last}$ (µM*min) |
|---|---|
| WT | 8.899 |
| 64 | 14.97 |
| PEG-WT | 275.5 |
| PEG-64 | 332.5 |

3.6 Discussion

The relative gain in $AUC_{last}$ conferred to WT by the mutation is 1.68X (WT vs. 64), most likely due to the higher protease resistance in the sub cute compartment. The relative gain in $AUC_{last}$ conferred to WT by PEGylation is 31X (WT vs. PEG-WT), mainly due to impaired renal filtration of the PEG conjugate, but also to protection from protease action. Putting together mutation and PEGylation yields a relative gain in $AUC_{last}$ of 37X (WT vs. PEG-64). Unexpectedly, the two modifications together have a positive effect on animal exposure to the protein that is superior to the sum of the contributions of the single modifications (i.e., 37X>1.68X+31X). Thus, single point mutation and PEGylation have a synergistic, cooperative effect on the pharmacokinetic profile of the native protein. A possible explanation of this phenomenon could be that PEGylated proteins are not completely protected from proteolysis in the sub cute compartment. The introduction of a single point mutation gives a boost to resistance in this compartment, allowing higher quantities of protein to enter blood circulation and to be then protected from renal filtration by the bulky PEG chain.

The invention claimed is:

1. A polymer conjugate comprising a polypeptide variant of the human and/or non human HMGB1 high affinity binding domain Box-A (HMGB1 Box-A) or of a biologically active fragment of HMGB1 Box-A, whereby the amino acid sequence of said polypeptide variant differs from the amino acid sequence of the wild type HMGB1 Box-A by the mutation of one or more single amino acid, wherein the polypeptide variant of the human HMGB1 Box-A is selected from the group consisting of amino acid sequences defined by SEQ ID NO: 35, 43, 57, 64, 69, and 104, and at least one linear or branched polymer moiety selected from the group consisting of polyalkylene glycol, polyalkylene oxide, polyacrylic acid, polyacrylate, polyacrylamide, N-alkyl polyacrylate derivatives, polymethacrylic acid, polymethacrylate, polyethylacrylic acid, polyethylacrylate, polyvinylpyrrolidone, poly (vinylalcohol), polyglycolic acid, polyactic acid, poly(lactic-co-glycolic) acid, dextran, chitosan and polyaminoacid.

2. The polymer conjugate of claim 1, wherein the amino acid sequence of said polypeptide variant of the human HMGB1 Box-A is defined by SEQ ID NO:64.

3. The polymer conjugate of claim 1, wherein the polymer is a linear or branched polymer moeity selected from polyethylene glycol (PEG) or methoxy polyethylene glycol (m-PEG).

4. A composition comprising the polymer conjugate of claim 1 as an active agent and a pharmaceutically acceptable carrier, adjuvant, diluent or additive.

5. The composition of claim 4, wherein the polymer conjugate is in combination with at least one further agent.

6. A medical device comprising surfaces, wherein the conjugate of claim 1 is reversibly immobilized on at least one of said surfaces.

* * * * *

SEQUENCE LISTING

<160> NUMBER OF SEQ ID NOS: 610

<210> SEQ ID NO 1
<211> LENGTH: 84
<212> TYPE: PRT
<213> ORGANISM: Homo sapiens

<400> SEQUENCE: 1

Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
            20                  25                  30
Ala Ser Val Asn Phe Ser Glu Phe Ser Lys Lys Cys Ser Glu Arg Trp
        35                  40                  45
Lys Thr Met Ser Ala Lys Glu Lys Gly Lys Phe Glu Asp Met Ala Lys
    50                  55                  60
Ala Asp Lys Ala Arg Tyr Glu Arg Glu Met Lys Thr Tyr Ile Pro Pro
65                  70                  75                  80
Lys Gly Glu Thr

<210> SEQ ID NO 2
<211> LENGTH: 84
<212> TYPE: PRT
<213> ORGANISM: Homo sapiens

<400> SEQUENCE: 2

Gly Asn Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
            20                  25                  30
Ala Ser Val Asn Phe Ser Glu Phe Ser Lys Lys Cys Ser Glu Arg Trp
        35                  40                  45
Lys Thr Met Ser Ala Lys Glu Lys Gly Lys Phe Glu Asp Met Ala Lys
    50                  55                  60
Ala Asp Lys Ala Arg Tyr Glu Arg Glu Met Lys Thr Tyr Ile Pro Pro
65                  70                  75                  80
Lys Gly Glu Thr

<210> SEQ ID NO 3
<211> LENGTH: 84
<212> TYPE: PRT
<213> ORGANISM: Homo sapiens

<400> SEQUENCE: 3

Gly Gln Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
            20                  25                  30
Ala Ser Val Asn Phe Ser Glu Phe Ser Lys Lys Cys Ser Glu Arg Trp
        35                  40                  45
Lys Thr Met Ser Ala Lys Glu Lys Gly Lys Phe Glu Asp Met Ala Lys
    50                  55                  60
Ala Asp Lys Ala Arg Tyr Glu Arg Glu Met Lys Thr Tyr Ile Pro Pro
65                  70                  75                  80
Lys Gly Glu Thr

<210> SEQ ID NO 4
<211> LENGTH: 84
<212> TYPE: PRT
<213> ORGANISM: Homo sapiens

<400> SEQUENCE: 4

Gly Lys Gly Asn Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 5
<211> LENGTH: 84
<212> TYPE: PRT
<213> ORGANISM: Homo sapiens

<400> SEQUENCE: 5

Gly Lys Gly Gln Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 6
<211> LENGTH: 84
<212> TYPE: PRT
<213> ORGANISM: Homo sapiens

<400> SEQUENCE: 6

Gly Lys Gly Asp Ala Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 7
<211> LENGTH: 84
<212> TYPE: PRT
<213> ORGANISM: Homo sapiens

-continued

```
<400> SEQUENCE: 7

Gly Lys Gly Asp Ser Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 8
<211> LENGTH: 84
<212> TYPE: PRT
<213> ORGANISM: Homo sapiens

<400> SEQUENCE: 8

Gly Lys Gly Asp Pro Asn Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 9
<211> LENGTH: 84
<212> TYPE: PRT
<213> ORGANISM: Homo sapiens

<400> SEQUENCE: 9

Gly Lys Gly Asp Pro Gln Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 10
<211> LENGTH: 84
<212> TYPE: PRT
<213> ORGANISM: Homo sapiens

<400> SEQUENCE: 10

Gly Lys Gly Asp Pro Lys Asn Pro Arg Gly Lys Met Ser Ser Tyr Ala
1               5                   10                  15
```

```
Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 11
<211> LENGTH: 84
<212> TYPE: PRT
<213> ORGANISM: Homo sapiens

<400> SEQUENCE: 11

Gly Lys Gly Asp Pro Lys Gln Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 12
<211> LENGTH: 84
<212> TYPE: PRT
<213> ORGANISM: Homo sapiens

<400> SEQUENCE: 12

Gly Lys Gly Asp Pro Lys Lys Ala Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 13
<211> LENGTH: 84
<212> TYPE: PRT
<213> ORGANISM: Homo sapiens

<400> SEQUENCE: 13

Gly Lys Gly Asp Pro Lys Lys Ser Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45
```

```
Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
 65                 70                  75                  80

Lys Gly Glu Thr

<210> SEQ ID NO 14
<211> LENGTH: 84
<212> TYPE: PRT
<213> ORGANISM: Homo sapiens

<400> SEQUENCE: 14

Gly Lys Gly Asp Pro Lys Lys Pro His Gly Lys Met Ser Ser Tyr Ala
  1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
 65                 70                  75                  80

Lys Gly Glu Thr

<210> SEQ ID NO 15
<211> LENGTH: 84
<212> TYPE: PRT
<213> ORGANISM: Homo sapiens

<400> SEQUENCE: 15

Gly Lys Gly Asp Pro Lys Lys Pro Gln Gly Lys Met Ser Ser Tyr Ala
  1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
 65                 70                  75                  80

Lys Gly Glu Thr

<210> SEQ ID NO 16
<211> LENGTH: 84
<212> TYPE: PRT
<213> ORGANISM: Homo sapiens

<400> SEQUENCE: 16

Gly Lys Gly Asp Pro Lys Lys Pro Arg Gly Asn Met Ser Ser Tyr Ala
  1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
```

Lys Gly Glu Thr

<210> SEQ ID NO 17
<211> LENGTH: 84
<212> TYPE: PRT
<213> ORGANISM: Homo sapiens

<400> SEQUENCE: 17

Gly Lys Gly Asp Pro Lys Lys Pro Arg Gly Gln Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 18
<211> LENGTH: 84
<212> TYPE: PRT
<213> ORGANISM: Homo sapiens

<400> SEQUENCE: 18

Gly Lys Gly Asp Pro Lys Lys Pro Arg Gly Lys Ile Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 19
<211> LENGTH: 84
<212> TYPE: PRT
<213> ORGANISM: Homo sapiens

<400> SEQUENCE: 19

Gly Lys Gly Asp Pro Lys Lys Pro Arg Gly Lys Val Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 20
<211> LENGTH: 84
<212> TYPE: PRT
<213> ORGANISM: Homo sapiens

<400> SEQUENCE: 20

Gly Lys Gly Asp Pro Lys Lys Pro Arg Gly Lys Met Ser Ser His Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 21
<211> LENGTH: 84
<212> TYPE: PRT
<213> ORGANISM: Homo sapiens

<400> SEQUENCE: 21

Gly Lys Gly Asp Pro Lys Lys Pro Arg Gly Lys Met Ser Ser Ile Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 22
<211> LENGTH: 84
<212> TYPE: PRT
<213> ORGANISM: Homo sapiens

<400> SEQUENCE: 22

Gly Lys Gly Asp Pro Lys Lys Pro Arg Gly Lys Met Ser Ser Tyr Ala
1               5                   10                  15

Ile Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 23
<211> LENGTH: 84
<212> TYPE: PRT
<213> ORGANISM: Homo sapiens -continued

<400> SEQUENCE: 23

Gly Lys Gly Asp Pro Lys Lys Pro Arg Gly Lys Met Ser Ser Tyr Ala
1               5                   10                  15

Val Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 24
<211> LENGTH: 84
<212> TYPE: PRT
<213> ORGANISM: Homo sapiens

<400> SEQUENCE: 24

Gly Lys Gly Asp Pro Lys Lys Pro Arg Gly Lys Met Ser Ser Tyr Ala
1               5                   10                  15

Phe Ile Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 25
<211> LENGTH: 84
<212> TYPE: PRT
<213> ORGANISM: Homo sapiens

<400> SEQUENCE: 25

Gly Lys Gly Asp Pro Lys Lys Pro Arg Gly Lys Met Ser Ser Tyr Ala
1               5                   10                  15

Phe Val Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 26
<211> LENGTH: 84
<212> TYPE: PRT
<213> ORGANISM: Homo sapiens

<400> SEQUENCE: 26

Gly Lys Gly Asp Pro Lys Lys Pro Arg Gly Lys Met Ser Ser Tyr Ala
1               5                   10                  15

```
Phe Phe Val Gln Thr Cys His Glu Glu His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Pro Pro
 65                  70                  75                  80

Lys Gly Glu Thr
```

<210> SEQ ID NO 27
<211> LENGTH: 84
<212> TYPE: PRT
<213> ORGANISM: Homo sapiens

<400> SEQUENCE: 27

```
Gly Lys Gly Asp Pro Lys Lys Pro Arg Gly Lys Met Ser Ser Tyr Ala
 1               5                  10                  15

Phe Phe Val Gln Thr Cys Gln Glu Glu His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Pro Pro
 65                  70                  75                  80

Lys Gly Glu Thr
```

<210> SEQ ID NO 28
<211> LENGTH: 84
<212> TYPE: PRT
<213> ORGANISM: Homo sapiens

<400> SEQUENCE: 28

```
Gly Lys Gly Asp Pro Lys Lys Pro Arg Gly Lys Met Ser Ser Tyr Ala
 1               5                  10                  15

Phe Phe Val Gln Thr Cys Arg Gln Glu His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Pro Pro
 65                  70                  75                  80

Lys Gly Glu Thr
```

<210> SEQ ID NO 29
<211> LENGTH: 84
<212> TYPE: PRT
<213> ORGANISM: Homo sapiens

<400> SEQUENCE: 29

```
Gly Lys Gly Asp Pro Lys Lys Pro Arg Gly Lys Met Ser Ser Tyr Ala
 1               5                  10                  15

Phe Phe Val Gln Thr Cys Arg His Glu His Lys Lys Lys His Pro Asp
                 20                  25                  30

Ala Ser Val Asn Phe Ser Glu Phe Ser Lys Lys Cys Ser Glu Arg Trp
             35                  40                  45
```

```
Lys Thr Met Ser Ala Lys Glu Lys Gly Lys Phe Glu Asp Met Ala Lys
         50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 30
<211> LENGTH: 84
<212> TYPE: PRT
<213> ORGANISM: Homo sapiens

<400> SEQUENCE: 30

Gly Lys Gly Asp Pro Lys Lys Pro Arg Gly Lys Met Ser Ser Tyr Ala
 1               5                  10                  15

Phe Phe Val Gln Thr Cys Arg Asn Glu His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
         50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 31
<211> LENGTH: 84
<212> TYPE: PRT
<213> ORGANISM: Homo sapiens

<400> SEQUENCE: 31

Gly Lys Gly Asp Pro Lys Lys Pro Arg Gly Lys Met Ser Ser Tyr Ala
 1               5                  10                  15

Phe Phe Val Gln Thr Cys Arg Glu Gln His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
         50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 32
<211> LENGTH: 84
<212> TYPE: PRT
<213> ORGANISM: Homo sapiens

<400> SEQUENCE: 32

Gly Lys Gly Asp Pro Lys Lys Pro Arg Gly Lys Met Ser Ser Tyr Ala
 1               5                  10                  15

Phe Phe Val Gln Thr Cys Arg Glu His His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
         50                  55                  60

Ala Asp Lys Ala Arg Tyr Glu Arg Glu Met Lys Thr Tyr Ile Pro Pro
```

65                  70                  75                  80

Lys Gly Glu Thr

<210> SEQ ID NO 33
<211> LENGTH: 84
<212> TYPE: PRT
<213> ORGANISM: Homo sapiens

<400> SEQUENCE: 33

Gly Lys Gly Asp Pro Lys Lys Pro Arg Gly Lys Met Ser Ser Tyr Ala
1               5                   10                  15

Phe Phe Val Gln Thr Cys Arg Glu Asn His Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 34
<211> LENGTH: 84
<212> TYPE: PRT
<213> ORGANISM: Homo sapiens

<400> SEQUENCE: 34

Gly Lys Gly Asp Pro Lys Lys Pro Arg Gly Lys Met Ser Ser Tyr Ala
1               5                   10                  15

Phe Phe Val Gln Thr Cys Arg Glu Glu His Asn Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 35
<211> LENGTH: 84
<212> TYPE: PRT
<213> ORGANISM: Homo sapiens

<400> SEQUENCE: 35

Gly Lys Gly Asp Pro Lys Lys Pro Arg Gly Lys Met Ser Ser Tyr Ala
1               5                   10                  15

Phe Phe Val Gln Thr Cys Arg Glu Glu Gln Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

```
<210> SEQ ID NO 36
<211> LENGTH: 84
<212> TYPE: PRT
<213> ORGANISM: Homo sapiens

<400> SEQUENCE: 36

Gly Lys Gly Asp Pro Lys Lys Pro Arg Gly Lys Met Ser Ser Tyr Ala
1               5                   10                  15

Phe Phe Val Gln Thr Cys Arg Glu Glu His Asn Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 37
<211> LENGTH: 84
<212> TYPE: PRT
<213> ORGANISM: Homo sapiens

<400> SEQUENCE: 37

Gly Lys Gly Asp Pro Lys Lys Pro Arg Gly Lys Met Ser Ser Tyr Ala
1               5                   10                  15

Phe Phe Val Gln Thr Cys Arg Glu Glu His Gln Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 38
<211> LENGTH: 84
<212> TYPE: PRT
<213> ORGANISM: Homo sapiens

<400> SEQUENCE: 38

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Asn His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 39
<211> LENGTH: 84
<212> TYPE: PRT
<213> ORGANISM: Homo sapiens
```

-continued

```
<400> SEQUENCE: 39

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Gln His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 40
<211> LENGTH: 84
<212> TYPE: PRT
<213> ORGANISM: Homo sapiens

<400> SEQUENCE: 40

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Ala Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 41
<211> LENGTH: 84
<212> TYPE: PRT
<213> ORGANISM: Homo sapiens

<400> SEQUENCE: 41

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Ser Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 42
<211> LENGTH: 84
<212> TYPE: PRT
<213> ORGANISM: Homo sapiens

<400> SEQUENCE: 42

Gly Lys Gly Asp Pro Lys Lys Pro Arg Gly Lys Met Ser Ser Tyr Ala
1               5                   10                  15
```

```
Phe Phe Val Gln Thr Cys Arg Glu Glu His Lys Lys Lys His Pro Asn
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 43
<211> LENGTH: 84
<212> TYPE: PRT
<213> ORGANISM: Homo sapiens

<400> SEQUENCE: 43

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Gln
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 44
<211> LENGTH: 84
<212> TYPE: PRT
<213> ORGANISM: Homo sapiens

<400> SEQUENCE: 44

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
            20                  25                  30

Ala Ser Val Asn Ile Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 45
<211> LENGTH: 84
<212> TYPE: PRT
<213> ORGANISM: Homo sapiens

<400> SEQUENCE: 45

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
            20                  25                  30

Ala Ser Val Asn Val Ser Glu Phe Ser Lys Lys Cys Ser Glu Arg Trp
            35                  40                  45
```

```
Lys Thr Met Ser Ala Lys Glu Lys Gly Lys Phe Glu Asp Met Ala Lys
         50                  55                  60
Ala Asp Lys Ala Arg Tyr Glu Arg Glu Met Lys Thr Tyr Ile Pro Pro
65                  70                  75                  80
Lys Gly Glu Thr
```

<210> SEQ ID NO 46
<211> LENGTH: 84
<212> TYPE: PRT
<213> ORGANISM: Homo sapiens

<400> SEQUENCE: 46

```
Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
                20                  25                  30
Ala Ser Val Asn Phe Ser Gln Phe Ser Lys Lys Cys Ser Glu Arg Trp
            35                  40                  45
Lys Thr Met Ser Ala Lys Glu Lys Gly Lys Phe Glu Asp Met Ala Lys
         50                  55                  60
Ala Asp Lys Ala Arg Tyr Glu Arg Glu Met Lys Thr Tyr Ile Pro Pro
65                  70                  75                  80
Lys Gly Glu Thr
```

<210> SEQ ID NO 47
<211> LENGTH: 84
<212> TYPE: PRT
<213> ORGANISM: Homo sapiens

<400> SEQUENCE: 47

```
Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
                20                  25                  30
Ala Ser Val Asn Phe Ser His Phe Ser Lys Lys Cys Ser Glu Arg Trp
            35                  40                  45
Lys Thr Met Ser Ala Lys Glu Lys Gly Lys Phe Glu Asp Met Ala Lys
         50                  55                  60
Ala Asp Lys Ala Arg Tyr Glu Arg Glu Met Lys Thr Tyr Ile Pro Pro
65                  70                  75                  80
Lys Gly Glu Thr
```

<210> SEQ ID NO 48
<211> LENGTH: 84
<212> TYPE: PRT
<213> ORGANISM: Homo sapiens

<400> SEQUENCE: 48

```
Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
                20                  25                  30
Ala Ser Val Asn Phe Ser Asn Phe Ser Lys Lys Cys Ser Glu Arg Trp
            35                  40                  45
Lys Thr Met Ser Ala Lys Glu Lys Gly Lys Phe Glu Asp Met Ala Lys
         50                  55                  60
Ala Asp Lys Ala Arg Tyr Glu Arg Glu Met Lys Thr Tyr Ile Pro Pro
```

```
                        65                  70                  75                  80
Lys Gly Glu Thr

<210> SEQ ID NO 49
<211> LENGTH: 84
<212> TYPE: PRT
<213> ORGANISM: Homo sapiens

<400> SEQUENCE: 49

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Ile Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 50
<211> LENGTH: 84
<212> TYPE: PRT
<213> ORGANISM: Homo sapiens

<400> SEQUENCE: 50

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Val Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 51
<211> LENGTH: 84
<212> TYPE: PRT
<213> ORGANISM: Homo sapiens

<400> SEQUENCE: 51

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Asn Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr
```

```
<210> SEQ ID NO 52
<211> LENGTH: 84
<212> TYPE: PRT
<213> ORGANISM: Homo sapiens

<400> SEQUENCE: 52

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Gln Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 53
<211> LENGTH: 84
<212> TYPE: PRT
<213> ORGANISM: Homo sapiens

<400> SEQUENCE: 53

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Asn Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 54
<211> LENGTH: 84
<212> TYPE: PRT
<213> ORGANISM: Homo sapiens

<400> SEQUENCE: 54

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Gln Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 55
<211> LENGTH: 84
<212> TYPE: PRT
<213> ORGANISM: Homo sapiens
```

<400> SEQUENCE: 55

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Gln Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 56
<211> LENGTH: 84
<212> TYPE: PRT
<213> ORGANISM: Homo sapiens

<400> SEQUENCE: 56

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser His Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 57
<211> LENGTH: 84
<212> TYPE: PRT
<213> ORGANISM: Homo sapiens

<400> SEQUENCE: 57

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Asn Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 58
<211> LENGTH: 84
<212> TYPE: PRT
<213> ORGANISM: Homo sapiens

<400> SEQUENCE: 58

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu His Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 59
<211> LENGTH: 84
<212> TYPE: PRT
<213> ORGANISM: Homo sapiens

<400> SEQUENCE: 59

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Gln Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 60
<211> LENGTH: 84
<212> TYPE: PRT
<213> ORGANISM: Homo sapiens

<400> SEQUENCE: 60

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Tyr
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 61
<211> LENGTH: 84
<212> TYPE: PRT
<213> ORGANISM: Homo sapiens

<400> SEQUENCE: 61

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Ser
        35                  40                  45

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 62
<211> LENGTH: 84
<212> TYPE: PRT
<213> ORGANISM: Homo sapiens

<400> SEQUENCE: 62

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Asn Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 63
<211> LENGTH: 84
<212> TYPE: PRT
<213> ORGANISM: Homo sapiens

<400> SEQUENCE: 63

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Gln Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 64
<211> LENGTH: 84
<212> TYPE: PRT
<213> ORGANISM: Homo sapiens

<400> SEQUENCE: 64

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Ile Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro

```
                65                  70                  75                  80
Lys Gly Glu Thr

<210> SEQ ID NO 65
<211> LENGTH: 84
<212> TYPE: PRT
<213> ORGANISM: Homo sapiens

<400> SEQUENCE: 65

Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
                20                  25                  30
Ala Ser Val Asn Phe Ser Glu Phe Ser Lys Lys Cys Ser Glu Arg Trp
            35                  40                  45
Lys Thr Val Ser Ala Lys Glu Lys Gly Lys Phe Glu Asp Met Ala Lys
        50                  55                  60
Ala Asp Lys Ala Arg Tyr Glu Arg Glu Met Lys Thr Tyr Ile Pro Pro
65                  70                  75                  80
Lys Gly Glu Thr

<210> SEQ ID NO 66
<211> LENGTH: 84
<212> TYPE: PRT
<213> ORGANISM: Homo sapiens

<400> SEQUENCE: 66

Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
                20                  25                  30
Ala Ser Val Asn Phe Ser Glu Phe Ser Lys Lys Cys Ser Glu Arg Trp
            35                  40                  45
Lys Thr Met Ser Ala Asn Glu Lys Gly Lys Phe Glu Asp Met Ala Lys
        50                  55                  60
Ala Asp Lys Ala Arg Tyr Glu Arg Glu Met Lys Thr Tyr Ile Pro Pro
65                  70                  75                  80
Lys Gly Glu Thr

<210> SEQ ID NO 67
<211> LENGTH: 84
<212> TYPE: PRT
<213> ORGANISM: Homo sapiens

<400> SEQUENCE: 67

Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
                20                  25                  30
Ala Ser Val Asn Phe Ser Glu Phe Ser Lys Lys Cys Ser Glu Arg Trp
            35                  40                  45
Lys Thr Met Ser Ala Gln Glu Lys Gly Lys Phe Glu Asp Met Ala Lys
        50                  55                  60
Ala Asp Lys Ala Arg Tyr Glu Arg Glu Met Lys Thr Tyr Ile Pro Pro
65                  70                  75                  80
Lys Gly Glu Thr
```

```
<210> SEQ ID NO 68
<211> LENGTH: 84
<212> TYPE: PRT
<213> ORGANISM: Homo sapiens

<400> SEQUENCE: 68

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Gln Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 69
<211> LENGTH: 84
<212> TYPE: PRT
<213> ORGANISM: Homo sapiens

<400> SEQUENCE: 69

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys His Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 70
<211> LENGTH: 84
<212> TYPE: PRT
<213> ORGANISM: Homo sapiens

<400> SEQUENCE: 70

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Asn Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 71
<211> LENGTH: 84
<212> TYPE: PRT
<213> ORGANISM: Homo sapiens
```

<400> SEQUENCE: 71

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Asn Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 72
<211> LENGTH: 84
<212> TYPE: PRT
<213> ORGANISM: Homo sapiens

<400> SEQUENCE: 72

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Gln Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 73
<211> LENGTH: 84
<212> TYPE: PRT
<213> ORGANISM: Homo sapiens

<400> SEQUENCE: 73

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Asn Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 74
<211> LENGTH: 84
<212> TYPE: PRT
<213> ORGANISM: Homo sapiens

<400> SEQUENCE: 74

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Gln Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 75
<211> LENGTH: 84
<212> TYPE: PRT
<213> ORGANISM: Homo sapiens

<400> SEQUENCE: 75

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Ile Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 76
<211> LENGTH: 84
<212> TYPE: PRT
<213> ORGANISM: Homo sapiens

<400> SEQUENCE: 76

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Val Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 77
<211> LENGTH: 84
<212> TYPE: PRT
<213> ORGANISM: Homo sapiens

<400> SEQUENCE: 77

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

```
Lys Thr Met Ser Ala Lys Glu Lys Gly Lys Phe Gln Asp Met Ala Lys
        50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 78
<211> LENGTH: 84
<212> TYPE: PRT
<213> ORGANISM: Homo sapiens

<400> SEQUENCE: 78

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe His Asp Met Ala Lys
        50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 79
<211> LENGTH: 84
<212> TYPE: PRT
<213> ORGANISM: Homo sapiens

<400> SEQUENCE: 79

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Asn Asp Met Ala Lys
        50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 80
<211> LENGTH: 84
<212> TYPE: PRT
<213> ORGANISM: Homo sapiens

<400> SEQUENCE: 80

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asn Met Ala Lys
        50                  55                  60

Ala Asp Lys Ala Arg Tyr Glu Arg Glu Met Lys Thr Tyr Ile Pro Pro
```

```
                65                  70                  75                  80

Lys Gly Glu Thr

<210> SEQ ID NO 81
<211> LENGTH: 84
<212> TYPE: PRT
<213> ORGANISM: Homo sapiens

<400> SEQUENCE: 81

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Gln Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 82
<211> LENGTH: 84
<212> TYPE: PRT
<213> ORGANISM: Homo sapiens

<400> SEQUENCE: 82

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Ile Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 83
<211> LENGTH: 84
<212> TYPE: PRT
<213> ORGANISM: Homo sapiens

<400> SEQUENCE: 83

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Val Ala Lys
    50                  55                  60

Ala Asp Lys Ala Arg Tyr Glu Arg Glu Met Lys Thr Tyr Ile Pro Pro
65                  70                  75                  80

Lys Gly Glu Thr
```

<210> SEQ ID NO 84
<211> LENGTH: 84
<212> TYPE: PRT
<213> ORGANISM: Homo sapiens

<400> SEQUENCE: 84

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Asn
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 85
<211> LENGTH: 84
<212> TYPE: PRT
<213> ORGANISM: Homo sapiens

<400> SEQUENCE: 85

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Gln
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 86
<211> LENGTH: 84
<212> TYPE: PRT
<213> ORGANISM: Homo sapiens

<400> SEQUENCE: 86

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asn Lys Ala Arg Tyr Glu Arg Glu Met Lys Thr Tyr Ile Pro Pro
65                  70                  75                  80

Lys Gly Glu Thr

<210> SEQ ID NO 87
<211> LENGTH: 84
<212> TYPE: PRT
<213> ORGANISM: Homo sapiens -continued

```
<400> SEQUENCE: 87

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Gln Lys Ala Arg Tyr Glu Arg Glu Met Lys Thr Tyr Ile Pro Pro
65                  70                  75                  80

Lys Gly Glu Thr

<210> SEQ ID NO 88
<211> LENGTH: 84
<212> TYPE: PRT
<213> ORGANISM: Homo sapiens

<400> SEQUENCE: 88

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Asn Ala Arg Tyr Glu Arg Glu Met Lys Thr Tyr Ile Pro Pro
65                  70                  75                  80

Lys Gly Glu Thr

<210> SEQ ID NO 89
<211> LENGTH: 84
<212> TYPE: PRT
<213> ORGANISM: Homo sapiens

<400> SEQUENCE: 89

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Gln Ala Arg Tyr Glu Arg Glu Met Lys Thr Tyr Ile Pro Pro
65                  70                  75                  80

Lys Gly Glu Thr

<210> SEQ ID NO 90
<211> LENGTH: 84
<212> TYPE: PRT
<213> ORGANISM: Homo sapiens

<400> SEQUENCE: 90

Gly Lys Gly Asp Pro Lys Lys Pro Arg Gly Lys Met Ser Ser Tyr Ala
1               5                   10                  15
```

Phe Phe Val Gln Thr Cys Arg Glu Glu His Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
50                  55                  60

Ala Asp Lys Ala His Tyr Glu Arg Glu Met Lys Thr Tyr Ile Pro Pro
65                  70                  75                  80

Lys Gly Glu Thr

<210> SEQ ID NO 91
<211> LENGTH: 84
<212> TYPE: PRT
<213> ORGANISM: Homo sapiens

<400> SEQUENCE: 91

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
50                  55                  60

Ala Asp Lys Ala Gln Tyr Glu Arg Glu Met Lys Thr Tyr Ile Pro Pro
65                  70                  75                  80

Lys Gly Glu Thr

<210> SEQ ID NO 92
<211> LENGTH: 84
<212> TYPE: PRT
<213> ORGANISM: Homo sapiens

<400> SEQUENCE: 92

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
50                  55                  60

Ala Asp Lys Ala Arg His Glu Arg Glu Met Lys Thr Tyr Ile Pro Pro
65                  70                  75                  80

Lys Gly Glu Thr

<210> SEQ ID NO 93
<211> LENGTH: 84
<212> TYPE: PRT
<213> ORGANISM: Homo sapiens

<400> SEQUENCE: 93

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

```
Lys Thr Met Ser Ala Lys Glu Lys Gly Lys Phe Glu Asp Met Ala Lys
     50                  55                  60
Ala Asp Lys Ala Arg Ile Glu Arg Glu Met Lys Thr Tyr Ile Pro Pro
 65                  70                  75                  80
Lys Gly Glu Thr

<210> SEQ ID NO 94
<211> LENGTH: 84
<212> TYPE: PRT
<213> ORGANISM: Homo sapiens

<400> SEQUENCE: 94

Gly Lys Gly Asp Pro Lys Lys Pro Arg Gly Lys Met Ser Ser Tyr Ala
 1                5                  10                  15
Phe Phe Val Gln Thr Cys Arg Glu Glu His Lys Lys Lys His Pro Asp
                 20                  25                  30
Ala Ser Val Asn Phe Ser Glu Phe Ser Lys Lys Cys Ser Glu Arg Trp
             35                  40                  45
Lys Thr Met Ser Ala Lys Glu Lys Gly Lys Phe Glu Asp Met Ala Lys
     50                  55                  60
Ala Asp Lys Ala Arg Tyr Gln Arg Glu Met Lys Thr Tyr Ile Pro Pro
 65                  70                  75                  80
Lys Gly Glu Thr

<210> SEQ ID NO 95
<211> LENGTH: 84
<212> TYPE: PRT
<213> ORGANISM: Homo sapiens

<400> SEQUENCE: 95

Gly Lys Gly Asp Pro Lys Lys Pro Arg Gly Lys Met Ser Ser Tyr Ala
 1                5                  10                  15
Phe Phe Val Gln Thr Cys Arg Glu Glu His Lys Lys Lys His Pro Asp
                 20                  25                  30
Ala Ser Val Asn Phe Ser Glu Phe Ser Lys Lys Cys Ser Glu Arg Trp
             35                  40                  45
Lys Thr Met Ser Ala Lys Glu Lys Gly Lys Phe Glu Asp Met Ala Lys
     50                  55                  60
Ala Asp Lys Ala Arg Tyr His Arg Glu Met Lys Thr Tyr Ile Pro Pro
 65                  70                  75                  80
Lys Gly Glu Thr

<210> SEQ ID NO 96
<211> LENGTH: 84
<212> TYPE: PRT
<213> ORGANISM: Homo sapiens

<400> SEQUENCE: 96

Gly Lys Gly Asp Pro Lys Lys Pro Arg Gly Lys Met Ser Ser Tyr Ala
 1                5                  10                  15
Phe Phe Val Gln Thr Cys Arg Glu Glu His Lys Lys Lys His Pro Asp
                 20                  25                  30
Ala Ser Val Asn Phe Ser Glu Phe Ser Lys Lys Cys Ser Glu Arg Trp
             35                  40                  45
Lys Thr Met Ser Ala Lys Glu Lys Gly Lys Phe Glu Asp Met Ala Lys
     50                  55                  60
Ala Asp Lys Ala Arg Tyr Asn Arg Glu Met Lys Thr Tyr Ile Pro Pro
```

```
                65                  70                  75                  80
Lys Gly Glu Thr

<210> SEQ ID NO 97
<211> LENGTH: 84
<212> TYPE: PRT
<213> ORGANISM: Homo sapiens

<400> SEQUENCE: 97

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu His Glu Met Lys Thr Tyr Ile Pro Pro
65                  70                  75                  80

Lys Gly Glu Thr

<210> SEQ ID NO 98
<211> LENGTH: 84
<212> TYPE: PRT
<213> ORGANISM: Homo sapiens

<400> SEQUENCE: 98

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Gln Glu Met Lys Thr Tyr Ile Pro Pro
65                  70                  75                  80

Lys Gly Glu Thr

<210> SEQ ID NO 99
<211> LENGTH: 84
<212> TYPE: PRT
<213> ORGANISM: Homo sapiens

<400> SEQUENCE: 99

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Gln Met Lys Thr Tyr Ile Pro Pro
65                  70                  75                  80

Lys Gly Glu Thr
```

<210> SEQ ID NO 100
<211> LENGTH: 84
<212> TYPE: PRT
<213> ORGANISM: Homo sapiens

<400> SEQUENCE: 100

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg His Met Lys Thr Tyr Ile Pro Pro
65                  70                  75                  80

Lys Gly Glu Thr

<210> SEQ ID NO 101
<211> LENGTH: 84
<212> TYPE: PRT
<213> ORGANISM: Homo sapiens

<400> SEQUENCE: 101

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Asn Met Lys Thr Tyr Ile Pro Pro
65                  70                  75                  80

Lys Gly Glu Thr

<210> SEQ ID NO 102
<211> LENGTH: 84
<212> TYPE: PRT
<213> ORGANISM: Homo sapiens

<400> SEQUENCE: 102

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Ile Lys Thr Tyr Ile Pro Pro
65                  70                  75                  80

Lys Gly Glu Thr

<210> SEQ ID NO 103
<211> LENGTH: 84
<212> TYPE: PRT
<213> ORGANISM: Homo sapiens -continued

```
<400> SEQUENCE: 103

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Val Lys Thr Tyr Ile Pro Pro
65                  70                  75                  80

Lys Gly Glu Thr

<210> SEQ ID NO 104
<211> LENGTH: 84
<212> TYPE: PRT
<213> ORGANISM: Homo sapiens

<400> SEQUENCE: 104

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Asn Thr Tyr Ile Pro Pro
65                  70                  75                  80

Lys Gly Glu Thr

<210> SEQ ID NO 105
<211> LENGTH: 84
<212> TYPE: PRT
<213> ORGANISM: Homo sapiens

<400> SEQUENCE: 105

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Gln Thr Tyr Ile Pro Pro
65                  70                  75                  80

Lys Gly Glu Thr

<210> SEQ ID NO 106
<211> LENGTH: 84
<212> TYPE: PRT
<213> ORGANISM: Homo sapiens

<400> SEQUENCE: 106

Gly Lys Gly Asp Pro Lys Lys Pro Arg Gly Lys Met Ser Ser Tyr Ala
1               5                   10                  15
```

```
Phe Phe Val Gln Thr Cys Arg Glu Glu His Lys Lys Lys His Pro Asp
         20                  25                  30

Ala Ser Val Asn Phe Ser Glu Phe Ser Lys Lys Cys Ser Glu Arg Trp
     35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr His Ile Pro Pro
 65                  70                  75                  80

Lys Gly Glu Thr

<210> SEQ ID NO 107
<211> LENGTH: 84
<212> TYPE: PRT
<213> ORGANISM: Homo sapiens

<400> SEQUENCE: 107

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
         20                  25                  30

Ala Ser Val Asn Phe Ser Glu Phe Ser Lys Lys Cys Ser Glu Arg Trp
     35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Ile Ile Pro Pro
 65                  70                  75                  80

Lys Gly Glu Thr

<210> SEQ ID NO 108
<211> LENGTH: 84
<212> TYPE: PRT
<213> ORGANISM: Homo sapiens

<400> SEQUENCE: 108

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
         20                  25                  30

Ala Ser Val Asn Phe Ser Glu Phe Ser Lys Lys Cys Ser Glu Arg Trp
     35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Ala Pro
 65                  70                  75                  80

Lys Gly Glu Thr

<210> SEQ ID NO 109
<211> LENGTH: 84
<212> TYPE: PRT
<213> ORGANISM: Homo sapiens

<400> SEQUENCE: 109

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
         20                  25                  30

Ala Ser Val Asn Phe Ser Glu Phe Ser Lys Lys Cys Ser Glu Arg Trp
     35                  40                  45
```

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Ser Pro
65                  70                  75                  80

Lys Gly Glu Thr

<210> SEQ ID NO 110
<211> LENGTH: 84
<212> TYPE: PRT
<213> ORGANISM: Homo sapiens

<400> SEQUENCE: 110

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Ala
65                  70                  75                  80

Lys Gly Glu Thr

<210> SEQ ID NO 111
<211> LENGTH: 84
<212> TYPE: PRT
<213> ORGANISM: Homo sapiens

<400> SEQUENCE: 111

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Ser
65                  70                  75                  80

Lys Gly Glu Thr

<210> SEQ ID NO 112
<211> LENGTH: 84
<212> TYPE: PRT
<213> ORGANISM: Homo sapiens

<400> SEQUENCE: 112

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro

```
                65                  70                  75                  80
Asn Gly Glu Thr

<210> SEQ ID NO 113
<211> LENGTH: 84
<212> TYPE: PRT
<213> ORGANISM: Homo sapiens

<400> SEQUENCE: 113

Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
            20                  25                  30
Ala Ser Val Asn Phe Ser Glu Phe Ser Lys Lys Cys Ser Glu Arg Trp
        35                  40                  45
Lys Thr Met Ser Ala Lys Glu Lys Gly Lys Phe Glu Asp Met Ala Lys
    50                  55                  60
Ala Asp Lys Ala Arg Tyr Glu Arg Glu Met Lys Thr Tyr Ile Pro Pro
65                  70                  75                  80
Gln Gly Glu Thr

<210> SEQ ID NO 114
<211> LENGTH: 84
<212> TYPE: PRT
<213> ORGANISM: Homo sapiens

<400> SEQUENCE: 114

Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
            20                  25                  30
Ala Ser Val Asn Phe Ser Glu Phe Ser Lys Lys Cys Ser Glu Arg Trp
        35                  40                  45
Lys Thr Met Ser Ala Lys Glu Lys Gly Lys Phe Glu Asp Met Ala Lys
    50                  55                  60
Ala Asp Lys Ala Arg Tyr Glu Arg Glu Met Lys Thr Tyr Ile Pro Pro
65                  70                  75                  80
Lys Gly Gln Thr

<210> SEQ ID NO 115
<211> LENGTH: 84
<212> TYPE: PRT
<213> ORGANISM: Homo sapiens

<400> SEQUENCE: 115

Gly Lys Gly Asp Pro Lys Lys Pro Arg Gly Lys Met Ser Ser Tyr Ala
1               5                   10                  15
Phe Phe Val Gln Thr Cys Arg Glu Glu His Lys Lys Lys His Pro Asp
            20                  25                  30
Ala Ser Val Asn Phe Ser Glu Phe Ser Lys Lys Cys Ser Glu Arg Trp
        35                  40                  45
Lys Thr Met Ser Ala Lys Glu Lys Gly Lys Phe Glu Asp Met Ala Lys
    50                  55                  60
Ala Asp Lys Ala Arg Tyr Glu Arg Glu Met Lys Thr Tyr Ile Pro Pro
65                  70                  75                  80
Lys Gly His Thr
```

<210> SEQ ID NO 116
<211> LENGTH: 84
<212> TYPE: PRT
<213> ORGANISM: Homo sapiens

<400> SEQUENCE: 116

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Asn Thr

<210> SEQ ID NO 117
<211> LENGTH: 77
<212> TYPE: PRT
<213> ORGANISM: Homo sapiens

<400> SEQUENCE: 117

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 118
<211> LENGTH: 77
<212> TYPE: PRT
<213> ORGANISM: Homo sapiens

<400> SEQUENCE: 118

Ala Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 119
<211> LENGTH: 77
<212> TYPE: PRT
<213> ORGANISM: Homo sapiens

<400> SEQUENCE: 119

Ser Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 120
<211> LENGTH: 77
<212> TYPE: PRT
<213> ORGANISM: Homo sapiens

<400> SEQUENCE: 120

Pro His Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 121
<211> LENGTH: 77
<212> TYPE: PRT
<213> ORGANISM: Homo sapiens

<400> SEQUENCE: 121

Pro Gln Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 122
<211> LENGTH: 77
<212> TYPE: PRT
<213> ORGANISM: Homo sapiens

<400> SEQUENCE: 122

Pro Arg Gly Asn Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr

-continued 65            70            75

<210> SEQ ID NO 123
<211> LENGTH: 77
<212> TYPE: PRT
<213> ORGANISM: Homo sapiens

<400> SEQUENCE: 123

Pro Arg Gly Gln Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 124
<211> LENGTH: 77
<212> TYPE: PRT
<213> ORGANISM: Homo sapiens

<400> SEQUENCE: 124

Pro Arg Gly Lys Ile Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 125
<211> LENGTH: 77
<212> TYPE: PRT
<213> ORGANISM: Homo sapiens

<400> SEQUENCE: 125

Pro Arg Gly Lys Val Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 126
<211> LENGTH: 77
<212> TYPE: PRT
<213> ORGANISM: Homo sapiens

<400> SEQUENCE: 126

Pro Arg Gly Lys Met Ser Ser His Ala Phe Phe Val Gln Thr Cys Arg

```
                1               5                   10                  15
Glu Glu His Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 127
<211> LENGTH: 77
<212> TYPE: PRT
<213> ORGANISM: Homo sapiens

<400> SEQUENCE: 127

Pro Arg Gly Lys Met Ser Ser Ile Ala Phe Phe Val Gln Thr Cys Arg
1               5                   10                  15

Glu Glu His Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 128
<211> LENGTH: 77
<212> TYPE: PRT
<213> ORGANISM: Homo sapiens

<400> SEQUENCE: 128

Pro Arg Gly Lys Met Ser Ser Tyr Ala Ile Phe Val Gln Thr Cys Arg
1               5                   10                  15

Glu Glu His Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 129
<211> LENGTH: 77
<212> TYPE: PRT
<213> ORGANISM: Homo sapiens

<400> SEQUENCE: 129

Pro Arg Gly Lys Met Ser Ser Tyr Ala Val Phe Val Gln Thr Cys Arg
1               5                   10                  15

Glu Glu His Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60
```

```
Arg Glu Met Lys Thr Tyr Ile Pro Pro Lys Gly Glu Thr
 65                  70                  75
```

<210> SEQ ID NO 130
<211> LENGTH: 77
<212> TYPE: PRT
<213> ORGANISM: Homo sapiens

<400> SEQUENCE: 130

```
Pro Arg Gly Lys Met Ser Ser Tyr Ala Phe Ile Val Gln Thr Cys Arg
 1               5                  10                  15

Glu Glu His Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75
```

<210> SEQ ID NO 131
<211> LENGTH: 77
<212> TYPE: PRT
<213> ORGANISM: Homo sapiens

<400> SEQUENCE: 131

```
Pro Arg Gly Lys Met Ser Ser Tyr Ala Phe Val Val Gln Thr Cys Arg
 1               5                  10                  15

Glu Glu His Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75
```

<210> SEQ ID NO 132
<211> LENGTH: 77
<212> TYPE: PRT
<213> ORGANISM: Homo sapiens

<400> SEQUENCE: 132

```
Pro Arg Gly Lys Met Ser Ser Tyr Ala Phe Phe Val Gln Thr Cys His
 1               5                  10                  15

Glu Glu His Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75
```

<210> SEQ ID NO 133
<211> LENGTH: 77
<212> TYPE: PRT
<213> ORGANISM: Homo sapiens

<400> SEQUENCE: 133

```
Pro Arg Gly Lys Met Ser Ser Tyr Ala Phe Val Gln Thr Cys Gln
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65              70                  75
```

<210> SEQ ID NO 134
<211> LENGTH: 77
<212> TYPE: PRT
<213> ORGANISM: Homo sapiens

<400> SEQUENCE: 134

```
Pro Arg Gly Lys Met Ser Ser Tyr Ala Phe Phe Val Gln Thr Cys Arg
1               5                   10                  15

Gln Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65              70                  75
```

<210> SEQ ID NO 135
<211> LENGTH: 77
<212> TYPE: PRT
<213> ORGANISM: Homo sapiens

<400> SEQUENCE: 135

```
Pro Arg Gly Lys Met Ser Ser Tyr Ala Phe Phe Val Gln Thr Cys Arg
1               5                   10                  15

His Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65              70                  75
```

<210> SEQ ID NO 136
<211> LENGTH: 77
<212> TYPE: PRT
<213> ORGANISM: Homo sapiens

<400> SEQUENCE: 136

```
Pro Arg Gly Lys Met Ser Ser Tyr Ala Phe Phe Val Gln Thr Cys Arg
1               5                   10                  15

Asn Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60
```

Arg Glu Met Lys Thr Tyr Ile Pro Pro Lys Gly Glu Thr
65                  70                  75

<210> SEQ ID NO 137
<211> LENGTH: 77
<212> TYPE: PRT
<213> ORGANISM: Homo sapiens

<400> SEQUENCE: 137

Pro Arg Gly Lys Met Ser Ser Tyr Ala Phe Phe Val Gln Thr Cys Arg
1               5                   10                  15

Glu Gln His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 138
<211> LENGTH: 77
<212> TYPE: PRT
<213> ORGANISM: Homo sapiens

<400> SEQUENCE: 138

Pro Arg Gly Lys Met Ser Ser Tyr Ala Phe Phe Val Gln Thr Cys Arg
1               5                   10                  15

Glu His His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 139
<211> LENGTH: 77
<212> TYPE: PRT
<213> ORGANISM: Homo sapiens

<400> SEQUENCE: 139

Pro Arg Gly Lys Met Ser Ser Tyr Ala Phe Phe Val Gln Thr Cys Arg
1               5                   10                  15

Glu Asn His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 140
<211> LENGTH: 77
<212> TYPE: PRT
<213> ORGANISM: Homo sapiens

<400> SEQUENCE: 140

Pro Arg Gly Lys Met Ser Ser Tyr Ala Phe Val Gln Thr Cys Arg
1               5                   10                  15

Glu Glu His Asn Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 141
<211> LENGTH: 77
<212> TYPE: PRT
<213> ORGANISM: Homo sapiens

<400> SEQUENCE: 141

Pro Arg Gly Lys Met Ser Ser Tyr Ala Phe Val Gln Thr Cys Arg
1               5                   10                  15

Glu Glu His Gln Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 142
<211> LENGTH: 77
<212> TYPE: PRT
<213> ORGANISM: Homo sapiens

<400> SEQUENCE: 142

Pro Arg Gly Lys Met Ser Ser Tyr Ala Phe Val Gln Thr Cys Arg
1               5                   10                  15

Glu Glu His Lys Asn Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 143
<211> LENGTH: 77
<212> TYPE: PRT
<213> ORGANISM: Homo sapiens

<400> SEQUENCE: 143

Pro Arg Gly Lys Met Ser Ser Tyr Ala Phe Val Gln Thr Cys Arg
1               5                   10                  15

Glu Glu His Lys Gln Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu

```
                    50                  55                  60
Arg Glu Met Lys Thr Tyr Ile Pro Pro Lys Gly Glu Thr
 65                  70                  75

<210> SEQ ID NO 144
<211> LENGTH: 77
<212> TYPE: PRT
<213> ORGANISM: Homo sapiens

<400> SEQUENCE: 144

Pro Arg Gly Lys Met Ser Ser Tyr Ala Phe Phe Val Gln Thr Cys Arg
  1               5                  10                  15

Glu Glu His Lys Lys Asn His Pro Asp Ala Ser Val Asn Phe Ser Glu
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75

<210> SEQ ID NO 145
<211> LENGTH: 77
<212> TYPE: PRT
<213> ORGANISM: Homo sapiens

<400> SEQUENCE: 145

Pro Arg Gly Lys Met Ser Ser Tyr Ala Phe Phe Val Gln Thr Cys Arg
  1               5                  10                  15

Glu Glu His Lys Lys Gln His Pro Asp Ala Ser Val Asn Phe Ser Glu
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75

<210> SEQ ID NO 146
<211> LENGTH: 77
<212> TYPE: PRT
<213> ORGANISM: Homo sapiens

<400> SEQUENCE: 146

Pro Arg Gly Lys Met Ser Ser Tyr Ala Phe Phe Val Gln Thr Cys Arg
  1               5                  10                  15

Glu Glu His Lys Lys Lys His Ala Asp Ala Ser Val Asn Phe Ser Glu
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75

<210> SEQ ID NO 147
<211> LENGTH: 77
<212> TYPE: PRT
<213> ORGANISM: Homo sapiens
```

<400> SEQUENCE: 147

Pro Arg Gly Lys Met Ser Ser Tyr Ala Phe Phe Val Gln Thr Cys Arg
1               5                   10                  15

Glu Glu His Lys Lys Lys His Ser Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 148
<211> LENGTH: 77
<212> TYPE: PRT
<213> ORGANISM: Homo sapiens

<400> SEQUENCE: 148

Pro Arg Gly Lys Met Ser Ser Tyr Ala Phe Phe Val Gln Thr Cys Arg
1               5                   10                  15

Glu Glu His Lys Lys Lys His Pro Asn Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 149
<211> LENGTH: 77
<212> TYPE: PRT
<213> ORGANISM: Homo sapiens

<400> SEQUENCE: 149

Pro Arg Gly Lys Met Ser Ser Tyr Ala Phe Phe Val Gln Thr Cys Arg
1               5                   10                  15

Glu Glu His Lys Lys Lys His Pro Gln Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 150
<211> LENGTH: 77
<212> TYPE: PRT
<213> ORGANISM: Homo sapiens

<400> SEQUENCE: 150

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Ile Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
            50                  55                  60

Arg Glu Met Lys Thr Tyr Ile Pro Pro Lys Gly Glu Thr
65                  70                  75

<210> SEQ ID NO 151
<211> LENGTH: 77
<212> TYPE: PRT
<213> ORGANISM: Homo sapiens

<400> SEQUENCE: 151

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Val Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
            50                  55                  60

Arg Glu Met Lys Thr Tyr Ile Pro Pro Lys Gly Glu Thr
65                  70                  75

<210> SEQ ID NO 152
<211> LENGTH: 77
<212> TYPE: PRT
<213> ORGANISM: Homo sapiens

<400> SEQUENCE: 152

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Gln
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
            50                  55                  60

Arg Glu Met Lys Thr Tyr Ile Pro Pro Lys Gly Glu Thr
65                  70                  75

<210> SEQ ID NO 153
<211> LENGTH: 77
<212> TYPE: PRT
<213> ORGANISM: Homo sapiens

<400> SEQUENCE: 153

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser His
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
            50                  55                  60

Arg Glu Met Lys Thr Tyr Ile Pro Pro Lys Gly Glu Thr
65                  70                  75

<210> SEQ ID NO 154
<211> LENGTH: 77
<212> TYPE: PRT
<213> ORGANISM: Homo sapiens -continued

```
<400> SEQUENCE: 154

Pro Arg Gly Lys Met Ser Ser Tyr Ala Phe Phe Val Gln Thr Cys Arg
1               5                   10                  15
Glu Glu His Lys Lys Lys His Pro Asp Ala Ser Val Asn Phe Ser Asn
            20                  25                  30
Phe Ser Lys Lys Cys Ser Glu Arg Trp Lys Thr Met Ser Ala Lys Glu
        35                  40                  45
Lys Gly Lys Phe Glu Asp Met Ala Lys Ala Asp Lys Ala Arg Tyr Glu
    50                  55                  60
Arg Glu Met Lys Thr Tyr Ile Pro Pro Lys Gly Glu Thr
65                  70                  75

<210> SEQ ID NO 155
<211> LENGTH: 77
<212> TYPE: PRT
<213> ORGANISM: Homo sapiens

<400> SEQUENCE: 155

Pro Arg Gly Lys Met Ser Ser Tyr Ala Phe Phe Val Gln Thr Cys Arg
1               5                   10                  15
Glu Glu His Lys Lys Lys His Pro Asp Ala Ser Val Asn Phe Ser Glu
            20                  25                  30
Ile Ser Lys Lys Cys Ser Glu Arg Trp Lys Thr Met Ser Ala Lys Glu
        35                  40                  45
Lys Gly Lys Phe Glu Asp Met Ala Lys Ala Asp Lys Ala Arg Tyr Glu
    50                  55                  60
Arg Glu Met Lys Thr Tyr Ile Pro Pro Lys Gly Glu Thr
65                  70                  75

<210> SEQ ID NO 156
<211> LENGTH: 77
<212> TYPE: PRT
<213> ORGANISM: Homo sapiens

<400> SEQUENCE: 156

Pro Arg Gly Lys Met Ser Ser Tyr Ala Phe Phe Val Gln Thr Cys Arg
1               5                   10                  15
Glu Glu His Lys Lys Lys His Pro Asp Ala Ser Val Asn Phe Ser Glu
            20                  25                  30
Val Ser Lys Lys Cys Ser Glu Arg Trp Lys Thr Met Ser Ala Lys Glu
        35                  40                  45
Lys Gly Lys Phe Glu Asp Met Ala Lys Ala Asp Lys Ala Arg Tyr Glu
    50                  55                  60
Arg Glu Met Lys Thr Tyr Ile Pro Pro Lys Gly Glu Thr
65                  70                  75

<210> SEQ ID NO 157
<211> LENGTH: 77
<212> TYPE: PRT
<213> ORGANISM: Homo sapiens

<400> SEQUENCE: 157

Pro Arg Gly Lys Met Ser Ser Tyr Ala Phe Phe Val Gln Thr Cys Arg
1               5                   10                  15
Glu Glu His Lys Lys Lys His Pro Asp Ala Ser Val Asn Phe Ser Glu
            20                  25                  30
Phe Ser Asn Lys Cys Ser Glu Arg Trp Lys Thr Met Ser Ala Lys Glu
        35                  40                  45
```

```
Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
 65              70                  75
```

<210> SEQ ID NO 158
<211> LENGTH: 77
<212> TYPE: PRT
<213> ORGANISM: Homo sapiens

<400> SEQUENCE: 158

```
Pro Arg Gly Lys Met Ser Ser Tyr Ala Phe Phe Val Gln Thr Cys Arg
 1               5                  10                  15

Glu Glu His Lys Lys His Pro Asp Ala Ser Val Asn Phe Ser Glu
                20                  25                  30

Phe Ser Gln Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
 65              70                  75
```

<210> SEQ ID NO 159
<211> LENGTH: 77
<212> TYPE: PRT
<213> ORGANISM: Homo sapiens

<400> SEQUENCE: 159

```
Pro Arg Gly Lys Met Ser Ser Tyr Ala Phe Phe Val Gln Thr Cys Arg
 1               5                  10                  15

Glu Glu His Lys Lys His Pro Asp Ala Ser Val Asn Phe Ser Glu
                20                  25                  30

Phe Ser Lys Asn Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
 65              70                  75
```

<210> SEQ ID NO 160
<211> LENGTH: 77
<212> TYPE: PRT
<213> ORGANISM: Homo sapiens

<400> SEQUENCE: 160

```
Pro Arg Gly Lys Met Ser Ser Tyr Ala Phe Phe Val Gln Thr Cys Arg
 1               5                  10                  15

Glu Glu His Lys Lys His Pro Asp Ala Ser Val Asn Phe Ser Glu
                20                  25                  30

Phe Ser Lys Gln Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
 65              70                  75
```

<210> SEQ ID NO 161
<211> LENGTH: 77
<212> TYPE: PRT

<213> ORGANISM: Homo sapiens

<400> SEQUENCE: 161

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Gln Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 162
<211> LENGTH: 77
<212> TYPE: PRT
<213> ORGANISM: Homo sapiens

<400> SEQUENCE: 162

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser His Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 163
<211> LENGTH: 77
<212> TYPE: PRT
<213> ORGANISM: Homo sapiens

<400> SEQUENCE: 163

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Asn Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 164
<211> LENGTH: 77
<212> TYPE: PRT
<213> ORGANISM: Homo sapiens

<400> SEQUENCE: 164

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu His Trp Lys Thr Met Ser Ala Lys Glu

```
            35                  40                  45
Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75

<210> SEQ ID NO 165
<211> LENGTH: 77
<212> TYPE: PRT
<213> ORGANISM: Homo sapiens

<400> SEQUENCE: 165

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
             20                  25                  30

Phe Ser Lys Lys Cys Ser Glu Gln Trp Lys Thr Met Ser Ala Lys Glu
         35                  40                  45

Lys Gly Lys Phe Glu Asp Met Ala Lys Ala Asp Lys Ala Arg Tyr Glu
     50                  55                  60

Arg Glu Met Lys Thr Tyr Ile Pro Pro Lys Gly Glu Thr
 65                  70                  75

<210> SEQ ID NO 166
<211> LENGTH: 77
<212> TYPE: PRT
<213> ORGANISM: Homo sapiens

<400> SEQUENCE: 166

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
             20                  25                  30

Phe Ser Lys Lys Cys Ser Glu Arg Tyr Lys Thr Met Ser Ala Lys Glu
         35                  40                  45

Lys Gly Lys Phe Glu Asp Met Ala Lys Ala Asp Lys Ala Arg Tyr Glu
     50                  55                  60

Arg Glu Met Lys Thr Tyr Ile Pro Pro Lys Gly Glu Thr
 65                  70                  75

<210> SEQ ID NO 167
<211> LENGTH: 77
<212> TYPE: PRT
<213> ORGANISM: Homo sapiens

<400> SEQUENCE: 167

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
             20                  25                  30

Phe Ser Lys Lys Cys Ser Glu Arg Ser Lys Thr Met Ser Ala Lys Glu
         35                  40                  45

Lys Gly Lys Phe Glu Asp Met Ala Lys Ala Asp Lys Ala Arg Tyr Glu
     50                  55                  60

Arg Glu Met Lys Thr Tyr Ile Pro Pro Lys Gly Glu Thr
 65                  70                  75

<210> SEQ ID NO 168
<211> LENGTH: 77
```

```
<212> TYPE: PRT
<213> ORGANISM: Homo sapiens

<400> SEQUENCE: 168

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Asn Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 169
<211> LENGTH: 77
<212> TYPE: PRT
<213> ORGANISM: Homo sapiens

<400> SEQUENCE: 169

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Gln Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 170
<211> LENGTH: 77
<212> TYPE: PRT
<213> ORGANISM: Homo sapiens

<400> SEQUENCE: 170

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Ile Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 171
<211> LENGTH: 77
<212> TYPE: PRT
<213> ORGANISM: Homo sapiens

<400> SEQUENCE: 171

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30
```

```
Phe Ser Lys Lys Cys Ser Glu Arg Trp Lys Thr Val Ser Ala Lys Glu
        35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 172
<211> LENGTH: 77
<212> TYPE: PRT
<213> ORGANISM: Homo sapiens

<400> SEQUENCE: 172

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Asn Glu
        35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 173
<211> LENGTH: 77
<212> TYPE: PRT
<213> ORGANISM: Homo sapiens

<400> SEQUENCE: 173

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Gln Glu
        35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 174
<211> LENGTH: 77
<212> TYPE: PRT
<213> ORGANISM: Homo sapiens

<400> SEQUENCE: 174

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Gln
        35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 175
```

```
<211> LENGTH: 77
<212> TYPE: PRT
<213> ORGANISM: Homo sapiens

<400> SEQUENCE: 175

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys His
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 176
<211> LENGTH: 77
<212> TYPE: PRT
<213> ORGANISM: Homo sapiens

<400> SEQUENCE: 176

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Asn
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 177
<211> LENGTH: 77
<212> TYPE: PRT
<213> ORGANISM: Homo sapiens

<400> SEQUENCE: 177

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Asn Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 178
<211> LENGTH: 77
<212> TYPE: PRT
<213> ORGANISM: Homo sapiens

<400> SEQUENCE: 178

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30
```

```
Phe Ser Lys Lys Cys Ser Glu Arg Trp Lys Thr Met Ser Ala Lys Glu
            35                  40                  45

Gln Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75
```

<210> SEQ ID NO 179
<211> LENGTH: 77
<212> TYPE: PRT
<213> ORGANISM: Homo sapiens

<400> SEQUENCE: 179

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Asn Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75
```

<210> SEQ ID NO 180
<211> LENGTH: 77
<212> TYPE: PRT
<213> ORGANISM: Homo sapiens

<400> SEQUENCE: 180

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Gln Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75
```

<210> SEQ ID NO 181
<211> LENGTH: 77
<212> TYPE: PRT
<213> ORGANISM: Homo sapiens

<400> SEQUENCE: 181

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Ile Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75
```

-continued

<210> SEQ ID NO 182
<211> LENGTH: 77
<212> TYPE: PRT
<213> ORGANISM: Homo sapiens

<400> SEQUENCE: 182

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Val Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 183
<211> LENGTH: 77
<212> TYPE: PRT
<213> ORGANISM: Homo sapiens

<400> SEQUENCE: 183

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Gln Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 184
<211> LENGTH: 77
<212> TYPE: PRT
<213> ORGANISM: Homo sapiens

<400> SEQUENCE: 184

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe His Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 185
<211> LENGTH: 77
<212> TYPE: PRT
<213> ORGANISM: Homo sapiens

<400> SEQUENCE: 185

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu

```
                    20                  25                  30

Phe Ser Lys Lys Cys Ser Glu Arg Trp Lys Thr Met Ser Ala Lys Glu
        35                  40                  45

Lys Gly Lys Phe Asn Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 186
<211> LENGTH: 77
<212> TYPE: PRT
<213> ORGANISM: Homo sapiens

<400> SEQUENCE: 186

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
        35                  40                  45

Lys Gly Lys Phe Glu Asn Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 187
<211> LENGTH: 77
<212> TYPE: PRT
<213> ORGANISM: Homo sapiens

<400> SEQUENCE: 187

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
        35                  40                  45

Lys Gly Lys Phe Glu Gln Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 188
<211> LENGTH: 77
<212> TYPE: PRT
<213> ORGANISM: Homo sapiens

<400> SEQUENCE: 188

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
        35                  40                  45

Lys Gly Lys Phe Glu Asp Ile Ala Lys Ala Asp Lys Ala Arg Tyr Glu
    50                  55                  60

Arg Glu Met Lys Thr Tyr Ile Pro Pro Lys Gly Glu Thr
65                  70                  75
```

```
<210> SEQ ID NO 189
<211> LENGTH: 77
<212> TYPE: PRT
<213> ORGANISM: Homo sapiens

<400> SEQUENCE: 189

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Val Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 190
<211> LENGTH: 77
<212> TYPE: PRT
<213> ORGANISM: Homo sapiens

<400> SEQUENCE: 190

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Asn Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 191
<211> LENGTH: 77
<212> TYPE: PRT
<213> ORGANISM: Homo sapiens

<400> SEQUENCE: 191

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Gln Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 192
<211> LENGTH: 77
<212> TYPE: PRT
<213> ORGANISM: Homo sapiens

<400> SEQUENCE: 192

Pro Arg Gly Lys Met Ser Ser Tyr Ala Phe Phe Val Gln Thr Cys Arg
1               5                   10                  15
```

-continued

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asn Lys Ala Arg Tyr Glu
    50                  55                  60

Arg Glu Met Lys Thr Tyr Ile Pro Pro Lys Gly Glu Thr
65                  70                  75

<210> SEQ ID NO 193
<211> LENGTH: 77
<212> TYPE: PRT
<213> ORGANISM: Homo sapiens

<400> SEQUENCE: 193

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Gln Lys Ala Arg Tyr Glu
    50                  55                  60

Arg Glu Met Lys Thr Tyr Ile Pro Pro Lys Gly Glu Thr
65                  70                  75

<210> SEQ ID NO 194
<211> LENGTH: 77
<212> TYPE: PRT
<213> ORGANISM: Homo sapiens

<400> SEQUENCE: 194

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Asn Ala Arg Tyr Glu
    50                  55                  60

Arg Glu Met Lys Thr Tyr Ile Pro Pro Lys Gly Glu Thr
65                  70                  75

<210> SEQ ID NO 195
<211> LENGTH: 77
<212> TYPE: PRT
<213> ORGANISM: Homo sapiens

<400> SEQUENCE: 195

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Gln Ala Arg Tyr Glu
    50                  55                  60

Arg Glu Met Lys Thr Tyr Ile Pro Pro Lys Gly Glu Thr
65                  70                  75

<210> SEQ ID NO 196
<211> LENGTH: 77
<212> TYPE: PRT
<213> ORGANISM: Homo sapiens

<400> SEQUENCE: 196

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala His Tyr Glu
    50                  55                  60

Arg Glu Met Lys Thr Tyr Ile Pro Pro Lys Gly Glu Thr
65                  70                  75

<210> SEQ ID NO 197
<211> LENGTH: 77
<212> TYPE: PRT
<213> ORGANISM: Homo sapiens

<400> SEQUENCE: 197

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Gln Tyr Glu
    50                  55                  60

Arg Glu Met Lys Thr Tyr Ile Pro Pro Lys Gly Glu Thr
65                  70                  75

<210> SEQ ID NO 198
<211> LENGTH: 77
<212> TYPE: PRT
<213> ORGANISM: Homo sapiens

<400> SEQUENCE: 198

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg His Glu
    50                  55                  60

Arg Glu Met Lys Thr Tyr Ile Pro Pro Lys Gly Glu Thr
65                  70                  75

<210> SEQ ID NO 199
<211> LENGTH: 77
<212> TYPE: PRT
<213> ORGANISM: Homo sapiens

<400> SEQUENCE: 199

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Ile Glu
    50                  55                  60

Arg Glu Met Lys Thr Tyr Ile Pro Pro Lys Gly Glu Thr
65                  70                  75

<210> SEQ ID NO 200
<211> LENGTH: 77
<212> TYPE: PRT
<213> ORGANISM: Homo sapiens

<400> SEQUENCE: 200

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Gln
    50                  55                  60

Arg Glu Met Lys Thr Tyr Ile Pro Pro Lys Gly Glu Thr
65                  70                  75

<210> SEQ ID NO 201
<211> LENGTH: 77
<212> TYPE: PRT
<213> ORGANISM: Homo sapiens

<400> SEQUENCE: 201

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr His
    50                  55                  60

Arg Glu Met Lys Thr Tyr Ile Pro Pro Lys Gly Glu Thr
65                  70                  75

<210> SEQ ID NO 202
<211> LENGTH: 77
<212> TYPE: PRT
<213> ORGANISM: Homo sapiens

<400> SEQUENCE: 202

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Asn
    50                  55                  60

Arg Glu Met Lys Thr Tyr Ile Pro Pro Lys Gly Glu Thr 65                  70                  75

<210> SEQ ID NO 203
<211> LENGTH: 77
<212> TYPE: PRT
<213> ORGANISM: Homo sapiens

<400> SEQUENCE: 203

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

His Glu Met Lys Thr Tyr Ile Pro Pro Lys Gly Glu Thr
65                  70                  75

<210> SEQ ID NO 204
<211> LENGTH: 77
<212> TYPE: PRT
<213> ORGANISM: Homo sapiens

<400> SEQUENCE: 204

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Gln Glu Met Lys Thr Tyr Ile Pro Pro Lys Gly Glu Thr
65                  70                  75

<210> SEQ ID NO 205
<211> LENGTH: 77
<212> TYPE: PRT
<213> ORGANISM: Homo sapiens

<400> SEQUENCE: 205

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Gln Met Lys Thr Tyr Ile Pro Pro Lys Gly Glu Thr
65                  70                  75

<210> SEQ ID NO 206
<211> LENGTH: 77
<212> TYPE: PRT
<213> ORGANISM: Homo sapiens

<400> SEQUENCE: 206

Pro Arg Gly Lys Met Ser Ser Tyr Ala Phe Phe Val Gln Thr Cys Arg

```
                1               5                  10                 15
Glu Glu His Lys Lys His Pro Asp Ala Ser Val Asn Phe Ser Glu
                20                  25                 30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg His Met Lys Thr Tyr Ile Pro Pro Lys Gly Glu Thr
65                  70                  75
```

<210> SEQ ID NO 207
<211> LENGTH: 77
<212> TYPE: PRT
<213> ORGANISM: Homo sapiens

<400> SEQUENCE: 207

```
Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Asn Met Lys Thr Tyr Ile Pro Pro Lys Gly Glu Thr
65                  70                  75
```

<210> SEQ ID NO 208
<211> LENGTH: 77
<212> TYPE: PRT
<213> ORGANISM: Homo sapiens

<400> SEQUENCE: 208

```
Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Ile Lys Thr Tyr Ile Pro Pro Lys Gly Glu Thr
65                  70                  75
```

<210> SEQ ID NO 209
<211> LENGTH: 77
<212> TYPE: PRT
<213> ORGANISM: Homo sapiens

<400> SEQUENCE: 209

```
Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60
```

Arg Glu Val Lys Thr Tyr Ile Pro Pro Lys Gly Glu Thr
65                  70                  75

<210> SEQ ID NO 210
<211> LENGTH: 77
<212> TYPE: PRT
<213> ORGANISM: Homo sapiens

<400> SEQUENCE: 210

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Asn Thr Tyr Ile Pro Pro Lys Gly Glu Thr
65                  70                  75

<210> SEQ ID NO 211
<211> LENGTH: 77
<212> TYPE: PRT
<213> ORGANISM: Homo sapiens

<400> SEQUENCE: 211

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Gln Thr Tyr Ile Pro Pro Lys Gly Glu Thr
65                  70                  75

<210> SEQ ID NO 212
<211> LENGTH: 77
<212> TYPE: PRT
<213> ORGANISM: Homo sapiens

<400> SEQUENCE: 212

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr His Ile Pro Pro Lys Gly Glu Thr
65                  70                  75

<210> SEQ ID NO 213
<211> LENGTH: 77
<212> TYPE: PRT
<213> ORGANISM: Homo sapiens

<400> SEQUENCE: 213

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Ile Ile Pro Pro Lys Gly Glu Thr
65                  70                  75
```

<210> SEQ ID NO 214
<211> LENGTH: 77
<212> TYPE: PRT
<213> ORGANISM: Homo sapiens

<400> SEQUENCE: 214

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Ala Pro Lys Gly Glu Thr
65                  70                  75
```

<210> SEQ ID NO 215
<211> LENGTH: 77
<212> TYPE: PRT
<213> ORGANISM: Homo sapiens

<400> SEQUENCE: 215

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Ser Pro Lys Gly Glu Thr
65                  70                  75
```

<210> SEQ ID NO 216
<211> LENGTH: 77
<212> TYPE: PRT
<213> ORGANISM: Homo sapiens

<400> SEQUENCE: 216

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60
```

```
Arg Glu Met Lys Thr Tyr Ile Pro Ala Lys Gly Glu Thr
 65                  70                  75
```

<210> SEQ ID NO 217
<211> LENGTH: 77
<212> TYPE: PRT
<213> ORGANISM: Homo sapiens

<400> SEQUENCE: 217

```
Pro Arg Gly Lys Met Ser Ser Tyr Ala Phe Phe Val Gln Thr Cys Arg
  1               5                  10                  15

Glu Glu His Lys Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
         35                  40                  45

Lys Gly Lys Phe Glu Asp Met Ala Lys Ala Asp Lys Ala Arg Tyr Glu
     50                  55                  60

Arg Glu Met Lys Thr Tyr Ile Pro Ser Lys Gly Glu Thr
 65                  70                  75
```

<210> SEQ ID NO 218
<211> LENGTH: 77
<212> TYPE: PRT
<213> ORGANISM: Homo sapiens

<400> SEQUENCE: 218

```
Pro Arg Gly Lys Met Ser Ser Tyr Ala Phe Phe Val Gln Thr Cys Arg
  1               5                  10                  15

Glu Glu His Lys Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
         35                  40                  45

Lys Gly Lys Phe Glu Asp Met Ala Lys Ala Asp Lys Ala Arg Tyr Glu
     50                  55                  60

Arg Glu Met Lys Thr Tyr Ile Pro Pro Asn Gly Glu Thr
 65                  70                  75
```

<210> SEQ ID NO 219
<211> LENGTH: 77
<212> TYPE: PRT
<213> ORGANISM: Homo sapiens

<400> SEQUENCE: 219

```
Pro Arg Gly Lys Met Ser Ser Tyr Ala Phe Phe Val Gln Thr Cys Arg
  1               5                  10                  15

Glu Glu His Lys Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
         35                  40                  45

Lys Gly Lys Phe Glu Asp Met Ala Lys Ala Asp Lys Ala Arg Tyr Glu
     50                  55                  60

Arg Glu Met Lys Thr Tyr Ile Pro Pro Gln Gly Glu Thr
 65                  70                  75
```

<210> SEQ ID NO 220
<211> LENGTH: 77
<212> TYPE: PRT
<213> ORGANISM: Homo sapiens

<400> SEQUENCE: 220

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Gln Thr
65                  70                  75

<210> SEQ ID NO 221
<211> LENGTH: 77
<212> TYPE: PRT
<213> ORGANISM: Homo sapiens

<400> SEQUENCE: 221

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly His Thr
65                  70                  75

<210> SEQ ID NO 222
<211> LENGTH: 77
<212> TYPE: PRT
<213> ORGANISM: Homo sapiens

<400> SEQUENCE: 222

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Asn Thr
65                  70                  75

<210> SEQ ID NO 223
<211> LENGTH: 54
<212> TYPE: PRT
<213> ORGANISM: Homo sapiens

<400> SEQUENCE: 223

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

```
<210> SEQ ID NO 224
<211> LENGTH: 54
<212> TYPE: PRT
<213> ORGANISM: Homo sapiens

<400> SEQUENCE: 224

Ala Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 225
<211> LENGTH: 54
<212> TYPE: PRT
<213> ORGANISM: Homo sapiens

<400> SEQUENCE: 225

Ser Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 226
<211> LENGTH: 54
<212> TYPE: PRT
<213> ORGANISM: Homo sapiens

<400> SEQUENCE: 226

Pro Asn Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 227
<211> LENGTH: 54
<212> TYPE: PRT
<213> ORGANISM: Homo sapiens

<400> SEQUENCE: 227

Pro Gln Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
```

```
<210> SEQ ID NO 228
<211> LENGTH: 54
<212> TYPE: PRT
<213> ORGANISM: Homo sapiens

<400> SEQUENCE: 228

Pro Asp Ala Ser Val Asn Ile Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 229
<211> LENGTH: 54
<212> TYPE: PRT
<213> ORGANISM: Homo sapiens

<400> SEQUENCE: 229

Pro Asp Ala Ser Val Asn Val Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 230
<211> LENGTH: 54
<212> TYPE: PRT
<213> ORGANISM: Homo sapiens

<400> SEQUENCE: 230

Pro Asp Ala Ser Val Asn Phe Ser Gln Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 231
<211> LENGTH: 54
<212> TYPE: PRT
<213> ORGANISM: Homo sapiens

<400> SEQUENCE: 231

Pro Asp Ala Ser Val Asn Phe Ser His Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
```

-continued

<210> SEQ ID NO 232
<211> LENGTH: 54
<212> TYPE: PRT
<213> ORGANISM: Homo sapiens

<400> SEQUENCE: 232

Pro Asp Ala Ser Val Asn Phe Ser Asn Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 233
<211> LENGTH: 54
<212> TYPE: PRT
<213> ORGANISM: Homo sapiens

<400> SEQUENCE: 233

Pro Asp Ala Ser Val Asn Phe Ser Glu Ile Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 234
<211> LENGTH: 54
<212> TYPE: PRT
<213> ORGANISM: Homo sapiens

<400> SEQUENCE: 234

Pro Asp Ala Ser Val Asn Phe Ser Glu Val Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 235
<211> LENGTH: 54
<212> TYPE: PRT
<213> ORGANISM: Homo sapiens

<400> SEQUENCE: 235

Pro Asp Ala Ser Val Asn Phe Ser Glu Phe Ser Asn Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

-continued

<210> SEQ ID NO 236
<211> LENGTH: 54
<212> TYPE: PRT
<213> ORGANISM: Homo sapiens

<400> SEQUENCE: 236

Pro Asp Ala Ser Val Asn Phe Ser Glu Phe Ser Gln Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 237
<211> LENGTH: 54
<212> TYPE: PRT
<213> ORGANISM: Homo sapiens

<400> SEQUENCE: 237

Pro Asp Ala Ser Val Asn Phe Ser Glu Phe Ser Lys Asn Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 238
<211> LENGTH: 54
<212> TYPE: PRT
<213> ORGANISM: Homo sapiens

<400> SEQUENCE: 238

Pro Asp Ala Ser Val Asn Phe Ser Glu Phe Ser Lys Gln Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 239
<211> LENGTH: 54
<212> TYPE: PRT
<213> ORGANISM: Homo sapiens

<400> SEQUENCE: 239

Pro Asp Ala Ser Val Asn Phe Ser Glu Phe Ser Lys Lys Cys Ser Gln
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

<210> SEQ ID NO 240
<211> LENGTH: 54
<212> TYPE: PRT
<213> ORGANISM: Homo sapiens

<400> SEQUENCE: 240

Pro Asp Ala Ser Val Asn Phe Ser Glu Phe Ser Lys Lys Cys Ser His
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 241
<211> LENGTH: 54
<212> TYPE: PRT
<213> ORGANISM: Homo sapiens

<400> SEQUENCE: 241

Pro Asp Ala Ser Val Asn Phe Ser Glu Phe Ser Lys Lys Cys Ser Asn
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 242
<211> LENGTH: 54
<212> TYPE: PRT
<213> ORGANISM: Homo sapiens

<400> SEQUENCE: 242

Pro Asp Ala Ser Val Asn Phe Ser Glu Phe Ser Lys Lys Cys Ser Glu
1               5                   10                  15

His Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 243
<211> LENGTH: 54
<212> TYPE: PRT
<213> ORGANISM: Homo sapiens

<400> SEQUENCE: 243

Pro Asp Ala Ser Val Asn Phe Ser Glu Phe Ser Lys Lys Cys Ser Glu
1               5                   10                  15

Gln Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

<210> SEQ ID NO 244
<211> LENGTH: 54
<212> TYPE: PRT
<213> ORGANISM: Homo sapiens

<400> SEQUENCE: 244

Pro Asp Ala Ser Val Asn Phe Ser Glu Phe Ser Lys Lys Cys Ser Glu
1               5                   10                  15

Arg Tyr Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 245
<211> LENGTH: 54
<212> TYPE: PRT
<213> ORGANISM: Homo sapiens

<400> SEQUENCE: 245

Pro Asp Ala Ser Val Asn Phe Ser Glu Phe Ser Lys Lys Cys Ser Glu
1               5                   10                  15

Arg Ser Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 246
<211> LENGTH: 54
<212> TYPE: PRT
<213> ORGANISM: Homo sapiens

<400> SEQUENCE: 246

Pro Asp Ala Ser Val Asn Phe Ser Glu Phe Ser Lys Lys Cys Ser Glu
1               5                   10                  15

Arg Trp Asn Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 247
<211> LENGTH: 54
<212> TYPE: PRT
<213> ORGANISM: Homo sapiens

<400> SEQUENCE: 247

Pro Asp Ala Ser Val Asn Phe Ser Glu Phe Ser Lys Lys Cys Ser Glu
1               5                   10                  15

Arg Trp Gln Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

<210> SEQ ID NO 248
<211> LENGTH: 54
<212> TYPE: PRT
<213> ORGANISM: Homo sapiens

<400> SEQUENCE: 248

Pro Asp Ala Ser Val Asn Phe Ser Glu Phe Ser Lys Lys Cys Ser Glu
1               5                   10                  15

Arg Trp Lys Thr Ile Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 249
<211> LENGTH: 54
<212> TYPE: PRT
<213> ORGANISM: Homo sapiens

<400> SEQUENCE: 249

Pro Asp Ala Ser Val Asn Phe Ser Glu Phe Ser Lys Lys Cys Ser Glu
1               5                   10                  15

Arg Trp Lys Thr Val Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 250
<211> LENGTH: 54
<212> TYPE: PRT
<213> ORGANISM: Homo sapiens

<400> SEQUENCE: 250

Pro Asp Ala Ser Val Asn Phe Ser Glu Phe Ser Lys Lys Cys Ser Glu
1               5                   10                  15

Arg Trp Lys Thr Met Ser Ala Asn Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 251
<211> LENGTH: 54
<212> TYPE: PRT
<213> ORGANISM: Homo sapiens

<400> SEQUENCE: 251

Pro Asp Ala Ser Val Asn Phe Ser Glu Phe Ser Lys Lys Cys Ser Glu
1               5                   10                  15

Arg Trp Lys Thr Met Ser Ala Gln Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

-continued

<210> SEQ ID NO 252
<211> LENGTH: 54
<212> TYPE: PRT
<213> ORGANISM: Homo sapiens

<400> SEQUENCE: 252

Pro Asp Ala Ser Val Asn Phe Ser Glu Phe Ser Lys Lys Cys Ser Glu
1               5                   10                  15

Arg Trp Lys Thr Met Ser Ala Lys Gln Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 253
<211> LENGTH: 54
<212> TYPE: PRT
<213> ORGANISM: Homo sapiens

<400> SEQUENCE: 253

Pro Asp Ala Ser Val Asn Phe Ser Glu Phe Ser Lys Lys Cys Ser Glu
1               5                   10                  15

Arg Trp Lys Thr Met Ser Ala Lys His Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 254
<211> LENGTH: 54
<212> TYPE: PRT
<213> ORGANISM: Homo sapiens

<400> SEQUENCE: 254

Pro Asp Ala Ser Val Asn Phe Ser Glu Phe Ser Lys Lys Cys Ser Glu
1               5                   10                  15

Arg Trp Lys Thr Met Ser Ala Lys Asn Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 255
<211> LENGTH: 54
<212> TYPE: PRT
<213> ORGANISM: Homo sapiens

<400> SEQUENCE: 255

Pro Asp Ala Ser Val Asn Phe Ser Glu Phe Ser Lys Lys Cys Ser Glu
1               5                   10                  15

Arg Trp Lys Thr Met Ser Ala Lys Glu Asn Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

```
<210> SEQ ID NO 256
<211> LENGTH: 54
<212> TYPE: PRT
<213> ORGANISM: Homo sapiens

<400> SEQUENCE: 256

Pro Asp Ala Ser Val Asn Phe Ser Glu Phe Ser Lys Lys Cys Ser Glu
1               5                   10                  15

Arg Trp Lys Thr Met Ser Ala Lys Glu Gln Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 257
<211> LENGTH: 54
<212> TYPE: PRT
<213> ORGANISM: Homo sapiens

<400> SEQUENCE: 257

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Asn Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 258
<211> LENGTH: 54
<212> TYPE: PRT
<213> ORGANISM: Homo sapiens

<400> SEQUENCE: 258

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Gln Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 259
<211> LENGTH: 54
<212> TYPE: PRT
<213> ORGANISM: Homo sapiens

<400> SEQUENCE: 259

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Ile Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
```

<210> SEQ ID NO 260
<211> LENGTH: 54
<212> TYPE: PRT
<213> ORGANISM: Homo sapiens

<400> SEQUENCE: 260

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Val Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 261
<211> LENGTH: 54
<212> TYPE: PRT
<213> ORGANISM: Homo sapiens

<400> SEQUENCE: 261

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Gln Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 262
<211> LENGTH: 54
<212> TYPE: PRT
<213> ORGANISM: Homo sapiens

<400> SEQUENCE: 262

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe His Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 263
<211> LENGTH: 54
<212> TYPE: PRT
<213> ORGANISM: Homo sapiens

<400> SEQUENCE: 263

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Asn Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

50

<210> SEQ ID NO 264
<211> LENGTH: 54
<212> TYPE: PRT
<213> ORGANISM: Homo sapiens

<400> SEQUENCE: 264

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asn Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 265
<211> LENGTH: 54
<212> TYPE: PRT
<213> ORGANISM: Homo sapiens

<400> SEQUENCE: 265

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Gln Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 266
<211> LENGTH: 54
<212> TYPE: PRT
<213> ORGANISM: Homo sapiens

<400> SEQUENCE: 266

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Ile
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 267
<211> LENGTH: 54
<212> TYPE: PRT
<213> ORGANISM: Homo sapiens

<400> SEQUENCE: 267

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Val
            20                  25                  30

Ala Lys Ala Asp Lys Ala Arg Tyr Glu Arg Glu Met Lys Thr Tyr Ile
        35                  40                  45

Pro Pro Lys Gly Glu Thr

<210> SEQ ID NO 268
<211> LENGTH: 54
<212> TYPE: PRT
<213> ORGANISM: Homo sapiens

<400> SEQUENCE: 268

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Asn Ala Asp Lys Ala Arg Tyr Glu Arg Glu Met Lys Thr Tyr Ile
        35                  40                  45

Pro Pro Lys Gly Glu Thr
    50

<210> SEQ ID NO 269
<211> LENGTH: 54
<212> TYPE: PRT
<213> ORGANISM: Homo sapiens

<400> SEQUENCE: 269

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Gln Ala Asp Lys Ala Arg Tyr Glu Arg Glu Met Lys Thr Tyr Ile
        35                  40                  45

Pro Pro Lys Gly Glu Thr
    50

<210> SEQ ID NO 270
<211> LENGTH: 54
<212> TYPE: PRT
<213> ORGANISM: Homo sapiens

<400> SEQUENCE: 270

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asn Lys Ala Arg Tyr Glu Arg Glu Met Lys Thr Tyr Ile
        35                  40                  45

Pro Pro Lys Gly Glu Thr
    50

<210> SEQ ID NO 271
<211> LENGTH: 54
<212> TYPE: PRT
<213> ORGANISM: Homo sapiens

<400> SEQUENCE: 271

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Gln Lys Ala Arg Tyr Glu Arg Glu Met Lys Thr Tyr Ile
        35                  40                  45

Pro Pro Lys Gly Glu Thr

<210> SEQ ID NO 272
<211> LENGTH: 54
<212> TYPE: PRT
<213> ORGANISM: Homo sapiens

<400> SEQUENCE: 272

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Asn Ala Arg Tyr Glu Arg Glu Met Lys Thr Tyr Ile
        35                  40                  45

Pro Pro Lys Gly Glu Thr
    50

<210> SEQ ID NO 273
<211> LENGTH: 54
<212> TYPE: PRT
<213> ORGANISM: Homo sapiens

<400> SEQUENCE: 273

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Gln Ala Arg Tyr Glu Arg Glu Met Lys Thr Tyr Ile
        35                  40                  45

Pro Pro Lys Gly Glu Thr
    50

<210> SEQ ID NO 274
<211> LENGTH: 54
<212> TYPE: PRT
<213> ORGANISM: Homo sapiens

<400> SEQUENCE: 274

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala His Tyr Glu Arg Glu Met Lys Thr Tyr Ile
        35                  40                  45

Pro Pro Lys Gly Glu Thr
    50

<210> SEQ ID NO 275
<211> LENGTH: 54
<212> TYPE: PRT
<213> ORGANISM: Homo sapiens

<400> SEQUENCE: 275

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Gln Tyr Glu Arg Glu Met Lys Thr Tyr Ile
        35                  40                  45

Pro Pro Lys Gly Glu Thr

50

<210> SEQ ID NO 276
<211> LENGTH: 54
<212> TYPE: PRT
<213> ORGANISM: Homo sapiens

<400> SEQUENCE: 276

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg His Glu Arg Glu Met Lys Thr Tyr Ile
        35                  40                  45

Pro Pro Lys Gly Glu Thr
    50

<210> SEQ ID NO 277
<211> LENGTH: 54
<212> TYPE: PRT
<213> ORGANISM: Homo sapiens

<400> SEQUENCE: 277

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Ile Glu Arg Glu Met Lys Thr Tyr Ile
        35                  40                  45

Pro Pro Lys Gly Glu Thr
    50

<210> SEQ ID NO 278
<211> LENGTH: 54
<212> TYPE: PRT
<213> ORGANISM: Homo sapiens

<400> SEQUENCE: 278

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Gln Arg Glu Met Lys Thr Tyr Ile
        35                  40                  45

Pro Pro Lys Gly Glu Thr
    50

<210> SEQ ID NO 279
<211> LENGTH: 54
<212> TYPE: PRT
<213> ORGANISM: Homo sapiens

<400> SEQUENCE: 279

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr His Arg Glu Met Lys Thr Tyr Ile
        35                  40                  45

Pro Pro Lys Gly Glu Thr

50

<210> SEQ ID NO 280
<211> LENGTH: 54
<212> TYPE: PRT
<213> ORGANISM: Homo sapiens

<400> SEQUENCE: 280

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Asn Arg Glu Met Lys Thr Tyr Ile
        35                  40                  45

Pro Pro Lys Gly Glu Thr
    50

<210> SEQ ID NO 281
<211> LENGTH: 54
<212> TYPE: PRT
<213> ORGANISM: Homo sapiens

<400> SEQUENCE: 281

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu His Glu Met Lys Thr Tyr Ile
        35                  40                  45

Pro Pro Lys Gly Glu Thr
    50

<210> SEQ ID NO 282
<211> LENGTH: 54
<212> TYPE: PRT
<213> ORGANISM: Homo sapiens

<400> SEQUENCE: 282

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Gln Glu Met Lys Thr Tyr Ile
        35                  40                  45

Pro Pro Lys Gly Glu Thr
    50

<210> SEQ ID NO 283
<211> LENGTH: 54
<212> TYPE: PRT
<213> ORGANISM: Homo sapiens

<400> SEQUENCE: 283

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Gln Met Lys Thr Tyr Ile
        35                  40                  45

Pro Pro Lys Gly Glu Thr

<210> SEQ ID NO 284
<211> LENGTH: 54
<212> TYPE: PRT
<213> ORGANISM: Homo sapiens

<400> SEQUENCE: 284

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg His Met Lys Thr Tyr Ile
        35                  40                  45

Pro Pro Lys Gly Glu Thr
    50

<210> SEQ ID NO 285
<211> LENGTH: 54
<212> TYPE: PRT
<213> ORGANISM: Homo sapiens

<400> SEQUENCE: 285

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Asn Met Lys Thr Tyr Ile
        35                  40                  45

Pro Pro Lys Gly Glu Thr
    50

<210> SEQ ID NO 286
<211> LENGTH: 54
<212> TYPE: PRT
<213> ORGANISM: Homo sapiens

<400> SEQUENCE: 286

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Ile Lys Thr Tyr Ile
        35                  40                  45

Pro Pro Lys Gly Glu Thr
    50

<210> SEQ ID NO 287
<211> LENGTH: 54
<212> TYPE: PRT
<213> ORGANISM: Homo sapiens

<400> SEQUENCE: 287

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Val Lys Thr Tyr Ile
        35                  40                  45

Pro Pro Lys Gly Glu Thr

50

<210> SEQ ID NO 288
<211> LENGTH: 54
<212> TYPE: PRT
<213> ORGANISM: Homo sapiens

<400> SEQUENCE: 288

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Asn Thr Tyr Ile
        35                  40                  45

Pro Pro Lys Gly Glu Thr
    50

<210> SEQ ID NO 289
<211> LENGTH: 54
<212> TYPE: PRT
<213> ORGANISM: Homo sapiens

<400> SEQUENCE: 289

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Gln Thr Tyr Ile
        35                  40                  45

Pro Pro Lys Gly Glu Thr
    50

<210> SEQ ID NO 290
<211> LENGTH: 54
<212> TYPE: PRT
<213> ORGANISM: Homo sapiens

<400> SEQUENCE: 290

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr His Ile
        35                  40                  45

Pro Pro Lys Gly Glu Thr
    50

<210> SEQ ID NO 291
<211> LENGTH: 54
<212> TYPE: PRT
<213> ORGANISM: Homo sapiens

<400> SEQUENCE: 291

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Ile Ile
        35                  40                  45

Pro Pro Lys Gly Glu Thr

<210> SEQ ID NO 292
<211> LENGTH: 54
<212> TYPE: PRT
<213> ORGANISM: Homo sapiens

<400> SEQUENCE: 292

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Ala Pro Lys Gly Glu Thr
    50

<210> SEQ ID NO 293
<211> LENGTH: 54
<212> TYPE: PRT
<213> ORGANISM: Homo sapiens

<400> SEQUENCE: 293

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Ser Pro Lys Gly Glu Thr
    50

<210> SEQ ID NO 294
<211> LENGTH: 54
<212> TYPE: PRT
<213> ORGANISM: Homo sapiens

<400> SEQUENCE: 294

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Ala Lys Gly Glu Thr
    50

<210> SEQ ID NO 295
<211> LENGTH: 54
<212> TYPE: PRT
<213> ORGANISM: Homo sapiens

<400> SEQUENCE: 295

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Ser Lys Gly Glu Thr

<210> SEQ ID NO 296
<211> LENGTH: 54
<212> TYPE: PRT
<213> ORGANISM: Homo sapiens

<400> SEQUENCE: 296

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Asn Gly Glu Thr
    50

<210> SEQ ID NO 297
<211> LENGTH: 54
<212> TYPE: PRT
<213> ORGANISM: Homo sapiens

<400> SEQUENCE: 297

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Gln Gly Glu Thr
    50

<210> SEQ ID NO 298
<211> LENGTH: 54
<212> TYPE: PRT
<213> ORGANISM: Homo sapiens

<400> SEQUENCE: 298

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Gln Thr
    50

<210> SEQ ID NO 299
<211> LENGTH: 54
<212> TYPE: PRT
<213> ORGANISM: Homo sapiens

<400> SEQUENCE: 299

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly His Thr

```
<210> SEQ ID NO 300
<211> LENGTH: 54
<212> TYPE: PRT
<213> ORGANISM: Homo sapiens

<400> SEQUENCE: 300

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Asn Thr
    50

<210> SEQ ID NO 301
<211> LENGTH: 84
<212> TYPE: PRT
<213> ORGANISM: Anopheles gambiae

<400> SEQUENCE: 301

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 302
<211> LENGTH: 84
<212> TYPE: PRT
<213> ORGANISM: Anopheles gambiae

<400> SEQUENCE: 302

Gly Asn Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 303
<211> LENGTH: 84
<212> TYPE: PRT
<213> ORGANISM: Anopheles gambiae

<400> SEQUENCE: 303
```

Gly Gln Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 304
<211> LENGTH: 84
<212> TYPE: PRT
<213> ORGANISM: Anopheles gambiae

<400> SEQUENCE: 304

Gly Lys Val Asn Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 305
<211> LENGTH: 84
<212> TYPE: PRT
<213> ORGANISM: Anopheles gambiae

<400> SEQUENCE: 305

Gly Lys Val Gln Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 306
<211> LENGTH: 84
<212> TYPE: PRT
<213> ORGANISM: Anopheles gambiae

<400> SEQUENCE: 306

Gly Lys Val Lys Asn Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

```
Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 307
<211> LENGTH: 84
<212> TYPE: PRT
<213> ORGANISM: Anopheles gambiae

<400> SEQUENCE: 307

Gly Lys Val Lys Gln Asn Lys Pro Arg Gly Arg Met Thr Ala Tyr Ala
 1               5                  10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 308
<211> LENGTH: 84
<212> TYPE: PRT
<213> ORGANISM: Anopheles gambiae

<400> SEQUENCE: 308

Gly Lys Val Lys Asp Asn Pro Arg Gly Arg Met Thr Ala Tyr Ala
 1               5                  10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 309
<211> LENGTH: 84
<212> TYPE: PRT
<213> ORGANISM: Anopheles gambiae

<400> SEQUENCE: 309

Gly Lys Val Lys Asp Asn Gln Pro Arg Gly Arg Met Thr Ala Tyr Ala
 1               5                  10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
```

-continued

```
                    50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 310
<211> LENGTH: 84
<212> TYPE: PRT
<213> ORGANISM: Anopheles gambiae

<400> SEQUENCE: 310

Gly Lys Val Lys Asp Asn Lys Ala Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 311
<211> LENGTH: 84
<212> TYPE: PRT
<213> ORGANISM: Anopheles gambiae

<400> SEQUENCE: 311

Gly Lys Val Lys Asp Asn Lys Ser Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 312
<211> LENGTH: 84
<212> TYPE: PRT
<213> ORGANISM: Anopheles gambiae

<400> SEQUENCE: 312

Gly Lys Val Lys Asp Asn Lys Pro His Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 313
<211> LENGTH: 84
<212> TYPE: PRT
<213> ORGANISM: Anopheles gambiae

<400> SEQUENCE: 313

Gly Lys Val Lys Asp Asn Lys Pro Gln Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 314
<211> LENGTH: 84
<212> TYPE: PRT
<213> ORGANISM: Anopheles gambiae

<400> SEQUENCE: 314

Gly Lys Val Lys Asp Asn Lys Pro Arg Gly His Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 315
<211> LENGTH: 84
<212> TYPE: PRT
<213> ORGANISM: Anopheles gambiae

<400> SEQUENCE: 315

Gly Lys Val Lys Asp Asn Lys Pro Arg Gly Gln Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 316
<211> LENGTH: 84

```
<212> TYPE: PRT
<213> ORGANISM: Anopheles gambiae

<400> SEQUENCE: 316

Gly Lys Val Lys Asp Asn Lys Pro Arg Gly Arg Ile Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 317
<211> LENGTH: 84
<212> TYPE: PRT
<213> ORGANISM: Anopheles gambiae

<400> SEQUENCE: 317

Gly Lys Val Lys Asp Asn Lys Pro Arg Gly Arg Val Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 318
<211> LENGTH: 84
<212> TYPE: PRT
<213> ORGANISM: Anopheles gambiae

<400> SEQUENCE: 318

Gly Lys Val Lys Asp Asn Lys Pro Arg Gly Arg Met Thr Ala His Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 319
<211> LENGTH: 84
<212> TYPE: PRT
<213> ORGANISM: Anopheles gambiae

<400> SEQUENCE: 319
```

-continued

Gly Lys Val Lys Asp Asn Lys Pro Arg Gly Arg Met Thr Ala Ile Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 320
<211> LENGTH: 84
<212> TYPE: PRT
<213> ORGANISM: Anopheles gambiae

<400> SEQUENCE: 320

Gly Lys Val Lys Asp Asn Lys Pro Arg Gly Arg Met Thr Ala Tyr Ala
1               5                   10                  15

Ile Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 321
<211> LENGTH: 84
<212> TYPE: PRT
<213> ORGANISM: Anopheles gambiae

<400> SEQUENCE: 321

Gly Lys Val Lys Asp Asn Lys Pro Arg Gly Arg Met Thr Ala Tyr Ala
1               5                   10                  15

Val Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 322
<211> LENGTH: 84
<212> TYPE: PRT
<213> ORGANISM: Anopheles gambiae

<400> SEQUENCE: 322

Gly Lys Val Lys Asp Asn Lys Pro Arg Gly Arg Met Thr Ala Tyr Ala
1               5                   10                  15

Phe Ile Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 323
<211> LENGTH: 84
<212> TYPE: PRT
<213> ORGANISM: Anopheles gambiae

<400> SEQUENCE: 323

Gly Lys Val Lys Asp Asn Lys Pro Arg Gly Arg Met Thr Ala Tyr Ala
 1               5                  10                  15

Phe Val Val Gln Thr Cys Arg Glu Glu His Lys Lys His Pro Glu
                 20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 324
<211> LENGTH: 84
<212> TYPE: PRT
<213> ORGANISM: Anopheles gambiae

<400> SEQUENCE: 324

Gly Lys Val Lys Asp Asn Lys Pro Arg Gly Arg Met Thr Ala Tyr Ala
 1               5                  10                  15

Phe Phe Val Gln Thr Cys His Glu Glu His Lys Lys His Pro Glu
                 20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 325
<211> LENGTH: 84
<212> TYPE: PRT
<213> ORGANISM: Anopheles gambiae

<400> SEQUENCE: 325

Gly Lys Val Lys Asp Asn Lys Pro Arg Gly Arg Met Thr Ala Tyr Ala
 1               5                  10                  15

Phe Phe Val Gln Thr Cys Gln Glu Glu His Lys Lys His Pro Glu
                 20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu

```
                    50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 326
<211> LENGTH: 84
<212> TYPE: PRT
<213> ORGANISM: Anopheles gambiae

<400> SEQUENCE: 326

Gly Lys Val Lys Asp Asn Lys Pro Arg Gly Arg Met Thr Ala Tyr Ala
  1               5                  10                  15

Phe Phe Val Gln Thr Cys Arg Gln Glu His Lys Lys Lys His Pro Glu
                 20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 327
<211> LENGTH: 84
<212> TYPE: PRT
<213> ORGANISM: Anopheles gambiae

<400> SEQUENCE: 327

Gly Lys Val Lys Asp Asn Lys Pro Arg Gly Arg Met Thr Ala Tyr Ala
  1               5                  10                  15

Phe Phe Val Gln Thr Cys Arg His Glu His Lys Lys Lys His Pro Glu
                 20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 328
<211> LENGTH: 84
<212> TYPE: PRT
<213> ORGANISM: Anopheles gambiae

<400> SEQUENCE: 328

Gly Lys Val Lys Asp Asn Lys Pro Arg Gly Arg Met Thr Ala Tyr Ala
  1               5                  10                  15

Phe Phe Val Gln Thr Cys Arg Asn Glu His Lys Lys Lys His Pro Glu
                 20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 329
<211> LENGTH: 84
<212> TYPE: PRT
<213> ORGANISM: Anopheles gambiae

<400> SEQUENCE: 329

Gly Lys Val Lys Asp Asn Lys Pro Arg Gly Arg Met Thr Ala Tyr Ala
1               5                   10                  15

Phe Phe Val Gln Thr Cys Arg Glu Gln His Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 330
<211> LENGTH: 84
<212> TYPE: PRT
<213> ORGANISM: Anopheles gambiae

<400> SEQUENCE: 330

Gly Lys Val Lys Asp Asn Lys Pro Arg Gly Arg Met Thr Ala Tyr Ala
1               5                   10                  15

Phe Phe Val Gln Thr Cys Arg Glu His His Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 331
<211> LENGTH: 84
<212> TYPE: PRT
<213> ORGANISM: Anopheles gambiae

<400> SEQUENCE: 331

Gly Lys Val Lys Asp Asn Lys Pro Arg Gly Arg Met Thr Ala Tyr Ala
1               5                   10                  15

Phe Phe Val Gln Thr Cys Arg Glu Asn His Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 332
<211> LENGTH: 84

```
<212> TYPE: PRT
<213> ORGANISM: Anopheles gambiae

<400> SEQUENCE: 332

Gly Lys Val Lys Asp Asn Lys Pro Arg Gly Arg Met Thr Ala Tyr Ala
1               5                   10                  15

Phe Phe Val Gln Thr Cys Arg Glu Glu His Asn Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 333
<211> LENGTH: 84
<212> TYPE: PRT
<213> ORGANISM: Anopheles gambiae

<400> SEQUENCE: 333

Gly Lys Val Lys Asp Asn Lys Pro Arg Gly Arg Met Thr Ala Tyr Ala
1               5                   10                  15

Phe Phe Val Gln Thr Cys Arg Glu Glu His Gln Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 334
<211> LENGTH: 84
<212> TYPE: PRT
<213> ORGANISM: Anopheles gambiae

<400> SEQUENCE: 334

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Asn Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 335
<211> LENGTH: 84
<212> TYPE: PRT
<213> ORGANISM: Anopheles gambiae

<400> SEQUENCE: 335
```

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Gln Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65              70                  75                  80

Lys Gly Ala Val

<210> SEQ ID NO 336
<211> LENGTH: 84
<212> TYPE: PRT
<213> ORGANISM: Anopheles gambiae

<400> SEQUENCE: 336

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Asn His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65              70                  75                  80

Lys Gly Ala Val

<210> SEQ ID NO 337
<211> LENGTH: 84
<212> TYPE: PRT
<213> ORGANISM: Anopheles gambiae

<400> SEQUENCE: 337

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Gln His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65              70                  75                  80

Lys Gly Ala Val

<210> SEQ ID NO 338
<211> LENGTH: 84
<212> TYPE: PRT
<213> ORGANISM: Anopheles gambiae

<400> SEQUENCE: 338

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Ala Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 339
<211> LENGTH: 84
<212> TYPE: PRT
<213> ORGANISM: Anopheles gambiae

<400> SEQUENCE: 339

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Ser Glu
                 20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 340
<211> LENGTH: 84
<212> TYPE: PRT
<213> ORGANISM: Anopheles gambiae

<400> SEQUENCE: 340

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Gln
                 20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 341
<211> LENGTH: 84
<212> TYPE: PRT
<213> ORGANISM: Anopheles gambiae

<400> SEQUENCE: 341

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro His
                 20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu

```
            50                  55                  60
Lys Asp Lys Ala Arg Tyr Glu Leu Glu Met Gln Ser Tyr Val Pro Pro
 65                  70                  75                  80

Lys Gly Ala Val
```

<210> SEQ ID NO 342
<211> LENGTH: 84
<212> TYPE: PRT
<213> ORGANISM: Anopheles gambiae

<400> SEQUENCE: 342

```
Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Asn
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val
```

<210> SEQ ID NO 343
<211> LENGTH: 84
<212> TYPE: PRT
<213> ORGANISM: Anopheles gambiae

<400> SEQUENCE: 343

```
Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Gln Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val
```

<210> SEQ ID NO 344
<211> LENGTH: 84
<212> TYPE: PRT
<213> ORGANISM: Anopheles gambiae

<400> SEQUENCE: 344

```
Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

His Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 345
<211> LENGTH: 84
<212> TYPE: PRT
<213> ORGANISM: Anopheles gambiae

<400> SEQUENCE: 345

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Asn Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 346
<211> LENGTH: 84
<212> TYPE: PRT
<213> ORGANISM: Anopheles gambiae

<400> SEQUENCE: 346

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Ile Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 347
<211> LENGTH: 84
<212> TYPE: PRT
<213> ORGANISM: Anopheles gambiae

<400> SEQUENCE: 347

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Val Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 348
<211> LENGTH: 84

```
<212> TYPE: PRT
<213> ORGANISM: Anopheles gambiae

<400> SEQUENCE: 348

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Gln Phe Ser Arg Lys Cys Ala Glu Arg Trp
                35                  40                  45

Lys Thr Met Leu Asp Lys Glu Lys Gln Arg Phe His Glu Met Ala Glu
50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 349
<211> LENGTH: 84
<212> TYPE: PRT
<213> ORGANISM: Anopheles gambiae

<400> SEQUENCE: 349

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala His Phe Ser Arg Lys Cys Ala Glu Arg Trp
                35                  40                  45

Lys Thr Met Leu Asp Lys Glu Lys Gln Arg Phe His Glu Met Ala Glu
50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 350
<211> LENGTH: 84
<212> TYPE: PRT
<213> ORGANISM: Anopheles gambiae

<400> SEQUENCE: 350

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Asn Phe Ser Arg Lys Cys Ala Glu Arg Trp
                35                  40                  45

Lys Thr Met Leu Asp Lys Glu Lys Gln Arg Phe His Glu Met Ala Glu
50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 351
<211> LENGTH: 84
<212> TYPE: PRT
<213> ORGANISM: Anopheles gambiae

<400> SEQUENCE: 351
```

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Ile Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65              70                  75                  80

Lys Gly Ala Val

<210> SEQ ID NO 352
<211> LENGTH: 84
<212> TYPE: PRT
<213> ORGANISM: Anopheles gambiae

<400> SEQUENCE: 352

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Val Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65              70                  75                  80

Lys Gly Ala Val

<210> SEQ ID NO 353
<211> LENGTH: 84
<212> TYPE: PRT
<213> ORGANISM: Anopheles gambiae

<400> SEQUENCE: 353

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser His Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65              70                  75                  80

Lys Gly Ala Val

<210> SEQ ID NO 354
<211> LENGTH: 84
<212> TYPE: PRT
<213> ORGANISM: Anopheles gambiae

<400> SEQUENCE: 354

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30
```

Glu Gln Val Ile Phe Ala Glu Phe Ser Gln Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 355
<211> LENGTH: 84
<212> TYPE: PRT
<213> ORGANISM: Anopheles gambiae

<400> SEQUENCE: 355

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Asn Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 356
<211> LENGTH: 84
<212> TYPE: PRT
<213> ORGANISM: Anopheles gambiae

<400> SEQUENCE: 356

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Gln Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 357
<211> LENGTH: 84
<212> TYPE: PRT
<213> ORGANISM: Anopheles gambiae

<400> SEQUENCE: 357

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Gln Arg Trp
            35                  40                  45

Lys Thr Met Leu Asp Lys Glu Lys Gln Arg Phe His Glu Met Ala Glu

```
            50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 358
<211> LENGTH: 84
<212> TYPE: PRT
<213> ORGANISM: Anopheles gambiae

<400> SEQUENCE: 358

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Glu Gln Val Ile Phe Ala Glu Phe Ser Arg Lys Cys Ala His Arg Trp
             35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 359
<211> LENGTH: 84
<212> TYPE: PRT
<213> ORGANISM: Anopheles gambiae

<400> SEQUENCE: 359

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Glu Gln Val Ile Phe Ala Glu Phe Ser Arg Lys Cys Ala Asn Arg Trp
             35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 360
<211> LENGTH: 84
<212> TYPE: PRT
<213> ORGANISM: Anopheles gambiae

<400> SEQUENCE: 360

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Glu Gln Val Ile Phe Ala Glu Phe Ser Arg Lys Cys Ala Glu His Trp
             35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 361
<211> LENGTH: 84
<212> TYPE: PRT
<213> ORGANISM: Anopheles gambiae

<400> SEQUENCE: 361

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Gln Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 362
<211> LENGTH: 84
<212> TYPE: PRT
<213> ORGANISM: Anopheles gambiae

<400> SEQUENCE: 362

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Tyr
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 363
<211> LENGTH: 84
<212> TYPE: PRT
<213> ORGANISM: Anopheles gambiae

<400> SEQUENCE: 363

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Ser
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 364
<211> LENGTH: 84

```
<212> TYPE: PRT
<213> ORGANISM: Anopheles gambiae

<400> SEQUENCE: 364

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Asn Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 365
<211> LENGTH: 84
<212> TYPE: PRT
<213> ORGANISM: Anopheles gambiae

<400> SEQUENCE: 365

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Gln Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 366
<211> LENGTH: 84
<212> TYPE: PRT
<213> ORGANISM: Anopheles gambiae

<400> SEQUENCE: 366

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Ile Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 367
<211> LENGTH: 84
<212> TYPE: PRT
<213> ORGANISM: Anopheles gambiae

<400> SEQUENCE: 367
```

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Val Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 368
<211> LENGTH: 84
<212> TYPE: PRT
<213> ORGANISM: Anopheles gambiae

<400> SEQUENCE: 368

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Ile Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 369
<211> LENGTH: 84
<212> TYPE: PRT
<213> ORGANISM: Anopheles gambiae

<400> SEQUENCE: 369

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Val Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 370
<211> LENGTH: 84
<212> TYPE: PRT
<213> ORGANISM: Anopheles gambiae

<400> SEQUENCE: 370

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30
```

Glu Gln Val Ile Phe Ala Glu Phe Ser Arg Lys Cys Ala Glu Arg Trp
            35                  40                  45

Lys Thr Met Leu Asn Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 371
<211> LENGTH: 84
<212> TYPE: PRT
<213> ORGANISM: Anopheles gambiae

<400> SEQUENCE: 371

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Gln Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 372
<211> LENGTH: 84
<212> TYPE: PRT
<213> ORGANISM: Anopheles gambiae

<400> SEQUENCE: 372

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Asn Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 373
<211> LENGTH: 84
<212> TYPE: PRT
<213> ORGANISM: Anopheles gambiae

<400> SEQUENCE: 373

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Gln Glu Lys Gln Arg Phe His Glu Met Ala Glu

```
            50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 374
<211> LENGTH: 84
<212> TYPE: PRT
<213> ORGANISM: Anopheles gambiae

<400> SEQUENCE: 374

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Gln Lys Gln Arg Phe His Glu Met Ala Glu
        50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 375
<211> LENGTH: 84
<212> TYPE: PRT
<213> ORGANISM: Anopheles gambiae

<400> SEQUENCE: 375

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys His Lys Gln Arg Phe His Glu Met Ala Glu
        50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 376
<211> LENGTH: 84
<212> TYPE: PRT
<213> ORGANISM: Anopheles gambiae

<400> SEQUENCE: 376

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Asn Lys Gln Arg Phe His Glu Met Ala Glu
        50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 377
<211> LENGTH: 84
<212> TYPE: PRT
<213> ORGANISM: Anopheles gambiae

<400> SEQUENCE: 377

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Asn Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 378
<211> LENGTH: 84
<212> TYPE: PRT
<213> ORGANISM: Anopheles gambiae

<400> SEQUENCE: 378

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Gln Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 379
<211> LENGTH: 84
<212> TYPE: PRT
<213> ORGANISM: Anopheles gambiae

<400> SEQUENCE: 379

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln His Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 380
<211> LENGTH: 84

```
<212> TYPE: PRT
<213> ORGANISM: Anopheles gambiae

<400> SEQUENCE: 380

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Gln Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 381
<211> LENGTH: 84
<212> TYPE: PRT
<213> ORGANISM: Anopheles gambiae

<400> SEQUENCE: 381

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Ile His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 382
<211> LENGTH: 84
<212> TYPE: PRT
<213> ORGANISM: Anopheles gambiae

<400> SEQUENCE: 382

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Val His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 383
<211> LENGTH: 84
<212> TYPE: PRT
<213> ORGANISM: Anopheles gambiae

<400> SEQUENCE: 383
```

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Gln Met Ala Glu
50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 384
<211> LENGTH: 84
<212> TYPE: PRT
<213> ORGANISM: Anopheles gambiae

<400> SEQUENCE: 384

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His His Met Ala Glu
50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 385
<211> LENGTH: 84
<212> TYPE: PRT
<213> ORGANISM: Anopheles gambiae

<400> SEQUENCE: 385

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Asn Met Ala Glu
50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 386
<211> LENGTH: 84
<212> TYPE: PRT
<213> ORGANISM: Anopheles gambiae

<400> SEQUENCE: 386

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Ile Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 387
<211> LENGTH: 84
<212> TYPE: PRT
<213> ORGANISM: Anopheles gambiae

<400> SEQUENCE: 387

Gly Lys Val Lys Asp Asn Lys Pro Arg Gly Arg Met Thr Ala Tyr Ala
 1                5                  10                  15

Phe Phe Val Gln Thr Cys Arg Glu Glu His Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Val Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 388
<211> LENGTH: 84
<212> TYPE: PRT
<213> ORGANISM: Anopheles gambiae

<400> SEQUENCE: 388

Gly Lys Val Lys Asp Asn Lys Pro Arg Gly Arg Met Thr Ala Tyr Ala
 1                5                  10                  15

Phe Phe Val Gln Thr Cys Arg Glu Glu His Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Gln
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 389
<211> LENGTH: 84
<212> TYPE: PRT
<213> ORGANISM: Anopheles gambiae

<400> SEQUENCE: 389

Gly Lys Val Lys Asp Asn Lys Pro Arg Gly Arg Met Thr Ala Tyr Ala
 1                5                  10                  15

Phe Phe Val Gln Thr Cys Arg Glu Glu His Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala His

```
                    50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 390
<211> LENGTH: 84
<212> TYPE: PRT
<213> ORGANISM: Anopheles gambiae

<400> SEQUENCE: 390

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Asn
        50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 391
<211> LENGTH: 84
<212> TYPE: PRT
<213> ORGANISM: Anopheles gambiae

<400> SEQUENCE: 391

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Asn Asp Lys Ala Arg Tyr Glu Leu Glu Met Gln Ser Tyr Val Pro Pro
 65                  70                  75                  80

Lys Gly Ala Val

<210> SEQ ID NO 392
<211> LENGTH: 84
<212> TYPE: PRT
<213> ORGANISM: Anopheles gambiae

<400> SEQUENCE: 392

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Gln Asp Lys Ala Arg Tyr Glu Leu Glu Met Gln Ser Tyr Val Pro Pro
 65                  70                  75                  80
```

-continued

Lys Gly Ala Val

<210> SEQ ID NO 393
<211> LENGTH: 84
<212> TYPE: PRT
<213> ORGANISM: Anopheles gambiae

<400> SEQUENCE: 393

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asn Lys Ala Arg Tyr Glu Leu Glu Met Gln Ser Tyr Val Pro Pro
65                  70                  75                  80

Lys Gly Ala Val

<210> SEQ ID NO 394
<211> LENGTH: 84
<212> TYPE: PRT
<213> ORGANISM: Anopheles gambiae

<400> SEQUENCE: 394

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Gln Lys Ala Arg Tyr Glu Leu Glu Met Gln Ser Tyr Val Pro Pro
65                  70                  75                  80

Lys Gly Ala Val

<210> SEQ ID NO 395
<211> LENGTH: 84
<212> TYPE: PRT
<213> ORGANISM: Anopheles gambiae

<400> SEQUENCE: 395

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Asn Ala Arg Tyr Glu Leu Glu Met Gln Ser Tyr Val Pro Pro
65                  70                  75                  80

Lys Gly Ala Val

<210> SEQ ID NO 396
<211> LENGTH: 84

```
<212> TYPE: PRT
<213> ORGANISM: Anopheles gambiae

<400> SEQUENCE: 396

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Gln Ala Arg Tyr Glu Leu Glu Met Gln Ser Tyr Val Pro Pro
65                  70                  75                  80

Lys Gly Ala Val

<210> SEQ ID NO 397
<211> LENGTH: 84
<212> TYPE: PRT
<213> ORGANISM: Anopheles gambiae

<400> SEQUENCE: 397

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala His Tyr Glu Leu Glu Met Gln Ser Tyr Val Pro Pro
65                  70                  75                  80

Lys Gly Ala Val

<210> SEQ ID NO 398
<211> LENGTH: 84
<212> TYPE: PRT
<213> ORGANISM: Anopheles gambiae

<400> SEQUENCE: 398

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Gln Tyr Glu Leu Glu Met Gln Ser Tyr Val Pro Pro
65                  70                  75                  80

Lys Gly Ala Val

<210> SEQ ID NO 399
<211> LENGTH: 84
<212> TYPE: PRT
<213> ORGANISM: Anopheles gambiae

<400> SEQUENCE: 399
```

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg His Glu Leu Glu Met Gln Ser Tyr Val Pro Pro
65                  70                  75                  80

Lys Gly Ala Val

<210> SEQ ID NO 400
<211> LENGTH: 84
<212> TYPE: PRT
<213> ORGANISM: Anopheles gambiae

<400> SEQUENCE: 400

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Ile Glu Leu Glu Met Gln Ser Tyr Val Pro Pro
65                  70                  75                  80

Lys Gly Ala Val

<210> SEQ ID NO 401
<211> LENGTH: 84
<212> TYPE: PRT
<213> ORGANISM: Anopheles gambiae

<400> SEQUENCE: 401

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Gln Leu Glu Met Gln Ser Tyr Val Pro Pro
65                  70                  75                  80

Lys Gly Ala Val

<210> SEQ ID NO 402
<211> LENGTH: 84
<212> TYPE: PRT
<213> ORGANISM: Anopheles gambiae

<400> SEQUENCE: 402

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30
```

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr His Leu Glu Met Gln Ser Tyr Val Pro Pro
 65                  70                  75                  80

Lys Gly Ala Val

<210> SEQ ID NO 403
<211> LENGTH: 84
<212> TYPE: PRT
<213> ORGANISM: Anopheles gambiae

<400> SEQUENCE: 403

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Asn Leu Glu Met Gln Ser Tyr Val Pro Pro
 65                  70                  75                  80

Lys Gly Ala Val

<210> SEQ ID NO 404
<211> LENGTH: 84
<212> TYPE: PRT
<213> ORGANISM: Anopheles gambiae

<400> SEQUENCE: 404

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Ile Glu Met Gln Ser Tyr Val Pro Pro
 65                  70                  75                  80

Lys Gly Ala Val

<210> SEQ ID NO 405
<211> LENGTH: 84
<212> TYPE: PRT
<213> ORGANISM: Anopheles gambiae

<400> SEQUENCE: 405

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu

```
                50                  55                  60
Lys Asp Lys Ala Arg Tyr Glu Val Glu Met Gln Ser Tyr Val Pro Pro
 65                  70                  75                  80

Lys Gly Ala Val

<210> SEQ ID NO 406
<211> LENGTH: 84
<212> TYPE: PRT
<213> ORGANISM: Anopheles gambiae

<400> SEQUENCE: 406

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Gln Met Gln Ser Tyr Val Pro Pro
 65                  70                  75                  80

Lys Gly Ala Val

<210> SEQ ID NO 407
<211> LENGTH: 84
<212> TYPE: PRT
<213> ORGANISM: Anopheles gambiae

<400> SEQUENCE: 407

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu His Met Gln Ser Tyr Val Pro Pro
 65                  70                  75                  80

Lys Gly Ala Val

<210> SEQ ID NO 408
<211> LENGTH: 84
<212> TYPE: PRT
<213> ORGANISM: Anopheles gambiae

<400> SEQUENCE: 408

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Asn Met Gln Ser Tyr Val Pro Pro
 65                  70                  75                  80
```

Lys Gly Ala Val

<210> SEQ ID NO 409
<211> LENGTH: 84
<212> TYPE: PRT
<213> ORGANISM: Anopheles gambiae

<400> SEQUENCE: 409

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Ile Gln Ser Tyr Val Pro Pro
65                  70                  75                  80

Lys Gly Ala Val

<210> SEQ ID NO 410
<211> LENGTH: 84
<212> TYPE: PRT
<213> ORGANISM: Anopheles gambiae

<400> SEQUENCE: 410

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Val Gln Ser Tyr Val Pro Pro
65                  70                  75                  80

Lys Gly Ala Val

<210> SEQ ID NO 411
<211> LENGTH: 84
<212> TYPE: PRT
<213> ORGANISM: Anopheles gambiae

<400> SEQUENCE: 411

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser His Val Pro Pro
65                  70                  75                  80

Lys Gly Ala Val

<210> SEQ ID NO 412
<211> LENGTH: 84

```
<212> TYPE: PRT
<213> ORGANISM: Anopheles gambiae

<400> SEQUENCE: 412

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Ile Val Pro Pro
65                  70                  75                  80

Lys Gly Ala Val

<210> SEQ ID NO 413
<211> LENGTH: 84
<212> TYPE: PRT
<213> ORGANISM: Anopheles gambiae

<400> SEQUENCE: 413

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Ala Pro
65                  70                  75                  80

Lys Gly Ala Val

<210> SEQ ID NO 414
<211> LENGTH: 84
<212> TYPE: PRT
<213> ORGANISM: Anopheles gambiae

<400> SEQUENCE: 414

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Ser Pro
65                  70                  75                  80

Lys Gly Ala Val

<210> SEQ ID NO 415
<211> LENGTH: 84
<212> TYPE: PRT
<213> ORGANISM: Anopheles gambiae

<400> SEQUENCE: 415
```

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Ala
65                  70                  75                  80

Lys Gly Ala Val

<210> SEQ ID NO 416
<211> LENGTH: 84
<212> TYPE: PRT
<213> ORGANISM: Anopheles gambiae

<400> SEQUENCE: 416

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Ser
65                  70                  75                  80

Lys Gly Ala Val

<210> SEQ ID NO 417
<211> LENGTH: 84
<212> TYPE: PRT
<213> ORGANISM: Anopheles gambiae

<400> SEQUENCE: 417

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65                  70                  75                  80

Asn Gly Ala Val

<210> SEQ ID NO 418
<211> LENGTH: 84
<212> TYPE: PRT
<213> ORGANISM: Anopheles gambiae

<400> SEQUENCE: 418

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
                35                  40                  45
Lys Thr Met Leu Asp Lys Glu Lys Gln Arg Phe His Glu Met Ala Glu
 50                  55                  60
Lys Asp Lys Ala Arg Tyr Glu Leu Glu Met Gln Ser Tyr Val Pro Pro
65                  70                  75                  80

Gln Gly Ala Val

<210> SEQ ID NO 419
<211> LENGTH: 77
<212> TYPE: PRT
<213> ORGANISM: Anopheles gambiae

<400> SEQUENCE: 419

Pro Arg Gly Arg Met Thr Ala Tyr Ala Phe Phe Val Gln Thr Cys Arg
1               5                   10                  15
Glu Glu His Lys Lys Lys His Pro Glu Glu Gln Val Ile Phe Ala Glu
                20                  25                  30
Phe Ser Arg Lys Cys Ala Glu Arg Trp Lys Thr Met Leu Asp Lys Glu
            35                  40                  45
Lys Gln Arg Phe His Glu Met Ala Glu Lys Asp Lys Ala Arg Tyr Glu
        50                  55                  60
Leu Glu Met Gln Ser Tyr Val Pro Pro Lys Gly Ala Val
65                  70                  75

<210> SEQ ID NO 420
<211> LENGTH: 77
<212> TYPE: PRT
<213> ORGANISM: Anopheles gambiae

<400> SEQUENCE: 420

Ala Arg Gly Arg Met Thr Ala Tyr Ala Phe Phe Val Gln Thr Cys Arg
1               5                   10                  15
Glu Glu His Lys Lys Lys His Pro Glu Glu Gln Val Ile Phe Ala Glu
                20                  25                  30
Phe Ser Arg Lys Cys Ala Glu Arg Trp Lys Thr Met Leu Asp Lys Glu
            35                  40                  45
Lys Gln Arg Phe His Glu Met Ala Glu Lys Asp Lys Ala Arg Tyr Glu
        50                  55                  60
Leu Glu Met Gln Ser Tyr Val Pro Pro Lys Gly Ala Val
65                  70                  75

<210> SEQ ID NO 421
<211> LENGTH: 77
<212> TYPE: PRT
<213> ORGANISM: Anopheles gambiae

<400> SEQUENCE: 421

Ser Arg Gly Arg Met Thr Ala Tyr Ala Phe Phe Val Gln Thr Cys Arg
1               5                   10                  15
Glu Glu His Lys Lys Lys His Pro Glu Glu Gln Val Ile Phe Ala Glu
                20                  25                  30
Phe Ser Arg Lys Cys Ala Glu Arg Trp Lys Thr Met Leu Asp Lys Glu
            35                  40                  45
Lys Gln Arg Phe His Glu Met Ala Glu Lys Asp Lys Ala Arg Tyr Glu
        50                  55                  60
Leu Glu Met Gln Ser Tyr Val Pro Pro Lys Gly Ala Val
65                  70                  75

<210> SEQ ID NO 422
<211> LENGTH: 77
<212> TYPE: PRT
<213> ORGANISM: Anopheles gambiae

<400> SEQUENCE: 422

Pro His Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 423
<211> LENGTH: 77
<212> TYPE: PRT
<213> ORGANISM: Anopheles gambiae

<400> SEQUENCE: 423

Pro Gln Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 424
<211> LENGTH: 77
<212> TYPE: PRT
<213> ORGANISM: Anopheles gambiae

<400> SEQUENCE: 424

Pro Arg Gly His Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 425
<211> LENGTH: 77
<212> TYPE: PRT
<213> ORGANISM: Anopheles gambiae

<400> SEQUENCE: 425

Pro Arg Gly Gln Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 426
<211> LENGTH: 77
<212> TYPE: PRT
<213> ORGANISM: Anopheles gambiae

<400> SEQUENCE: 426

Pro Arg Gly Arg Ile Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 427
<211> LENGTH: 77
<212> TYPE: PRT
<213> ORGANISM: Anopheles gambiae

<400> SEQUENCE: 427

Pro Arg Gly Arg Val Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 428
<211> LENGTH: 77
<212> TYPE: PRT
<213> ORGANISM: Anopheles gambiae

<400> SEQUENCE: 428

Pro Arg Gly Arg Met Thr Ala His Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val 65                70                75

<210> SEQ ID NO 429
<211> LENGTH: 77
<212> TYPE: PRT
<213> ORGANISM: Anopheles gambiae

<400> SEQUENCE: 429

Pro Arg Gly Arg Met Thr Ala Ile Ala Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 430
<211> LENGTH: 77
<212> TYPE: PRT
<213> ORGANISM: Anopheles gambiae

<400> SEQUENCE: 430

Pro Arg Gly Arg Met Thr Ala Tyr Ala Ile Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 431
<211> LENGTH: 77
<212> TYPE: PRT
<213> ORGANISM: Anopheles gambiae

<400> SEQUENCE: 431

Pro Arg Gly Arg Met Thr Ala Tyr Ala Val Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 432
<211> LENGTH: 77
<212> TYPE: PRT
<213> ORGANISM: Anopheles gambiae

<400> SEQUENCE: 432

Pro Arg Gly Arg Met Thr Ala Tyr Ala Phe Ile Val Gln Thr Cys Arg

```
                1               5                  10                 15
Glu Glu His Lys Lys His Pro Glu Glu Gln Val Ile Phe Ala Glu
            20                  25                 30

Phe Ser Arg Lys Cys Ala Glu Arg Trp Lys Thr Met Leu Asp Lys Glu
            35                  40                 45

Lys Gln Arg Phe His Glu Met Ala Glu Lys Asp Lys Ala Arg Tyr Glu
            50                  55                 60

Leu Glu Met Gln Ser Tyr Val Pro Pro Lys Gly Ala Val
65                  70                  75

<210> SEQ ID NO 433
<211> LENGTH: 77
<212> TYPE: PRT
<213> ORGANISM: Anopheles gambiae

<400> SEQUENCE: 433

Pro Arg Gly Arg Met Thr Ala Tyr Ala Phe Val Val Gln Thr Cys Arg
1               5                   10                 15

Glu Glu His Lys Lys His Pro Glu Glu Gln Val Ile Phe Ala Glu
            20                  25                 30

Phe Ser Arg Lys Cys Ala Glu Arg Trp Lys Thr Met Leu Asp Lys Glu
            35                  40                 45

Lys Gln Arg Phe His Glu Met Ala Glu Lys Asp Lys Ala Arg Tyr Glu
            50                  55                 60

Leu Glu Met Gln Ser Tyr Val Pro Pro Lys Gly Ala Val
65                  70                  75

<210> SEQ ID NO 434
<211> LENGTH: 77
<212> TYPE: PRT
<213> ORGANISM: Anopheles gambiae

<400> SEQUENCE: 434

Pro Arg Gly Arg Met Thr Ala Tyr Ala Phe Val Gln Thr Cys His
1               5                   10                 15

Glu Glu His Lys Lys His Pro Glu Glu Gln Val Ile Phe Ala Glu
            20                  25                 30

Phe Ser Arg Lys Cys Ala Glu Arg Trp Lys Thr Met Leu Asp Lys Glu
            35                  40                 45

Lys Gln Arg Phe His Glu Met Ala Glu Lys Asp Lys Ala Arg Tyr Glu
            50                  55                 60

Leu Glu Met Gln Ser Tyr Val Pro Pro Lys Gly Ala Val
65                  70                  75

<210> SEQ ID NO 435
<211> LENGTH: 77
<212> TYPE: PRT
<213> ORGANISM: Anopheles gambiae

<400> SEQUENCE: 435

Pro Arg Gly Arg Met Thr Ala Tyr Ala Phe Phe Val Gln Thr Cys Gln
1               5                   10                 15

Glu Glu His Lys Lys His Pro Glu Glu Gln Val Ile Phe Ala Glu
            20                  25                 30

Phe Ser Arg Lys Cys Ala Glu Arg Trp Lys Thr Met Leu Asp Lys Glu
            35                  40                 45

Lys Gln Arg Phe His Glu Met Ala Glu Lys Asp Lys Ala Arg Tyr Glu
            50                  55                 60
```

Leu Glu Met Gln Ser Tyr Val Pro Pro Lys Gly Ala Val
65                  70                  75

<210> SEQ ID NO 436
<211> LENGTH: 77
<212> TYPE: PRT
<213> ORGANISM: Anopheles gambiae

<400> SEQUENCE: 436

Pro Arg Gly Arg Met Thr Ala Tyr Ala Phe Phe Val Gln Thr Cys Arg
1               5                   10                  15

Gln Glu His Lys Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 437
<211> LENGTH: 77
<212> TYPE: PRT
<213> ORGANISM: Anopheles gambiae

<400> SEQUENCE: 437

Pro Arg Gly Arg Met Thr Ala Tyr Ala Phe Phe Val Gln Thr Cys Arg
1               5                   10                  15

His Glu His Lys Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 438
<211> LENGTH: 77
<212> TYPE: PRT
<213> ORGANISM: Anopheles gambiae

<400> SEQUENCE: 438

Pro Arg Gly Arg Met Thr Ala Tyr Ala Phe Phe Val Gln Thr Cys Arg
1               5                   10                  15

Asn Glu His Lys Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 439
<211> LENGTH: 77
<212> TYPE: PRT
<213> ORGANISM: Anopheles gambiae

<400> SEQUENCE: 439

```
Pro Arg Gly Arg Met Thr Ala Tyr Ala Phe Phe Val Gln Thr Cys Arg
1               5                   10                  15

Glu Gln His Lys Lys His Pro Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Lys Gly Ala Val
65                  70                  75
```

```
<210> SEQ ID NO 440
<211> LENGTH: 77
<212> TYPE: PRT
<213> ORGANISM: Anopheles gambiae

<400> SEQUENCE: 440

Pro Arg Gly Arg Met Thr Ala Tyr Ala Phe Phe Val Gln Thr Cys Arg
1               5                   10                  15

Glu His His Lys Lys His Pro Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Lys Gly Ala Val
65                  70                  75
```

```
<210> SEQ ID NO 441
<211> LENGTH: 77
<212> TYPE: PRT
<213> ORGANISM: Anopheles gambiae

<400> SEQUENCE: 441

Pro Arg Gly Arg Met Thr Ala Tyr Ala Phe Phe Val Gln Thr Cys Arg
1               5                   10                  15

Glu Asn His Lys Lys His Pro Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Lys Gly Ala Val
65                  70                  75
```

```
<210> SEQ ID NO 442
<211> LENGTH: 77
<212> TYPE: PRT
<213> ORGANISM: Anopheles gambiae

<400> SEQUENCE: 442

Pro Arg Gly Arg Met Thr Ala Tyr Ala Phe Phe Val Gln Thr Cys Arg
1               5                   10                  15

Glu Glu His Asn Lys Lys His Pro Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
            50                  55                  60
```

```
Leu Glu Met Gln Ser Tyr Val Pro Pro Lys Gly Ala Val
 65                  70                  75

<210> SEQ ID NO 443
<211> LENGTH: 77
<212> TYPE: PRT
<213> ORGANISM: Anopheles gambiae

<400> SEQUENCE: 443

Pro Arg Gly Arg Met Thr Ala Tyr Ala Phe Phe Val Gln Thr Cys Arg
  1               5                  10                  15

Glu Glu His Gln Lys Lys His Pro Glu Glu Gln Val Ile Phe Ala Glu
             20                  25                  30

Phe Ser Arg Lys Cys Ala Glu Arg Trp Lys Thr Met Leu Asp Lys Glu
         35                  40                  45

Lys Gln Arg Phe His Glu Met Ala Glu Lys Asp Lys Ala Arg Tyr Glu
     50                  55                  60

Leu Glu Met Gln Ser Tyr Val Pro Pro Lys Gly Ala Val
 65                  70                  75

<210> SEQ ID NO 444
<211> LENGTH: 77
<212> TYPE: PRT
<213> ORGANISM: Anopheles gambiae

<400> SEQUENCE: 444

Pro Arg Gly Arg Met Thr Ala Tyr Ala Phe Phe Val Gln Thr Cys Arg
  1               5                  10                  15

Glu Glu His Lys Asn Lys His Pro Glu Glu Gln Val Ile Phe Ala Glu
             20                  25                  30

Phe Ser Arg Lys Cys Ala Glu Arg Trp Lys Thr Met Leu Asp Lys Glu
         35                  40                  45

Lys Gln Arg Phe His Glu Met Ala Glu Lys Asp Lys Ala Arg Tyr Glu
     50                  55                  60

Leu Glu Met Gln Ser Tyr Val Pro Pro Lys Gly Ala Val
 65                  70                  75

<210> SEQ ID NO 445
<211> LENGTH: 77
<212> TYPE: PRT
<213> ORGANISM: Anopheles gambiae

<400> SEQUENCE: 445

Pro Arg Gly Arg Met Thr Ala Tyr Ala Phe Phe Val Gln Thr Cys Arg
  1               5                  10                  15

Glu Glu His Lys Gln Lys His Pro Glu Glu Gln Val Ile Phe Ala Glu
             20                  25                  30

Phe Ser Arg Lys Cys Ala Glu Arg Trp Lys Thr Met Leu Asp Lys Glu
         35                  40                  45

Lys Gln Arg Phe His Glu Met Ala Glu Lys Asp Lys Ala Arg Tyr Glu
     50                  55                  60

Leu Glu Met Gln Ser Tyr Val Pro Pro Lys Gly Ala Val
 65                  70                  75

<210> SEQ ID NO 446
<211> LENGTH: 77
<212> TYPE: PRT
<213> ORGANISM: Anopheles gambiae

<400> SEQUENCE: 446
```

Pro Arg Gly Arg Met Thr Ala Tyr Ala Phe Phe Val Gln Thr Cys Arg
1               5                   10                  15

Glu Glu His Lys Lys Asn His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 447
<211> LENGTH: 77
<212> TYPE: PRT
<213> ORGANISM: Anopheles gambiae

<400> SEQUENCE: 447

Pro Arg Gly Arg Met Thr Ala Tyr Ala Phe Phe Val Gln Thr Cys Arg
1               5                   10                  15

Glu Glu His Lys Lys Gln His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 448
<211> LENGTH: 77
<212> TYPE: PRT
<213> ORGANISM: Anopheles gambiae

<400> SEQUENCE: 448

Pro Arg Gly Arg Met Thr Ala Tyr Ala Phe Phe Val Gln Thr Cys Arg
1               5                   10                  15

Glu Glu His Lys Lys His Ala Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 449
<211> LENGTH: 77
<212> TYPE: PRT
<213> ORGANISM: Anopheles gambiae

<400> SEQUENCE: 449

Pro Arg Gly Arg Met Thr Ala Tyr Ala Phe Phe Val Gln Thr Cys Arg
1               5                   10                  15

Glu Glu His Lys Lys Lys His Ser Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu

```
                    50                  55                  60
Leu Glu Met Gln Ser Tyr Val Pro Pro Lys Gly Ala Val
 65                  70                  75

<210> SEQ ID NO 450
<211> LENGTH: 77
<212> TYPE: PRT
<213> ORGANISM: Anopheles gambiae

<400> SEQUENCE: 450

Pro Arg Gly Arg Met Thr Ala Tyr Ala Phe Phe Val Gln Thr Cys Arg
  1               5                  10                  15

Glu Glu His Lys Lys Lys His Pro Gln Glu Gln Val Ile Phe Ala Glu
                 20                  25                  30

Phe Ser Arg Lys Cys Ala Glu Arg Trp Lys Thr Met Leu Asp Lys Glu
             35                  40                  45

Lys Gln Arg Phe His Glu Met Ala Glu Lys Asp Lys Ala Arg Tyr Glu
         50                  55                  60

Leu Glu Met Gln Ser Tyr Val Pro Pro Lys Gly Ala Val
 65                  70                  75

<210> SEQ ID NO 451
<211> LENGTH: 77
<212> TYPE: PRT
<213> ORGANISM: Anopheles gambiae

<400> SEQUENCE: 451

Pro Arg Gly Arg Met Thr Ala Tyr Ala Phe Phe Val Gln Thr Cys Arg
  1               5                  10                  15

Glu Glu His Lys Lys Lys His Pro His Glu Gln Val Ile Phe Ala Glu
                 20                  25                  30

Phe Ser Arg Lys Cys Ala Glu Arg Trp Lys Thr Met Leu Asp Lys Glu
             35                  40                  45

Lys Gln Arg Phe His Glu Met Ala Glu Lys Asp Lys Ala Arg Tyr Glu
         50                  55                  60

Leu Glu Met Gln Ser Tyr Val Pro Pro Lys Gly Ala Val
 65                  70                  75

<210> SEQ ID NO 452
<211> LENGTH: 77
<212> TYPE: PRT
<213> ORGANISM: Anopheles gambiae

<400> SEQUENCE: 452

Pro Arg Gly Arg Met Thr Ala Tyr Ala Phe Phe Val Gln Thr Cys Arg
  1               5                  10                  15

Glu Glu His Lys Lys Lys His Pro Asn Glu Gln Val Ile Phe Ala Glu
                 20                  25                  30

Phe Ser Arg Lys Cys Ala Glu Arg Trp Lys Thr Met Leu Asp Lys Glu
             35                  40                  45

Lys Gln Arg Phe His Glu Met Ala Glu Lys Asp Lys Ala Arg Tyr Glu
         50                  55                  60

Leu Glu Met Gln Ser Tyr Val Pro Pro Lys Gly Ala Val
 65                  70                  75

<210> SEQ ID NO 453
<211> LENGTH: 77
<212> TYPE: PRT
<213> ORGANISM: Anopheles gambiae
```

<400> SEQUENCE: 453

Pro Arg Gly Arg Met Thr Ala Tyr Ala Phe Phe Val Gln Thr Cys Arg
1               5                   10                  15

Glu Glu His Lys Lys Lys His Pro Glu Gln Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 454
<211> LENGTH: 77
<212> TYPE: PRT
<213> ORGANISM: Anopheles gambiae

<400> SEQUENCE: 454

Pro Arg Gly Arg Met Thr Ala Tyr Ala Phe Phe Val Gln Thr Cys Arg
1               5                   10                  15

Glu Glu His Lys Lys Lys His Pro Glu His Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 455
<211> LENGTH: 77
<212> TYPE: PRT
<213> ORGANISM: Anopheles gambiae

<400> SEQUENCE: 455

Pro Arg Gly Arg Met Thr Ala Tyr Ala Phe Phe Val Gln Thr Cys Arg
1               5                   10                  15

Glu Glu His Lys Lys Lys His Pro Glu Asn Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 456
<211> LENGTH: 77
<212> TYPE: PRT
<213> ORGANISM: Anopheles gambiae

<400> SEQUENCE: 456

Pro Arg Gly Arg Met Thr Ala Tyr Ala Phe Phe Val Gln Thr Cys Arg
1               5                   10                  15

Glu Glu His Lys Lys Lys His Pro Glu Gln Val Ile Ile Ala Glu
            20                  25                  30

Phe Ser Arg Lys Cys Ala Glu Arg Trp Lys Thr Met Leu Asp Lys Glu
        35                  40                  45

-continued

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 457
<211> LENGTH: 77
<212> TYPE: PRT
<213> ORGANISM: Anopheles gambiae

<400> SEQUENCE: 457

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Val Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 458
<211> LENGTH: 77
<212> TYPE: PRT
<213> ORGANISM: Anopheles gambiae

<400> SEQUENCE: 458

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Gln
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 459
<211> LENGTH: 77
<212> TYPE: PRT
<213> ORGANISM: Anopheles gambiae

<400> SEQUENCE: 459

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala His
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 460
<211> LENGTH: 77
<212> TYPE: PRT
<213> ORGANISM: Anopheles gambiae

<400> SEQUENCE: 460

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Asn
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 461
<211> LENGTH: 77
<212> TYPE: PRT
<213> ORGANISM: Anopheles gambiae

<400> SEQUENCE: 461

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Ile Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 462
<211> LENGTH: 77
<212> TYPE: PRT
<213> ORGANISM: Anopheles gambiae

<400> SEQUENCE: 462

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Val Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 463
<211> LENGTH: 77
<212> TYPE: PRT
<213> ORGANISM: Anopheles gambiae

<400> SEQUENCE: 463

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser His Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 464
<211> LENGTH: 77
<212> TYPE: PRT
<213> ORGANISM: Anopheles gambiae

<400> SEQUENCE: 464

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
                20                  25                  30

Phe Ser Gln Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 465
<211> LENGTH: 77
<212> TYPE: PRT
<213> ORGANISM: Anopheles gambiae

<400> SEQUENCE: 465

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
                20                  25                  30

Phe Ser Arg Asn Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 466
<211> LENGTH: 77
<212> TYPE: PRT
<213> ORGANISM: Anopheles gambiae

<400> SEQUENCE: 466

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
                20                  25                  30

Phe Ser Arg Gln Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 467
<211> LENGTH: 77
<212> TYPE: PRT

<213> ORGANISM: Anopheles gambiae

<400> SEQUENCE: 467

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Gln Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 468
<211> LENGTH: 77
<212> TYPE: PRT
<213> ORGANISM: Anopheles gambiae

<400> SEQUENCE: 468

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala His Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 469
<211> LENGTH: 77
<212> TYPE: PRT
<213> ORGANISM: Anopheles gambiae

<400> SEQUENCE: 469

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Asn Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 470
<211> LENGTH: 77
<212> TYPE: PRT
<213> ORGANISM: Anopheles gambiae

<400> SEQUENCE: 470

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu His Trp Lys Thr Met Leu Asp Lys Glu

-continued

```
                35                  40                  45

Lys Gln Arg Phe His Glu Met Ala Glu Lys Asp Lys Ala Arg Tyr Glu
         50                  55                  60

Leu Glu Met Gln Ser Tyr Val Pro Pro Lys Gly Ala Val
 65                  70                  75

<210> SEQ ID NO 471
<211> LENGTH: 77
<212> TYPE: PRT
<213> ORGANISM: Anopheles gambiae

<400> SEQUENCE: 471

Pro Arg Gly Arg Met Thr Ala Tyr Ala Phe Phe Val Gln Thr Cys Arg
  1               5                  10                  15

Glu Glu His Lys Lys Lys His Pro Glu Glu Gln Val Ile Phe Ala Glu
                 20                  25                  30

Phe Ser Arg Lys Cys Ala Glu Gln Trp Lys Thr Met Leu Asp Lys Glu
             35                  40                  45

Lys Gln Arg Phe His Glu Met Ala Glu Lys Asp Lys Ala Arg Tyr Glu
         50                  55                  60

Leu Glu Met Gln Ser Tyr Val Pro Pro Lys Gly Ala Val
 65                  70                  75

<210> SEQ ID NO 472
<211> LENGTH: 77
<212> TYPE: PRT
<213> ORGANISM: Anopheles gambiae

<400> SEQUENCE: 472

Pro Arg Gly Arg Met Thr Ala Tyr Ala Phe Phe Val Gln Thr Cys Arg
  1               5                  10                  15

Glu Glu His Lys Lys Lys His Pro Glu Glu Gln Val Ile Phe Ala Glu
                 20                  25                  30

Phe Ser Arg Lys Cys Ala Glu Arg Tyr Lys Thr Met Leu Asp Lys Glu
             35                  40                  45

Lys Gln Arg Phe His Glu Met Ala Glu Lys Asp Lys Ala Arg Tyr Glu
         50                  55                  60

Leu Glu Met Gln Ser Tyr Val Pro Pro Lys Gly Ala Val
 65                  70                  75

<210> SEQ ID NO 473
<211> LENGTH: 77
<212> TYPE: PRT
<213> ORGANISM: Anopheles gambiae

<400> SEQUENCE: 473

Pro Arg Gly Arg Met Thr Ala Tyr Ala Phe Phe Val Gln Thr Cys Arg
  1               5                  10                  15

Glu Glu His Lys Lys Lys His Pro Glu Glu Gln Val Ile Phe Ala Glu
                 20                  25                  30

Phe Ser Arg Lys Cys Ala Glu Arg Ser Lys Thr Met Leu Asp Lys Glu
             35                  40                  45

Lys Gln Arg Phe His Glu Met Ala Glu Lys Asp Lys Ala Arg Tyr Glu
         50                  55                  60

Leu Glu Met Gln Ser Tyr Val Pro Pro Lys Gly Ala Val
 65                  70                  75

<210> SEQ ID NO 474
<211> LENGTH: 77
```

```
<212> TYPE: PRT
<213> ORGANISM: Anopheles gambiae

<400> SEQUENCE: 474

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Asn Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 475
<211> LENGTH: 77
<212> TYPE: PRT
<213> ORGANISM: Anopheles gambiae

<400> SEQUENCE: 475

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Gln Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 476
<211> LENGTH: 77
<212> TYPE: PRT
<213> ORGANISM: Anopheles gambiae

<400> SEQUENCE: 476

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Ile Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 477
<211> LENGTH: 77
<212> TYPE: PRT
<213> ORGANISM: Anopheles gambiae

<400> SEQUENCE: 477

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30
```

```
Phe Ser Arg Lys Cys Ala Glu Arg Trp Lys Thr Val Leu Asp Lys Glu
         35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 478
<211> LENGTH: 77
<212> TYPE: PRT
<213> ORGANISM: Anopheles gambiae

<400> SEQUENCE: 478

Pro Arg Gly Arg Met Thr Ala Tyr Ala Phe Phe Val Gln Thr Cys Arg
 1               5                  10                  15

Glu Glu His Lys Lys His Pro Glu Glu Gln Val Ile Phe Ala Glu
             20                  25                  30

Phe Ser Arg Lys Cys Ala Glu Arg Trp Lys Thr Met Ile Asp Lys Glu
         35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 479
<211> LENGTH: 77
<212> TYPE: PRT
<213> ORGANISM: Anopheles gambiae

<400> SEQUENCE: 479

Pro Arg Gly Arg Met Thr Ala Tyr Ala Phe Phe Val Gln Thr Cys Arg
 1               5                  10                  15

Glu Glu His Lys Lys His Pro Glu Glu Gln Val Ile Phe Ala Glu
             20                  25                  30

Phe Ser Arg Lys Cys Ala Glu Arg Trp Lys Thr Met Val Asp Lys Glu
         35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 480
<211> LENGTH: 77
<212> TYPE: PRT
<213> ORGANISM: Anopheles gambiae

<400> SEQUENCE: 480

Pro Arg Gly Arg Met Thr Ala Tyr Ala Phe Phe Val Gln Thr Cys Arg
 1               5                  10                  15

Glu Glu His Lys Lys His Pro Glu Glu Gln Val Ile Phe Ala Glu
             20                  25                  30

Phe Ser Arg Lys Cys Ala Glu Arg Trp Lys Thr Met Leu Asn Lys Glu
         35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 481
```

```
<211> LENGTH: 77
<212> TYPE: PRT
<213> ORGANISM: Anopheles gambiae

<400> SEQUENCE: 481

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Gln Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 482
<211> LENGTH: 77
<212> TYPE: PRT
<213> ORGANISM: Anopheles gambiae

<400> SEQUENCE: 482

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Asn Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 483
<211> LENGTH: 77
<212> TYPE: PRT
<213> ORGANISM: Anopheles gambiae

<400> SEQUENCE: 483

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Gln Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 484
<211> LENGTH: 77
<212> TYPE: PRT
<213> ORGANISM: Anopheles gambiae

<400> SEQUENCE: 484

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30
```

```
Phe Ser Arg Lys Cys Ala Glu Arg Trp Lys Thr Met Leu Asp Lys Gln
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75

<210> SEQ ID NO 485
<211> LENGTH: 77
<212> TYPE: PRT
<213> ORGANISM: Anopheles gambiae

<400> SEQUENCE: 485

Pro Arg Gly Arg Met Thr Ala Tyr Ala Phe Phe Val Gln Thr Cys Arg
 1               5                  10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys His
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75

<210> SEQ ID NO 486
<211> LENGTH: 77
<212> TYPE: PRT
<213> ORGANISM: Anopheles gambiae

<400> SEQUENCE: 486

Pro Arg Gly Arg Met Thr Ala Tyr Ala Phe Phe Val Gln Thr Cys Arg
 1               5                  10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Asn
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75

<210> SEQ ID NO 487
<211> LENGTH: 77
<212> TYPE: PRT
<213> ORGANISM: Anopheles gambiae

<400> SEQUENCE: 487

Pro Arg Gly Arg Met Thr Ala Tyr Ala Phe Phe Val Gln Thr Cys Arg
 1               5                  10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Asn Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75
```

<210> SEQ ID NO 488
<211> LENGTH: 77
<212> TYPE: PRT
<213> ORGANISM: Anopheles gambiae

<400> SEQUENCE: 488

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Gln Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 489
<211> LENGTH: 77
<212> TYPE: PRT
<213> ORGANISM: Anopheles gambiae

<400> SEQUENCE: 489

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln His Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 490
<211> LENGTH: 77
<212> TYPE: PRT
<213> ORGANISM: Anopheles gambiae

<400> SEQUENCE: 490

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Gln Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 491
<211> LENGTH: 77
<212> TYPE: PRT
<213> ORGANISM: Anopheles gambiae

<400> SEQUENCE: 491

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu

```
            20                  25                  30

Phe Ser Arg Lys Cys Ala Glu Arg Trp Lys Thr Met Leu Asp Lys Glu
            35                  40                  45

Lys Gln Arg Ile His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 492
<211> LENGTH: 77
<212> TYPE: PRT
<213> ORGANISM: Anopheles gambiae

<400> SEQUENCE: 492

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Val His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 493
<211> LENGTH: 77
<212> TYPE: PRT
<213> ORGANISM: Anopheles gambiae

<400> SEQUENCE: 493

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Gln Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 494
<211> LENGTH: 77
<212> TYPE: PRT
<213> ORGANISM: Anopheles gambiae

<400> SEQUENCE: 494

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His His Met Ala Glu Lys Asp Lys Ala Arg Tyr Glu
        50                  55                  60

Leu Glu Met Gln Ser Tyr Val Pro Pro Lys Gly Ala Val
65                  70                  75
```

```
<210> SEQ ID NO 495
<211> LENGTH: 77
<212> TYPE: PRT
<213> ORGANISM: Anopheles gambiae

<400> SEQUENCE: 495

Pro Arg Gly Arg Met Thr Ala Tyr Ala Phe Phe Val Gln Thr Cys Arg
1               5                   10                  15

Glu Glu His Lys Lys His Pro Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Asn Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 496
<211> LENGTH: 77
<212> TYPE: PRT
<213> ORGANISM: Anopheles gambiae

<400> SEQUENCE: 496

Pro Arg Gly Arg Met Thr Ala Tyr Ala Phe Phe Val Gln Thr Cys Arg
1               5                   10                  15

Glu Glu His Lys Lys His Pro Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Ile Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 497
<211> LENGTH: 77
<212> TYPE: PRT
<213> ORGANISM: Anopheles gambiae

<400> SEQUENCE: 497

Pro Arg Gly Arg Met Thr Ala Tyr Ala Phe Phe Val Gln Thr Cys Arg
1               5                   10                  15

Glu Glu His Lys Lys His Pro Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Val Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 498
<211> LENGTH: 77
<212> TYPE: PRT
<213> ORGANISM: Anopheles gambiae

<400> SEQUENCE: 498

Pro Arg Gly Arg Met Thr Ala Tyr Ala Phe Phe Val Gln Thr Cys Arg
1               5                   10                  15
```

Glu Glu His Lys Lys His Pro Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Gln Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 499
<211> LENGTH: 77
<212> TYPE: PRT
<213> ORGANISM: Anopheles gambiae

<400> SEQUENCE: 499

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala His Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 500
<211> LENGTH: 77
<212> TYPE: PRT
<213> ORGANISM: Anopheles gambiae

<400> SEQUENCE: 500

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Asn Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 501
<211> LENGTH: 77
<212> TYPE: PRT
<213> ORGANISM: Anopheles gambiae

<400> SEQUENCE: 501

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Asn Asp Lys Ala Arg Tyr Glu
    50                  55                  60

Leu Glu Met Gln Ser Tyr Val Pro Pro Lys Gly Ala Val
65                  70                  75

<210> SEQ ID NO 502
<211> LENGTH: 77
<212> TYPE: PRT
<213> ORGANISM: Anopheles gambiae

<400> SEQUENCE: 502

Pro Arg Gly Arg Met Thr Ala Tyr Ala Phe Phe Val Gln Thr Cys Arg
1               5                   10                  15

Glu Glu His Lys Lys Lys His Pro Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Gln Asp Lys Ala Arg Tyr Glu
            50                  55                  60

Leu Glu Met Gln Ser Tyr Val Pro Pro Lys Gly Ala Val
65                  70                  75

<210> SEQ ID NO 503
<211> LENGTH: 77
<212> TYPE: PRT
<213> ORGANISM: Anopheles gambiae

<400> SEQUENCE: 503

Pro Arg Gly Arg Met Thr Ala Tyr Ala Phe Phe Val Gln Thr Cys Arg
1               5                   10                  15

Glu Glu His Lys Lys Lys His Pro Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asn Lys Ala Arg Tyr Glu
            50                  55                  60

Leu Glu Met Gln Ser Tyr Val Pro Pro Lys Gly Ala Val
65                  70                  75

<210> SEQ ID NO 504
<211> LENGTH: 77
<212> TYPE: PRT
<213> ORGANISM: Anopheles gambiae

<400> SEQUENCE: 504

Pro Arg Gly Arg Met Thr Ala Tyr Ala Phe Phe Val Gln Thr Cys Arg
1               5                   10                  15

Glu Glu His Lys Lys Lys His Pro Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Gln Lys Ala Arg Tyr Glu
            50                  55                  60

Leu Glu Met Gln Ser Tyr Val Pro Pro Lys Gly Ala Val
65                  70                  75

<210> SEQ ID NO 505
<211> LENGTH: 77
<212> TYPE: PRT
<213> ORGANISM: Anopheles gambiae

<400> SEQUENCE: 505

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Asn Ala Arg Tyr Glu
    50                  55                  60

Leu Glu Met Gln Ser Tyr Val Pro Pro Lys Gly Ala Val
65                  70                  75

<210> SEQ ID NO 506
<211> LENGTH: 77
<212> TYPE: PRT
<213> ORGANISM: Anopheles gambiae

<400> SEQUENCE: 506

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Gln Ala Arg Tyr Glu
    50                  55                  60

Leu Glu Met Gln Ser Tyr Val Pro Pro Lys Gly Ala Val
65                  70                  75

<210> SEQ ID NO 507
<211> LENGTH: 77
<212> TYPE: PRT
<213> ORGANISM: Anopheles gambiae

<400> SEQUENCE: 507

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala His Tyr Glu
    50                  55                  60

Leu Glu Met Gln Ser Tyr Val Pro Pro Lys Gly Ala Val
65                  70                  75

<210> SEQ ID NO 508
<211> LENGTH: 77
<212> TYPE: PRT
<213> ORGANISM: Anopheles gambiae

<400> SEQUENCE: 508

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Gln Tyr Glu
    50                  55                  60

Leu Glu Met Gln Ser Tyr Val Pro Pro Lys Gly Ala Val 65            70             75

<210> SEQ ID NO 509
<211> LENGTH: 77
<212> TYPE: PRT
<213> ORGANISM: Anopheles gambiae

<400> SEQUENCE: 509

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg His Glu
    50                  55                  60

Leu Glu Met Gln Ser Tyr Val Pro Pro Lys Gly Ala Val
65              70              75

<210> SEQ ID NO 510
<211> LENGTH: 77
<212> TYPE: PRT
<213> ORGANISM: Anopheles gambiae

<400> SEQUENCE: 510

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Ile Glu
    50                  55                  60

Leu Glu Met Gln Ser Tyr Val Pro Pro Lys Gly Ala Val
65              70              75

<210> SEQ ID NO 511
<211> LENGTH: 77
<212> TYPE: PRT
<213> ORGANISM: Anopheles gambiae

<400> SEQUENCE: 511

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Gln
    50                  55                  60

Leu Glu Met Gln Ser Tyr Val Pro Pro Lys Gly Ala Val
65              70              75

<210> SEQ ID NO 512
<211> LENGTH: 77
<212> TYPE: PRT
<213> ORGANISM: Anopheles gambiae

<400> SEQUENCE: 512

Pro Arg Gly Arg Met Thr Ala Tyr Ala Phe Phe Val Gln Thr Cys Arg

```
                1               5                   10                  15
Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr His
        50                  55                  60

Leu Glu Met Gln Ser Tyr Val Pro Pro Lys Gly Ala Val
65                  70                  75

<210> SEQ ID NO 513
<211> LENGTH: 77
<212> TYPE: PRT
<213> ORGANISM: Anopheles gambiae

<400> SEQUENCE: 513

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Asn
        50                  55                  60

Leu Glu Met Gln Ser Tyr Val Pro Pro Lys Gly Ala Val
65                  70                  75

<210> SEQ ID NO 514
<211> LENGTH: 77
<212> TYPE: PRT
<213> ORGANISM: Anopheles gambiae

<400> SEQUENCE: 514

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Ile Glu Met Gln Ser Tyr Val Pro Pro Lys Gly Ala Val
65                  70                  75

<210> SEQ ID NO 515
<211> LENGTH: 77
<212> TYPE: PRT
<213> ORGANISM: Anopheles gambiae

<400> SEQUENCE: 515

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60
```

Val Glu Met Gln Ser Tyr Val Pro Pro Lys Gly Ala Val
65                  70                  75

<210> SEQ ID NO 516
<211> LENGTH: 77
<212> TYPE: PRT
<213> ORGANISM: Anopheles gambiae

<400> SEQUENCE: 516

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Gln Met Gln Ser Tyr Val Pro Pro Lys Gly Ala Val
65                  70                  75

<210> SEQ ID NO 517
<211> LENGTH: 77
<212> TYPE: PRT
<213> ORGANISM: Anopheles gambiae

<400> SEQUENCE: 517

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu His Met Gln Ser Tyr Val Pro Pro Lys Gly Ala Val
65                  70                  75

<210> SEQ ID NO 518
<211> LENGTH: 77
<212> TYPE: PRT
<213> ORGANISM: Anopheles gambiae

<400> SEQUENCE: 518

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Asn Met Gln Ser Tyr Val Pro Pro Lys Gly Ala Val
65                  70                  75

<210> SEQ ID NO 519
<211> LENGTH: 77
<212> TYPE: PRT
<213> ORGANISM: Anopheles gambiae

<400> SEQUENCE: 519

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Ile Gln Ser Tyr Val Pro Pro Lys Gly Ala Val
65                  70                  75

<210> SEQ ID NO 520
<211> LENGTH: 77
<212> TYPE: PRT
<213> ORGANISM: Anopheles gambiae

<400> SEQUENCE: 520

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Val Gln Ser Tyr Val Pro Pro Lys Gly Ala Val
65                  70                  75

<210> SEQ ID NO 521
<211> LENGTH: 77
<212> TYPE: PRT
<213> ORGANISM: Anopheles gambiae

<400> SEQUENCE: 521

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser His Val Pro Pro Lys Gly Ala Val
65                  70                  75

<210> SEQ ID NO 522
<211> LENGTH: 77
<212> TYPE: PRT
<213> ORGANISM: Anopheles gambiae

<400> SEQUENCE: 522

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

```
Leu Glu Met Gln Ser Ile Val Pro Pro Lys Gly Ala Val
 65                  70                  75

<210> SEQ ID NO 523
<211> LENGTH: 77
<212> TYPE: PRT
<213> ORGANISM: Anopheles gambiae

<400> SEQUENCE: 523

Pro Arg Gly Arg Met Thr Ala Tyr Ala Phe Phe Val Gln Thr Cys Arg
  1               5                  10                  15

Glu Glu His Lys Lys His Pro Glu Glu Gln Val Ile Phe Ala Glu
             20                  25                  30

Phe Ser Arg Lys Cys Ala Glu Arg Trp Lys Thr Met Leu Asp Lys Glu
         35                  40                  45

Lys Gln Arg Phe His Glu Met Ala Glu Lys Asp Lys Ala Arg Tyr Glu
     50                  55                  60

Leu Glu Met Gln Ser Tyr Val Ala Pro Lys Gly Ala Val
 65                  70                  75

<210> SEQ ID NO 524
<211> LENGTH: 77
<212> TYPE: PRT
<213> ORGANISM: Anopheles gambiae

<400> SEQUENCE: 524

Pro Arg Gly Arg Met Thr Ala Tyr Ala Phe Phe Val Gln Thr Cys Arg
  1               5                  10                  15

Glu Glu His Lys Lys His Pro Glu Glu Gln Val Ile Phe Ala Glu
             20                  25                  30

Phe Ser Arg Lys Cys Ala Glu Arg Trp Lys Thr Met Leu Asp Lys Glu
         35                  40                  45

Lys Gln Arg Phe His Glu Met Ala Glu Lys Asp Lys Ala Arg Tyr Glu
     50                  55                  60

Leu Glu Met Gln Ser Tyr Val Ser Pro Lys Gly Ala Val
 65                  70                  75

<210> SEQ ID NO 525
<211> LENGTH: 77
<212> TYPE: PRT
<213> ORGANISM: Anopheles gambiae

<400> SEQUENCE: 525

Pro Arg Gly Arg Met Thr Ala Tyr Ala Phe Phe Val Gln Thr Cys Arg
  1               5                  10                  15

Glu Glu His Lys Lys His Pro Glu Glu Gln Val Ile Phe Ala Glu
             20                  25                  30

Phe Ser Arg Lys Cys Ala Glu Arg Trp Lys Thr Met Leu Asp Lys Glu
         35                  40                  45

Lys Gln Arg Phe His Glu Met Ala Glu Lys Asp Lys Ala Arg Tyr Glu
     50                  55                  60

Leu Glu Met Gln Ser Tyr Val Pro Ala Lys Gly Ala Val
 65                  70                  75

<210> SEQ ID NO 526
<211> LENGTH: 77
<212> TYPE: PRT
<213> ORGANISM: Anopheles gambiae

<400> SEQUENCE: 526
```

```
Pro Arg Gly Arg Met Thr Ala Tyr Ala Phe Val Gln Thr Cys Arg
1               5                  10                 15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
            50                  55                  60

Leu Glu Met Gln Ser Tyr Val Pro Ser Lys Gly Ala Val
65                  70                  75

<210> SEQ ID NO 527
<211> LENGTH: 77
<212> TYPE: PRT
<213> ORGANISM: Anopheles gambiae

<400> SEQUENCE: 527

Pro Arg Gly Arg Met Thr Ala Tyr Ala Phe Val Gln Thr Cys Arg
1               5                  10                 15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Asn Gly Ala Val
65                  70                  75

<210> SEQ ID NO 528
<211> LENGTH: 77
<212> TYPE: PRT
<213> ORGANISM: Anopheles gambiae

<400> SEQUENCE: 528

Pro Arg Gly Arg Met Thr Ala Tyr Ala Phe Val Gln Thr Cys Arg
1               5                  10                 15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Gln Gly Ala Val
65                  70                  75

<210> SEQ ID NO 529
<211> LENGTH: 54
<212> TYPE: PRT
<213> ORGANISM: Anopheles gambiae

<400> SEQUENCE: 529

Pro Glu Glu Gln Val Ile Phe Ala Glu Phe Ser Arg Lys Cys Ala Glu
1               5                  10                 15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
            35                  40                  45

Pro Pro Lys Gly Ala Val
```

```
<210> SEQ ID NO 530
<211> LENGTH: 54
<212> TYPE: PRT
<213> ORGANISM: Anopheles gambiae

<400> SEQUENCE: 530

Ala Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 531
<211> LENGTH: 54
<212> TYPE: PRT
<213> ORGANISM: Anopheles gambiae

<400> SEQUENCE: 531

Ser Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 532
<211> LENGTH: 54
<212> TYPE: PRT
<213> ORGANISM: Anopheles gambiae

<400> SEQUENCE: 532

Pro Gln Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 533
<211> LENGTH: 54
<212> TYPE: PRT
<213> ORGANISM: Anopheles gambiae

<400> SEQUENCE: 533

Pro His Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
```

```
<210> SEQ ID NO 534
<211> LENGTH: 54
<212> TYPE: PRT
<213> ORGANISM: Anopheles gambiae

<400> SEQUENCE: 534

Pro Asn Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 535
<211> LENGTH: 54
<212> TYPE: PRT
<213> ORGANISM: Anopheles gambiae

<400> SEQUENCE: 535

Pro Glu Gln Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 536
<211> LENGTH: 54
<212> TYPE: PRT
<213> ORGANISM: Anopheles gambiae

<400> SEQUENCE: 536

Pro Glu His Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 537
<211> LENGTH: 54
<212> TYPE: PRT
<213> ORGANISM: Anopheles gambiae

<400> SEQUENCE: 537

Pro Glu Asn Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
```

-continued

<210> SEQ ID NO 538
<211> LENGTH: 54
<212> TYPE: PRT
<213> ORGANISM: Anopheles gambiae

<400> SEQUENCE: 538

Pro Glu Glu Gln Val Ile Ile Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 539
<211> LENGTH: 54
<212> TYPE: PRT
<213> ORGANISM: Anopheles gambiae

<400> SEQUENCE: 539

Pro Glu Glu Gln Val Ile Val Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 540
<211> LENGTH: 54
<212> TYPE: PRT
<213> ORGANISM: Anopheles gambiae

<400> SEQUENCE: 540

Pro Glu Glu Gln Val Ile Phe Ala Gln Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 541
<211> LENGTH: 54
<212> TYPE: PRT
<213> ORGANISM: Anopheles gambiae

<400> SEQUENCE: 541

Pro Glu Glu Gln Val Ile Phe Ala His Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val

<210> SEQ ID NO 542
<211> LENGTH: 54
<212> TYPE: PRT
<213> ORGANISM: Anopheles gambiae

<400> SEQUENCE: 542

Pro Glu Glu Gln Val Ile Phe Ala Asn Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 543
<211> LENGTH: 54
<212> TYPE: PRT
<213> ORGANISM: Anopheles gambiae

<400> SEQUENCE: 543

Pro Glu Glu Gln Val Ile Phe Ala Glu Ile Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 544
<211> LENGTH: 54
<212> TYPE: PRT
<213> ORGANISM: Anopheles gambiae

<400> SEQUENCE: 544

Pro Glu Glu Gln Val Ile Phe Ala Glu Val Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 545
<211> LENGTH: 54
<212> TYPE: PRT
<213> ORGANISM: Anopheles gambiae

<400> SEQUENCE: 545

Pro Glu Glu Gln Val Ile Phe Ala Glu Phe Ser His Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val

50

<210> SEQ ID NO 546
<211> LENGTH: 54
<212> TYPE: PRT
<213> ORGANISM: Anopheles gambiae

<400> SEQUENCE: 546

Pro Glu Glu Gln Val Ile Phe Ala Glu Phe Ser Gln Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 547
<211> LENGTH: 54
<212> TYPE: PRT
<213> ORGANISM: Anopheles gambiae

<400> SEQUENCE: 547

Pro Glu Glu Gln Val Ile Phe Ala Glu Phe Ser Arg Asn Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 548
<211> LENGTH: 54
<212> TYPE: PRT
<213> ORGANISM: Anopheles gambiae

<400> SEQUENCE: 548

Pro Glu Glu Gln Val Ile Phe Ala Glu Phe Ser Arg Gln Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 549
<211> LENGTH: 54
<212> TYPE: PRT
<213> ORGANISM: Anopheles gambiae

<400> SEQUENCE: 549

Pro Glu Glu Gln Val Ile Phe Ala Glu Phe Ser Arg Lys Cys Ala Gln
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val

```
<210> SEQ ID NO 550
<211> LENGTH: 54
<212> TYPE: PRT
<213> ORGANISM: Anopheles gambiae

<400> SEQUENCE: 550

Pro Glu Glu Gln Val Ile Phe Ala Glu Phe Ser Arg Lys Cys Ala His
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 551
<211> LENGTH: 54
<212> TYPE: PRT
<213> ORGANISM: Anopheles gambiae

<400> SEQUENCE: 551

Pro Glu Glu Gln Val Ile Phe Ala Glu Phe Ser Arg Lys Cys Ala Asn
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 552
<211> LENGTH: 54
<212> TYPE: PRT
<213> ORGANISM: Anopheles gambiae

<400> SEQUENCE: 552

Pro Glu Glu Gln Val Ile Phe Ala Glu Phe Ser Arg Lys Cys Ala Glu
1               5                   10                  15

His Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 553
<211> LENGTH: 54
<212> TYPE: PRT
<213> ORGANISM: Anopheles gambiae

<400> SEQUENCE: 553

Pro Glu Glu Gln Val Ile Phe Ala Glu Phe Ser Arg Lys Cys Ala Glu
1               5                   10                  15

Gln Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
```

<210> SEQ ID NO 554
<211> LENGTH: 54
<212> TYPE: PRT
<213> ORGANISM: Anopheles gambiae

<400> SEQUENCE: 554

Pro Glu Glu Gln Val Ile Phe Ala Glu Phe Ser Arg Lys Cys Ala Glu
1               5                   10                  15

Arg Tyr Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 555
<211> LENGTH: 54
<212> TYPE: PRT
<213> ORGANISM: Anopheles gambiae

<400> SEQUENCE: 555

Pro Glu Glu Gln Val Ile Phe Ala Glu Phe Ser Arg Lys Cys Ala Glu
1               5                   10                  15

Arg Ser Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 556
<211> LENGTH: 54
<212> TYPE: PRT
<213> ORGANISM: Anopheles gambiae

<400> SEQUENCE: 556

Pro Glu Glu Gln Val Ile Phe Ala Glu Phe Ser Arg Lys Cys Ala Glu
1               5                   10                  15

Arg Trp Asn Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 557
<211> LENGTH: 54
<212> TYPE: PRT
<213> ORGANISM: Anopheles gambiae

<400> SEQUENCE: 557

Pro Glu Glu Gln Val Ile Phe Ala Glu Phe Ser Arg Lys Cys Ala Glu
1               5                   10                  15

Arg Trp Gln Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val

<210> SEQ ID NO 558
<211> LENGTH: 54
<212> TYPE: PRT
<213> ORGANISM: Anopheles gambiae

<400> SEQUENCE: 558

Pro Glu Glu Gln Val Ile Phe Ala Glu Phe Ser Arg Lys Cys Ala Glu
1               5                   10                  15

Arg Trp Lys Thr Ile Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 559
<211> LENGTH: 54
<212> TYPE: PRT
<213> ORGANISM: Anopheles gambiae

<400> SEQUENCE: 559

Pro Glu Glu Gln Val Ile Phe Ala Glu Phe Ser Arg Lys Cys Ala Glu
1               5                   10                  15

Arg Trp Lys Thr Val Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 560
<211> LENGTH: 54
<212> TYPE: PRT
<213> ORGANISM: Anopheles gambiae

<400> SEQUENCE: 560

Pro Glu Glu Gln Val Ile Phe Ala Glu Phe Ser Arg Lys Cys Ala Glu
1               5                   10                  15

Arg Trp Lys Thr Met Ile Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 561
<211> LENGTH: 54
<212> TYPE: PRT
<213> ORGANISM: Anopheles gambiae

<400> SEQUENCE: 561

Pro Glu Glu Gln Val Ile Phe Ala Glu Phe Ser Arg Lys Cys Ala Glu
1               5                   10                  15

Arg Trp Lys Thr Met Val Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val

```
<210> SEQ ID NO 562
<211> LENGTH: 54
<212> TYPE: PRT
<213> ORGANISM: Anopheles gambiae

<400> SEQUENCE: 562

Pro Glu Glu Gln Val Ile Phe Ala Glu Phe Ser Arg Lys Cys Ala Glu
1               5                   10                  15

Arg Trp Lys Thr Met Leu Asn Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 563
<211> LENGTH: 54
<212> TYPE: PRT
<213> ORGANISM: Anopheles gambiae

<400> SEQUENCE: 563

Pro Glu Glu Gln Val Ile Phe Ala Glu Phe Ser Arg Lys Cys Ala Glu
1               5                   10                  15

Arg Trp Lys Thr Met Leu Gln Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 564
<211> LENGTH: 54
<212> TYPE: PRT
<213> ORGANISM: Anopheles gambiae

<400> SEQUENCE: 564

Pro Glu Glu Gln Val Ile Phe Ala Glu Phe Ser Arg Lys Cys Ala Glu
1               5                   10                  15

Arg Trp Lys Thr Met Leu Asp Asn Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 565
<211> LENGTH: 54
<212> TYPE: PRT
<213> ORGANISM: Anopheles gambiae

<400> SEQUENCE: 565

Pro Glu Glu Gln Val Ile Phe Ala Glu Phe Ser Arg Lys Cys Ala Glu
1               5                   10                  15

Arg Trp Lys Thr Met Leu Asp Gln Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
```

<210> SEQ ID NO 566
<211> LENGTH: 54
<212> TYPE: PRT
<213> ORGANISM: Anopheles gambiae

<400> SEQUENCE: 566

Pro Glu Glu Gln Val Ile Phe Ala Glu Phe Ser Arg Lys Cys Ala Glu
1               5                   10                  15

Arg Trp Lys Thr Met Leu Asp Lys Gln Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 567
<211> LENGTH: 54
<212> TYPE: PRT
<213> ORGANISM: Anopheles gambiae

<400> SEQUENCE: 567

Pro Glu Glu Gln Val Ile Phe Ala Glu Phe Ser Arg Lys Cys Ala Glu
1               5                   10                  15

Arg Trp Lys Thr Met Leu Asp Lys His Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 568
<211> LENGTH: 54
<212> TYPE: PRT
<213> ORGANISM: Anopheles gambiae

<400> SEQUENCE: 568

Pro Glu Glu Gln Val Ile Phe Ala Glu Phe Ser Arg Lys Cys Ala Glu
1               5                   10                  15

Arg Trp Lys Thr Met Leu Asp Lys Asn Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 569
<211> LENGTH: 54
<212> TYPE: PRT
<213> ORGANISM: Anopheles gambiae

<400> SEQUENCE: 569

Pro Glu Glu Gln Val Ile Phe Ala Glu Phe Ser Arg Lys Cys Ala Glu
1               5                   10                  15

Arg Trp Lys Thr Met Leu Asp Lys Glu Asn Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val

```
<210> SEQ ID NO 570
<211> LENGTH: 54
<212> TYPE: PRT
<213> ORGANISM: Anopheles gambiae

<400> SEQUENCE: 570

Pro Glu Glu Gln Val Ile Phe Ala Glu Phe Ser Arg Lys Cys Ala Glu
1               5                   10                  15

Arg Trp Lys Thr Met Leu Asp Lys Glu Gln Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 571
<211> LENGTH: 54
<212> TYPE: PRT
<213> ORGANISM: Anopheles gambiae

<400> SEQUENCE: 571

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln His Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 572
<211> LENGTH: 54
<212> TYPE: PRT
<213> ORGANISM: Anopheles gambiae

<400> SEQUENCE: 572

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Gln Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 573
<211> LENGTH: 54
<212> TYPE: PRT
<213> ORGANISM: Anopheles gambiae

<400> SEQUENCE: 573

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Ile His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
```

<210> SEQ ID NO 574
<211> LENGTH: 54
<212> TYPE: PRT
<213> ORGANISM: Anopheles gambiae

<400> SEQUENCE: 574

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Val His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 575
<211> LENGTH: 54
<212> TYPE: PRT
<213> ORGANISM: Anopheles gambiae

<400> SEQUENCE: 575

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Gln Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 576
<211> LENGTH: 54
<212> TYPE: PRT
<213> ORGANISM: Anopheles gambiae

<400> SEQUENCE: 576

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His His Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 577
<211> LENGTH: 54
<212> TYPE: PRT
<213> ORGANISM: Anopheles gambiae

<400> SEQUENCE: 577

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Asn Met
            20                  25                  30

Ala Glu Lys Asp Lys Ala Arg Tyr Glu Leu Glu Met Gln Ser Tyr Val
        35                  40                  45

Pro Pro Lys Gly Ala Val

-continued

<210> SEQ ID NO 578
<211> LENGTH: 54
<212> TYPE: PRT
<213> ORGANISM: Anopheles gambiae

<400> SEQUENCE: 578

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Ile
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 579
<211> LENGTH: 54
<212> TYPE: PRT
<213> ORGANISM: Anopheles gambiae

<400> SEQUENCE: 579

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Val
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 580
<211> LENGTH: 54
<212> TYPE: PRT
<213> ORGANISM: Anopheles gambiae

<400> SEQUENCE: 580

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Gln Lys Asp Lys Ala Arg Tyr Glu Leu Glu Met Gln Ser Tyr Val
        35                  40                  45

Pro Pro Lys Gly Ala Val
    50

<210> SEQ ID NO 581
<211> LENGTH: 54
<212> TYPE: PRT
<213> ORGANISM: Anopheles gambiae

<400> SEQUENCE: 581

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala His Lys Asp Lys Ala Arg Tyr Glu Leu Glu Met Gln Ser Tyr Val
        35                  40                  45

Pro Pro Lys Gly Ala Val

50

<210> SEQ ID NO 582
<211> LENGTH: 54
<212> TYPE: PRT
<213> ORGANISM: Anopheles gambiae

<400> SEQUENCE: 582

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Asn Lys Asp Lys Ala Arg Tyr Glu Leu Glu Met Gln Ser Tyr Val
        35                  40                  45

Pro Pro Lys Gly Ala Val
    50

<210> SEQ ID NO 583
<211> LENGTH: 54
<212> TYPE: PRT
<213> ORGANISM: Anopheles gambiae

<400> SEQUENCE: 583

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Asn Asp Lys Ala Arg Tyr Glu Leu Glu Met Gln Ser Tyr Val
        35                  40                  45

Pro Pro Lys Gly Ala Val
    50

<210> SEQ ID NO 584
<211> LENGTH: 54
<212> TYPE: PRT
<213> ORGANISM: Anopheles gambiae

<400> SEQUENCE: 584

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Gln Asp Lys Ala Arg Tyr Glu Leu Glu Met Gln Ser Tyr Val
        35                  40                  45

Pro Pro Lys Gly Ala Val
    50

<210> SEQ ID NO 585
<211> LENGTH: 54
<212> TYPE: PRT
<213> ORGANISM: Anopheles gambiae

<400> SEQUENCE: 585

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asn Lys Ala Arg Tyr Glu Leu Glu Met Gln Ser Tyr Val
        35                  40                  45

Pro Pro Lys Gly Ala Val

<210> SEQ ID NO 586
<211> LENGTH: 54
<212> TYPE: PRT
<213> ORGANISM: Anopheles gambiae

<400> SEQUENCE: 586

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Gln Lys Ala Arg Tyr Glu Leu Glu Met Gln Ser Tyr Val
        35                  40                  45

Pro Pro Lys Gly Ala Val
    50

<210> SEQ ID NO 587
<211> LENGTH: 54
<212> TYPE: PRT
<213> ORGANISM: Anopheles gambiae

<400> SEQUENCE: 587

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Asn Ala Arg Tyr Glu Leu Glu Met Gln Ser Tyr Val
        35                  40                  45

Pro Pro Lys Gly Ala Val
    50

<210> SEQ ID NO 588
<211> LENGTH: 54
<212> TYPE: PRT
<213> ORGANISM: Anopheles gambiae

<400> SEQUENCE: 588

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Gln Ala Arg Tyr Glu Leu Glu Met Gln Ser Tyr Val
        35                  40                  45

Pro Pro Lys Gly Ala Val
    50

<210> SEQ ID NO 589
<211> LENGTH: 54
<212> TYPE: PRT
<213> ORGANISM: Anopheles gambiae

<400> SEQUENCE: 589

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala His Tyr Glu Leu Glu Met Gln Ser Tyr Val
        35                  40                  45

Pro Pro Lys Gly Ala Val

-continued

<210> SEQ ID NO 590
<211> LENGTH: 54
<212> TYPE: PRT
<213> ORGANISM: Anopheles gambiae

<400> SEQUENCE: 590

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Gln Tyr Glu Leu Glu Met Gln Ser Tyr Val
        35                  40                  45

Pro Pro Lys Gly Ala Val
    50

<210> SEQ ID NO 591
<211> LENGTH: 54
<212> TYPE: PRT
<213> ORGANISM: Anopheles gambiae

<400> SEQUENCE: 591

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg His Glu Leu Glu Met Gln Ser Tyr Val
        35                  40                  45

Pro Pro Lys Gly Ala Val
    50

<210> SEQ ID NO 592
<211> LENGTH: 54
<212> TYPE: PRT
<213> ORGANISM: Anopheles gambiae

<400> SEQUENCE: 592

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Ile Glu Leu Glu Met Gln Ser Tyr Val
        35                  40                  45

Pro Pro Lys Gly Ala Val
    50

<210> SEQ ID NO 593
<211> LENGTH: 54
<212> TYPE: PRT
<213> ORGANISM: Anopheles gambiae

<400> SEQUENCE: 593

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Gln Leu Glu Met Gln Ser Tyr Val
        35                  40                  45

Pro Pro Lys Gly Ala Val

<210> SEQ ID NO 594
<211> LENGTH: 54
<212> TYPE: PRT
<213> ORGANISM: Anopheles gambiae

<400> SEQUENCE: 594

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr His Leu Glu Met Gln Ser Tyr Val
        35                  40                  45

Pro Pro Lys Gly Ala Val
    50

<210> SEQ ID NO 595
<211> LENGTH: 54
<212> TYPE: PRT
<213> ORGANISM: Anopheles gambiae

<400> SEQUENCE: 595

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Asn Leu Glu Met Gln Ser Tyr Val
        35                  40                  45

Pro Pro Lys Gly Ala Val
    50

<210> SEQ ID NO 596
<211> LENGTH: 54
<212> TYPE: PRT
<213> ORGANISM: Anopheles gambiae

<400> SEQUENCE: 596

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Ile Glu Met Gln Ser Tyr Val
        35                  40                  45

Pro Pro Lys Gly Ala Val
    50

<210> SEQ ID NO 597
<211> LENGTH: 54
<212> TYPE: PRT
<213> ORGANISM: Anopheles gambiae

<400> SEQUENCE: 597

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Val Glu Met Gln Ser Tyr Val
        35                  40                  45

Pro Pro Lys Gly Ala Val

<210> SEQ ID NO 598
<211> LENGTH: 54
<212> TYPE: PRT
<213> ORGANISM: Anopheles gambiae

<400> SEQUENCE: 598

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Gln Met Gln Ser Tyr Val
        35                  40                  45

Pro Pro Lys Gly Ala Val
    50

<210> SEQ ID NO 599
<211> LENGTH: 54
<212> TYPE: PRT
<213> ORGANISM: Anopheles gambiae

<400> SEQUENCE: 599

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu His Met Gln Ser Tyr Val
        35                  40                  45

Pro Pro Lys Gly Ala Val
    50

<210> SEQ ID NO 600
<211> LENGTH: 54
<212> TYPE: PRT
<213> ORGANISM: Anopheles gambiae

<400> SEQUENCE: 600

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Asn Met Gln Ser Tyr Val
        35                  40                  45

Pro Pro Lys Gly Ala Val
    50

<210> SEQ ID NO 601
<211> LENGTH: 54
<212> TYPE: PRT
<213> ORGANISM: Anopheles gambiae

<400> SEQUENCE: 601

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Ile Gln Ser Tyr Val
        35                  40                  45

Pro Pro Lys Gly Ala Val

<210> SEQ ID NO 602
<211> LENGTH: 54
<212> TYPE: PRT
<213> ORGANISM: Anopheles gambiae

<400> SEQUENCE: 602

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Val Gln Ser Tyr Val
        35                  40                  45

Pro Pro Lys Gly Ala Val
    50

<210> SEQ ID NO 603
<211> LENGTH: 54
<212> TYPE: PRT
<213> ORGANISM: Anopheles gambiae

<400> SEQUENCE: 603

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser His Val
        35                  40                  45

Pro Pro Lys Gly Ala Val
    50

<210> SEQ ID NO 604
<211> LENGTH: 54
<212> TYPE: PRT
<213> ORGANISM: Anopheles gambiae

<400> SEQUENCE: 604

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Ile Val
        35                  40                  45

Pro Pro Lys Gly Ala Val
    50

<210> SEQ ID NO 605
<211> LENGTH: 54
<212> TYPE: PRT
<213> ORGANISM: Anopheles gambiae

<400> SEQUENCE: 605

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Ala Pro Lys Gly Ala Val

<210> SEQ ID NO 606
<211> LENGTH: 54
<212> TYPE: PRT
<213> ORGANISM: Anopheles gambiae

<400> SEQUENCE: 606

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Ser Pro Lys Gly Ala Val
    50

<210> SEQ ID NO 607
<211> LENGTH: 54
<212> TYPE: PRT
<213> ORGANISM: Anopheles gambiae

<400> SEQUENCE: 607

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Ala Lys Gly Ala Val
    50

<210> SEQ ID NO 608
<211> LENGTH: 54
<212> TYPE: PRT
<213> ORGANISM: Anopheles gambiae

<400> SEQUENCE: 608

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Ser Lys Gly Ala Val
    50

<210> SEQ ID NO 609
<211> LENGTH: 54
<212> TYPE: PRT
<213> ORGANISM: Anopheles gambiae

<400> SEQUENCE: 609

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Asn Gly Ala Val

-continued

```
    50

<210> SEQ ID NO 610
<211> LENGTH: 54
<212> TYPE: PRT
<213> ORGANISM: Anopheles gambiae

<400> SEQUENCE: 610

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Gln Gly Ala Val
    50
```